US008945584B2

(12) United States Patent
Gottwein et al.

(10) Patent No.: US 8,945,584 B2
(45) Date of Patent: Feb. 3, 2015

(54) CELL CULTURE SYSTEM OF A HEPATITIS C GENOTYPE 3A AND 2A CHIMERA

(75) Inventors: Judith M. Gottwein, Frederiksberg (DK); Troels Kasper Høyer Scheel, Copenhagen (DK); Jesper Eugen-Olsen, Hellerup (DK); Jens Bukh, Præstø (DK)

(73) Assignee: Hvidovre Hospital, Hvidovre (DK)

( * ) Notice: Subject to any disclaimer, the term of this patent is extended or adjusted under 35 U.S.C. 154(b) by 587 days.

(21) Appl. No.: 12/595,822

(22) PCT Filed: Apr. 11, 2008

(86) PCT No.: PCT/DK2008/050083
§ 371 (c)(1),
(2), (4) Date: Dec. 8, 2009

(87) PCT Pub. No.: WO2008/125117
PCT Pub. Date: Oct. 23, 2008

(65) Prior Publication Data
US 2010/0093841 A1 Apr. 15, 2010

(30) Foreign Application Priority Data

Apr. 13, 2007 (DK) .................................. 2007 00544
Jul. 27, 2007 (DK) .................................. 2007 01100

(51) Int. Cl.
| | |
|---|---|
| A61K 39/29 | (2006.01) |
| A61K 39/12 | (2006.01) |
| C12N 7/02 | (2006.01) |
| C12N 15/06 | (2006.01) |
| C12Q 1/02 | (2006.01) |
| C07H 21/00 | (2006.01) |
| C12N 7/00 | (2006.01) |
| A61K 39/00 | (2006.01) |

(52) U.S. Cl.
CPC ............ *C12N 7/00* (2013.01); *A61K 2039/5254* (2013.01); *C12N 2770/24251* (2013.01)
USPC ................... 424/228.1; 424/192.1; 424/199.1; 424/202.1; 435/5; 435/235.1; 435/239; 435/320.1; 435/455; 536/23.72

(58) Field of Classification Search
CPC ........... C12N 7/00; C12N 2770/24221; C12N 2770/24222; C12N 2770/24234; C12N 2710/24143; C12N 2770/24211; C12N 2770/24251; C07K 14/005; C07K 16/109; A61K 2039/525; A61K 39/29; A61K 2039/53; A61K 2039/5254; C12Q 1/707
USPC ........................ 435/5, 235.1, 239, 320.1, 455; 424/192.1, 199.1, 228.1; 536/23.72
See application file for complete search history.

(56) References Cited

U.S. PATENT DOCUMENTS

| | | | |
|---|---|---|---|
| 5,428,145 A | 6/1995 | Okamoto et al. | |
| 6,638,714 B1 | 10/2003 | Linnen et al. | |
| 2007/0073039 A1 | 3/2007 | Chisari | |
| 2010/0227311 A1* | 9/2010 | Han et al. ........................ | 435/5 |

FOREIGN PATENT DOCUMENTS

| | | |
|---|---|---|
| EP | 1 801 209 A1 | 6/2007 |
| EP | 1 930 416 A1 | 6/2008 |
| WO | WO 99/04008 A2 | 1/1999 |
| WO | WO 01/21807 A1 | 3/2001 |
| WO | WO 02/052015 A2 | 7/2002 |
| WO | WO 02/059321 A2 | 8/2002 |
| WO | WO 2005/047463 A2 | 5/2005 |
| WO | WO 2005/053516 A2 | 6/2005 |
| WO | WO 2006/096459 A2 | 9/2006 |
| WO | WO 2007/037429 A1 | 4/2007 |
| WO | WO 2007/041487 A2 | 4/2007 |
| WO | WO 2007/073039 A1 | 6/2007 |
| WO | WO 2008/125117 A1 | 10/2008 |
| WO | WO 2008/125119 A1 | 10/2008 |
| WO | WO 2008/141651 A1 | 11/2008 |
| WO | WO 2009/080052 A1 | 7/2009 |
| WO | WO 2009/080053 A1 | 7/2009 |

OTHER PUBLICATIONS

Kunkel, Proc. Natl. Acad. Sci. 1986, 82, 488-492.*
Skolnick et al Trends in Biotech, 2000, 18, 34-39.*
Krieger et al J. Virology, 2001, 75(10), 4614-4624.*
Lanford Virology, 2002, 293, 1-9.*
Verma (Annual Review of Biochem, 2005, 74, 711-738).*
Verma and Somia (1997) Nature 389:239-242.*
Pietsmann PNAS, 2006, 103, 7408-7413.*
Appel, Nicole et al., "Mutational Analysis of Hepatitis C Virus Nonstructural Protein 5A: Potential Role of Differential Phosphorylation in RNA Replication and Identification of a Genetically Flexible Domain" Journal of Virology, Mar. 2005, pp. 3187-3194, vol. 79, No. 5.
Appel, Nicole et al., "Essential Role of Domain III of Nonstructural Protein 5A for Hepatitis C Virus Infectious Particle Assembly" PLOS Pathogens, Mar. 2008, pp. 1-14, vol. 4, Issue 3.
Bukh, Jens et al., "Mutations that permit efficient replication of hepatitis C virus RNA in Huh-7 cells prevent productive replication in chimpanzees" Proc. Natl. Acad. Sci., Oct. 29, 2002, pp. 14416-14421, vol. 99, No. 22.
Chamberlain, Richard W. et al., "Complete nucleotide sequence of a type 4 hepatitis C virus variant, the predominant genotype in the Middle East" Journal of General Virology, 1997, pp. 1341-1347, vol. 78.

(Continued)

*Primary Examiner* — Anoop Singh
(74) *Attorney, Agent, or Firm* — Thompson Coburn LLP; Charles P. Romano

(57) ABSTRACT

A robust and genetically stable cell culture system for Hepatitis C Virus (HCV) genotype 3a is provided. A genotype 3a/2a (S52/JFH1) recombinant containing the structural genes (Core, E1, E2), p7 and NS2 of strain S52 was constructed and characterized in Huh7.5 cells. S52/JFH1 and J6/JFH viruses passaged in cell culture had comparable growth kinetics and yielded similar peak HCV RNA titers and infectivity titers. Direct genome sequencing of cell culture derived S52/JFH1 viruses identified putative adaptive mutations in Core, E2, p7, NS3, and NS5A; clonal analysis revealed that all genomes analyzed exhibited different combinations of these mutations. Finally, viruses resulting from transfection with RNA transcripts of five S52/JFH1 recombinants containing these combinations of putative adaptive mutations performed as efficiently as J6/JFH viruses in Huh7.5 cells and were all genetically stable after viral passage.

15 Claims, 10 Drawing Sheets

(56) References Cited

OTHER PUBLICATIONS

Figure 1:
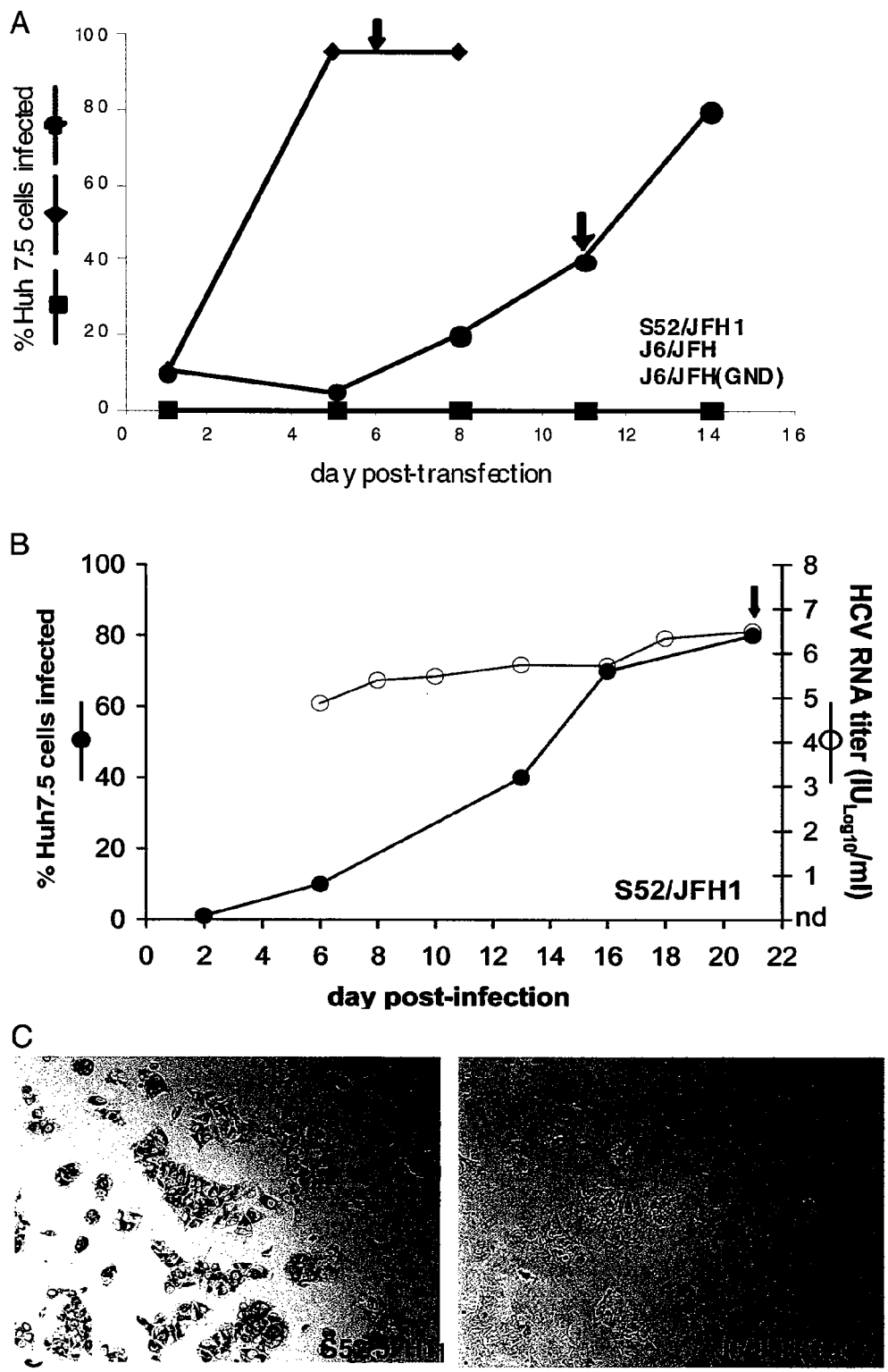
Figure 2:
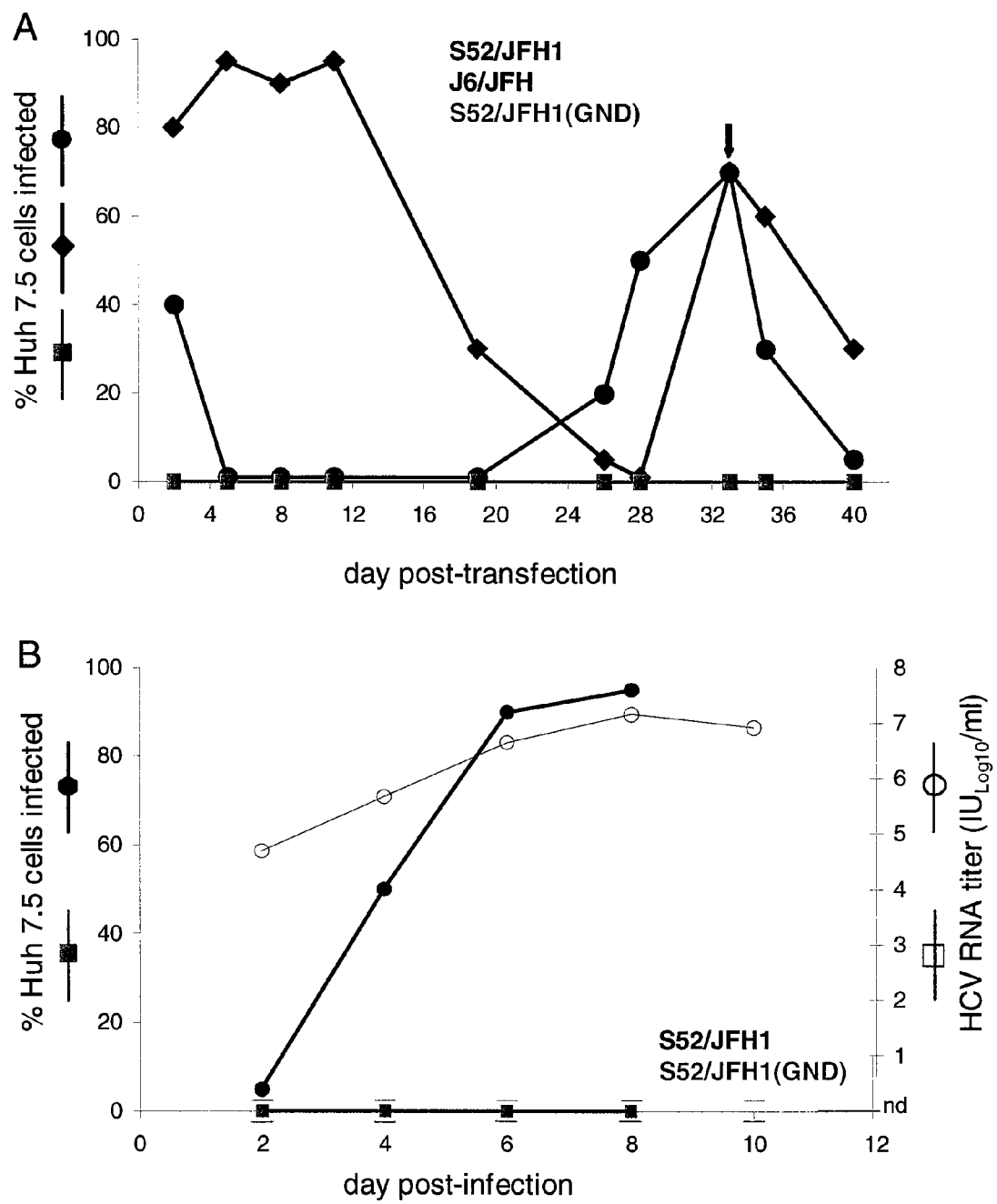

Forns, Xavier et al., "Hepatitis C virus lacking the hypervariable region 1 of the second envelope protein is infectious and causes acute resolving or persistent infection in chimpanzees" Proceedings of the National Academy of Sciences of the United States of America, Nov. 21, 2000, pp. 13318-13323, vol. 97, No. 24.

Gottwein, Judith M. et al., "Robust Hepatitis C Genotype 3a Cell Culture Releasing Adapted Intergenotypic 3a/2a (S52/JFH1) Viruses" Gastroenterology, 2007, pp. 1614-1626, vol. 133.

Gottwein, Judith M. et al., "Development and Characterization of Hepatitis C Virus Genotype 1-7 Cell Culture Systems: Role of CD81 and Scavenger Receptor Class B Type I and Effect of Antiviral Drugs" Hepatology, Oct. 9, 2008, pp. 364-377, vol. 49, No. 2.

Gottwein, Judith M. et al., "Monocistronic Hepatitis C Reporter Virus Recombinants of All Major Genotypes Expressing Enhanced Green Fluorescent Protein Tagged NS5A Protein" Journal of Hepatology, Apr. 2009, p. S33, vol. 50, No. sup1.

Gottwein, Judith M. et al., "Novel Chimeric Cell Culture Systems for Hepatitis C Genotypes 1A, 1B, 3A and 4A" J. Hepatology, Apr. 2007, p. S30, vol. 46.

Graham, Donald J. et al., "A genotype 2b NS5B polymerase with novel substitutions supports replication of a chimeric HCV 1b:2b replicon containing a genotype 1b NS3-5A background" Antiviral Research, 2006, pp. 24-30, vol. 69.

Hou, Wei et al., "A recombinant replication-competent hepatitis C virus expressing Azami-Green, a bright green-emitting fluorescent protein, suitable for visualization of infected cells" Biochemical and Biophysical Research Communications, Sep. 9, 2008, pp. 7-11, vol. 377, No. 1.

Jensen, Tanja Bertelsen "Efficient cell culture system for Hepatitis C Virus genotype 5a" Department of Infectious Diseases and Clinical Research Unit, Copenhagen University Hospital, Master Thesis, Mar. 2007, pp. 1-60.

Jensen, Tanja B. et al., "Highly Efficient JFH1-Based Cell-Culture System for Hepatitis C Virus Genotype 5a: Failure of Homologous Neutralizing-Antibody Treatment to Control Infection" Journal of Infectious Diseases, Dec. 15, 2008, pp. 1756-1765, vol. 198.

Kato, Takanobu et al., "Sequence Analysis of Hepatitis C Virus Isolated From a Fulminant Hepatitis Patient" Journal of Medical Virology, 2001, pp. 334-339, vol. 64.

Kato, Takanobu et al., "Efficient Replication of the Genotype 2a Hepatitis C Virus Subgenomic Replicon" Gastroenterology, 2003, pp. 1808-1817, vol. 125.

Kaul, Artur et al., "Cell Culture Adaptation of Hepatitis C Virus and In Vivo Viability of an Adapted Variant" Journal of Virology, Dec. 2007, pp. 13168-13179, vol. 81, No. 23.

Kim, Chon Saeng et al., "Monitoring the Antiviral Effect of Alpha Interferon on Individual Cells" Journal of Virology, Aug. 2007, pp. 8814-8820, vol. 81, No. 16.

Krieger, Nicole et al., "Enhancement of Hepatitis C Virus RNA Replication by Cell Culture-Adaptive Mutations" Journal of Virology, May 2001, pp. 4614-4624, vol. 75, No. 10.

Lindenbach, Brett D. et al., "Complete Replication of Hepatitis C Virus in Cell Culture" Science, Jul. 22, 2005, pp. 623-626, vol. 309.

Lohmann, Volker at al., "Mutations in Hepatitis C Virus RNAs Conferring Cell Culture Adaptation" Journal of Virology, Feb. 2001, pp. 1437-1449, vol. 75, No. 3.

Moradpour, Darius et al., "Insertion of Green Fluorescent Protein into Nonstructural Protein 5A Allows Direct Visualization of Functional Hepatitis C Virus Replication Complexes" Journal of Virology, Jul. 2004, pp. 7400-7409, vol. 78, No. 14.

Murphy, D. "Hepatitis C virus isolate QC69 polyprotein gene, complete cds" Database EMBL E.B.I. Hinxton U.K., Nov. 7, 2007.

Murphy, Donald et al., "A New Genotype of Hepatitis C Virus Originating From Central Africa" Hepatology, Oct. 2007, p. 623A, vol. 64, No. 4.

Pietschmann, Thomas et al., "Construction and characterization of infectious intragenotypic and intergenotypic hepatitis C virus chimeras" Proc. Natl. Acad. Sci., May 9, 2006, pp. 7408-7413, vol. 103, No. 19.

Prentoe, Jannick C. et al., "HCV entry related studies" Booklet, 4th Smögen Summer Symposium on Virology, Aug. 2008, p. 23.

Schaller, Torsten et al., "Analysis of Hepatitis C Virus Superinfection Exclusion by Using Novel Fluorochrome Gene-Tagged Viral Genomes" Journal of Virology, May 2007, pp. 4591-4603, vol. 81, No. 9.

Scheel, Troels K. H. et al., "Development of JFH1-based cell culture systems for hepatitis C virus genotype 4a and evidence for cross-genotype neutralization" Proceedings of the National Academy of Sciences, Jan. 22, 2008, pp. 997-1002, vol. 105, No. 3.

Simmonds, Peter et al., "Consensus Proposals for a Unified System of Nomenclature of Hepatitis C Virus Genotypes" Hepatology, Oct. 2005, pp. 962-973, vol. 42, No. 4.

Suzuki, T. et al., "Novel Chimeric hepatitis C virus genome comprising nucleic acid encoding epitope tag peptide at hypervariable region 1 of E2 protein, useful as vaccine for preventing or treating hepatitis-c viral infection" Database WPI Week 200914, Thomson Scientific, AN 2009-E03534, Jan. 22, 2009.

Wakita, Takaji et al., "Production of infectious hepatitis C Virus in tissue culture from a cloned viral genome" Nature Medicine, Jul. 2005, pp. 791-796, vol. 11, No. 7.

Yanagi, Masayuki et al., "Transcripts of a Chimeric cDNA Clone of Hepatitis C Virus Genotype 1b Are Infectious in Vivo" Virology, 1998, pp. 161-172, vol. 244.

Yi, Minkyung et al., "Compensatory Mutations in E1, p7, NS2, and NS3 Enhance Yields of Cell Culture-Infectious Intergenotypic Chimeric Hepatitis C Virus" Journal of Virology, Jan. 2007, pp. 629-638, vol. 81, No. 2.

Evans et al., "Claudin-1 is a Hepatitis C Virus Co-Receptor Required for a Late Step in Entry", Journal, Apr. 2007, pp. 801-805, vol. 446/12, Nature Publishing Group.

Gottwein et al., "Novel Infectious cDNA Clones of Hepatitis C Virus Genotype 3a (Strain S52) and 4a (Strain ED43): Genetic Analyses and In Vivo Pathogenesis Studies", Journal of Virology, May 2010, pp. 5277-5293, vol. 84, No. 10, American Society for Microbiology.

Kolykhalov et al., "Transmission of Hepatitis C by Intrahepatic Inoculation with Transcribed RNA", Journal—Science, Jul. 25, 1997, pp. 570-574, vol. 277.

Kremsdorf et al., "New Animal Models for Hepatitis C Viral Infections and Pathogenesis Studies", Journal—World Journal of Gastroenterology, May 7, 2007, pp. 2427-2435, vol. 13, No. 17.

Lindenbach et al., "Cell Culture-Grown Hepatitis C Virus is Infectious In Vivo and can be Recultured In Vitro", Journal—PNAS, Mar. 7, 2006, pp. 3805-3809, vol. 103, No. 10.

Pietschmann et al., "Production of Infectious Genotype 1b Virus Particles in Cell Culture and Impairment by Replication Enhancing Mutations", Journal—PLoS Pathogens, Jun. 2009, pp. 1-14, vol. 5, Issue 6.

Scheel et al., "Efficient Culture Adaptation of Hepatitis C Virus Recombinants with Genotype-Specific Core-NS2 by Using Previously Identified Mutations", Journal of Virology, Mar. 2011, pp. 2891-2906, vol. 85, No. 6.

Yanagi et al., "Transcripts from a Single Full-Length cDNA Clone of Hepatitis C Virus are Infectious When Directly Transfected into the Liver of a Chimpanzee", Journal—Proc. Natl. Acad. Sci., Aug. 1997, pp. 8738-8743, vol. 94, Medical Sciences.

\* cited by examiner

SEQUENCE LISTING

```
<160> NUMBER OF SEQ ID NOS: 67

<210> SEQ ID NO 1
<211> LENGTH: 9684
<212> TYPE: DNA
<213> ORGANISM: Hepatitis C virus

<400> SEQUENCE: 1
acctgcccct aatagggcg acactccgcc atgaatcact ccctgtgag gaactactgt      60 cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgccccggga ggtctcgtag accgtgcacc atgagcacac ttcctaaacc     360
tcaaagaaaa accaaaagaa acaccatccg tcgcccacag gacgttaagt tcccgggtgg     420
cggacagatc gttggtggag tatacgtgtt gccgcgcagg ggcccacgat tgggtgtgcg     480
cgcgacgcgt aaaacttctg aacggtcaca gcctcgcgga cgacgacagc ctatccccaa     540
ggcgcgtcgg agcgaaggcc ggtcctgggc tcagcccggg tacccttggc ccctctatgg     600
taatgagggc tgcgggtggg cagggtggct cctgtccccg cgcggctccc gtccatcttg     660
gggcccaaac gaccccggc ggaggtcccg caatttgggt aaagtcatcg ataccttac      720 gtgcggattc gccgacctca tggggtacat cccgctcgtc ggcgctcccg taggaggcgt     780
cgcaagagcc ctcgcgcatg gcgtgagggc ccttgaagac gggataaatt ttgcaacagg     840
gaacttgccc ggttgctcct tttctatctt ccttcttgct ctgttctcct gcttagttca     900
tcctgcagct agtcttgagt ggcggaatac gtctggcctc tatgtcctta ccaacgactg     960
ttccaatagc agtattgtgt atgaggccga tgacgtcatt ctgcacacac ccggctgtgt    1020
accttgtgtt caggacgaca atacatccac gtgctggacc ccagtgacac ctacggtggc    1080
agtcaggtac gtcggagcaa ccaccgcttc gatacgcagt catgtggacc tattagtggg    1140
cgcggccacg ctgtgctctg cgctctatgt gggtgatatg tgtggggccg tctttctcgt    1200
gggacaagcc ttcacgttca gacctcgtcg ccatcaaacg gtccagacct gtaactgctc    1260
gctgtaccca ggccatgttt caggacatcg aatggcttgg gatatgatga tgaattggtc    1320 cccgctgtg ggtatggtgg tggcgcacat cctgcgattg cccagacct tgtttgacat    1380 actggccggg gccattgggg gcatcttggc gggcctagcc tattattcta tgcagggcaa    1440
```

```
ctgggccaag gtcgctattg tcatgattat gttttcaggg gtcgatgctg aaacatatgt   1500
caccggtggc agtgtagctc atagtgccag agggttaact agcctttta gtatgggcgc    1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
ggggtggggc cccttgacag atgctaacat caccggtcct tctgatgata gaccgtattg   1800
ctggcactac gcacctagac cttgtagtgt tgtcccggca tcaagtgtct gcggccctgt   1860
gtactgcttc acaccatcgc cagtggtcgt aggcactact gatatcaaag gcaagccgac   1920
ctacaactgg ggtgagaatg agacagatgt gttcctgctg gagtccctgc ggcctcccag   1980
tggccggtgt tttggatgcg cgtggatgaa ctccacgggg ttcctcaaga cgtgtggagc   2040
tcccccttgt aacatctatg ggggtgaggg ggatcccgaa aatgagacag acctcttctg   2100
ccccaccgac tgcttcagga aacatcctga ggccacatac agccggtgtg gtgcggggcc   2160
ctggttgaca cctcgctgca tggtcgacta tccataccgg ctttggcatt acccatgtac   2220
agtcaatttc acattgttca aggtgaggat gtttgtgggc ggatttgaac accggtttac   2280
cgccgcttgt aactggacca ggggggagcg ctgcaatatc gaggatcgtg atcgcagcga   2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct tggagaacct tgtcacgctg aacgccgtcg ctgctgctgg   2640
gacacatggt attggttggt acctggtagc cttttgcgcg gcgtggtacg tgcggggtaa   2700
acttgtcccg ctgacgatct acggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940
cccccccttta cttgcacgcg ggagtaggga cggtgtcatc ctgctaacaa gcttgcttta   3000
tccatcctta atttttgaca tcactaagct gctgatagca gtaataggcc cattatactt   3060
aatacaggct gccatcacta ccaccccta ctttgtgcgc gcacatgtac tggtccgcct    3120
ttgcatgctc gtgcgctccg tgatgggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcgggctgcc   3360
ggtctccgcg cgattaggcc gtgaggtatt gttgggacct gctgatgatt atcgggaaat   3420
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcgggggttt tgtggactgt   3600
ttaccacgga gctggcaaca agactctagc cggcttacgg ggtccggtca cgcagatgta   3660
ctcgagtgct gaggggggact tggtaggctg gcccagcccc cctgggacca agtctttgga   3720
gccgtgcaag tgtggagccg tcgacctata tctggtcacg cggaacgctg atgtcatccc   3780
```

```
ggctcggaga cgcggggaca agcggggagc attgctctcc ccgagaccca tttcgacctt    3840
gaagggtcc tcgggggggc cggtgctctg ccctagggc cacgtcgttg ggctcttccg    3900
agcagctgtg tgctctcggg gcgtggccaa atccatcgat ttcatcccg ttgagacact    3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aaccccctcgg tagctgccac    4140
cctggggttt ggggcgtacc tatccaaggc acatggcatc aatcccaaca ttaggactgg    4200
agtcaggacc gtgatgaccg gggaggccat cacgtactcc acatatggca aatttctcgc    4260
cgatggggc tgcgctagcg gcgcctatga catcatcata tgcgatgaat gccacgctgt    4320
ggatgctacc tccattctcg gcatcggaac ggtccttgat caagcagaga cagccggggt    4380
cagactaact gtgctggcta cggccacacc ccccgggtca gtgacaaccc ccatcccga    4440
tatagaagag gtaggcctcg gcgggaggg tgagatcccc ttctatggga gggcgattcc    4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcacccctca cacacctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accacccgcg ggggccaccg gctttgtcgt cagtggcctg gtggggctg ccgtgggcag    5880
cataggcctg ggtaaggtgc tgtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggagggg cgcggtccaa tggatgaaca ggcttattgc    6120
ctttgcttcc agaggaaacc acgtcgcccc tactcactac gtgacggagt cggatgcgtc    6180
```

```
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc    6540
tatcaattgc tacacggagg gccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctccccagg agcgggtttc cacgggcctt    7200
accggcttgg gcacggcctg actacaaccc gccgctcgtg aatcgtggga ggaggccaga    7260
ttaccaaccg cccaccgttg ctggttgtgc tctcccccc cccaagaagg ccccgacgcc    7320
tcccccaagg agacgccgga cagtgggtct gagcgagagc accatatcag aagccctcca    7380
gcaactggcc atcaagacct ttggccagcc cccctcgagc ggtgatgcag gctcgtccac    7440
gggggcgggc gccgccgaat ccggcggtcc gacgtcccct ggtgagccgg cccctcaga    7500 gacaggttcc gcctcctcta tgccccccct cgaggggag cctggagatc cggacctgga    7560
gtctgatcag gtagagcttc aacctccccc ccagggggg ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740
caaccctttg agtaactcgc tgttgcgata ccataacaag gtgtactgta caacatcaaa    7800
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca gtatggatt     7980 cggggccaag gaggtccgca gcttgtccgg gagggccgtt aaccacatca gtccgtgtg    8040 gaaggacctc ctggaagacc cacaaacacc aattcccaca accatcatgg ccaaaaatga    8100
ggtgttctgc gtggacccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactgctg actgagagac tttacgtagg    8460
agggcccatg ttcaacagca gggtcaaac ctgcggttac agacgttgcc gcgccagcgg    8520
```

-continued

```
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc cccagaccg gaatatgacc tggagctaat     8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct tctccattct catggtccaa gacacctgg accagaacct     9000
caactttgag atgtatggat cagtatactc cgtgaatcct ttggaccttc cagccataat    9060
tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttttcacag    9360
cgtgtcgcgc gcccgacccc gctcattact cttcggccta ctcctacttt tcgtaggggt    9420
aggcctcttc ctactccccg ctcggtagag cggcacacac taggtacact ccatagctaa    9480
ctgttccttt ttttttttt ttttttttt ttttttttt ttttttttt cttttttttt        9540
ttttccctc tttcttccct tctcatctta ttctactttc tttcttggtg gctccatctt     9600
agccctagtc acggctagct gtgaaaggtc cgtgagccgc atgactgcag agagtgccgt    9660
aactggtctc tctgcagatc atgt                                           9684
```

<210> SEQ ID NO 2
<211> LENGTH: 3035
<212> TYPE: PRT
<213> ORGANISM: Hepatitis C virus

<400> SEQUENCE: 2

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
```

```
              165                 170                 175
Phe Leu Leu Ala Leu Phe Ser Cys Leu Val His Pro Ala Ala Ser Leu
                180                 185                 190

Glu Trp Arg Asn Thr Ser Gly Leu Tyr Val Leu Thr Asn Asp Cys Ser
                195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
                260                 265                 270

Ser Ala Leu Tyr Val Gly Asp Met Cys Gly Ala Val Phe Leu Val Gly
                275                 280                 285

Gln Ala Phe Thr Phe Arg Pro Arg Arg His Gln Thr Val Gln Thr Cys
                290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
                340                 345                 350

Trp Gly Ile Leu Ala Gly Leu Ala Tyr Tyr Ser Met Gln Gly Asn Trp
                355                 360                 365

Ala Lys Val Ala Ile Val Met Ile Met Phe Ser Gly Val Asp Ala Glu
                370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
                435                 440                 445

Ser Thr Gly Cys Pro Gln Arg Leu Ser Ser Cys Lys Pro Ile Ile Ser
                450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
                500                 505                 510

Ser Pro Val Val Val Gly Thr Thr Asp Ile Lys Gly Lys Pro Thr Tyr
                515                 520                 525

Asn Trp Gly Glu Asn Glu Thr Asp Val Phe Leu Leu Glu Ser Leu Arg
                530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
                580                 585                 590
```

-continued

```
Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
                660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
                740                 745                 750

Ala Leu Glu Asn Leu Val Thr Leu Asn Ala Val Ala Ala Gly Thr
        755                 760                 765

His Gly Ile Gly Trp Tyr Leu Val Ala Phe Cys Ala Ala Trp Tyr Val
        770                 775                 780

Arg Gly Lys Leu Val Pro Leu Thr Ile Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
                820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
    850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
                900                 905                 910

Thr Thr Thr Pro Tyr Phe Val Arg Ala His Val Leu Val Arg Leu Cys
        915                 920                 925

Met Leu Val Arg Ser Val Met Gly Gly Lys Tyr Phe Gln Met Ala Ile
    930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
                980                 985                 990

Gly Ala Asp Thr Ala Ala Cys Gly Asp Ile Leu Cys Gly Leu Pro Val
        995                 1000                1005
```

```
Ser Ala Arg Leu Gly Arg Glu Val Leu Leu Gly Pro Ala Asp Asp
    1010                1015                1020

Tyr Arg Glu Met Gly Trp Arg Leu Leu Ala Pro Ile Thr Ala Tyr
    1025                1030                1035

Ala Gln Gln Thr Arg Gly Leu Leu Gly Ala Ile Val Val Ser Met
    1040                1045                1050

Thr Gly Arg Asp Arg Thr Glu Gln Ala Gly Glu Val Gln Ile Leu
    1055                1060                1065

Ser Thr Val Ser Gln Ser Phe Leu Gly Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Pro Gly Thr Lys Ser Leu Glu Pro
    1115                1120                1125

Cys Lys Cys Gly Ala Val Asp Leu Tyr Leu Val Thr Arg Asn Ala
    1130                1135                1140

Asp Val Ile Pro Ala Arg Arg Gly Asp Lys Arg Gly Ala Leu
    1145                1150                1155

Leu Ser Pro Arg Pro Ile Ser Thr Leu Lys Gly Ser Ser Gly Gly
    1160                1165                1170

Pro Val Leu Cys Pro Arg Gly His Val Val Gly Leu Phe Arg Ala
    1175                1180                1185

Ala Val Cys Ser Arg Gly Val Ala Lys Ser Ile Asp Phe Ile Pro
    1190                1195                1200

Val Glu Thr Leu Asp Val Val Thr Arg Ser Pro Thr Phe Ser Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Lys Val Pro Val
    1235                1240                1245

Ala Tyr Ala Ala Gln Gly Tyr Lys Val Leu Val Leu Asn Pro Ser
    1250                1255                1260

Val Ala Ala Thr Leu Gly Phe Gly Ala Tyr Leu Ser Lys Ala His
    1265                1270                1275

Gly Ile Asn Pro Asn Ile Arg Thr Gly Val Arg Thr Val Met Thr
    1280                1285                1290

Gly Glu Ala Ile Thr Tyr Ser Thr Tyr Gly Lys Phe Leu Ala Asp
    1295                1300                1305

Gly Gly Cys Ala Ser Gly Ala Tyr Asp Ile Ile Ile Cys Asp Glu
    1310                1315                1320

Cys His Ala Val Asp Ala Thr Ser Ile Leu Gly Ile Gly Thr Val
    1325                1330                1335

Leu Asp Gln Ala Glu Thr Ala Gly Val Arg Leu Thr Val Leu Ala
    1340                1345                1350

Thr Ala Thr Pro Pro Gly Ser Val Thr Thr Pro His Pro Asp Ile
    1355                1360                1365

Glu Glu Val Gly Leu Gly Arg Glu Gly Glu Ile Pro Phe Tyr Gly
    1370                1375                1380

Arg Ala Ile Pro Leu Ser Cys Ile Lys Gly Gly Arg His Leu Ile
    1385                1390                1395

Phe Cys His Ser Lys Lys Lys Cys Asp Glu Leu Ala Ala Ala Leu
```

-continued

```
              1400                1405                1410
Arg Gly Met Gly Leu Asn Ala Val Ala Tyr Tyr Arg Gly Leu Asp
    1415                1420                1425

Val Ser Ile Ile Pro Ala Gln Gly Asp Val Val Val Ala Thr
    1430                1435                1440

Asp Ala Leu Met Thr Gly Tyr Thr Gly Asp Phe Asp Ser Val Ile
    1445                1450                1455

Asp Cys Asn Val Ala Val Thr Gln Ala Val Asp Phe Ser Leu Asp
    1460                1465                1470

Pro Thr Phe Thr Ile Thr Thr Gln Thr Val Pro Gln Asp Ala Val
    1475                1480                1485

Ser Arg Ser Gln Arg Arg Gly Arg Thr Gly Arg Gly Arg Gln Gly
    1490                1495                1500

Thr Tyr Arg Tyr Val Ser Thr Gly Glu Arg Ala Ser Gly Met Phe
    1505                1510                1515

Asp Ser Val Val Leu Cys Glu Cys Tyr Asp Ala Gly Ala Ala Trp
    1520                1525                1530

Tyr Asp Leu Thr Pro Ala Glu Thr Thr Val Arg Leu Arg Ala Tyr
    1535                1540                1545

Phe Asn Thr Pro Gly Leu Pro Val Cys Gln Asp His Leu Glu Phe
    1550                1555                1560

Trp Glu Ala Val Phe Thr Gly Leu Thr His Ile Asp Ala His Phe
    1565                1570                1575

Leu Ser Gln Thr Lys Gln Ala Gly Glu Asn Phe Ala Tyr Leu Val
    1580                1585                1590

Ala Tyr Gln Ala Thr Val Cys Ala Arg Ala Lys Ala Pro Pro Pro
    1595                1600                1605

Ser Trp Asp Ala Met Trp Lys Cys Leu Ala Arg Leu Lys Pro Thr
    1610                1615                1620

Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680

Gly Cys Val Ser Ile Ile Gly Arg Leu His Val Asn Gln Arg Val
    1685                1690                1695

Val Val Ala Pro Asp Lys Glu Val Leu Tyr Glu Ala Phe Asp Glu
    1700                1705                1710

Met Glu Glu Cys Ala Ser Arg Ala Ala Leu Ile Glu Glu Gly Gln
    1715                1720                1725

Arg Ile Ala Glu Met Leu Lys Ser Lys Ile Gln Gly Leu Leu Gln
    1730                1735                1740

Gln Ala Ser Lys Gln Ala Gln Asp Ile Gln Pro Ala Met Gln Ala
    1745                1750                1755

Ser Trp Pro Lys Val Glu Gln Phe Trp Ala Arg His Met Trp Asn
    1760                1765                1770

Phe Ile Ser Gly Ile Gln Tyr Leu Ala Gly Leu Ser Thr Leu Pro
    1775                1780                1785

Gly Asn Pro Ala Val Ala Ser Met Met Ala Phe Ser Ala Ala Leu
    1790                1795                1800
```

```
Thr Ser Pro Leu Ser Thr Ser Thr Thr Ile Leu Leu Asn Ile Met
1805             1810              1815

Gly Gly Trp Leu Ala Ser Gln Ile Ala Pro Pro Ala Gly Ala Thr
1820             1825              1830

Gly Phe Val Val Ser Gly Leu Val Gly Ala Ala Val Gly Ser Ile
1835             1840              1845

Gly Leu Gly Lys Val Leu Val Asp Ile Leu Ala Gly Tyr Gly Ala
1850             1855              1860

Gly Ile Ser Gly Ala Leu Val Ala Phe Lys Ile Met Ser Gly Glu
1865             1870              1875

Lys Pro Ser Met Glu Asp Val Ile Asn Leu Leu Pro Gly Ile Leu
1880             1885              1890

Ser Pro Gly Ala Leu Val Val Gly Val Ile Cys Ala Ala Ile Leu
1895             1900              1905

Arg Arg His Val Gly Pro Gly Glu Gly Ala Val Gln Trp Met Asn
1910             1915              1920

Arg Leu Ile Ala Phe Ala Ser Arg Gly Asn His Val Ala Pro Thr
1925             1930              1935

His Tyr Val Thr Glu Ser Asp Ala Ser Gln Arg Val Thr Gln Leu
1940             1945              1950

Leu Gly Ser Leu Thr Ile Thr Ser Leu Leu Arg Arg Leu His Asn
1955             1960              1965

Trp Ile Thr Glu Asp Cys Pro Ile Pro Cys Ser Gly Ser Trp Leu
1970             1975              1980

Arg Asp Val Trp Asp Trp Val Cys Thr Ile Leu Thr Asp Phe Lys
1985             1990              1995

Asn Trp Leu Thr Ser Lys Leu Phe Pro Lys Leu Pro Gly Leu Pro
2000             2005              2010

Phe Ile Ser Cys Gln Lys Gly Tyr Lys Gly Val Trp Ala Gly Thr
2015             2020              2025

Gly Ile Met Thr Thr Arg Cys Pro Cys Gly Ala Asn Ile Ser Gly
2030             2035              2040

Asn Val Arg Leu Gly Ser Met Arg Ile Thr Gly Pro Lys Thr Cys
2045             2050              2055

Met Asn Thr Trp Gln Gly Thr Phe Pro Ile Asn Cys Tyr Thr Glu
2060             2065              2070

Gly Gln Cys Ala Pro Lys Pro Pro Thr Asn Tyr Lys Thr Ala Ile
2075             2080              2085

Trp Arg Val Ala Ala Ser Glu Tyr Ala Glu Val Thr Gln His Gly
2090             2095              2100

Ser Tyr Ser Tyr Val Thr Gly Leu Thr Thr Asp Asn Leu Lys Ile
2105             2110              2115

Pro Cys Gln Leu Pro Ser Pro Glu Phe Phe Ser Trp Val Asp Gly
2120             2125              2130

Val Gln Ile His Arg Phe Ala Pro Thr Pro Lys Pro Phe Phe Arg
2135             2140              2145

Asp Glu Val Ser Phe Cys Val Gly Leu Asn Ser Tyr Ala Val Gly
2150             2155              2160

Ser Gln Leu Pro Cys Glu Pro Glu Pro Asp Ala Asp Val Leu Arg
2165             2170              2175

Ser Met Leu Thr Asp Pro Pro His Ile Thr Ala Glu Thr Ala Ala
2180             2185              2190
```

```
Arg Arg Leu Ala Arg Gly Ser Pro Pro Ser Glu Ala Ser Ser Ser
2195                2200                2205

Val Ser Gln Leu Ser Ala Pro Ser Leu Arg Ala Thr Cys Thr Thr
2210                2215                2220

His Ser Asn Thr Tyr Asp Val Asp Met Val Asp Ala Asn Leu Leu
2225                2230                2235

Met Glu Gly Gly Val Ala Gln Thr Glu Pro Glu Ser Arg Val Pro
2240                2245                2250

Val Leu Asp Phe Leu Glu Pro Met Ala Glu Glu Ser Asp Leu
2255                2260                2265

Glu Pro Ser Ile Pro Ser Glu Cys Met Leu Pro Arg Ser Gly Phe
2270                2275                2280

Pro Arg Ala Leu Pro Ala Trp Ala Arg Pro Asp Tyr Asn Pro Pro
2285                2290                2295

Leu Val Glu Ser Trp Arg Arg Pro Asp Tyr Gln Pro Pro Thr Val
2300                2305                2310

Ala Gly Cys Ala Leu Pro Pro Lys Lys Ala Pro Thr Pro Pro
2315                2320                2325

Pro Arg Arg Arg Arg Thr Val Gly Leu Ser Glu Ser Thr Ile Ser
2330                2335                2340

Glu Ala Leu Gln Gln Leu Ala Ile Lys Thr Phe Gly Gln Pro Pro
2345                2350                2355

Ser Ser Gly Asp Ala Gly Ser Ser Thr Gly Ala Gly Ala Ala Glu
2360                2365                2370

Ser Gly Gly Pro Thr Ser Pro Gly Glu Pro Ala Pro Ser Glu Thr
2375                2380                2385

Gly Ser Ala Ser Ser Met Pro Pro Leu Glu Gly Glu Pro Gly Asp
2390                2395                2400

Pro Asp Leu Glu Ser Asp Gln Val Glu Leu Gln Pro Pro Pro Gln
2405                2410                2415

Gly Gly Gly Val Ala Pro Gly Ser Gly Ser Gly Ser Trp Ser Thr
2420                2425                2430

Cys Ser Glu Glu Asp Asp Thr Thr Val Cys Cys Ser Met Ser Tyr
2435                2440                2445

Ser Trp Thr Gly Ala Leu Ile Thr Pro Cys Ser Pro Glu Glu Glu
2450                2455                2460

Lys Leu Pro Ile Asn Pro Leu Ser Asn Ser Leu Leu Arg Tyr His
2465                2470                2475

Asn Lys Val Tyr Cys Thr Thr Ser Lys Ser Ala Ser Gln Arg Ala
2480                2485                2490

Lys Lys Val Thr Phe Asp Arg Thr Gln Val Leu Asp Ala His Tyr
2495                2500                2505

Asp Ser Val Leu Lys Asp Ile Lys Leu Ala Ala Ser Lys Val Ser
2510                2515                2520

Ala Arg Leu Leu Thr Leu Glu Glu Ala Cys Gln Leu Thr Pro Pro
2525                2530                2535

His Ser Ala Arg Ser Lys Tyr Gly Phe Gly Ala Lys Glu Val Arg
2540                2545                2550

Ser Leu Ser Gly Arg Ala Val Asn His Ile Lys Ser Val Trp Lys
2555                2560                2565

Asp Leu Leu Glu Asp Pro Gln Thr Pro Ile Pro Thr Thr Ile Met
2570                2575                2580

Ala Lys Asn Glu Val Phe Cys Val Asp Pro Ala Lys Gly Gly Lys
```

```
              2585                2590                2595

Lys Pro  Ala Arg Leu Ile  Val Tyr Pro Asp  Leu Gly Val Arg Val
    2600                 2605                 2610

Cys Glu  Lys Met Ala Leu  Tyr Asp Ile Thr  Gln Lys Leu Pro Gln
    2615                 2620                 2625

Ala Val  Met Gly Ala Ser  Tyr Gly Phe Gln  Tyr Ser Pro Ala Gln
    2630                 2635                 2640

Arg Val  Glu Tyr Leu Leu  Lys Ala Trp Ala  Glu Lys Lys Asp Pro
    2645                 2650                 2655

Met Gly  Phe Ser Tyr Asp  Thr Arg Cys Phe  Asp Ser Thr Val Thr
    2660                 2665                 2670

Glu Arg  Asp Ile Arg Thr  Glu Glu Ser Ile  Tyr Gln Ala Cys Ser
    2675                 2680                 2685

Leu Pro  Glu Glu Ala Arg  Thr Ala Ile His  Ser Leu Thr Glu Arg
    2690                 2695                 2700

Leu Tyr  Val Gly Gly Pro  Met Phe Asn Ser  Lys Gly Gln Thr Cys
    2705                 2710                 2715

Gly Tyr  Arg Arg Cys Arg  Ala Ser Gly Val  Leu Thr Thr Ser Met
    2720                 2725                 2730

Gly Asn  Thr Ile Thr Cys  Tyr Val Lys Ala  Leu Ala Ala Cys Lys
    2735                 2740                 2745

Ala Ala  Gly Ile Val Ala  Pro Thr Met Leu  Val Cys Gly Asp Asp
    2750                 2755                 2760

Leu Val  Val Ile Ser Glu  Ser Gln Gly Thr  Glu Glu Asp Glu Arg
    2765                 2770                 2775

Asn Leu  Arg Ala Phe Thr  Glu Ala Met Thr  Arg Tyr Ser Ala Pro
    2780                 2785                 2790

Pro Gly  Asp Pro Pro Arg  Pro Glu Tyr Asp  Leu Glu Leu Ile Thr
    2795                 2800                 2805

Ser Cys  Ser Ser Asn Val  Ser Val Ala Leu  Gly Pro Arg Gly Arg
    2810                 2815                 2820

Arg Arg  Tyr Tyr Leu Thr  Arg Asp Pro Thr  Thr Pro Leu Ala Arg
    2825                 2830                 2835

Ala Ala  Trp Glu Thr Val  Arg His Ser Pro  Ile Asn Ser Trp Leu
    2840                 2845                 2850

Gly Asn  Ile Ile Gln Tyr  Ala Pro Thr Ile  Trp Val Arg Met Val
    2855                 2860                 2865

Leu Met  Thr His Phe Phe  Ser Ile Leu Met  Val Gln Asp Thr Leu
    2870                 2875                 2880

Asp Gln  Asn Leu Asn Phe  Glu Met Tyr Gly  Ser Val Tyr Ser Val
    2885                 2890                 2895

Asn Pro  Leu Asp Leu Pro  Ala Ile Ile Glu  Arg Leu His Gly Leu
    2900                 2905                 2910

Asp Ala  Phe Ser Met His  Thr Tyr Ser His  His Glu Leu Thr Arg
    2915                 2920                 2925

Val Ala  Ser Ala Leu Arg  Lys Leu Gly Ala  Pro Pro Leu Arg Val
    2930                 2935                 2940

Trp Lys  Ser Arg Ala Arg  Ala Val Arg Ala  Ser Leu Ile Ser Arg
    2945                 2950                 2955

Gly Gly  Lys Ala Ala Val  Cys Gly Arg Tyr  Leu Phe Asn Trp Ala
    2960                 2965                 2970

Val Lys  Thr Lys Leu Lys  Leu Thr Pro Leu  Pro Glu Ala Arg Leu
    2975                 2980                 2985
```

| Leu | Asp | Leu | Ser | Ser | Trp | Phe | Thr | Val | Gly | Ala | Gly | Gly | Gly | Asp |
| | 2990 | | | | 2995 | | | | | 3000 | | | | |

| Ile | Phe | His | Ser | Val | Ser | Arg | Ala | Arg | Pro | Arg | Ser | Leu | Leu | Phe |
| 3005 | | | | | 3010 | | | | | 3015 | | | | |

| Gly | Leu | Leu | Leu | Leu | Phe | Val | Gly | Val | Gly | Leu | Phe | Leu | Leu | Pro |
| | 3020 | | | | | 3025 | | | | | 3030 | | | |

Ala Arg
    3035

<210> SEQ ID NO 3
<211> LENGTH: 9684
<212> TYPE: DNA
<213> ORGANISM: Hepatitis C virus

<400> SEQUENCE: 3

```
acctgcccct aatagggcg acactccgcc atgaatcact ccctgtgag gaactactgt      60
cttcacgcag aaagcgccta gccatggcgt tagtatgagt gtcgtacagc ctccaggccc    120
cccctcccg ggagagccat agtggtctgc ggaaccggtg agtacaccgg aattgccggg    180
aagactgggt cctttcttgg ataaacccac tctatgcccg ccatttgggc gtgcccccg    240
caagactgct agccgagtag cgttgggttg cgaaaggcct tgtggtactg cctgataggg    300
tgcttgcgag tgccccggga ggtctcgtag accgtgcacc atgagcacac ttcctaaacc    360
tcaaagaaaa accaaaagaa acaccatccg tcgcccacag gacgttaagt tcccgggtgg    420
cggacagatc gttggtggag tatacgtgtt gccgcgcagg ggcccacgat gggtgtgcg    480
cgcgacgcgt aaaacttctg aacggtcaca gcctcgcgga cgacgacagc ctatccccaa    540
ggcgcgtcgg agcgaaggcc ggtcctgggc tcagcccggg tacccttggc ccctctatgg    600
taatgagggc tgcgggtggg cagggtggct cctgtccccg cgcggctccc gtccatcttg    660
gggcccaaac gacccccggc ggaggtcccg caatttgggt aaagtcatcg ataccctatc    720
gtgcggactc gccgacctca tggggtacat cccgctcgtc ggcgctcccg taggaggcgt    780
cgcaagagcc ctcgcgcatg gcgtgagggc ccttgaagac gggataaaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg gtatggtgg tggcgcacat cctgcgattg cccagacct tgtttgacat    1380
actggccggg gcccattggg gcatcttggc gggcctagcc tattattcta tgcagggcaa   1440
ctgggcaag gtcgctattg tcatgattat gttttcaggg gtcgatgctg aaacatatgt    1500
caccggtggc agtgtagctc atagtgccag agggttaact agccttttta gtgtgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
```

```
ggggtggggc cccttgacag atgctaacat caccggtcct tctgatgata gaccgtattg    1800
ctggcactac gcacctagac cttgtagtgt tgtcccggca tcaagtgtct gcggccctgt    1860
gtactgcttc acaccatcgc cagtggtcgt aggcactact gatatccaag gcaagccgac    1920
ctacaactgg ggtgagaatg agacagatgt gttcctgctg gagtccctgc ggcctcccag    1980
tggccggtgg tttggatgcg cgtggatgaa ctccacgggg ttcctcaaga cgtgtggagc    2040
tcccccttgt aacatctatg ggggtgaggg ggatcccgaa aatgagacag acctcttctg    2100
ccccaccgac tgcttcagga aacatcctga ggccacatac agccggtgtg gtgcggggcc    2160
ctggttgaca cctcgctgca tggtcgacta tccataccgg cttttggcatt acccatgtac    2220 agtcaatttc acattgttca aggtgaggat gtttgtgggc ggatttgaac accggtttac    2280
cgccgcttgt aactggacca gggggagcg ctgcaatatc gaggatcgtg atcgcagcga    2340
gcaacatccg ctgctgcatt caacaactga gcttgctata ctgccttgct ctttcacgcc    2400
catgcctgca ttgtcaacag gtctaataca cctccaccaa aatatcgtgg atgtccaata    2460
cctttatggt gttggatctg acatggtggg atgggcgctg aaatgggagt tcgtcatcct    2520
cgttttcctc ctcctggcag acgcacgcgt gtgcgttgcc ctttggctga tgctgatggt    2580
atcacaagca gaagcagcct ggagaacct tgtcacgctg aacgccgtcg ctgctgctgg    2640
gacacatggt attggttggt acctggtagc cttttgcgcg cgtggtacg tgcggggtaa    2700 acttgtcccg ctgacgagct acggcctgac gggtctttgg tccctagcat tgcttgtcct    2760
cttgctcccc caacgggcgt atgcttggtc gggtgaagac agcgctactc tcggcgctgg    2820
ggtcttggcc ctcttcggct tctttacctt atcaccctgg tacaagcatt ggatcggccg    2880
cctcatgtgg tggaaccagt acactatatg tagatgcgag gccgcccttc aagtgtgggt    2940 cccccccctta cttgcacgcg ggagtaggga cggtgtcatc ctgctaacaa gcttgcttta    3000
tccatcctta attttttgaca tcactaagct gctgatagca gtaataggcc cattatactt    3060
aatacaggct gccatcacta ccaccccccta cttttgtgcgc gcacatgtac tggtccgcct    3120
ttgcatgctc gtgcgctccg tgatgggggg aaagtacttc cagatggcca tactgagcat    3180
tggcagatgg ttcaacacct acctatatga ccacctagcg ccaatgcaac attgggccgc    3240
agctggcctc aaagacctag cagtggccac tgaacctgta atatttagtc ccatggaaat    3300
taaggtcatc acctggggcg cggacacagc ggcttgcgga gatattcttt gcgggctgcc    3360
ggtctccgcg cgattaggcc gtgaggtatt gttgggacct gctgatgatt atcgggaaat    3420
gggttggcgt ctgttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gagggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840 gaagggggtcc tcgggggggc cggtgctctg ccctagggggc cacgtcgttg ggctcttccg    3900
agcagctgtg tgctctcggg gcgtggccaa atccatcgat ttcatcccccg ttgagacact    3960 cgacgttgtt acaaggtctc ccactttcag tgacaacagc acgccaccgg ctgtgccccca    4020 gacctatcag gtcgggtact tgcatgctcc aactggcagt ggaaagagca ccaaggtccc    4080
tgtcgcgtat gccgcccagg ggtacaaagt actagtgctt aaccccctcgg tagctgccac    4140
```

```
cctgggttt ggggcgtacc tatccaaggc acatggcatc aatcccaaca ttaggactgg    4200
agtcaggacc gtgatgaccg gggaggccat cacgtactcc acatatggca aatttctcgc    4260 cgatggggc tgcgctagcg gcgcctatga catcatcata tgcgatgaat gccacgctgt     4320
ggatgctacc tccattctcg gcatcggaac ggtccttgat caagcagaga cagccggggt    4380
cagactaact gtgctggcta cggccacacc ccccgggtca gtgacaaccc cccatcccga    4440
tatagaagag gtaggcctcg gcgggaggg tgagatcccc ttctatggga gggcgattcc     4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680 gacgggtac actggagact ttgactccgt gatcgactgc aatgtagcgg tcacccaagc     4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcgggga     5100 gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820 accaccgcg ggggccaccg gctttgtcgt cagtggcctg gtgggggctg ccgtgggcag     5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggagg cgcggtccaa tggatgaaca ggcttattgc      6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaagggg tacaagggtg tgtgggccgg    6420
cactggcatc atgaccacgc gctgcccttg cggcgccaac atctctggca atgtccgcct    6480
```

```
gggctctatg aggatcacag ggcctaaaac ctgcatgaac acctggcagg ggacctttcc    6540
tatcaattgc tacacggagg gccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccac cggagtgcat gctccccagg agcgggtttc cacgggcctt    7200
accggcttgg gcacggcctg actacaaccc gccgctcgtg aatcgtggga ggaggccaga    7260
ttaccaaccg cccaccgttg ctggttgtgc tctcccccccc cccaagaagg ccccgacgcc    7320
tcccccaagg agacgccgga cagtgggtct gagcgagagc accatatcag aagccctcca    7380
gcaactggcc atcaagacct ttggccagcc ccctcgagc ggtgatgcag gctcgtccac    7440
gggggcgggc gccgccgaat ccggcggtcc gacgtcccct ggtgagccgg ccccctcaga    7500
gacaggttcc gcctcctcta tgcccccccct cgaggggggag cctggagatc cggacctgga    7560
gtctgatcag gtagagcttc aacctccccc caggggggg ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740 caacccttg agtaactcgc tgttgcgata ccataacaag gtgtactgta caacatcaaa    7800
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920 cacccttggag gaggcgtgcc agttgactcc accccattct gcaagatcca agtatggatt    7980 cgggccaag gaggtccgca gcttgtccgg gagggccgtt aaccacatca gtccgtgtg    8040 gaaggacctc ctggaagacc cacaaacacc aattcccaca accatcatgg ccaaaaatga    8100
ggtgttctgc gtggaccccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttcgtagg    8460 agggcccatg ttcaacagca agggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc cagggggactg aggaggacga gcggaacctg agagccttca cggaggccat    8700
gaccaggtac tctgcccctc ctggtgatcc cccagaccg gaatatgacc tggagctaat    8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
```

-continued

```
ccctatcaat tcatggctgg gaaacatcat ccagtatgct ccaaccatat gggttcgcat    8940
ggtcctaatg acacacttct tctccattct catggtccaa gacaccctgg accagaacct    9000
caactttgag atgtatggat cagtatactc cgtgaatcct ttggaccttc cagccataat    9060
tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca tttttcacag    9360
cgtgtcgcgc gcccgacccc gctcattact cttcggccta ctcctacttt cgtaggggt    9420
aggcctcttc ctactccccg ctcggtagag cggcacacac taggtacact ccatagctaa    9480
ctgttccttt tttttttttt tttttttttt tttttttttt tttttttttt cttttttttt    9540
ttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                           9684
```

<210> SEQ ID NO 4
<211> LENGTH: 3035
<212> TYPE: PRT
<213> ORGANISM: Hepatitis C virus

<400> SEQUENCE: 4

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220
```

-continued

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
            245                 250                 255

Ser Ile Arg Ser His Val Asp Leu Leu Val Gly Ala Ala Thr Leu Cys
        260                 265                 270

Ser Ala Leu Tyr Val Gly Asp Met Cys Gly Ala Val Phe Leu Val Gly
    275                 280                 285

Gln Ala Phe Thr Phe Arg Pro Arg Arg His Gln Thr Val Gln Thr Cys
290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
    370                 375                 380

Thr Tyr Val Thr Gly Gly Ser Val Ala His Ser Ala Arg Gly Leu Thr
385                 390                 395                 400

Ser Leu Phe Ser Val Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Gly Thr Thr Asp Ile Gln Gly Lys Pro Thr Tyr
    515                 520                 525

Asn Trp Gly Glu Asn Glu Thr Asp Val Phe Leu Leu Glu Ser Leu Arg
530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
            565                 570                 575

Gly Asp Pro Glu Asn Glu Thr Asp Leu Phe Cys Pro Thr Asp Cys Phe
        580                 585                 590

Arg Lys His Pro Glu Ala Thr Tyr Ser Arg Cys Gly Ala Gly Pro Trp
    595                 600                 605

Leu Thr Pro Arg Cys Met Val Asp Tyr Pro Tyr Arg Leu Trp His Tyr
610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu

```
                645                 650                 655
Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
            690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
                740                 745                 750

Ala Leu Glu Asn Leu Val Thr Leu Asn Ala Val Ala Ala Gly Thr
            755                 760                 765

His Gly Ile Gly Trp Tyr Leu Val Ala Phe Cys Ala Ala Trp Tyr Val
            770                 775                 780

Arg Gly Lys Leu Val Pro Leu Thr Ser Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
            835                 840                 845

Met Trp Trp Asn Gln Tyr Thr Ile Cys Arg Cys Glu Ala Ala Leu Gln
850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
            900                 905                 910

Thr Thr Thr Pro Tyr Phe Val Arg Ala His Val Leu Val Arg Leu Cys
            915                 920                 925

Met Leu Val Arg Ser Val Met Gly Gly Lys Tyr Phe Gln Met Ala Ile
            930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
            965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
            995                 1000                1005

Ser Ala Arg Leu Gly Arg Glu Val Leu Leu Gly Pro Ala Asp Asp
            1010                1015                1020

Tyr Arg Glu Met Gly Trp Arg Leu Leu Ala Pro Ile Thr Ala Tyr
            1025                1030                1035

Ala Gln Gln Thr Arg Gly Leu Leu Gly Ala Ile Val Val Ser Met
            1040                1045                1050

Thr Gly Arg Asp Arg Thr Glu Gln Ala Gly Glu Val Gln Ile Leu
            1055                1060                1065
```

```
Ser Thr Val Ser Gln Ser Phe Leu Gly Thr Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Pro Gly Thr Lys Ser Leu Glu Pro
    1115                1120                1125

Cys Lys Cys Gly Ala Val Asp Leu Tyr Leu Val Thr Arg Asn Ala
    1130                1135                1140

Asp Val Ile Pro Ala Arg Arg Arg Gly Asp Lys Arg Gly Ala Leu
    1145                1150                1155

Leu Ser Pro Arg Pro Ile Ser Thr Leu Lys Gly Ser Ser Gly Gly
    1160                1165                1170

Pro Val Leu Cys Pro Arg Gly His Val Val Gly Leu Phe Arg Ala
    1175                1180                1185

Ala Val Cys Ser Arg Gly Val Ala Lys Ser Ile Asp Phe Ile Pro
    1190                1195                1200

Val Glu Thr Leu Asp Val Val Thr Arg Ser Pro Thr Phe Ser Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Lys Val Pro Val
    1235                1240                1245

Ala Tyr Ala Ala Gln Gly Tyr Lys Val Leu Val Leu Asn Pro Ser
    1250                1255                1260

Val Ala Ala Thr Leu Gly Phe Gly Ala Tyr Leu Ser Lys Ala His
    1265                1270                1275

Gly Ile Asn Pro Asn Ile Arg Thr Gly Val Arg Thr Val Met Thr
    1280                1285                1290

Gly Glu Ala Ile Thr Tyr Ser Thr Tyr Gly Lys Phe Leu Ala Asp
    1295                1300                1305

Gly Gly Cys Ala Ser Gly Ala Tyr Asp Ile Ile Ile Cys Asp Glu
    1310                1315                1320

Cys His Ala Val Asp Ala Thr Ser Ile Leu Gly Ile Gly Thr Val
    1325                1330                1335

Leu Asp Gln Ala Glu Thr Ala Gly Val Arg Leu Thr Val Leu Ala
    1340                1345                1350

Thr Ala Thr Pro Pro Gly Ser Val Thr Thr Pro His Pro Asp Ile
    1355                1360                1365

Glu Glu Val Gly Leu Gly Arg Glu Gly Glu Ile Pro Phe Tyr Gly
    1370                1375                1380

Arg Ala Ile Pro Leu Ser Cys Ile Lys Gly Gly Arg His Leu Ile
    1385                1390                1395

Phe Cys His Ser Lys Lys Lys Cys Asp Glu Leu Ala Ala Ala Leu
    1400                1405                1410

Arg Gly Met Gly Leu Asn Ala Val Ala Tyr Tyr Arg Gly Leu Asp
    1415                1420                1425

Val Ser Ile Ile Pro Ala Gln Gly Asp Val Val Val Ala Thr
    1430                1435                1440

Asp Ala Leu Met Thr Gly Tyr Thr Gly Asp Phe Asp Ser Val Ile
    1445                1450                1455
```

```
Asp Cys Asn Val Ala Val Thr Gln Ala Val Asp Phe Ser Leu Asp
    1460                1465                1470

Pro Thr Phe Thr Ile Thr Thr Gln Thr Val Pro Gln Asp Ala Val
    1475                1480                1485

Ser Arg Ser Gln Arg Arg Gly Arg Thr Gly Arg Gly Arg Gln Gly
    1490                1495                1500

Thr Tyr Arg Tyr Val Ser Thr Gly Glu Arg Ala Ser Gly Met Phe
    1505                1510                1515

Asp Ser Val Val Leu Cys Glu Cys Tyr Asp Ala Gly Ala Ala Trp
    1520                1525                1530

Tyr Asp Leu Thr Pro Ala Glu Thr Thr Val Arg Leu Arg Ala Tyr
    1535                1540                1545

Phe Asn Thr Pro Gly Leu Pro Val Cys Gln Asp His Leu Glu Phe
    1550                1555                1560

Trp Glu Ala Val Phe Thr Gly Leu Thr His Ile Asp Ala His Phe
    1565                1570                1575

Leu Ser Gln Thr Lys Gln Ala Gly Glu Asn Phe Ala Tyr Leu Val
    1580                1585                1590

Ala Tyr Gln Ala Thr Val Cys Ala Arg Ala Lys Ala Pro Pro Pro
    1595                1600                1605

Ser Trp Asp Ala Met Trp Lys Cys Leu Ala Arg Leu Lys Pro Thr
    1610                1615                1620

Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680

Gly Cys Val Ser Ile Ile Gly Arg Leu His Val Asn Gln Arg Val
    1685                1690                1695

Val Val Ala Pro Asp Lys Glu Val Leu Tyr Glu Ala Phe Asp Glu
    1700                1705                1710

Met Glu Glu Cys Ala Ser Arg Ala Ala Leu Ile Glu Glu Gly Gln
    1715                1720                1725

Arg Ile Ala Glu Met Leu Lys Ser Lys Ile Gln Gly Leu Leu Gln
    1730                1735                1740

Gln Ala Ser Lys Gln Ala Gln Asp Ile Gln Pro Ala Met Gln Ala
    1745                1750                1755

Ser Trp Pro Lys Val Glu Gln Phe Trp Ala Arg His Met Trp Asn
    1760                1765                1770

Phe Ile Ser Gly Ile Gln Tyr Leu Ala Gly Leu Ser Thr Leu Pro
    1775                1780                1785

Gly Asn Pro Ala Val Ala Ser Met Met Ala Phe Ser Ala Ala Leu
    1790                1795                1800

Thr Ser Pro Leu Ser Thr Ser Thr Thr Ile Leu Leu Asn Ile Met
    1805                1810                1815

Gly Gly Trp Leu Ala Ser Gln Ile Ala Pro Pro Ala Gly Ala Thr
    1820                1825                1830

Gly Phe Val Val Ser Gly Leu Val Gly Ala Ala Val Gly Ser Ile
    1835                1840                1845

Gly Leu Gly Lys Val Leu Val Asp Ile Leu Ala Gly Tyr Gly Ala
```

```
              1850                1855                1860
Gly Ile Ser Gly Ala Leu Val Ala Phe Lys Ile Met Ser Gly Glu
    1865                1870                1875
Lys Pro Ser Met Glu Asp Val Ile Asn Leu Leu Pro Gly Ile Leu
    1880                1885                1890
Ser Pro Gly Ala Leu Val Val Gly Val Ile Cys Ala Ala Ile Leu
    1895                1900                1905
Arg Arg His Val Gly Pro Gly Glu Gly Ala Val Gln Trp Met Asn
    1910                1915                1920
Arg Leu Ile Ala Phe Ala Ser Arg Gly Asn His Val Ala Pro Thr
    1925                1930                1935
His Tyr Val Thr Glu Ser Asp Ala Ser Gln Arg Val Thr Gln Leu
    1940                1945                1950
Leu Gly Ser Leu Thr Ile Thr Ser Leu Leu Arg Arg Leu His Asn
    1955                1960                1965
Trp Ile Thr Glu Asp Cys Pro Ile Pro Cys Ser Gly Ser Trp Leu
    1970                1975                1980
Arg Asp Val Trp Asp Trp Val Cys Thr Ile Leu Thr Asp Phe Lys
    1985                1990                1995
Asn Trp Leu Thr Ser Lys Leu Phe Pro Lys Leu Pro Gly Leu Pro
    2000                2005                2010
Phe Ile Ser Cys Gln Lys Gly Tyr Lys Gly Val Trp Ala Gly Thr
    2015                2020                2025
Gly Ile Met Thr Thr Arg Cys Pro Cys Gly Ala Asn Ile Ser Gly
    2030                2035                2040
Asn Val Arg Leu Gly Ser Met Arg Ile Thr Gly Pro Lys Thr Cys
    2045                2050                2055
Met Asn Thr Trp Gln Gly Thr Phe Pro Ile Asn Cys Tyr Thr Glu
    2060                2065                2070
Gly Gln Cys Ala Pro Lys Pro Pro Thr Asn Tyr Lys Thr Ala Ile
    2075                2080                2085
Trp Arg Val Ala Ala Ser Glu Tyr Ala Glu Val Thr Gln His Gly
    2090                2095                2100
Ser Tyr Ser Tyr Val Thr Gly Leu Thr Thr Asp Asn Leu Lys Ile
    2105                2110                2115
Pro Cys Gln Leu Pro Ser Pro Glu Phe Phe Ser Trp Val Asp Gly
    2120                2125                2130
Val Gln Ile His Arg Phe Ala Pro Thr Pro Lys Pro Phe Phe Arg
    2135                2140                2145
Asp Glu Val Ser Phe Cys Val Gly Leu Asn Ser Tyr Ala Val Gly
    2150                2155                2160
Ser Gln Leu Pro Cys Glu Pro Glu Pro Asp Ala Asp Val Leu Arg
    2165                2170                2175
Ser Met Leu Thr Asp Pro Pro His Ile Thr Ala Glu Thr Ala Ala
    2180                2185                2190
Arg Arg Leu Ala Arg Gly Ser Pro Pro Ser Glu Ala Ser Ser Ser
    2195                2200                2205
Val Ser Gln Leu Ser Ala Pro Ser Leu Arg Ala Thr Cys Thr Thr
    2210                2215                2220
His Ser Asn Thr Tyr Asp Val Asp Met Val Asp Ala Asn Leu Leu
    2225                2230                2235
Met Glu Gly Gly Val Ala Gln Thr Glu Pro Glu Ser Arg Val Pro
    2240                2245                2250
```

```
Val Leu Asp Phe Leu Glu Pro Met Ala Glu Glu Ser Asp Leu
2255                2260                2265

Glu Pro Ser Ile Pro Pro Glu Cys Met Leu Pro Arg Ser Gly Phe
2270                2275                2280

Pro Arg Ala Leu Pro Ala Trp Ala Arg Pro Asp Tyr Asn Pro
2285                2290                2295

Leu Val Glu Ser Trp Arg Arg Pro Asp Tyr Gln Pro Pro Thr Val
2300                2305                2310

Ala Gly Cys Ala Leu Pro Pro Lys Lys Ala Pro Thr Pro Pro
2315                2320                2325

Pro Arg Arg Arg Arg Thr Val Gly Leu Ser Glu Ser Thr Ile Ser
2330                2335                2340

Glu Ala Leu Gln Gln Leu Ala Ile Lys Thr Phe Gly Gln Pro Pro
2345                2350                2355

Ser Ser Gly Asp Ala Gly Ser Ser Thr Gly Ala Gly Ala Ala Glu
2360                2365                2370

Ser Gly Gly Pro Thr Ser Pro Gly Glu Pro Ala Pro Ser Glu Thr
2375                2380                2385

Gly Ser Ala Ser Ser Met Pro Pro Leu Glu Gly Glu Pro Gly Asp
2390                2395                2400

Pro Asp Leu Glu Ser Asp Gln Val Glu Leu Gln Pro Pro Pro Gln
2405                2410                2415

Gly Gly Gly Val Ala Pro Gly Ser Gly Ser Gly Ser Trp Ser Thr
2420                2425                2430

Cys Ser Glu Glu Asp Asp Thr Thr Val Cys Cys Ser Met Ser Tyr
2435                2440                2445

Ser Trp Thr Gly Ala Leu Ile Thr Pro Cys Ser Pro Glu Glu Glu
2450                2455                2460

Lys Leu Pro Ile Asn Pro Leu Ser Asn Ser Leu Leu Arg Tyr His
2465                2470                2475

Asn Lys Val Tyr Cys Thr Thr Ser Lys Ser Ala Ser Gln Arg Ala
2480                2485                2490

Lys Lys Val Thr Phe Asp Arg Thr Gln Val Leu Asp Ala His Tyr
2495                2500                2505

Asp Ser Val Leu Lys Asp Ile Lys Leu Ala Ala Ser Lys Val Ser
2510                2515                2520

Ala Arg Leu Leu Thr Leu Glu Glu Ala Cys Gln Leu Thr Pro Pro
2525                2530                2535

His Ser Ala Arg Ser Lys Tyr Gly Phe Gly Ala Lys Glu Val Arg
2540                2545                2550

Ser Leu Ser Gly Arg Ala Val Asn His Ile Lys Ser Val Trp Lys
2555                2560                2565

Asp Leu Leu Glu Asp Pro Gln Thr Pro Ile Pro Thr Thr Ile Met
2570                2575                2580

Ala Lys Asn Glu Val Phe Cys Val Asp Pro Ala Lys Gly Gly Lys
2585                2590                2595

Lys Pro Ala Arg Leu Ile Val Tyr Pro Asp Leu Gly Val Arg Val
2600                2605                2610

Cys Glu Lys Met Ala Leu Tyr Asp Ile Thr Gln Lys Leu Pro Gln
2615                2620                2625

Ala Val Met Gly Ala Ser Tyr Gly Phe Gln Tyr Ser Pro Ala Gln
2630                2635                2640
```

```
Arg Val Glu Tyr Leu Leu Lys Ala Trp Ala Glu Lys Lys Asp Pro
2645                2650                2655

Met Gly Phe Ser Tyr Asp Thr Arg Cys Phe Asp Ser Thr Val Thr
2660                2665                2670

Glu Arg Asp Ile Arg Thr Glu Glu Ser Ile Tyr Gln Ala Cys Ser
2675                2680                2685

Leu Pro Glu Glu Ala Arg Thr Ala Ile His Ser Leu Thr Glu Arg
2690                2695                2700

Leu Tyr Val Gly Gly Pro Met Phe Asn Ser Lys Gly Gln Thr Cys
2705                2710                2715

Gly Tyr Arg Arg Cys Arg Ala Ser Gly Val Leu Thr Thr Ser Met
2720                2725                2730

Gly Asn Thr Ile Thr Cys Tyr Val Lys Ala Leu Ala Ala Cys Lys
2735                2740                2745

Ala Ala Gly Ile Val Ala Pro Thr Met Leu Val Cys Gly Asp Asp
2750                2755                2760

Leu Val Val Ile Ser Glu Ser Gln Gly Thr Glu Glu Asp Glu Arg
2765                2770                2775

Asn Leu Arg Ala Phe Thr Glu Ala Met Thr Arg Tyr Ser Ala Pro
2780                2785                2790

Pro Gly Asp Pro Pro Arg Pro Glu Tyr Asp Leu Glu Leu Ile Thr
2795                2800                2805

Ser Cys Ser Ser Asn Val Ser Val Ala Leu Gly Pro Arg Gly Arg
2810                2815                2820

Arg Arg Tyr Tyr Leu Thr Arg Asp Pro Thr Thr Pro Leu Ala Arg
2825                2830                2835

Ala Ala Trp Glu Thr Val Arg His Ser Pro Ile Asn Ser Trp Leu
2840                2845                2850

Gly Asn Ile Ile Gln Tyr Ala Pro Thr Ile Trp Val Arg Met Val
2855                2860                2865

Leu Met Thr His Phe Phe Ser Ile Leu Met Val Gln Asp Thr Leu
2870                2875                2880

Asp Gln Asn Leu Asn Phe Glu Met Tyr Gly Ser Val Tyr Ser Val
2885                2890                2895

Asn Pro Leu Asp Leu Pro Ala Ile Ile Glu Arg Leu His Gly Leu
2900                2905                2910

Asp Ala Phe Ser Met His Thr Tyr Ser His His Glu Leu Thr Arg
2915                2920                2925

Val Ala Ser Ala Leu Arg Lys Leu Gly Ala Pro Pro Leu Arg Val
2930                2935                2940

Trp Lys Ser Arg Ala Arg Ala Val Arg Ala Ser Leu Ile Ser Arg
2945                2950                2955

Gly Gly Lys Ala Ala Val Cys Gly Arg Tyr Leu Phe Asn Trp Ala
2960                2965                2970

Val Lys Thr Lys Leu Lys Leu Thr Pro Leu Pro Glu Ala Arg Leu
2975                2980                2985

Leu Asp Leu Ser Ser Trp Phe Thr Val Gly Ala Gly Gly Gly Asp
2990                2995                3000

Ile Phe His Ser Val Ser Arg Ala Arg Pro Arg Ser Leu Leu Phe
3005                3010                3015

Gly Leu Leu Leu Leu Phe Val Gly Val Gly Leu Phe Leu Leu Pro
3020                3025                3030

Ala Arg
```

<210> SEQ ID NO 5
<211> LENGTH: 9684
<212> TYPE: DNA
<213> ORGANISM: Hepatitis C virus

<400> SEQUENCE: 5

```
acctgcccct aatagggggcg acactccgcc atgaatcact cccctgtgag gaactactgt      60
cttcacgcag aaagcgccta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgccccggga ggtctcgtag accgtgcacc atgagcacac ttcctaaacc     360
tcaaagaaaa accaaaagaa acaccatccg tcgcccacag gacgttaagt tcccgggtgg     420
cggacagatc gttggtggag tatacgtgtt gccgcgcagg ggcccacgat ggggtgtgcg     480
cgcgacgcgt aaaacttctg aacggtcaca gcctcgcgga cgacgacagc ctatccccaa     540
ggcgcgtcgg agcgaaggcc ggtcctgggc tcagcccggg tacccttggc ccctctatgg     600
taatgagggc tgcgggtggg cagggtggct cctgtccccg cgcggctccc gtccatcttg     660
gggcccaaac gaccccggc ggaggtcccg caatttgggt aaagtcatcg atacccttac     720
gtgcggactc gccgacctca tggggtacat cccgctcgtc ggcgctcccg taggaggcgt     780
cgcaagagcc ctcgcgcatg gcgtgagggc ccttgaagac gggataaatt ttgcaacagg     840
gaacttgccc ggttgctcct tttctatctt ccttcttgct ctgttctcct gcttagttca     900
tcctgcagct agtcttgagt ggcggaatac gtctggcctc tatgtcctta ccaacgactg     960
ttccaatagc agtattgtgt atgaggccga tgacgtcatt ctgcacacac ccggctgtgt    1020
accttgtgtt caggacgaca atacatccac gtgctggacc ccagtgacac ctacggtggc    1080
agtcaggtac gtcggagcaa ccaccgcttc gatacgcagt catgtggacc tattagtggg    1140
cgcggccacg ctgtgctctg cgctctatgt gggtgatatg tgtggggccg tcttctctgt    1200
gggacaagcc ttcacgttca gacctcgtcg ccatcaaacg gtccagacct gtaactgctc    1260
gctgtaccca ggccatgttt caggacatcg aatggcttgg gatatgatga tgaattggtc    1320
ccccgctgtg ggtatggtgg tggcgcacat cctgcgattg ccccagacct tgtttgacat    1380
actggccggg gcccattggg gcatcttggc gggcctagcc tattattcta tgcagggcaa    1440
ctggggccaag gtcgctattg tcatgattat gttttcaggg gtcgatgctg aaacatatgt    1500
caccggtggc agtgtagctc atagtgccag agggttaact agccttttta gtgtgggcgc    1560
caagcagaaa ctgcaattgg tcaacaccaa tggctcgtgg cacatcaaca gtactgccct    1620
gaactgcaat gagtccataa acaccgggtt catagctggg ttgttttatt accataagtt    1680
caactctact ggatgtcctc aaaggcttag cagctgcaag cccatcattt ccttcaggca    1740
ggggtggggc cccttgacag atgctaacat caccggtcct tctgatgata accgtattg    1800
ctggcactac gcacctagac cttgtagtgt tgtcccggca tcaagtgtct gcggccctgt    1860
gtactgcttc acaccatcgc cagtggtcgt aggcactact gatatccaag gcaagccgac    1920
ctacaactgg ggtgagaatg agacagatgt gttcctgctg gagtccctgc ggcctcccag    1980
tggcggtgg tttggatgcg cgtggatgaa ctccacgggg ttcctcaaga cgtgtggagc    2040
tcccccttgt aacatctatg ggggtgaggg ggatcccgaa aatgagacag acctcttctg    2100
```

```
ccccaccgac tgcttcagga aacatcctga ggccacatac agccggtgtg gtgcggggcc   2160
ctggttgaca cctcgctgca tggtcgacta tccataccgg ctttggcatt acccatgtac   2220
agtcaatttc acattgttca aggtgaggat gtttgtgggc ggatttgaac accggtttac   2280
cgccgcttgt aactggacca ggggggagcg ctgcaatatc gaggatcgtg atcgcagcga   2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct ggagaacct tgtcacgctg aacgccgtcg ctgctgctgg    2640
gacacatggt attggttggt acctggtagc cttttgcgcg cgtggtacg tgcggggtaa    2700
acttgtcccg ctgacgatct gcggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940
ccccccctta cttgcacgcg ggagtaggga cggtgtcatc ctgctaacaa gcttgcttta   3000
tccatcctta atttttgaca tcactaagct gctgatagca gtaataggcc cattatactt   3060
aatacaggct gccatcacta ccacccccta ctttgtgcgc gcacatgtac tggtccgcct   3120
ttgcatgctc gtgcgctccg tgatgggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcgggctgcc   3360
ggtctccgcg cgattaggcc gtgaggtatt gttgggacct gctgatgatt atcgggaaat   3420
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcgggggttt tgtggactgt   3600
ttaccacgga gctggcaaca agactctagc cggcttacgg ggtccggtca cgcagatgta   3660
ctcgagtgct gaggggact tggtaggctg cccagcccc cctgggacca agtctttgga    3720
gccgtgcaag tgtggagccg tcgacctata tctggtcacg cggaacgctg atgtcatccc   3780
ggctcggaga cgcggggaca agcggggagc attgctctcc ccgagaccca tttcgacctt   3840
gaaggggtcc tcggggggc cggtgctctg ccctagggggc cacgtcgttg gctcttccg    3900
agcagctgtg tgctctcggg gcgtggccaa atccatcgat ttcatccccg ttgagacact   3960
cgacgttgtt acaaggtctc ccactttcag tgacaacagc acgccaccgg ctgtgcccca   4020
gacctatcag gtcgggtact tgcatgctcc aactggcagt ggaaagagca ccaaggtccc   4080
tgtcgcgtat gccgcccagg ggtacaaagt actagtgctt aacccctcgg tagctgccac   4140
cctggggttt ggggcgtacc tatccaaggc acatggcatc aatcccaaca ttaggactgg   4200
agtcaggacc gtgatgaccg gggaggccat cacgtactcc acatatgcaa atttctcgc    4260
cgatgggggc tgcgctagcg gcgcctatga catcatcata tgcgatgaat gccacgctgt   4320
ggatgctacc tccattctcg gcatcggaac ggtccttgat caagcagaga cagccggggt   4380
cagactaact gtgctggcta cggccacacc ccccgggtca gtgacaaccc cccatcccga   4440
```

```
tatagaagag gtaggcctcg ggcgggaggg tgagatcccc ttctatggga gggcgattcc    4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact tgactccgt gatcgactgc aatgtagcgg tcacccaagc     4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgccggcc tacccgtgtg tcaagaccat cttgaatttt gggaggcagt     5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac ccgcggtgg cttccatgat ggcattcagt gccgccctca ccagtccgtt     5760
gtcgaccagt accaccatcc ttctcaacat catgggaggc tggttagcgt cccagatcgc    5820
accacccgcg ggggccaccg gctttgtcgt cagtggcctg gtggggggctg ccgtgggcag    5880 cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg gggtcatct gcgcggccat     6060 tctgcgccgc cacgtgggac cggggagg cgcggtccaa tggatgaaca ggcttattgc      6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcacgtgtg    6300 ggactgggtt tgcaccatct tgacagactt caaaaattgg ctgacctcta aattgttccc    6360
caagctgccc ggcctcccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg ggaccttttcc   6540 tatcaattgc tacacggagg gccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactaccct ctccagagtt    6720
tttctcctgg gtgacggtg tgcagatcca taggtttgca cccacaccaa agccgttttt    6780
ccgggatgag gtctcgttct cgttgggct taattcctat gctgtcgggt cccagcttcc    6840
```

```
ctgtgaacct gagcccgacg cagacgtatt gaggtccatg ctaacagatc cgccccacat  6900
cacggcggag actgcggcgc ggcgcttggc acggggatca cctccatctg aggcgagctc  6960
ctcagtgagc cagctatcag caccgtcgct gcgggccacc tgcaccaccc acagcaacac  7020
ctatgacgtg gacatggtcg atgccaacct gctcatggag ggcggtgtgg ctcagacaga  7080
gcctgagtcc agggtgcccg ttctggactt tctcgagcca atggccgagg aagagagcga  7140
ccttgagccc tcaataccac cggagtgcat gctccccagg agcgggtttc cacgggcctt  7200
accggcttgg gcacggcctg actacaaccc gccgctcgtg gaatcgtgga ggaggccaga  7260
ttaccaaccg cccaccgttg ctggttgtgc tctcccccc cccaagaagg ccccgacgcc   7320
tcccccaagg agacgccgga cagtgggtct gagcgagagc accatatcag aagccctcca  7380
gcaactggcc atcaagacct ttggccagcc cccctcgagc ggtgatgcag gctcgtccac  7440
gggggcgggc gccgccgaat ccggcggtcc gacgtcccct ggtgagccgg cccctcaga   7500
gacaggttcc gcctcctcta tgccccccct cgagggggag cctggagatc cggacctgga  7560
gtctgatcag gtagagcttc aacctccccc ccaggggggg ggggtagctc ccggttcggg  7620
ctcggggtct tggtctactt gctccgagga ggacgatacc accgtgtgct gctccatgtc  7680
atactcctgg accggggctc taataactcc ctgtagcccc gaagaggaaa agttgccaat  7740
caaccctttg agtaactcgc tgttgcgata ccataacaag gtgtactgta caacatcaaa  7800
gagcgcctca cagagggcta aaaggtaac ttttgacagg acgcaagtgc tcgacgccca   7860
ttatgactca gtcttaaagg acatcaagct agcggcttcc aaggtcagcg caaggctcct  7920
cacccttggag gaggcgtgcc agttgactcc accccattct gcaagatcca gtatggatt   7980
cggggccaag gaggtccgca gcttgtccgg gagggccgtt aaccacatca gtccgtgtg   8040
gaaggacctc ctggaagacc cacaaacacc aattcccaca accatcatgg ccaaaaatga  8100
ggtgttctgc gtggacccc ccaagggggg taagaaacca gctcgcctca tcgtttaccc   8160
tgacctcggc gtccgggtct gcgagaaaat ggccctctat gacattacac aaaagcttcc  8220
tcaggcggta atgggagctt cctatggctt ccagtactcc cctgcccaac gggtggagta  8280
tctcttgaaa gcatgggcgg aaaagaagga ccccatgggt ttttcgtatg atacccgatg  8340
cttcgactca accgtcactg agagagacat caggaccgag gagtccatat accaggcctg  8400
ctccctgccc gaggaggccc gcactgccat acactcgctg actgagagac tttacgtagg  8460
agggcccatg ttcaacagca agggtcaaac ctgcggttac agacgttgcc gcgccagcgg  8520
ggtgctaacc actagcatgg gtaacaccat cacatgctat gtgaaagccc tagcggcctg  8580
caaggctgcg gggatagttg cgcccacaat gctggtatgc ggcgatgacc tagtagtcat  8640
ctcagaaagc caggggactg aggaggacga gcggaacctg agagccttca cggaggccat  8700
gaccaggtac tctgcccctc ctggtgatcc ccccagaccg aatatgacc tggagctaat   8760
aacatcctgt tcctcaaatg tgtctgtggc gttgggcccg cggggccgcc gcagatacta  8820
cctgaccaga gacccaacca ctccactcgc ccgggctgcc tgggaaacag ttagacactc  8880
ccctatcaat tcatggctgg gaaacatcat ccagtatgct ccaaccatat gggttcgcat  8940
ggtcctaatg acacacttct tctccattct catggtccaa gacaccctgg accagaacct  9000
caactttgag atgtatggat cagtatactc cgtgaatcct ttggaccttc agccataat   9060
tgagaggtta cacggcttg acgccttttc tatgcacaca tactctcacc acgaactgac  9120
gcgggtggct tcagccctca gaaaacttgg ggcgccaccc ctcagggtgt ggaagagtcg  9180
```

-continued

```
ggctcgcgca gtcagggcgt ccctcatctc ccgtggaggg aaagcggccg tttgcggccg      9240
atatctcttc aattgggcgg tgaagaccaa gctcaaactc actccattgc cggaggcgcg      9300
cctactggac ttatccagtt ggttcaccgt cggcgccggc gggggcgaca tttttcacag      9360
cgtgtcgcgc gcccgacccc gctcattact cttcggccta ctcctacttt cgtaggggt       9420 aggcctcttc ctactccccg ctcggtagag cggcacacac taggtacact ccatagctaa      9480
ctgttccttt tttttttttt tttttttttt tttttttttt tttttttttt cttttttttt      9540
tttttccctc tttcttccct tctcatctta ttctactttc tttcttggtg gctccatctt      9600
agccctagtc acggctagct gtgaaaggtc cgtgagccgc atgactgcag agagtgccgt      9660
aactggtctc tctgcagatc atgt                                             9684
```

<210> SEQ ID NO 6
<211> LENGTH: 3035
<212> TYPE: PRT
<213> ORGANISM: Hepatitis C virus

<400> SEQUENCE: 6

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285
```

```
Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
    370                 375                 380

Thr Tyr Val Thr Gly Gly Ser Val Ala His Ser Ala Arg Gly Leu Thr
385                 390                 395                 400

Ser Leu Phe Ser Val Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Gly Thr Thr Asp Ile Gln Gly Lys Pro Thr Tyr
        515                 520                 525

Asn Trp Gly Glu Asn Glu Thr Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700
```

-continued

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
            725                 730                 735

Val Cys Val Ala Leu Trp Leu Met Leu Met Val Ser Gln Ala Glu Ala
                740                 745                 750

Ala Leu Glu Asn Leu Val Thr Leu Asn Ala Val Ala Ala Gly Thr
        755                 760                 765

His Gly Ile Gly Trp Tyr Leu Val Ala Phe Cys Ala Ala Trp Tyr Val
    770                 775                 780

Arg Gly Lys Leu Val Pro Leu Thr Ile Cys Gly Leu Thr Gly Leu Trp
785                 790                 795                 800

Ser Leu Ala Leu Leu Val Leu Leu Pro Gln Arg Ala Tyr Ala Trp
        805                 810                 815

Ser Gly Glu Asp Ser Ala Thr Leu Gly Ala Gly Val Leu Ala Leu Phe
                820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
        900                 905                 910

Thr Thr Thr Pro Tyr Phe Val Arg Ala His Val Leu Val Arg Leu Cys
        915                 920                 925

Met Leu Val Arg Ser Val Met Gly Gly Lys Tyr Phe Gln Met Ala Ile
        930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
            965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
            995                 1000                1005

Ser Ala Arg Leu Gly Arg Glu Val Leu Leu Gly Pro Ala Asp Asp
    1010                1015                1020

Tyr Arg Glu Met Gly Trp Arg Leu Leu Ala Pro Ile Thr Ala Tyr
    1025                1030                1035

Ala Gln Gln Thr Arg Gly Leu Leu Gly Ala Ile Val Val Ser Met
    1040                1045                1050

Thr Gly Arg Asp Arg Thr Glu Gln Ala Gly Glu Val Gln Ile Leu
    1055                1060                1065

Ser Thr Val Ser Gln Ser Phe Leu Gly Thr Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Pro Gly Thr Lys Ser Leu Glu Pro

-continued

```
            1115                1120                1125
Cys  Lys  Cys  Gly  Ala  Val  Asp  Leu  Tyr  Leu  Val  Thr  Arg  Asn  Ala
            1130                1135                1140

Asp  Val  Ile  Pro  Ala  Arg  Arg  Gly  Asp  Lys  Arg  Gly  Ala  Leu
       1145                1150                1155

Leu  Ser  Pro  Arg  Pro  Ile  Ser  Thr  Leu  Lys  Gly  Ser  Ser  Gly  Gly
            1160                1165                1170

Pro  Val  Leu  Cys  Pro  Arg  Gly  His  Val  Val  Gly  Leu  Phe  Arg  Ala
            1175                1180                1185

Ala  Val  Cys  Ser  Arg  Gly  Val  Ala  Lys  Ser  Ile  Asp  Phe  Ile  Pro
            1190                1195                1200

Val  Glu  Thr  Leu  Asp  Val  Val  Thr  Arg  Ser  Pro  Thr  Phe  Ser  Asp
            1205                1210                1215

Asn  Ser  Thr  Pro  Pro  Ala  Val  Pro  Gln  Thr  Tyr  Gln  Val  Gly  Tyr
            1220                1225                1230

Leu  His  Ala  Pro  Thr  Gly  Ser  Gly  Lys  Ser  Thr  Lys  Val  Pro  Val
            1235                1240                1245

Ala  Tyr  Ala  Ala  Gln  Gly  Tyr  Lys  Val  Leu  Val  Leu  Asn  Pro  Ser
            1250                1255                1260

Val  Ala  Ala  Thr  Leu  Gly  Phe  Gly  Ala  Tyr  Leu  Ser  Lys  Ala  His
            1265                1270                1275

Gly  Ile  Asn  Pro  Asn  Ile  Arg  Thr  Gly  Val  Arg  Thr  Val  Met  Thr
            1280                1285                1290

Gly  Glu  Ala  Ile  Thr  Tyr  Ser  Thr  Tyr  Gly  Lys  Phe  Leu  Ala  Asp
            1295                1300                1305

Gly  Gly  Cys  Ala  Ser  Gly  Ala  Tyr  Asp  Ile  Ile  Ile  Cys  Asp  Glu
            1310                1315                1320

Cys  His  Ala  Val  Asp  Ala  Thr  Ser  Ile  Leu  Gly  Ile  Gly  Thr  Val
            1325                1330                1335

Leu  Asp  Gln  Ala  Glu  Thr  Ala  Gly  Val  Arg  Leu  Thr  Val  Leu  Ala
            1340                1345                1350

Thr  Ala  Thr  Pro  Pro  Gly  Ser  Val  Thr  Thr  Pro  His  Pro  Asp  Ile
            1355                1360                1365

Glu  Glu  Val  Gly  Leu  Gly  Arg  Glu  Gly  Glu  Ile  Pro  Phe  Tyr  Gly
            1370                1375                1380

Arg  Ala  Ile  Pro  Leu  Ser  Cys  Ile  Lys  Gly  Gly  Arg  His  Leu  Ile
            1385                1390                1395

Phe  Cys  His  Ser  Lys  Lys  Lys  Cys  Asp  Glu  Leu  Ala  Ala  Ala  Leu
            1400                1405                1410

Arg  Gly  Met  Gly  Leu  Asn  Ala  Val  Ala  Tyr  Tyr  Arg  Gly  Leu  Asp
            1415                1420                1425

Val  Ser  Ile  Ile  Pro  Ala  Gln  Gly  Asp  Val  Val  Val  Ala  Thr
            1430                1435                1440

Asp  Ala  Leu  Met  Thr  Gly  Tyr  Thr  Gly  Asp  Phe  Asp  Ser  Val  Ile
            1445                1450                1455

Asp  Cys  Asn  Val  Ala  Val  Thr  Gln  Ala  Val  Asp  Phe  Ser  Leu  Asp
            1460                1465                1470

Pro  Thr  Phe  Thr  Ile  Thr  Thr  Gln  Thr  Val  Pro  Gln  Asp  Ala  Val
            1475                1480                1485

Ser  Arg  Ser  Gln  Arg  Arg  Gly  Arg  Thr  Gly  Arg  Gly  Arg  Gln  Gly
            1490                1495                1500

Thr  Tyr  Arg  Tyr  Val  Ser  Thr  Gly  Glu  Arg  Ala  Ser  Gly  Met  Phe
            1505                1510                1515
```

```
Asp Ser Val Val Leu Cys Glu Cys Tyr Asp Ala Gly Ala Ala Trp
    1520             1525             1530

Tyr Asp Leu Thr Pro Ala Glu Thr Thr Val Arg Leu Arg Ala Tyr
    1535             1540             1545

Phe Asn Thr Pro Gly Leu Pro Val Cys Gln Asp His Leu Glu Phe
    1550             1555             1560

Trp Glu Ala Val Phe Thr Gly Leu Thr His Ile Asp Ala His Phe
    1565             1570             1575

Leu Ser Gln Thr Lys Gln Ala Gly Glu Asn Phe Ala Tyr Leu Val
    1580             1585             1590

Ala Tyr Gln Ala Thr Val Cys Ala Arg Ala Lys Ala Pro Pro Pro
    1595             1600             1605

Ser Trp Asp Ala Met Trp Lys Cys Leu Ala Arg Leu Lys Pro Thr
    1610             1615             1620

Leu Ala Gly Pro Thr Pro Leu Leu Tyr Arg Leu Gly Pro Ile Thr
    1625             1630             1635

Asn Glu Val Thr Leu Thr His Pro Gly Thr Lys Tyr Ile Ala Thr
    1640             1645             1650

Cys Met Gln Ala Asp Leu Glu Val Met Thr Ser Thr Trp Val Leu
    1655             1660             1665

Ala Gly Gly Val Leu Ala Ala Val Ala Ala Tyr Cys Leu Ala Thr
    1670             1675             1680

Gly Cys Val Ser Ile Ile Gly Arg Leu His Val Asn Gln Arg Val
    1685             1690             1695

Val Val Ala Pro Asp Lys Glu Val Leu Tyr Glu Ala Phe Asp Glu
    1700             1705             1710

Met Glu Glu Cys Ala Ser Arg Ala Ala Leu Ile Glu Glu Gly Gln
    1715             1720             1725

Arg Ile Ala Glu Met Leu Lys Ser Lys Ile Gln Gly Leu Leu Gln
    1730             1735             1740

Gln Ala Ser Lys Gln Ala Gln Asp Ile Gln Pro Ala Met Gln Ala
    1745             1750             1755

Ser Trp Pro Lys Val Glu Gln Phe Trp Ala Arg His Met Trp Asn
    1760             1765             1770

Phe Ile Ser Gly Ile Gln Tyr Leu Ala Gly Leu Ser Thr Leu Pro
    1775             1780             1785

Gly Asn Pro Ala Val Ala Ser Met Met Ala Phe Ser Ala Ala Leu
    1790             1795             1800

Thr Ser Pro Leu Ser Thr Ser Thr Thr Ile Leu Leu Asn Ile Met
    1805             1810             1815

Gly Gly Trp Leu Ala Ser Gln Ile Ala Pro Pro Ala Gly Ala Thr
    1820             1825             1830

Gly Phe Val Val Ser Gly Leu Val Gly Ala Ala Val Gly Ser Ile
    1835             1840             1845

Gly Leu Gly Lys Val Leu Val Asp Ile Leu Ala Gly Tyr Gly Ala
    1850             1855             1860

Gly Ile Ser Gly Ala Leu Val Ala Phe Lys Ile Met Ser Gly Glu
    1865             1870             1875

Lys Pro Ser Met Glu Asp Val Ile Asn Leu Leu Pro Gly Ile Leu
    1880             1885             1890

Ser Pro Gly Ala Leu Val Val Gly Val Ile Cys Ala Ala Ile Leu
    1895             1900             1905
```

```
Arg Arg His Val Gly Pro Gly Glu Gly Ala Val Gln Trp Met Asn
1910                1915                1920

Arg Leu Ile Ala Phe Ala Ser Arg Gly Asn His Val Ala Pro Thr
1925                1930                1935

His Tyr Val Thr Glu Ser Asp Ala Ser Gln Arg Val Thr Gln Leu
1940                1945                1950

Leu Gly Ser Leu Thr Ile Thr Ser Leu Leu Arg Arg Leu His Asn
1955                1960                1965

Trp Ile Thr Glu Asp Cys Pro Ile Pro Cys Ser Gly Ser Trp Leu
1970                1975                1980

Arg Asp Val Trp Asp Trp Val Cys Thr Ile Leu Thr Asp Phe Lys
1985                1990                1995

Asn Trp Leu Thr Ser Lys Leu Phe Pro Lys Leu Pro Gly Leu Pro
2000                2005                2010

Phe Ile Ser Cys Gln Lys Gly Tyr Lys Gly Val Trp Ala Gly Thr
2015                2020                2025

Gly Ile Met Thr Thr Arg Cys Pro Cys Gly Ala Asn Ile Ser Gly
2030                2035                2040

Asn Val Arg Leu Gly Ser Met Arg Ile Thr Gly Pro Lys Thr Cys
2045                2050                2055

Met Asn Thr Trp Gln Gly Thr Phe Pro Ile Asn Cys Tyr Thr Glu
2060                2065                2070

Gly Gln Cys Ala Pro Lys Pro Pro Thr Asn Tyr Lys Thr Ala Ile
2075                2080                2085

Trp Arg Val Ala Ala Ser Glu Tyr Ala Glu Val Thr Gln His Gly
2090                2095                2100

Ser Tyr Ser Tyr Val Thr Gly Leu Thr Thr Asp Asn Leu Lys Ile
2105                2110                2115

Pro Cys Gln Leu Pro Ser Pro Glu Phe Phe Ser Trp Val Asp Gly
2120                2125                2130

Val Gln Ile His Arg Phe Ala Pro Thr Pro Lys Pro Phe Phe Arg
2135                2140                2145

Asp Glu Val Ser Phe Cys Val Gly Leu Asn Ser Tyr Ala Val Gly
2150                2155                2160

Ser Gln Leu Pro Cys Glu Pro Glu Pro Asp Ala Asp Val Leu Arg
2165                2170                2175

Ser Met Leu Thr Asp Pro Pro His Ile Thr Ala Glu Thr Ala Ala
2180                2185                2190

Arg Arg Leu Ala Arg Gly Ser Pro Pro Ser Glu Ala Ser Ser Ser
2195                2200                2205

Val Ser Gln Leu Ser Ala Pro Ser Leu Arg Ala Thr Cys Thr Thr
2210                2215                2220

His Ser Asn Thr Tyr Asp Val Asp Met Val Asp Ala Asn Leu Leu
2225                2230                2235

Met Glu Gly Gly Val Ala Gln Thr Glu Pro Glu Ser Arg Val Pro
2240                2245                2250

Val Leu Asp Phe Leu Glu Pro Met Ala Glu Glu Glu Ser Asp Leu
2255                2260                2265

Glu Pro Ser Ile Pro Pro Glu Cys Met Leu Pro Arg Ser Gly Phe
2270                2275                2280

Pro Arg Ala Leu Pro Ala Trp Ala Arg Pro Asp Tyr Asn Pro Pro
2285                2290                2295

Leu Val Glu Ser Trp Arg Arg Pro Asp Tyr Gln Pro Pro Thr Val
```

```
                    2300                2305                2310

Ala Gly Cys Ala Leu Pro Pro Lys Lys Ala Pro Thr Pro Pro
    2315                2320                2325

Pro Arg Arg Arg Arg Thr Val Gly Leu Ser Glu Ser Thr Ile Ser
    2330                2335                2340

Glu Ala Leu Gln Gln Leu Ala Ile Lys Thr Phe Gly Gln Pro Pro
    2345                2350                2355

Ser Ser Gly Asp Ala Gly Ser Ser Thr Gly Ala Gly Ala Ala Glu
    2360                2365                2370

Ser Gly Gly Pro Thr Ser Pro Gly Glu Pro Ala Pro Ser Glu Thr
    2375                2380                2385

Gly Ser Ala Ser Ser Met Pro Pro Leu Glu Gly Glu Pro Gly Asp
    2390                2395                2400

Pro Asp Leu Glu Ser Asp Gln Val Glu Leu Gln Pro Pro Pro Gln
    2405                2410                2415

Gly Gly Gly Val Ala Pro Gly Ser Gly Ser Gly Ser Trp Ser Thr
    2420                2425                2430

Cys Ser Glu Glu Asp Asp Thr Thr Val Cys Cys Ser Met Ser Tyr
    2435                2440                2445

Ser Trp Thr Gly Ala Leu Ile Thr Pro Cys Ser Pro Glu Glu Glu
    2450                2455                2460

Lys Leu Pro Ile Asn Pro Leu Ser Asn Ser Leu Leu Arg Tyr His
    2465                2470                2475

Asn Lys Val Tyr Cys Thr Thr Ser Lys Ser Ala Ser Gln Arg Ala
    2480                2485                2490

Lys Lys Val Thr Phe Asp Arg Thr Gln Val Leu Asp Ala His Tyr
    2495                2500                2505

Asp Ser Val Leu Lys Asp Ile Lys Leu Ala Ala Ser Lys Val Ser
    2510                2515                2520

Ala Arg Leu Leu Thr Leu Glu Glu Ala Cys Gln Leu Thr Pro Pro
    2525                2530                2535

His Ser Ala Arg Ser Lys Tyr Gly Phe Gly Ala Lys Glu Val Arg
    2540                2545                2550

Ser Leu Ser Gly Arg Ala Val Asn His Ile Lys Ser Val Trp Lys
    2555                2560                2565

Asp Leu Leu Glu Asp Pro Gln Thr Pro Ile Pro Thr Thr Ile Met
    2570                2575                2580

Ala Lys Asn Glu Val Phe Cys Val Asp Pro Ala Lys Gly Gly Lys
    2585                2590                2595

Lys Pro Ala Arg Leu Ile Val Tyr Pro Asp Leu Gly Val Arg Val
    2600                2605                2610

Cys Glu Lys Met Ala Leu Tyr Asp Ile Thr Gln Lys Leu Pro Gln
    2615                2620                2625

Ala Val Met Gly Ala Ser Tyr Gly Phe Gln Tyr Ser Pro Ala Gln
    2630                2635                2640

Arg Val Glu Tyr Leu Leu Lys Ala Trp Ala Glu Lys Lys Asp Pro
    2645                2650                2655

Met Gly Phe Ser Tyr Asp Thr Arg Cys Phe Asp Ser Thr Val Thr
    2660                2665                2670

Glu Arg Asp Ile Arg Thr Glu Glu Ser Ile Tyr Gln Ala Cys Ser
    2675                2680                2685

Leu Pro Glu Glu Ala Arg Thr Ala Ile His Ser Leu Thr Glu Arg
    2690                2695                2700
```

| Leu | Tyr | Val | Gly | Gly | Pro | Met | Phe | Asn | Ser | Lys | Gly | Gln | Thr | Cys |
| | 2705 | | | | 2710 | | | | | 2715 | | | | |
| Gly | Tyr | Arg | Arg | Cys | Arg | Ala | Ser | Gly | Val | Leu | Thr | Thr | Ser | Met |
| 2720 | | | | | 2725 | | | | | 2730 | | | | |
| Gly | Asn | Thr | Ile | Thr | Cys | Tyr | Val | Lys | Ala | Leu | Ala | Ala | Cys | Lys |
| 2735 | | | | | 2740 | | | | | 2745 | | | | |
| Ala | Ala | Gly | Ile | Val | Ala | Pro | Thr | Met | Leu | Val | Cys | Gly | Asp | Asp |
| 2750 | | | | | 2755 | | | | | 2760 | | | | |
| Leu | Val | Val | Ile | Ser | Glu | Ser | Gln | Gly | Thr | Glu | Glu | Asp | Glu | Arg |
| 2765 | | | | | 2770 | | | | | 2775 | | | | |
| Asn | Leu | Arg | Ala | Phe | Thr | Glu | Ala | Met | Thr | Arg | Tyr | Ser | Ala | Pro |
| 2780 | | | | | 2785 | | | | | 2790 | | | | |
| Pro | Gly | Asp | Pro | Pro | Arg | Pro | Glu | Tyr | Asp | Leu | Glu | Leu | Ile | Thr |
| 2795 | | | | | 2800 | | | | | 2805 | | | | |
| Ser | Cys | Ser | Ser | Asn | Val | Ser | Val | Ala | Leu | Gly | Pro | Arg | Gly | Arg |
| 2810 | | | | | 2815 | | | | | 2820 | | | | |
| Arg | Arg | Tyr | Tyr | Leu | Thr | Arg | Asp | Pro | Thr | Thr | Pro | Leu | Ala | Arg |
| 2825 | | | | | 2830 | | | | | 2835 | | | | |
| Ala | Ala | Trp | Glu | Thr | Val | Arg | His | Ser | Pro | Ile | Asn | Ser | Trp | Leu |
| 2840 | | | | | 2845 | | | | | 2850 | | | | |
| Gly | Asn | Ile | Ile | Gln | Tyr | Ala | Pro | Thr | Ile | Trp | Val | Arg | Met | Val |
| 2855 | | | | | 2860 | | | | | 2865 | | | | |
| Leu | Met | Thr | His | Phe | Phe | Ser | Ile | Leu | Met | Val | Gln | Asp | Thr | Leu |
| 2870 | | | | | 2875 | | | | | 2880 | | | | |
| Asp | Gln | Asn | Leu | Asn | Phe | Glu | Met | Tyr | Gly | Ser | Val | Tyr | Ser | Val |
| 2885 | | | | | 2890 | | | | | 2895 | | | | |
| Asn | Pro | Leu | Asp | Leu | Pro | Ala | Ile | Ile | Glu | Arg | Leu | His | Gly | Leu |
| 2900 | | | | | 2905 | | | | | 2910 | | | | |
| Asp | Ala | Phe | Ser | Met | His | Thr | Tyr | Ser | His | His | Glu | Leu | Thr | Arg |
| 2915 | | | | | 2920 | | | | | 2925 | | | | |
| Val | Ala | Ser | Ala | Leu | Arg | Lys | Leu | Gly | Ala | Pro | Pro | Leu | Arg | Val |
| 2930 | | | | | 2935 | | | | | 2940 | | | | |
| Trp | Lys | Ser | Arg | Ala | Arg | Ala | Val | Arg | Ala | Ser | Leu | Ile | Ser | Arg |
| 2945 | | | | | 2950 | | | | | 2955 | | | | |
| Gly | Gly | Lys | Ala | Ala | Val | Cys | Gly | Arg | Tyr | Leu | Phe | Asn | Trp | Ala |
| 2960 | | | | | 2965 | | | | | 2970 | | | | |
| Val | Lys | Thr | Lys | Leu | Lys | Leu | Thr | Pro | Leu | Pro | Glu | Ala | Arg | Leu |
| 2975 | | | | | 2980 | | | | | 2985 | | | | |
| Leu | Asp | Leu | Ser | Ser | Trp | Phe | Thr | Val | Gly | Ala | Gly | Gly | Gly | Asp |
| 2990 | | | | | 2995 | | | | | 3000 | | | | |
| Ile | Phe | His | Ser | Val | Ser | Arg | Ala | Arg | Pro | Arg | Ser | Leu | Leu | Phe |
| 3005 | | | | | 3010 | | | | | 3015 | | | | |
| Gly | Leu | Leu | Leu | Leu | Phe | Val | Gly | Val | Gly | Leu | Phe | Leu | Leu | Pro |
| 3020 | | | | | 3025 | | | | | 3030 | | | | |
| Ala | Arg | | | | | | | | | | | | | |
| 3035 | | | | | | | | | | | | | | |

<210> SEQ ID NO 7
<211> LENGTH: 9684
<212> TYPE: DNA
<213> ORGANISM: Hepatitis C virus

<400> SEQUENCE: 7
acctgcccct aatagggggcg acactccgcc atgaatcact cccctgtgag gaactactgt    60

-continued

```
cttcacgcag aaagcgccta gccatggcgt tagtatgagt gtcgtacagc ctccaggccc    120 cccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacac ttcctaaacc    360
tcaaagaaaa accaaaagaa acaccatccg tcgcccacag gacgttaagt tcccgggtgg    420
cggacagatc gttggtggag tatacgtgtt gccgcgcagg ggcccacgat tgggtgtgcg    480
cgcgacgcgt aaaacttctg aacggtcaca gcctcgcgga cgacgacagc ctatccccaa    540
ggcgcgtcgg agcgaaggcc ggtcctgggc tcagcccggg tacccttggc ccctctatgg    600
taatgagggc tgcgggtggg cagggtggct cctgtcccg cgcggctccc gtccatcttg    660
gggcccaaac gaccccggc ggaggtcccg caatttgggt aaagtcatcg atacccttac    720
gtgcggactc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260 gctgtacccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agccttttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
ggggtggggc cccttgacag atgctaacat caccggtcct tctgatgata accgtattg    1800 ctggcactac gcacctagac cttgtagtgt tgtcccggca tcaagtgtct gcggccctgt   1860
gtactgcttc acaccatcgc cagtggtcgt aggcactact gatatcaaag caagccgac    1920 ctacaactgg ggtgagaatg agacagatgt gttcctgctg gagtccctgc ggcctcccag   1980 tggccggtg tttggatgcg cgtggatgaa ctccacgggg ttcctcaaga cgtgtggagc    2040 tccccccttgt aacatctatg ggggtgaggg ggatcccgaa aatgagacag acctcttctg   2100
ccccaccgac tgcttcagga acatcctga ggccacatac agccggtgtg gtgcggggcc    2160
ctggttgaca cctcgctgca tggtcgacta tccataccgg ctttggcatt acccatgtac   2220
agtcaatttc acattgttca aggtgaggat gtttgtgggc ggatttgaac accggtttac   2280
cgccgcttgt aactggacca ggggggagcg ctgcaatatc gaggatcgtg atcgcagcga   2340
gcaacatccg ctgctgcatt caacaactga gcttgctata ctgccttgct ctttcacgcc   2400
```

```
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct tggagaacct tgtcacgctg aacgccgtcg ctgctgctgg   2640
gacacatggt attggttggt acctggtagc cttttgcgcg gcgtggtacg tgcgggtaa    2700 acttgtcccg ctgacgagct acggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940 cccccccctta cttgcacgcg ggagtaggga cggtgtcatc ctgctaacaa gcttgcttta   3000
tccatcctta atttttgaca tcactaagct gctgatagca gtaataggcc cattatactt   3060
aatacaggct gccatcacta ccaccccta ctttgtgcgc gcacatgtac tggtccgcct   3120
ttgcatgctc gtgcgctccg tgatggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcgggctgcc   3360
ggtctccgcg cgattaggcc gtgaggtatt gttgggacct gctgatgatt atcgggaaat   3420
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcgggggttt tgtggactgt   3600
ttaccacgga gctggcaaca agactctagc cggcttacgg ggtccggtca cgcagatgta   3660
ctcgagtgct gagggggact tggtaggctg gcccagcccc cctgggacca agtctttgga   3720
gccgtgcaag tgtggagccg tcgacctata tctggtcacg cggaacgctg atgtcatccc   3780
ggctcggaga cgcggggaca agcggggagc attgctctcc ccgagaccca tttcgacctt   3840 gaagggtcc tcgggggggc cggtgctctg ccctagggc cacgtcgttg gctcttccg    3900 agcagctgtg tgctctcggg gcgtggccaa atccatcgat ttcatccccg ttgagacact   3960
cgacgttgtt acaaggtctc ccactttcag tgacaacagc acgccaccgg ctgtgcccca   4020
gacctatcag gtcgggtact tgcatgctcc aactggcagt ggaaagagca ccaaggtccc   4080
tgtcgcgtat gccgcccagg gtacaaaagt actagtgctt aaccctcgg tagctgccac   4140 cctggggttt ggggcgtacc tatccaaggc acatggcatc aatcccaaca ttaggactgg   4200
agtcaggacc gtgatgaccg gggaggccat cacgtactcc acatatggca aatttctcgc   4260
cgatgggggc tgcgctagcg gcgcctatga catcatcata tgcgatgaat gccacgctgt   4320
ggatgctacc tccattctcg gcatcggaac ggtccttgat caagcagaga cagccggggt   4380
cagactaact gtgctggcta cggccacacc cccgggtca gtgacaaccc cccatcccga   4440
tatagaagag gtaggcctcg gcgggaggg tgagatcccc ttctatggga gggcgattcc   4500
cctatcctgc atcaagggag ggagacacct gattttctgc cactcaaaga aaagtgtga    4560 cgagctcgcg gcggcccttc ggggcatggg cttgaatgcc gtggcatact atagagggtt   4620
ggacgtctcc ataataccag ctcagggaga tgtggtggtc gtcgccaccg acgccctcat   4680
gacggggtac actggagact ttgactccgt gatcgactgc aatgtagcgg tcacccaagc   4740
tgtcgacttc agcctggacc ccaccttcac tataaccaca cagactgtcc cacaagacgc   4800
```

```
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accaccgcg ggggccaccg gctttgtcgt cagtggcctg gtgggggctg ccgtgggcag    5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cgggggaggg cgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc    6540
tatcaattgc tacacggagg ccagtgcgc gccgaaaccc ccacgaact acaagaccgc    6600
catctggagg gtgcggcct cggagtacg ggaggtgacg cagcatgggt cgtactccta    6660
tgtaacagga ctgaccactg acaatctgaa aattccttgc caactacctt ctccagagtt    6720
tttctcctgg gtgacggtg tgcagatcca taggtttgca cccacaccaa agccgttttt    6780
ccgggatgag gtctcgttct cgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
```

```
ccttgagccc tcaataccac cggagtgcat gctccccagg agcgggtttc cacgggcctt   7200
accggcttgg gcacggcctg actacaaccc gccgctcgtg gaatcgtgga ggaggccaga   7260
ttaccaaccg cccaccgttg ctggttgtgc tctccccccc cccaagaagg ccccgacgcc   7320
tcccccaagg agacgccgga cagtgggtct gagcgagagc accatatcag aagccctcca   7380
gcaactggcc atcaagacct tggccagcc ccctcgagc ggtgatgcag gctcgtccac    7440 ggggcgggc gccgccgaat ccggcggtcc gacgtccct ggtgagccgg cccctcaga    7500 gacaggttcc gcctcctcta tgcccccct cgaggggag cctggagatc cggacctgga    7560
gtctgatcag gtagagcttc aacctcccc ccaggggggg ggtagctc ccggttcggg    7620 ctcggggtct tggtctactt gctccgagga ggacgatacc accgtgtgct gctccatgtc    7680
atactcctgg accggggctc taataactcc ctgtagcccc gaagaggaaa agttgccaat    7740
caaccctttg agtaactcgc tgttgcgata ccataacaag gtgtactgta caacatcaaa    7800
gagcgcctca cagagggcta aaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca gtatggatt    7980 cggggccaag gaggtccgca gcttgtccgg gagggccgtt aaccacatca gtccgtgtg    8040 gaaggacctc ctggaagacc cacaaacacc aattcccaca accatcatgg ccaaaaatga    8100
ggtgttctgc gtggacccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
agggcccatg ttcaacagca aggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgccccctc ctggtgatcc ccccagaccg gaatatgacc tggagctaat    8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct tctccattct catggtccaa gacacctgg accagaacct    9000 caactttgag atgtatggat cagtatactc cgtgaatcct ttggaccttc cagccataat    9060
tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttttcacag    9360 cgtgtcgcgc gcccgacccc gctcattact cttcggccta ctcctacttt tcgtaggggt    9420
aggcctcttc ctactcccg ctcggtagag cggcacacac taggtacact ccatagctaa    9480
ctgttccttt ttttttttt tttttttttt ttttttttt ttttttttt ctttttttt     9540
```

```
ttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                            9684
```

<210> SEQ ID NO 8
<211> LENGTH: 3035
<212> TYPE: PRT
<213> ORGANISM: Hepatitis C virus

<400> SEQUENCE: 8

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
```

```
                 340                 345                 350
Trp Gly Ile Leu Ala Gly Leu Ala Tyr Tyr Ser Met Gln Gly Asn Trp
            355                 360                 365

Ala Lys Val Ala Ile Val Met Ile Met Phe Ser Gly Val Asp Ala Glu
    370                 375                 380

Thr Tyr Val Thr Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Lys Pro Thr Tyr
        515                 520                 525

Asn Trp Gly Glu Asn Glu Thr Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Gly Thr
        755                 760                 765
```

His Gly Ile Gly Trp Tyr Leu Val Ala Phe Cys Ala Ala Trp Tyr Val
770                 775                 780

Arg Gly Lys Leu Val Pro Leu Thr Ser Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
                820                 825                 830

Gly Phe Phe Thr Leu Ser Pro Trp Tyr Lys His Trp Ile Gly Arg Leu
                835                 840                 845

Met Trp Trp Asn Gln Tyr Thr Ile Cys Arg Cys Glu Ala Ala Leu Gln
                850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
                900                 905                 910

Thr Thr Thr Pro Tyr Phe Val Arg Ala His Val Leu Val Arg Leu Cys
                915                 920                 925

Met Leu Val Arg Ser Val Met Gly Gly Lys Tyr Phe Gln Met Ala Ile
                930                 935                 940

Leu Ser Ile Gly Arg Trp Phe Asn Thr Tyr Leu Tyr Asp His Leu Ala
945                 950                 955                 960

Pro Met Gln His Trp Ala Ala Gly Leu Lys Asp Leu Ala Val Ala
                965                 970                 975

Thr Glu Pro Val Ile Phe Ser Pro Met Glu Ile Lys Val Ile Thr Trp
                980                 985                 990

Gly Ala Asp Thr Ala Ala Cys Gly Asp Ile Leu Cys Gly Leu Pro Val
                995                 1000                1005

Ser Ala Arg Leu Gly Arg Glu Val Leu Leu Gly Pro Ala Asp Asp
                1010                1015                1020

Tyr Arg Glu Met Gly Trp Arg Leu Leu Ala Pro Ile Thr Ala Tyr
                1025                1030                1035

Ala Gln Gln Thr Arg Gly Leu Leu Gly Ala Ile Val Val Ser Met
                1040                1045                1050

Thr Gly Arg Asp Arg Thr Glu Gln Ala Gly Glu Val Gln Ile Leu
                1055                1060                1065

Ser Thr Val Ser Gln Ser Phe Leu Gly Thr Thr Ile Ser Gly Val
                1070                1075                1080

Leu Trp Thr Val Tyr His Gly Ala Gly Asn Lys Thr Leu Ala Gly
                1085                1090                1095

Leu Arg Gly Pro Val Thr Gln Met Tyr Ser Ser Ala Glu Gly Asp
                1100                1105                1110

Leu Val Gly Trp Pro Ser Pro Pro Gly Thr Lys Ser Leu Glu Pro
                1115                1120                1125

Cys Lys Cys Gly Ala Val Asp Leu Tyr Leu Val Thr Arg Asn Ala
                1130                1135                1140

Asp Val Ile Pro Ala Arg Arg Gly Asp Lys Arg Gly Ala Leu
                1145                1150                1155

Leu Ser Pro Arg Pro Ile Ser Thr Leu Lys Gly Ser Ser Gly Gly
                1160                1165                1170

```
Pro Val Leu Cys Pro Arg Gly His Val Gly Leu Phe Arg Ala
1175                1180                1185

Ala Val Cys Ser Arg Gly Val Ala Lys Ser Ile Asp Phe Ile Pro
1190                1195                1200

Val Glu Thr Leu Asp Val Val Thr Arg Ser Pro Thr Phe Ser Asp
1205                1210                1215

Asn Ser Thr Pro Pro Ala Val Pro Gln Thr Tyr Gln Val Gly Tyr
1220                1225                1230

Leu His Ala Pro Thr Gly Ser Gly Lys Ser Thr Lys Val Pro Val
1235                1240                1245

Ala Tyr Ala Ala Gln Gly Tyr Lys Val Leu Val Leu Asn Pro Ser
1250                1255                1260

Val Ala Ala Thr Leu Gly Phe Gly Ala Tyr Leu Ser Lys Ala His
1265                1270                1275

Gly Ile Asn Pro Asn Ile Arg Thr Gly Val Arg Thr Val Met Thr
1280                1285                1290

Gly Glu Ala Ile Thr Tyr Ser Thr Tyr Gly Lys Phe Leu Ala Asp
1295                1300                1305

Gly Gly Cys Ala Ser Gly Ala Tyr Asp Ile Ile Ile Cys Asp Glu
1310                1315                1320

Cys His Ala Val Asp Ala Thr Ser Ile Leu Gly Ile Gly Thr Val
1325                1330                1335

Leu Asp Gln Ala Glu Thr Ala Gly Val Arg Leu Thr Val Leu Ala
1340                1345                1350

Thr Ala Thr Pro Pro Gly Ser Val Thr Thr Pro His Pro Asp Ile
1355                1360                1365

Glu Glu Val Gly Leu Gly Arg Glu Gly Glu Ile Pro Phe Tyr Gly
1370                1375                1380

Arg Ala Ile Pro Leu Ser Cys Ile Lys Gly Gly Arg His Leu Ile
1385                1390                1395

Phe Cys His Ser Lys Lys Lys Cys Asp Glu Leu Ala Ala Ala Leu
1400                1405                1410

Arg Gly Met Gly Leu Asn Ala Val Ala Tyr Tyr Arg Gly Leu Asp
1415                1420                1425

Val Ser Ile Ile Pro Ala Gln Gly Asp Val Val Val Ala Thr
1430                1435                1440

Asp Ala Leu Met Thr Gly Tyr Thr Gly Asp Phe Asp Ser Val Ile
1445                1450                1455

Asp Cys Asn Val Ala Val Thr Gln Ala Val Asp Phe Ser Leu Asp
1460                1465                1470

Pro Thr Phe Thr Ile Thr Gln Thr Val Pro Gln Asp Ala Val
1475                1480                1485

Ser Arg Ser Gln Arg Arg Gly Arg Thr Gly Arg Gly Arg Gln Gly
1490                1495                1500

Thr Tyr Arg Tyr Val Ser Thr Gly Glu Arg Ala Ser Gly Met Phe
1505                1510                1515

Asp Ser Val Val Leu Cys Glu Cys Tyr Asp Ala Gly Ala Ala Trp
1520                1525                1530

Tyr Asp Leu Thr Pro Ala Glu Thr Thr Val Arg Leu Arg Ala Tyr
1535                1540                1545

Phe Asn Thr Pro Gly Leu Pro Val Cys Gln Asp His Leu Glu Phe
1550                1555                1560

Trp Glu Ala Val Phe Thr Gly Leu Thr His Ile Asp Ala His Phe
```

```
                  1565                1570                 1575
Leu Ser Gln Thr Lys Gln Ala Gly Glu Asn Phe Ala Tyr Leu Val
        1580                1585                1590
Ala Tyr Gln Ala Thr Val Cys Ala Arg Ala Lys Ala Pro Pro Pro
        1595                1600                1605
Ser Trp Asp Ala Met Trp Lys Cys Leu Ala Arg Leu Lys Pro Thr
        1610                1615                1620
Leu Ala Gly Pro Thr Pro Leu Leu Tyr Arg Leu Gly Pro Ile Thr
        1625                1630                1635
Asn Glu Val Thr Leu Thr His Pro Gly Thr Lys Tyr Ile Ala Thr
        1640                1645                1650
Cys Met Gln Ala Asp Leu Glu Val Met Thr Ser Thr Trp Val Leu
        1655                1660                1665
Ala Gly Gly Val Leu Ala Ala Val Ala Ala Tyr Cys Leu Ala Thr
        1670                1675                1680
Gly Cys Val Ser Ile Ile Gly Arg Leu His Val Asn Gln Arg Val
        1685                1690                1695
Val Val Ala Pro Asp Lys Glu Val Leu Tyr Glu Ala Phe Asp Glu
        1700                1705                1710
Met Glu Glu Cys Ala Ser Arg Ala Ala Leu Ile Glu Glu Gly Gln
        1715                1720                1725
Arg Ile Ala Glu Met Leu Lys Ser Lys Ile Gln Gly Leu Leu Gln
        1730                1735                1740
Gln Ala Ser Lys Gln Ala Gln Asp Ile Gln Pro Ala Met Gln Ala
        1745                1750                1755
Ser Trp Pro Lys Val Glu Gln Phe Trp Ala Arg His Met Trp Asn
        1760                1765                1770
Phe Ile Ser Gly Ile Gln Tyr Leu Ala Gly Leu Ser Thr Leu Pro
        1775                1780                1785
Gly Asn Pro Ala Val Ala Ser Met Met Ala Phe Ser Ala Ala Leu
        1790                1795                1800
Thr Ser Pro Leu Ser Thr Ser Thr Thr Ile Leu Leu Asn Ile Met
        1805                1810                1815
Gly Gly Trp Leu Ala Ser Gln Ile Ala Pro Pro Ala Gly Ala Thr
        1820                1825                1830
Gly Phe Val Val Ser Gly Leu Val Gly Ala Ala Val Gly Ser Ile
        1835                1840                1845
Gly Leu Gly Lys Val Leu Val Asp Ile Leu Ala Gly Tyr Gly Ala
        1850                1855                1860
Gly Ile Ser Gly Ala Leu Val Ala Phe Lys Ile Met Ser Gly Glu
        1865                1870                1875
Lys Pro Ser Met Glu Asp Val Ile Asn Leu Leu Pro Gly Ile Leu
        1880                1885                1890
Ser Pro Gly Ala Leu Val Val Gly Val Ile Cys Ala Ala Ile Leu
        1895                1900                1905
Arg Arg His Val Gly Pro Gly Glu Gly Ala Val Gln Trp Met Asn
        1910                1915                1920
Arg Leu Ile Ala Phe Ala Ser Arg Gly Asn His Val Ala Pro Thr
        1925                1930                1935
His Tyr Val Thr Glu Ser Asp Ala Ser Gln Arg Val Thr Gln Leu
        1940                1945                1950
Leu Gly Ser Leu Thr Ile Thr Ser Leu Leu Arg Arg Leu His Asn
        1955                1960                1965
```

-continued

```
Trp Ile Thr Glu Asp Cys Pro Ile Pro Cys Ser Gly Ser Trp Leu
1970            1975            1980

Arg Asp Val Trp Asp Trp Val Cys Thr Ile Leu Thr Asp Phe Lys
1985            1990            1995

Asn Trp Leu Thr Ser Lys Leu Phe Pro Lys Leu Pro Gly Leu Pro
2000            2005            2010

Phe Ile Ser Cys Gln Lys Gly Tyr Lys Gly Val Trp Ala Gly Thr
2015            2020            2025

Gly Ile Met Thr Thr Arg Cys Pro Cys Gly Ala Asn Ile Ser Gly
2030            2035            2040

Asn Val Arg Leu Gly Ser Met Arg Ile Thr Gly Pro Lys Thr Cys
2045            2050            2055

Met Asn Thr Trp Gln Gly Thr Phe Pro Ile Asn Cys Tyr Thr Glu
2060            2065            2070

Gly Gln Cys Ala Pro Lys Pro Pro Thr Asn Tyr Lys Thr Ala Ile
2075            2080            2085

Trp Arg Val Ala Ala Ser Glu Tyr Ala Glu Val Thr Gln His Gly
2090            2095            2100

Ser Tyr Ser Tyr Val Thr Gly Leu Thr Thr Asp Asn Leu Lys Ile
2105            2110            2115

Pro Cys Gln Leu Pro Ser Pro Glu Phe Phe Ser Trp Val Asp Gly
2120            2125            2130

Val Gln Ile His Arg Phe Ala Pro Thr Pro Lys Pro Phe Phe Arg
2135            2140            2145

Asp Glu Val Ser Phe Cys Val Gly Leu Asn Ser Tyr Ala Val Gly
2150            2155            2160

Ser Gln Leu Pro Cys Glu Pro Glu Pro Asp Ala Asp Val Leu Arg
2165            2170            2175

Ser Met Leu Thr Asp Pro Pro His Ile Thr Ala Glu Thr Ala Ala
2180            2185            2190

Arg Arg Leu Ala Arg Gly Ser Pro Pro Ser Glu Ala Ser Ser Ser
2195            2200            2205

Val Ser Gln Leu Ser Ala Pro Ser Leu Arg Ala Thr Cys Thr Thr
2210            2215            2220

His Ser Asn Thr Tyr Asp Val Asp Met Val Asp Ala Asn Leu Leu
2225            2230            2235

Met Glu Gly Gly Val Ala Gln Thr Glu Pro Glu Ser Arg Val Pro
2240            2245            2250

Val Leu Asp Phe Leu Glu Pro Met Ala Glu Glu Glu Ser Asp Leu
2255            2260            2265

Glu Pro Ser Ile Pro Pro Glu Cys Met Leu Pro Arg Ser Gly Phe
2270            2275            2280

Pro Arg Ala Leu Pro Ala Trp Ala Arg Pro Asp Tyr Asn Pro Pro
2285            2290            2295

Leu Val Glu Ser Trp Arg Arg Pro Asp Tyr Gln Pro Pro Thr Val
2300            2305            2310

Ala Gly Cys Ala Leu Pro Pro Pro Lys Lys Ala Pro Thr Pro Pro
2315            2320            2325

Pro Arg Arg Arg Arg Thr Val Gly Leu Ser Glu Ser Thr Ile Ser
2330            2335            2340

Glu Ala Leu Gln Gln Leu Ala Ile Lys Thr Phe Gly Gln Pro Pro
2345            2350            2355
```

```
Ser Ser Gly Asp Ala Gly Ser Ser Thr Gly Ala Gly Ala Ala Glu
    2360                2365            2370

Ser Gly Gly Pro Thr Ser Pro Gly Glu Pro Ala Pro Ser Glu Thr
    2375                2380            2385

Gly Ser Ala Ser Ser Met Pro Pro Leu Glu Gly Glu Pro Gly Asp
    2390                2395            2400

Pro Asp Leu Glu Ser Asp Gln Val Glu Leu Gln Pro Pro Pro Gln
    2405                2410            2415

Gly Gly Gly Val Ala Pro Gly Ser Gly Ser Gly Ser Trp Ser Thr
    2420                2425            2430

Cys Ser Glu Glu Asp Asp Thr Thr Val Cys Cys Ser Met Ser Tyr
    2435                2440            2445

Ser Trp Thr Gly Ala Leu Ile Thr Pro Cys Ser Pro Glu Glu Glu
    2450                2455            2460

Lys Leu Pro Ile Asn Pro Leu Ser Asn Ser Leu Leu Arg Tyr His
    2465                2470            2475

Asn Lys Val Tyr Cys Thr Thr Ser Lys Ser Ala Ser Gln Arg Ala
    2480                2485            2490

Lys Lys Val Thr Phe Asp Arg Thr Gln Val Leu Asp Ala His Tyr
    2495                2500            2505

Asp Ser Val Leu Lys Asp Ile Lys Leu Ala Ala Ser Lys Val Ser
    2510                2515            2520

Ala Arg Leu Leu Thr Leu Glu Glu Ala Cys Gln Leu Thr Pro Pro
    2525                2530            2535

His Ser Ala Arg Ser Lys Tyr Gly Phe Gly Ala Lys Glu Val Arg
    2540                2545            2550

Ser Leu Ser Gly Arg Ala Val Asn His Ile Lys Ser Val Trp Lys
    2555                2560            2565

Asp Leu Leu Glu Asp Pro Gln Thr Pro Ile Pro Thr Thr Ile Met
    2570                2575            2580

Ala Lys Asn Glu Val Phe Cys Val Asp Pro Ala Lys Gly Gly Lys
    2585                2590            2595

Lys Pro Ala Arg Leu Ile Val Tyr Pro Asp Leu Gly Val Arg Val
    2600                2605            2610

Cys Glu Lys Met Ala Leu Tyr Asp Ile Thr Gln Lys Leu Pro Gln
    2615                2620            2625

Ala Val Met Gly Ala Ser Tyr Gly Phe Gln Tyr Ser Pro Ala Gln
    2630                2635            2640

Arg Val Glu Tyr Leu Leu Lys Ala Trp Ala Glu Lys Lys Asp Pro
    2645                2650            2655

Met Gly Phe Ser Tyr Asp Thr Arg Cys Phe Asp Ser Thr Val Thr
    2660                2665            2670

Glu Arg Asp Ile Arg Thr Glu Glu Ser Ile Tyr Gln Ala Cys Ser
    2675                2680            2685

Leu Pro Glu Glu Ala Arg Thr Ala Ile His Ser Leu Thr Glu Arg
    2690                2695            2700

Leu Tyr Val Gly Gly Pro Met Phe Asn Ser Lys Gly Gln Thr Cys
    2705                2710            2715

Gly Tyr Arg Arg Cys Arg Ala Ser Gly Val Leu Thr Thr Ser Met
    2720                2725            2730

Gly Asn Thr Ile Thr Cys Tyr Val Lys Ala Leu Ala Ala Cys Lys
    2735                2740            2745

Ala Ala Gly Ile Val Ala Pro Thr Met Leu Val Cys Gly Asp Asp
```

```
        2750                2755                2760
Leu Val Val Ile Ser Glu Ser Gln Gly Thr Glu Glu Asp Glu Arg
        2765                2770                2775

Asn Leu Arg Ala Phe Thr Glu Ala Met Thr Arg Tyr Ser Ala Pro
        2780                2785                2790

Pro Gly Asp Pro Pro Arg Pro Glu Tyr Asp Leu Glu Leu Ile Thr
        2795                2800                2805

Ser Cys Ser Ser Asn Val Ser Val Ala Leu Gly Pro Arg Gly Arg
        2810                2815                2820

Arg Arg Tyr Tyr Leu Thr Arg Asp Pro Thr Thr Pro Leu Ala Arg
        2825                2830                2835

Ala Ala Trp Glu Thr Val Arg His Ser Pro Ile Asn Ser Trp Leu
        2840                2845                2850

Gly Asn Ile Ile Gln Tyr Ala Pro Thr Ile Trp Val Arg Met Val
        2855                2860                2865

Leu Met Thr His Phe Phe Ser Ile Leu Met Val Gln Asp Thr Leu
        2870                2875                2880

Asp Gln Asn Leu Asn Phe Glu Met Tyr Gly Ser Val Tyr Ser Val
        2885                2890                2895

Asn Pro Leu Asp Leu Pro Ala Ile Ile Glu Arg Leu His Gly Leu
        2900                2905                2910

Asp Ala Phe Ser Met His Thr Tyr Ser His His Glu Leu Thr Arg
        2915                2920                2925

Val Ala Ser Ala Leu Arg Lys Leu Gly Ala Pro Pro Leu Arg Val
        2930                2935                2940

Trp Lys Ser Arg Ala Arg Ala Val Arg Ala Ser Leu Ile Ser Arg
        2945                2950                2955

Gly Gly Lys Ala Ala Val Cys Gly Arg Tyr Leu Phe Asn Trp Ala
        2960                2965                2970

Val Lys Thr Lys Leu Lys Leu Thr Pro Leu Pro Glu Ala Arg Leu
        2975                2980                2985

Leu Asp Leu Ser Ser Trp Phe Thr Val Gly Ala Gly Gly Gly Asp
        2990                2995                3000

Ile Phe His Ser Val Ser Arg Ala Arg Pro Arg Ser Leu Leu Phe
        3005                3010                3015

Gly Leu Leu Leu Leu Phe Val Gly Val Gly Leu Phe Leu Leu Pro
        3020                3025                3030

Ala Arg
        3035

<210> SEQ ID NO 9
<211> LENGTH: 9684
<212> TYPE: DNA
<213> ORGANISM: Hepatitis C virus

<400> SEQUENCE: 9
acctgcccct aatagggggcg acactccgcc atgaatcact cccctgtgag gaactactgt      60
cttcacgcag aaagcgccta gccatggcgt tagtatgagt gtcgtacagc ctccaggccc     120
ccccctcccg ggagagccat agtggtctgc ggaaccggtg agtacaccgg aattgccggg     180
aagactgggt cctttcttgg ataaacccac tctatgcccg gccatttggg cgtgccccccg     240 caagactgct agccgagtag cgttgggttg cgaaaggcct tgtggtactg cctgataggg     300
tgcttgcgag tgccccggga ggtctcgtag accgtgcacc atgagcacac ttcctaaacc     360
```

```
tcaaagaaaa accaaaagaa acaccatccg tcgcccacag gacgttaagt tcccgggtgg    420
cggacagatc gttggtggag tatacgtgtt gccgcgcagg ggcccacgat tgggtgtgcg    480
cgcgacgcgt aaaacttctg aacggtcaca gcctcgcgga cgacgacagc ctatcccaa     540 ggcgcgtcgg agcgaaggcc ggtcctgggc tcagcccggg tacccttggc ccctctatgg    600
taatgagggc tgcgggtggg cagggtggct cctgtccccg cgcggctccc gtccatcttg    660
gggcccaaac gaccccggc ggaggtcccg caatttgggt aaagtcatcg atacccttac     720
gtgcggattc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tcttcctcgt    1200
gggacaagcc ttcacgttca gcctcgtcg ccatcaaacg gtccagacct gtaactgctc    1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gccattgggg gcatcttggc gggcctagcc tattattcta tgcagggcaa    1440
ctgggccaag gtcgctattg tcatgattat gttttcaggg gtcgatgctg aaacatatgt    1500
caccggtggc agtgtagctc atagtgccag agggttaact agcctttta gtgtgggcgc     1560 caagcagaaa ctgcaattgg tcaacaccaa tggctcgtgg cacatcaaca gtactgccct   1620
gaactgcaat gagtccataa acaccgggtt catagctggg ttgttttatt accataagtt    1680
caactctact ggatgtcctc aaaggcttag cagctgcaag cccatcattt ccttcaggca    1740
ggggtggggc cccttgacag atgctaacat caccggtcct tctgatgata accgtattg     1800 ctggcactac gcacctagac cttgtagtgt tgtcccggca tcaagtgtct gcggccctgt    1860
gtactgcttc acaccatcgc cagtggtcgt aggcactact gatatcaaag gcaagccgac   1920
ctacaactgg ggtgagaatg agacagatgt gttcctgctg gagtccctgc ggcctcccag    1980
tggccggtgg tttggatgcg cgtggatgaa ctccacgggg ttcctcaaga cgtgtggagc    2040 tccccttgt aacatctatg ggggtgaggg ggatcccgaa aatgagacag acctcttctg    2100
ccccaccgac tgcttcagga aacatcctga ggccacatac agccggtgtg gtgcggggcc   2160
ctggttgaca cctcgctgca tggtcgacta tccataccgg cttggcatt acccatgtac    2220 agtcaatttc acattgttca aggtgaggat gtttgtgggc ggatttgaac accggtttac   2280
cgccgcttgt aactgaccaca ggggggagcg ctgcaatatc gaggatcgtg atcgcagcga   2340
gcaacatccg ctgctgcatt caacaactga gcttgctata ctgccttgct ctttcacgcc    2400
catgcctgca ttgtcaacag gtctaataca cctccaccaa aatatcgtgg atgtccaata    2460
cctttatggt gttggatctg acatggtggg atgggcgctg aaatgggagt tcgtcatcct    2520
cgttttcctc ctcctggcag acgcacgcgt gtgcgttgcc ctttggctga tgctgatggt    2580
atcacaagca gaagcagcct tggagaacct tgtcacgctg aacgccgtcg ctgctgctgg   2640
gacacatggt attggttggt acctggtagc cttttgcgcg gcgtggtacg tgcggggtaa    2700
acttgtcccg ctgacgatct gcggcctgac gggtctttgg tccctagcat tgcttgtcct    2760
```

```
cttgctcccc caacgggcgt atgcttggtc gggtgaagac agcgctactc tcggcgctgg    2820
ggtcttggcc ctcttcggct tctttacctt atcaccctgg tacaagcatt ggatcggccg    2880
cctcatgtgg tggaaccagt acactatatg tagatgcgag gccgcccttc aagtgtgggt    2940
ccccccctta cttgcacgcg ggagtaggga cggtgtcatc ctgctaacaa gcttgcttta    3000
tccatcctta attttgtgaca tcactaagct gctgatagca gtaataggcc cattatactt   3060
aatacaggct gccatcacta ccacccccta ctttgtgcgc gcacatgtac tggtccgcct    3120
ttgcatgctc gtgcgctccg tgatgggggg aaagtacttc cagatggcca tactgagcat    3180
tggcagatgg ttcaacacct acctatatga ccacctagcg ccaatgcaac attgggccgc    3240
agctggcctc aaagacctag cagtggccac tgaacctgta atatttagtc ccatggaaat    3300
taaggtcatc acctggggcg cggacacagc ggcttgcgga gatattcttt gcgggctgcc    3360
ggtctccgcg cgattaggcc gtgaggtatt gttgggacct gctgatgatt atcgggaaat    3420
gggttggcgt ctgttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gaggggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840
gaaggggtcc tcgggggggc cggtgctctg ccctaggggc cacgtcgttg ggctcttccg    3900
agcagctgtg tgctctcggg gcgtggccaa atccatcgat ttcatccccg ttgagacact    3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aaccctcgg tagctgccac    4140 cctgggggttt ggggcgtacc tatccaaggc acatggcatc aatcccaaca ttaggactgg    4200
agtcaggacc gtgatgaccg gggaggccat cacgtactcc acatatggca aatttctcgc    4260 cgatggggc tgcgctagcg gcgcctatga catcatcata tgcgatgaat gccacgctgt    4320
ggatgctacc tccattctcg gcatcggaac ggtccttgat caagcagaga cagccggggt    4380
cagactaact gtgctggcta cggccacacc ccccgggtca gtgacaaccc cccatcccga    4440
tatagaagag gtaggcctcg gcgggaggg tgagatcccc ttctatggga gggcgattcc    4500
cctatcctgc atcaagggag ggagacacct gatttctgc cactcaaaga aaagtgtga    4560 cgagctcgcg gcgccccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agactgggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgccggcc tacccgtgtg tcaagaccat cttgaatttt gggaggcagt    5040
tttcaccggc ctcacacaca tagacgccca cttcctctcc caaacaaagc aagcggggga    5100
```

```
gaacttcgcg tacctagtag cctaccaagc tacggtgtgc gccagagcca aggcccctcc   5160
cccgtcctgg gacgccatgt ggaagtgcct ggcccgactc aagcctacgc ttgcgggccc   5220
cacacctctc ctgtaccgtt tgggccctat taccaatgag gtcaccctca cacaccctgg   5280
gacgaagtac atcgccacat gcatgcaagc tgaccttgag gtcatgacca gcacgtgggt   5340
cctagctgga ggagtcctgg cagccgtcgc cgcatattgc ctggcgactg gatgcgtttc   5400
catcatcggc cgcttgcacg tcaaccagcg agtcgtcgtt gcgccggata aggaggtcct   5460
gtatgaggct tttgatgaga tggaggaatg cgcctctagg gcggctctca tcgaagaggg   5520
gcagcggata gccgagatgt tgaagtccaa gatccaaggc ttgctgcagc aggcctctaa   5580
gcaggcccag gacatacaac ccgctatgca ggcttcatgg cccaaagtgg aacaattttg   5640
ggccagacac atgtgaact tcattagcgg catccaatac ctcgcaggat tgtcaacact   5700
gccagggaac cccgcggtgg cttccatgat ggcattcagt gccgccctca ccagtccgtt   5760
gtcgaccagt accaccatcc ttctcaacat catgggaggc tggttagcgt cccagatcgc   5820
accacccgcg ggggccaccg gctttgtcgt cagtggcctg gtgggggctg ccgtgggcag   5880
cataggcctg ggtaaggtgc tggtggacat cctggcagga tatggtgcgg gcatttcggg   5940
ggccctcgtc gcattcaaga tcatgtctgg cgagaagccc tctatggaag atgtcatcaa   6000
tctactgcct gggatcctgt ctccgggagc cctggtggtg ggggtcatct gcgcggccat   6060
tctgcgccgc cacgtgggac cggggagggg cgcggtccaa tggatgaaca ggcttattgc   6120
ctttgcttcc agaggaaacc acgtcgcccc tactcactac gtgacggagt cggatgcgtc   6180
gcagcgtgtg acccaactac ttggctctct tactataacc agcctactca gaagactcca   6240
caattggata actgaggact gccccatccc atgctccgga tcctggctcc gcgacgtgtg   6300
ggactgggtt tgcaccatct tgacagactt caaaaattgg ctgacctcta aattgttccc   6360
caagctgccc ggcctcccct tcatctcttg tcaaaggggg tacaagggtg tgtgggccgg   6420
cactggcatc atgaccacgc gctgcccttg cggcgccaac atctctggca atgtccgcct   6480
gggctctatg aggatcacag ggcctaaaac ctgcatgaac acctggcagg gaccttttcc   6540
tatcaattgc tacacggagg gccagtgcgc gccgaaaccc cccacgaact acaagaccgc   6600
catctggagg gtggcggcct cggagtacgc ggaggtgacg cagcatgggt cgtactccta   6660
tgtaacagga ctgaccactg acaatctgaa aattccttgc caactacctt ctccagagtt   6720
tttctcctgg gtggacggtg tgcagatcca taggtttgca cccacaccaa agccgttttt   6780
ccgggatgag gtctcgttct cgcgttgggct taattcctat gctgtcgggt cccagcttcc   6840
ctgtgaacct gagcccgacg cagacgtatt gaggtccatg ctaacagatc cgccccacat   6900
cacggcggag actgcggcgc ggcgcttggc acgggatca cctccatctg aggcgagctc   6960
ctcagtgagc cagctatcag caccgtcgct gcgggccacc tgcaccaccc acagcaacac   7020
ctatgacgtg gacatggtcg atgccaacct gctcatggag ggcggtgtgg ctcagacaga   7080
gcctgagtcc agggtgcccg ttctggactt tctcgagcca atggccgagg aagagagcga   7140
ccttgagccc tcaataccat cggagtgcat gctcccagg agcgggtttc cacgggcctt   7200
accggcttgg gcacggcctg actacaaccc gccgctcgtg gaatcgtgga ggaggccaga   7260
ttaccaaccg cccaccgttg ctggttgtgc tctccccccc cccaagaagg ccccgacgcc   7320
tcccccaagg agacgccgga cagtgggtct gagcgagagc accatatcag aagccctcca   7380
gcaactggca atcaagacct ttggccagcc cccctcgagc ggtgatgcag gctcgtccac   7440
gggggcgggc gccgccgaat ccggcggtcc gacgtcccct ggtgagccgg ccccctcaga   7500
```

```
gacaggttcc gcctcctcta tgcccccct cgagggggag cctggagatc cggacctgga   7560
gtctgatcag gtagagcttc aacctcccc ccagggggg ggggtagctc ccggttcggg    7620 ctcgggtct tggtctactt gctccgagga ggacgatacc accgtgtgct gctccatgtc    7680
atactcctgg accggggctc taataactcc ctgtagcccc gaagaggaaa agttgccaat   7740 caacccttg agtaactcgc tgttgcgata ccataacaag gtgtactgta caacatcaaa   7800
gagcgcctca cagagggcta aaaaggtaac ttttgacagg acgcaagtgc tcgacgccca   7860
ttatgactca gtcttaaagg acatcaagct agcggcttcc aaggtcagcg caaggctcct   7920
caccttggag gaggcgtgcc agttgactcc accccattct gcaagatcca agtatggatt   7980
cggggccaag gaggtccgca gcttgtccgg gagggccgtt aaccacatca gtccgtgtg    8040 gaaggacctc ctggaagacc cacaaacacc aattcccaca accatcatgg ccaaaaatga   8100
ggtgttctgc gtggaccccg ccaagggggg taagaaacca gctcgcctca tcgtttaccc   8160
tgacctcggc gtccgggtct gcgagaaaat ggccctctat gacattacac aaaagcttcc   8220
tcaggcggta atgggagctt cctatggctt ccagtactcc cctgcccaac gggtggagta   8280
tctcttgaaa gcatgggcgg aaaagaagga ccccatgggt ttttcgtatg atacccgatg   8340
cttcgactca accgtcactg agagagacat caggaccgag gagtccatat accaggcctg   8400
ctccctgccc gaggaggccc gcactgccat acactcgctg actgagagac tttacgtagg   8460
agggcccatg ttcaacagca agggtcaaac ctgcggttac agacgttgcc gcgccagcgg   8520
ggtgctaacc actagcatgg gtaacaccat cacatgctat gtgaaagccc tagcggcctg   8580
caaggctgcg gggatagttg cgcccacaat gctggtatgc ggcgatgacc tagtagtcat   8640
ctcagaaagc caggggactg aggaggacga gcggaacctg agagccttca cggaggccat   8700
gaccaggtac tctgcccctc ctggtgatcc ccccagaccg gaatatgacc tggagctaat   8760
aacatcctgt tcctcaaatg tgtctgtggc gttgggcccg cggggccgcc gcagatacta   8820
cctgaccaga gacccaacca ctccactcgc ccgggctgcc tgggaaacag ttagacactc   8880
ccctatcaat tcatggctgg aaacatcat ccagtatgct ccaaccatat gggttcgcat   8940
ggtcctaatg acacacttct ctccattct catggtccaa gacaccctgg accagaacct   9000
caactttgag atgtatggat cagtatactc cgtgaatcct ttggaccttc agccataat    9060 tgagaggtta cacgggcttg acgcctttc tatgcacaca tactctcacc acgaactgac   9120
gcgggtggct tcagccctca gaaaacttgg ggcgccaccc ctcagggtgt ggaagagtcg   9180
ggctcgcgca gtcagggcgt ccctcatctc ccgtggaggg aaagcggccg tttgcggccg   9240
atatctcttc aattgggcgg tgaagaccaa gctcaaactc actccattgc cggaggcgcg   9300
cctactggac ttatccagtt ggttcaccgt cggcgccggc gggggcgaca tttttcacag   9360
cgtgtcgcgc gcccgacccc gctcattact cttcggccta ctcctactt tcgtaggggt    9420 aggcctcttc ctactcccg ctcggtagag cggcacacac taggtacact ccatagctaa   9480
ctgttccttt ttttttttt ttttttttt ttttttttt ttttttttt cttttttt        9540 tttttccctc tttcttccct tctcatctta ttctactttc tttcttggtg gctccatctt   9600
agccctagtc acggctagct gtgaaaggtc cgtgagccgc atgactgcag agagtgccgt   9660
aactggtctc tctgcagatc atgt                                          9684
```

<210> SEQ ID NO 10
<211> LENGTH: 3035
<212> TYPE: PRT

<213> ORGANISM: Hepatitis C virus

<400> SEQUENCE: 10

Met Ser Thr Leu Pro Lys Pro Gln Arg Lys Thr Lys Arg Asn Thr Ile
1 5 10 15

Arg Arg Pro Gln Asp Val Lys Phe Pro Gly Gly Gly Gln Ile Val Gly
20 25 30

Gly Val Tyr Val Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Ser Glu Gly Arg Ser Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Asn Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Val
130 135 140

Gly Gly Val Ala Arg Ala Leu Ala His Gly Val Arg Ala Leu Glu Asp
145 150 155 160

Gly Ile Asn Phe Ala Thr Gly Asn Leu Pro Gly Cys Ser Phe Ser Ile
165 170 175

Phe Leu Leu Ala Leu Phe Ser Cys Leu Val His Pro Ala Ala Ser Leu
180 185 190

Glu Trp Arg Asn Thr Ser Gly Leu Tyr Val Leu Thr Asn Asp Cys Ser
195 200 205

Asn Ser Ser Ile Val Tyr Glu Ala Asp Asp Val Ile Leu His Thr Pro
210 215 220

Gly Cys Val Pro Cys Val Gln Asp Asp Asn Thr Ser Thr Cys Trp Thr
225 230 235 240

Pro Val Thr Pro Thr Val Ala Val Arg Tyr Val Gly Ala Thr Thr Ala
245 250 255

Ser Ile Arg Ser His Val Asp Leu Leu Val Gly Ala Ala Thr Leu Cys
260 265 270

Ser Ala Leu Tyr Val Gly Asp Met Cys Gly Ala Val Phe Leu Val Gly
275 280 285

Gln Ala Phe Thr Phe Arg Pro Arg Arg His Gln Thr Val Gln Thr Cys
290 295 300

Asn Cys Ser Leu Tyr Pro Gly His Val Ser Gly His Arg Met Ala Trp
305 310 315 320

Asp Met Met Met Asn Trp Ser Pro Ala Val Gly Met Val Val Ala His
325 330 335

Ile Leu Arg Leu Pro Gln Thr Leu Phe Asp Ile Leu Ala Gly Ala His
340 345 350

Trp Gly Ile Leu Ala Gly Leu Ala Tyr Tyr Ser Met Gln Gly Asn Trp
355 360 365

Ala Lys Val Ala Ile Val Met Ile Met Phe Ser Gly Val Asp Ala Glu
370 375 380

Thr Tyr Val Thr Gly Gly Ser Val Ala His Ser Ala Arg Gly Leu Thr
385 390 395 400

```
Ser Leu Phe Ser Val Gly Ala Lys Gln Lys Leu Gln Leu Val Asn Thr
            405                 410                 415
Asn Gly Ser Trp His Ile Asn Ser Thr Ala Leu Asn Cys Asn Glu Ser
        420                 425                 430
Ile Asn Thr Gly Phe Ile Ala Gly Leu Phe Tyr Tyr His Lys Phe Asn
                435                 440                 445
Ser Thr Gly Cys Pro Gln Arg Leu Ser Ser Cys Lys Pro Ile Ile Ser
    450                 455                 460
Phe Arg Gln Gly Trp Gly Pro Leu Thr Asp Ala Asn Ile Thr Gly Pro
465                 470                 475                 480
Ser Asp Asp Arg Pro Tyr Cys Trp His Tyr Ala Pro Arg Pro Cys Ser
                485                 490                 495
Val Val Pro Ala Ser Ser Val Cys Gly Pro Val Tyr Cys Phe Thr Pro
            500                 505                 510
Ser Pro Val Val Gly Thr Thr Asp Ile Lys Gly Lys Pro Thr Tyr
        515                 520                 525
Asn Trp Gly Glu Asn Glu Thr Asp Val Phe Leu Leu Glu Ser Leu Arg
    530                 535                 540
Pro Pro Ser Gly Arg Trp Phe Gly Cys Ala Trp Met Asn Ser Thr Gly
545                 550                 555                 560
Phe Leu Lys Thr Cys Gly Ala Pro Pro Cys Asn Ile Tyr Gly Gly Glu
                565                 570                 575
Gly Asp Pro Glu Asn Glu Thr Asp Leu Phe Cys Pro Thr Asp Cys Phe
            580                 585                 590
Arg Lys His Pro Glu Ala Thr Tyr Ser Arg Cys Gly Ala Gly Pro Trp
        595                 600                 605
Leu Thr Pro Arg Cys Met Val Asp Tyr Pro Tyr Arg Leu Trp His Tyr
    610                 615                 620
Pro Cys Thr Val Asn Phe Thr Leu Phe Lys Val Arg Met Phe Val Gly
625                 630                 635                 640
Gly Phe Glu His Arg Phe Thr Ala Ala Cys Asn Trp Thr Arg Gly Glu
                645                 650                 655
Arg Cys Asn Ile Glu Asp Arg Asp Arg Ser Glu Gln His Pro Leu Leu
            660                 665                 670
His Ser Thr Thr Glu Leu Ala Ile Leu Pro Cys Ser Phe Thr Pro Met
        675                 680                 685
Pro Ala Leu Ser Thr Gly Leu Ile His Leu His Gln Asn Ile Val Asp
690                 695                 700
Val Gln Tyr Leu Tyr Gly Val Gly Ser Asp Met Val Gly Trp Ala Leu
705                 710                 715                 720
Lys Trp Glu Phe Val Ile Leu Val Phe Leu Leu Leu Ala Asp Ala Arg
                725                 730                 735
Val Cys Val Ala Leu Trp Leu Met Leu Met Val Ser Gln Ala Glu Ala
            740                 745                 750
Ala Leu Glu Asn Leu Val Thr Leu Asn Ala Val Ala Ala Ala Gly Thr
        755                 760                 765
His Gly Ile Gly Trp Tyr Leu Val Ala Phe Cys Ala Ala Trp Tyr Val
    770                 775                 780
Arg Gly Lys Leu Val Pro Leu Thr Ile Cys Gly Leu Thr Gly Leu Trp
785                 790                 795                 800
Ser Leu Ala Leu Leu Val Leu Leu Pro Gln Arg Ala Tyr Ala Trp
                805                 810                 815
Ser Gly Glu Asp Ser Ala Thr Leu Gly Ala Gly Val Leu Ala Leu Phe
```

-continued

```
                820                 825                 830
Gly Phe Phe Thr Leu Ser Pro Trp Tyr Lys His Trp Ile Gly Arg Leu
            835                 840                 845
Met Trp Trp Asn Gln Tyr Thr Ile Cys Arg Cys Glu Ala Ala Leu Gln
    850                 855                 860
Val Trp Val Pro Pro Leu Leu Ala Arg Gly Ser Arg Asp Gly Val Ile
865                 870                 875                 880
Leu Leu Thr Ser Leu Leu Tyr Pro Ser Leu Ile Phe Asp Ile Thr Lys
                885                 890                 895
Leu Leu Ile Ala Val Ile Gly Pro Leu Tyr Leu Ile Gln Ala Ala Ile
            900                 905                 910
Thr Thr Thr Pro Tyr Phe Val Arg Ala His Val Leu Val Arg Leu Cys
        915                 920                 925
Met Leu Val Arg Ser Val Met Gly Gly Lys Tyr Phe Gln Met Ala Ile
    930                 935                 940
Leu Ser Ile Gly Arg Trp Phe Asn Thr Tyr Leu Tyr Asp His Leu Ala
945                 950                 955                 960
Pro Met Gln His Trp Ala Ala Ala Gly Leu Lys Asp Leu Ala Val Ala
                965                 970                 975
Thr Glu Pro Val Ile Phe Ser Pro Met Glu Ile Lys Val Ile Thr Trp
            980                 985                 990
Gly Ala Asp Thr Ala Ala Cys Gly Asp Ile Leu Cys Gly Leu Pro Val
        995                 1000                1005
Ser Ala Arg Leu Gly Arg Glu Val Leu Leu Gly Pro Ala Asp Asp
    1010                1015                1020
Tyr Arg Glu Met Gly Trp Arg Leu Leu Ala Pro Ile Thr Ala Tyr
    1025                1030                1035
Ala Gln Gln Thr Arg Gly Leu Leu Gly Ala Ile Val Val Ser Met
    1040                1045                1050
Thr Gly Arg Asp Arg Thr Glu Gln Ala Gly Glu Val Gln Ile Leu
    1055                1060                1065
Ser Thr Val Ser Gln Ser Phe Leu Gly Thr Thr Ile Ser Gly Val
    1070                1075                1080
Leu Trp Thr Val Tyr His Gly Ala Gly Asn Lys Thr Leu Ala Gly
    1085                1090                1095
Leu Arg Gly Pro Val Thr Gln Met Tyr Ser Ser Ala Glu Gly Asp
    1100                1105                1110
Leu Val Gly Trp Pro Ser Pro Pro Gly Thr Lys Ser Leu Glu Pro
    1115                1120                1125
Cys Lys Cys Gly Ala Val Asp Leu Tyr Leu Val Thr Arg Asn Ala
    1130                1135                1140
Asp Val Ile Pro Ala Arg Arg Arg Gly Asp Lys Arg Gly Ala Leu
    1145                1150                1155
Leu Ser Pro Arg Pro Ile Ser Thr Leu Lys Gly Ser Ser Gly Gly
    1160                1165                1170
Pro Val Leu Cys Pro Arg Gly His Val Val Gly Leu Phe Arg Ala
    1175                1180                1185
Ala Val Cys Ser Arg Gly Val Ala Lys Ser Ile Asp Phe Ile Pro
    1190                1195                1200
Val Glu Thr Leu Asp Val Val Thr Arg Ser Pro Thr Phe Ser Asp
    1205                1210                1215
Asn Ser Thr Pro Pro Ala Val Pro Gln Thr Tyr Gln Val Gly Tyr
    1220                1225                1230
```

```
Leu His Ala Pro Thr Gly Ser Gly Lys Ser Thr Lys Val Pro Val
    1235            1240             1245

Ala Tyr Ala Ala Gln Gly Tyr Lys Val Leu Val Leu Asn Pro Ser
    1250            1255             1260

Val Ala Ala Thr Leu Gly Phe Gly Ala Tyr Leu Ser Lys Ala His
    1265            1270             1275

Gly Ile Asn Pro Asn Ile Arg Thr Gly Val Arg Thr Val Met Thr
    1280            1285             1290

Gly Glu Ala Ile Thr Tyr Ser Thr Tyr Gly Lys Phe Leu Ala Asp
    1295            1300             1305

Gly Gly Cys Ala Ser Gly Ala Tyr Asp Ile Ile Ile Cys Asp Glu
    1310            1315             1320

Cys His Ala Val Asp Ala Thr Ser Ile Leu Gly Ile Gly Thr Val
    1325            1330             1335

Leu Asp Gln Ala Glu Thr Ala Gly Val Arg Leu Thr Val Leu Ala
    1340            1345             1350

Thr Ala Thr Pro Pro Gly Ser Val Thr Thr Pro His Pro Asp Ile
    1355            1360             1365

Glu Glu Val Gly Leu Gly Arg Glu Gly Glu Ile Pro Phe Tyr Gly
    1370            1375             1380

Arg Ala Ile Pro Leu Ser Cys Ile Lys Gly Gly Arg His Leu Ile
    1385            1390             1395

Phe Cys His Ser Lys Lys Lys Cys Asp Glu Leu Ala Ala Ala Leu
    1400            1405             1410

Arg Gly Met Gly Leu Asn Ala Val Ala Tyr Tyr Arg Gly Leu Asp
    1415            1420             1425

Val Ser Ile Ile Pro Ala Gln Gly Asp Val Val Val Ala Thr
    1430            1435             1440

Asp Ala Leu Met Thr Gly Tyr Thr Gly Asp Phe Asp Ser Val Ile
    1445            1450             1455

Asp Cys Asn Val Ala Val Thr Gln Ala Val Asp Phe Ser Leu Asp
    1460            1465             1470

Pro Thr Phe Thr Ile Thr Thr Gln Thr Val Pro Gln Asp Ala Val
    1475            1480             1485

Ser Arg Ser Gln Arg Arg Gly Arg Thr Gly Arg Gly Arg Leu Gly
    1490            1495             1500

Thr Tyr Arg Tyr Val Ser Thr Gly Glu Arg Ala Ser Gly Met Phe
    1505            1510             1515

Asp Ser Val Val Leu Cys Glu Cys Tyr Asp Ala Gly Ala Ala Trp
    1520            1525             1530

Tyr Asp Leu Thr Pro Ala Glu Thr Thr Val Arg Leu Arg Ala Tyr
    1535            1540             1545

Phe Asn Thr Pro Gly Leu Pro Val Cys Gln Asp His Leu Glu Phe
    1550            1555             1560

Trp Glu Ala Val Phe Thr Gly Leu Thr His Ile Asp Ala His Phe
    1565            1570             1575

Leu Ser Gln Thr Lys Gln Ala Gly Glu Asn Phe Ala Tyr Leu Val
    1580            1585             1590

Ala Tyr Gln Ala Thr Val Cys Ala Arg Ala Lys Ala Pro Pro Pro
    1595            1600             1605

Ser Trp Asp Ala Met Trp Lys Cys Leu Ala Arg Leu Lys Pro Thr
    1610            1615             1620
```

-continued

```
Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680

Gly Cys Val Ser Ile Ile Gly Arg Leu His Val Asn Gln Arg Val
    1685                1690                1695

Val Val Ala Pro Asp Lys Glu Val Leu Tyr Glu Ala Phe Asp Glu
    1700                1705                1710

Met Glu Glu Cys Ala Ser Arg Ala Ala Leu Ile Glu Glu Gly Gln
    1715                1720                1725

Arg Ile Ala Glu Met Leu Lys Ser Lys Ile Gln Gly Leu Leu Gln
    1730                1735                1740

Gln Ala Ser Lys Gln Ala Gln Asp Ile Gln Pro Ala Met Gln Ala
    1745                1750                1755

Ser Trp Pro Lys Val Glu Gln Phe Trp Ala Arg His Met Trp Asn
    1760                1765                1770

Phe Ile Ser Gly Ile Gln Tyr Leu Ala Gly Leu Ser Thr Leu Pro
    1775                1780                1785

Gly Asn Pro Ala Val Ala Ser Met Met Ala Phe Ser Ala Ala Leu
    1790                1795                1800

Thr Ser Pro Leu Ser Thr Ser Thr Thr Ile Leu Leu Asn Ile Met
    1805                1810                1815

Gly Gly Trp Leu Ala Ser Gln Ile Ala Pro Pro Ala Gly Ala Thr
    1820                1825                1830

Gly Phe Val Val Ser Gly Leu Val Gly Ala Ala Val Gly Ser Ile
    1835                1840                1845

Gly Leu Gly Lys Val Leu Val Asp Ile Leu Ala Gly Tyr Gly Ala
    1850                1855                1860

Gly Ile Ser Gly Ala Leu Val Ala Phe Lys Ile Met Ser Gly Glu
    1865                1870                1875

Lys Pro Ser Met Glu Asp Val Ile Asn Leu Leu Pro Gly Ile Leu
    1880                1885                1890

Ser Pro Gly Ala Leu Val Val Gly Val Ile Cys Ala Ala Ile Leu
    1895                1900                1905

Arg Arg His Val Gly Pro Gly Glu Gly Ala Val Gln Trp Met Asn
    1910                1915                1920

Arg Leu Ile Ala Phe Ala Ser Arg Gly Asn His Val Ala Pro Thr
    1925                1930                1935

His Tyr Val Thr Glu Ser Asp Ala Ser Gln Arg Val Thr Gln Leu
    1940                1945                1950

Leu Gly Ser Leu Thr Ile Thr Ser Leu Leu Arg Arg Leu His Asn
    1955                1960                1965

Trp Ile Thr Glu Asp Cys Pro Ile Pro Cys Ser Gly Ser Trp Leu
    1970                1975                1980

Arg Asp Val Trp Asp Trp Val Cys Thr Ile Leu Thr Asp Phe Lys
    1985                1990                1995

Asn Trp Leu Thr Ser Lys Leu Phe Pro Lys Leu Pro Gly Leu Pro
    2000                2005                2010

Phe Ile Ser Cys Gln Lys Gly Tyr Lys Gly Val Trp Ala Gly Thr
```

-continued

```
            2015                2020                2025
Gly Ile Met Thr Thr Arg Cys Pro Cys Gly Ala Asn Ile Ser Gly
            2030                2035                2040
Asn Val Arg Leu Gly Ser Met Arg Ile Thr Gly Pro Lys Thr Cys
            2045                2050                2055
Met Asn Thr Trp Gln Gly Thr Phe Pro Ile Asn Cys Tyr Thr Glu
            2060                2065                2070
Gly Gln Cys Ala Pro Lys Pro Pro Thr Asn Tyr Lys Thr Ala Ile
            2075                2080                2085
Trp Arg Val Ala Ala Ser Glu Tyr Ala Glu Val Thr Gln His Gly
            2090                2095                2100
Ser Tyr Ser Tyr Val Thr Gly Leu Thr Thr Asp Asn Leu Lys Ile
            2105                2110                2115
Pro Cys Gln Leu Pro Ser Pro Glu Phe Phe Ser Trp Val Asp Gly
            2120                2125                2130
Val Gln Ile His Arg Phe Ala Pro Thr Pro Lys Pro Phe Phe Arg
            2135                2140                2145
Asp Glu Val Ser Phe Cys Val Gly Leu Asn Ser Tyr Ala Val Gly
            2150                2155                2160
Ser Gln Leu Pro Cys Glu Pro Glu Pro Asp Ala Asp Val Leu Arg
            2165                2170                2175
Ser Met Leu Thr Asp Pro Pro His Ile Thr Ala Glu Thr Ala Ala
            2180                2185                2190
Arg Arg Leu Ala Arg Gly Ser Pro Pro Ser Glu Ala Ser Ser Ser
            2195                2200                2205
Val Ser Gln Leu Ser Ala Pro Ser Leu Arg Ala Thr Cys Thr Thr
            2210                2215                2220
His Ser Asn Thr Tyr Asp Val Asp Met Val Asp Ala Asn Leu Leu
            2225                2230                2235
Met Glu Gly Gly Val Ala Gln Thr Glu Pro Glu Ser Arg Val Pro
            2240                2245                2250
Val Leu Asp Phe Leu Glu Pro Met Ala Glu Glu Ser Asp Leu
            2255                2260                2265
Glu Pro Ser Ile Pro Ser Glu Cys Met Leu Pro Arg Ser Gly Phe
            2270                2275                2280
Pro Arg Ala Leu Pro Ala Trp Ala Arg Pro Asp Tyr Asn Pro Pro
            2285                2290                2295
Leu Val Glu Ser Trp Arg Arg Pro Asp Tyr Gln Pro Pro Thr Val
            2300                2305                2310
Ala Gly Cys Ala Leu Pro Pro Lys Lys Ala Pro Thr Pro Pro
            2315                2320                2325
Pro Arg Arg Arg Arg Thr Val Gly Leu Ser Glu Ser Thr Ile Ser
            2330                2335                2340
Glu Ala Leu Gln Gln Leu Ala Ile Lys Thr Phe Gly Gln Pro Pro
            2345                2350                2355
Ser Ser Gly Asp Ala Gly Ser Ser Thr Gly Ala Gly Ala Ala Glu
            2360                2365                2370
Ser Gly Gly Pro Thr Ser Pro Gly Glu Pro Ala Pro Ser Glu Thr
            2375                2380                2385
Gly Ser Ala Ser Ser Met Pro Pro Leu Glu Gly Glu Pro Gly Asp
            2390                2395                2400
Pro Asp Leu Glu Ser Asp Gln Val Glu Leu Gln Pro Pro Pro Gln
            2405                2410                2415
```

```
Gly Gly Gly Val Ala Pro Gly Ser Gly Ser Trp Ser Thr
2420          2425          2430

Cys Ser Glu Glu Asp Asp Thr Thr Val Cys Cys Ser Met Ser Tyr
2435              2440              2445

Ser Trp Thr Gly Ala Leu Ile Thr Pro Cys Ser Pro Glu Glu Glu
2450              2455              2460

Lys Leu Pro Ile Asn Pro Leu Ser Asn Ser Leu Leu Arg Tyr His
2465              2470              2475

Asn Lys Val Tyr Cys Thr Thr Ser Lys Ser Ala Ser Gln Arg Ala
2480              2485              2490

Lys Lys Val Thr Phe Asp Arg Thr Gln Val Leu Asp Ala His Tyr
2495              2500              2505

Asp Ser Val Leu Lys Asp Ile Lys Leu Ala Ala Ser Lys Val Ser
2510              2515              2520

Ala Arg Leu Leu Thr Leu Glu Glu Ala Cys Gln Leu Thr Pro Pro
2525              2530              2535

His Ser Ala Arg Ser Lys Tyr Gly Phe Gly Ala Lys Glu Val Arg
2540              2545              2550

Ser Leu Ser Gly Arg Ala Val Asn His Ile Lys Ser Val Trp Lys
2555              2560              2565

Asp Leu Leu Glu Asp Pro Gln Thr Pro Ile Pro Thr Thr Ile Met
2570              2575              2580

Ala Lys Asn Glu Val Phe Cys Val Asp Pro Ala Lys Gly Gly Lys
2585              2590              2595

Lys Pro Ala Arg Leu Ile Val Tyr Pro Asp Leu Gly Val Arg Val
2600              2605              2610

Cys Glu Lys Met Ala Leu Tyr Asp Ile Thr Gln Lys Leu Pro Gln
2615              2620              2625

Ala Val Met Gly Ala Ser Tyr Gly Phe Gln Tyr Ser Pro Ala Gln
2630              2635              2640

Arg Val Glu Tyr Leu Leu Lys Ala Trp Ala Glu Lys Lys Asp Pro
2645              2650              2655

Met Gly Phe Ser Tyr Asp Thr Arg Cys Phe Asp Ser Thr Val Thr
2660              2665              2670

Glu Arg Asp Ile Arg Thr Glu Glu Ser Ile Tyr Gln Ala Cys Ser
2675              2680              2685

Leu Pro Glu Glu Ala Arg Thr Ala Ile His Ser Leu Thr Glu Arg
2690              2695              2700

Leu Tyr Val Gly Gly Pro Met Phe Asn Ser Lys Gly Gln Thr Cys
2705              2710              2715

Gly Tyr Arg Arg Cys Arg Ala Ser Gly Val Leu Thr Thr Ser Met
2720              2725              2730

Gly Asn Thr Ile Thr Cys Tyr Val Lys Ala Leu Ala Ala Cys Lys
2735              2740              2745

Ala Ala Gly Ile Val Ala Pro Thr Met Leu Val Cys Gly Asp Asp
2750              2755              2760

Leu Val Val Ile Ser Glu Ser Gln Gly Thr Glu Glu Asp Glu Arg
2765              2770              2775

Asn Leu Arg Ala Phe Thr Glu Ala Met Thr Arg Tyr Ser Ala Pro
2780              2785              2790

Pro Gly Asp Pro Pro Arg Pro Glu Tyr Asp Leu Glu Leu Ile Thr
2795              2800              2805
```

| | | | | | | | | | | | | |
|---|---|---|---|---|---|---|---|---|---|---|---|---|
| Ser | Cys | Ser | Ser | Asn | Val | Ser | Val | Ala | Leu | Gly | Pro | Arg Gly Arg |
| | 2810 | | | | 2815 | | | | 2820 | | | |
| Arg | Arg | Tyr | Tyr | Leu | Thr | Arg | Asp | Pro | Thr | Thr | Pro | Leu Ala Arg |
| 2825 | | | | | 2830 | | | | | 2835 | | |
| Ala | Ala | Trp | Glu | Thr | Val | Arg | His | Ser | Pro | Ile | Asn | Ser Trp Leu |
| 2840 | | | | | 2845 | | | | | 2850 | | |
| Gly | Asn | Ile | Ile | Gln | Tyr | Ala | Pro | Thr | Ile | Trp | Val | Arg Met Val |
| 2855 | | | | | 2860 | | | | | 2865 | | |
| Leu | Met | Thr | His | Phe | Phe | Ser | Ile | Leu | Met | Val | Gln | Asp Thr Leu |
| 2870 | | | | | 2875 | | | | | 2880 | | |
| Asp | Gln | Asn | Leu | Asn | Phe | Glu | Met | Tyr | Gly | Ser | Val | Tyr Ser Val |
| 2885 | | | | | 2890 | | | | | 2895 | | |
| Asn | Pro | Leu | Asp | Leu | Pro | Ala | Ile | Ile | Glu | Arg | Leu | His Gly Leu |
| 2900 | | | | | 2905 | | | | | 2910 | | |
| Asp | Ala | Phe | Ser | Met | His | Thr | Tyr | Ser | His | His | Glu | Leu Thr Arg |
| 2915 | | | | | 2920 | | | | | 2925 | | |
| Val | Ala | Ser | Ala | Leu | Arg | Lys | Leu | Gly | Ala | Pro | Pro | Leu Arg Val |
| 2930 | | | | | 2935 | | | | | 2940 | | |
| Trp | Lys | Ser | Arg | Ala | Arg | Ala | Val | Arg | Ala | Ser | Leu | Ile Ser Arg |
| 2945 | | | | | 2950 | | | | | 2955 | | |
| Gly | Gly | Lys | Ala | Ala | Val | Cys | Gly | Arg | Tyr | Leu | Phe | Asn Trp Ala |
| 2960 | | | | | 2965 | | | | | 2970 | | |
| Val | Lys | Thr | Lys | Leu | Lys | Leu | Thr | Pro | Leu | Pro | Glu | Ala Arg Leu |
| 2975 | | | | | 2980 | | | | | 2985 | | |
| Leu | Asp | Leu | Ser | Ser | Trp | Phe | Thr | Val | Gly | Ala | Gly | Gly Gly Asp |
| 2990 | | | | | 2995 | | | | | 3000 | | |
| Ile | Phe | His | Ser | Val | Ser | Arg | Ala | Arg | Pro | Arg | Ser | Leu Leu Phe |
| 3005 | | | | | 3010 | | | | | 3015 | | |
| Gly | Leu | Leu | Leu | Leu | Phe | Val | Gly | Val | Gly | Leu | Phe | Leu Leu Pro |
| 3020 | | | | | 3025 | | | | | 3030 | | |
| Ala | Arg | | | | | | | | | | | |
| 3035 | | | | | | | | | | | | |

```
<210> SEQ ID NO 11
<211> LENGTH: 9684
<212> TYPE: DNA
<213> ORGANISM: Hepatitis C virus

<400> SEQUENCE: 11
acctgcccct aatagggggcg acactccgcc atgaatcact cccctgtgag gaactactgt      60
cttcacgcag aaagcgccta gccatggcgt tagtatgagt gtcgtacagc ctccaggccc     120 cccctcccg  ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgccccggga ggtctcgtag accgtgcacc atgagcacac ttcctaaacc     360
tcaaagaaaa accaaaagaa acaccatccg tcgcccacag gacgttaagt tcccgggtgg     420
cggacagatc gttggtggag tatacgtgtt ccgcgcagg  ggcccacgat gggtgtgcg      480 cgcgacgcgt aaaacttctg aacggtcaca gcctcgcgga cgacgacagc ctatccccaa     540
ggcgcgtcgg agcgaaggcc ggtcctgggc tcagcccggg tacccttggc ccctctatgg     600
taatgagggc tgcggtgggg cagggtggct cctgtccccg cgcggctccc gtccatcttg     660
gggcccaaac gaccccggc  ggaggtcccg caatttgggt aaagtcatcg ataccctta      720
```

```
gtgcggattc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agccttttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
ggggtggggc cccttgacag atgctaacat caccggtcct tctgatgata gaccgtattg   1800
ctggcactac gcacctagac cttgtagtgt tgtcccggca tcaagtgtct gcggccctgt   1860
gtactgcttc acaccatcgc cagtggtcgt aggcactact gatatcaaag gcaagccgac   1920
ctacaactgg ggtgagaatg agacagatgt gttcctgctg gagtccctgc ggcctcccag   1980
tggccggtgg tttggatgcg cgtggatgaa ctccacgggg ttcctcaaga cgtgtggagc   2040
tcccccttgt aacatctatg ggggtgaggg ggatcccgaa aatgagacag acctcttctg   2100
ccccaccgac tgcttcagga aacatcctga ggccacatac agccggtgtg gtgcggggcc   2160
ctggttgaca cctcgctgca tggtcgacta tccataccgg cttggcatt acccatgtac   2220
agtcaatttc acattgttca aggtgaggat gtttgtgggc ggatttgaac accggtttac   2280
cgccgcttgt aactggacca gggggagcg ctgcaatatc gaggatcgtg atcgcagcga   2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct tggagaacct tgtcacgctg aacgccgtcg ctgctgctgg   2640
gacacatggt attggttggt acctggtagc cttttgcgcg cgtgtggtacg tgcggggtaa   2700
acttgtcccg ctgacgatct gcggcctgac gggtcttttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940
cccccccttta cttgcacgcg ggagtaggga cggtgtcatc ctgctaacaa gcttgcttta   3000
tccatcctta atttttgaca tcactaagct gctgatagca gtaataggcc cattatactt   3060
```

```
aatacaggct gccatcacta ccacccccta ctttgtgcgc gcacatgtac tggtccgcct    3120
ttgcatgctc gtgcgctccg tgatgggggg aaagtacttc cagatggcca tactgagcat    3180
tggcagatgg ttcaacacct acctatatga ccacctagcg ccaatgcaac attgggccgc    3240
agctggcctc aaagacctag cagtggccac tgaacctgta atatttagtc ccatggaaat    3300
taaggtcatc acctggggcg cggacacagc ggcttgcgga gatattcttt gcgggctgcc    3360
ggtctccgcg cgattaggcc gtgaggtatt gttgggacct gctgatgatt atcgggaaat    3420
gggttggcgt ctgttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gaggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840
gaaggggtcc tcggggggc cggtgctctg ccctaggggc cacgtcgttg ggctcttccg    3900
agcagctgtg tgctctcggg gcgtggccaa atccatcgat ttcatccccg ttgagacact    3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aaccctcgg tagctgccac    4140
cctggggttt gggggcgtacc tatccaaggc acatggcatc aatcccaaca ttaggactgg    4200
agtcaggacc gtgatgaccg gggaggccat cacgtactcc acatatggca aatttctcgc    4260
cgatgggggc tgcgctagcg gcgccctatga catcatcata tgcgatgaat gccacgctgt    4320
ggatgctacc tccattctcg gcatcggaac ggtccttgat caagcagaga cagccggggt    4380
cagactaact gtgctggcta cggccacacc ccccgggtca gtgacaaccc cccatcccga    4440
tatagaagag gtaggcctcg gcgggagg tgagatcccc ttctatggga gggcgattcc    4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agactgggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggccgactc aagcctacgc ttgcgggccc    5220
cacacctctc ctgtaccgtt tgggccctat taccaatgag gtcacccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
```

```
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtgaact tcattagcgg catccaatac ctcgcaggat tgtcaacact     5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accacccgcg ggggccaccg gctttgtcgt cagtggcctg gtgggggctg ccgtgggcag    5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggaggg cgcggtccaa tggatgaaca ggcttattgc     6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc     6540
tatcaattgc tacacggagg gccagtgcgc gccgaaaccc ccacgaact acaagaccgc     6600 catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgcccacat    6900 cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctcccagg agcgggtttc cacgggcctt    7200
accggcttgg gcacggcctg actacaaccc gccgctcgtg aatcgtgga ggaggccaga    7260 ttaccaaccg cccaccgttg ctggttgtgc tctcccccc cccaagaagg ccccgacgcc     7320
tcccccaagg agacgccgga cagtgggtct gagcgagagc accatatcag aagccctcca    7380
gcaactggcc atcaagacct ttggccagcc ccctcgagc ggtgatgcag gctcgtccac     7440
gggggcgggc gccgccgaat ccggcggtcc gacgtcccct ggtgagccgg ccccctcaga    7500
gacaggttcc gcctcctcta tgccccccct cgagggggag cctggagatc cggacctgga    7560
gtctgatcag gtagagcttc aacctccccc ccaggggggg ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740 caacccttg agtaactcgc tgttgcgata ccataacaag gtgtactgta caacatcaaa     7800
```

```
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca agtatggatt    7980
cggggccaag gaggtccgca gcttgtccgg gagggccgtt aaccacatca agtccgtgtg    8040
gaaggacctc ctggaagacc cacaaacacc aattcccaca accatcatgg ccaaaaatga    8100
ggtgttctgc gtggaccccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctcccctgcc gaggaggccc gcactgccat acactcgctg actgagagac tttacgtagg    8460
agggcccatg ttcaacagca agggtcaaac ctgcggttac agacgttgcc gcgccagcgg    8520
ggtgctaacc actagcatgg gtaacaccat acatgtctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc ccccagaccg gaatatgacc tggagctaat    8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct tctccattct catggtccaa gacaccctgg accagaacct    9000
caactttgag atgtatggat cagtatactc cgtgaatcct ttggaccttc agccataat    9060 tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttttcacag    9360 cgtgtcgcgc gcccgacccc gctcattact cttcggccta ctcctacttt tcgtagggggt    9420 aggcctcttc ctactccccg ctcggtagag cggcacacac taggtacact ccatagctaa    9480
ctgttccttt ttttttttt ttttttttt ttttttttt ttttttttt ctttttttt    9540 tttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                           9684
```

<210> SEQ ID NO 12
<211> LENGTH: 3035
<212> TYPE: PRT
<213> ORGANISM: Hepatitis C virus

<400> SEQUENCE: 12

Met Ser Thr Leu Pro Lys Pro Gln Arg Lys Thr Lys Arg Asn Thr Ile
 1               5                  10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala

```
                 35                  40                  45
Thr Arg Lys Thr Ser Glu Arg Ser Gln Pro Arg Gly Arg Gln Pro
 50                  55                  60
Ile Pro Lys Ala Arg Arg Ser Glu Gly Arg Ser Trp Ala Gln Pro Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro Ser Trp Gly Pro Asn Asp Pro
                100                 105                 110
Arg Arg Arg Ser Arg Asn Leu Gly Lys Val Ile Asp Thr Leu Thr Cys
        115                 120                 125
Gly Phe Ala Asp Leu Met Gly Tyr Ile Pro Leu Val Gly Ala Pro Val
        130                 135                 140
Gly Gly Val Ala Arg Ala Leu Ala His Gly Val Arg Ala Leu Glu Asp
145                 150                 155                 160
Gly Ile Asn Phe Ala Thr Gly Asn Leu Pro Gly Cys Ser Phe Ser Ile
                165                 170                 175
Phe Leu Leu Ala Leu Phe Ser Cys Leu Val His Pro Ala Ala Ser Leu
                180                 185                 190
Glu Trp Arg Asn Thr Ser Gly Leu Tyr Val Leu Thr Asn Asp Cys Ser
        195                 200                 205
Asn Ser Ser Ile Val Tyr Glu Ala Asp Asp Val Ile Leu His Thr Pro
210                 215                 220
Gly Cys Val Pro Cys Val Gln Asp Asp Asn Thr Ser Thr Cys Trp Thr
225                 230                 235                 240
Pro Val Thr Pro Thr Val Ala Val Arg Tyr Val Gly Ala Thr Thr Ala
                245                 250                 255
Ser Ile Arg Ser His Val Asp Leu Leu Val Gly Ala Ala Thr Leu Cys
        260                 265                 270
Ser Ala Leu Tyr Val Gly Asp Met Cys Gly Ala Val Phe Leu Val Gly
        275                 280                 285
Gln Ala Phe Thr Phe Arg Pro Arg Arg His Gln Thr Val Gln Thr Cys
        290                 295                 300
Asn Cys Ser Leu Tyr Pro Gly His Val Ser Gly His Arg Met Ala Trp
305                 310                 315                 320
Asp Met Met Met Asn Trp Ser Pro Ala Val Gly Met Val Val Ala His
                325                 330                 335
Ile Leu Arg Leu Pro Gln Thr Leu Phe Asp Ile Leu Ala Gly Ala His
                340                 345                 350
Trp Gly Ile Leu Ala Gly Leu Ala Tyr Tyr Ser Met Gln Gly Asn Trp
        355                 360                 365
Ala Lys Val Ala Ile Val Met Ile Met Phe Ser Gly Val Asp Ala Glu
        370                 375                 380
Thr Tyr Val Thr Gly Gly Ser Val Ala His Ser Ala Arg Gly Leu Thr
385                 390                 395                 400
Ser Leu Phe Ser Met Gly Ala Lys Gln Lys Leu Gln Leu Val Asn Thr
                405                 410                 415
Asn Gly Ser Trp His Ile Asn Ser Thr Ala Leu Asn Cys Asn Glu Ser
                420                 425                 430
Ile Asn Thr Gly Phe Ile Ala Gly Leu Phe Tyr Tyr His Lys Phe Asn
        435                 440                 445
Ser Thr Gly Cys Pro Gln Arg Leu Ser Ser Cys Lys Pro Ile Ile Ser
        450                 455                 460
```

```
Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Gly Thr Thr Asp Ile Lys Gly Lys Pro Thr Tyr
            515                 520                 525

Asn Trp Gly Glu Asn Glu Thr Asp Val Phe Leu Leu Glu Ser Leu Arg
530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
                660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Gly Thr
            755                 760                 765

His Gly Ile Gly Trp Tyr Leu Val Ala Phe Cys Ala Ala Trp Tyr Val
            770                 775                 780

Arg Gly Lys Leu Val Pro Leu Thr Ile Cys Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
            835                 840                 845

Met Trp Trp Asn Gln Tyr Thr Ile Cys Arg Cys Glu Ala Ala Leu Gln
            850                 855                 860

Val Trp Val Pro Pro Leu Leu Ala Arg Gly Ser Arg Asp Gly Val Ile
865                 870                 875                 880
```

```
Leu Leu Thr Ser Leu Leu Tyr Pro Ser Leu Ile Phe Asp Ile Thr Lys
            885                 890                 895

Leu Leu Ile Ala Val Ile Gly Pro Leu Tyr Leu Ile Gln Ala Ala Ile
            900                 905                 910

Thr Thr Thr Pro Tyr Phe Val Arg Ala His Val Leu Arg Leu Cys
            915                 920                 925

Met Leu Val Arg Ser Val Met Gly Gly Lys Tyr Phe Gln Met Ala Ile
            930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
            965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
            995                 1000                1005

Ser Ala Arg Leu Gly Arg Glu Val Leu Leu Gly Pro Ala Asp Asp
    1010                1015                1020

Tyr Arg Glu Met Gly Trp Arg Leu Leu Ala Pro Ile Thr Ala Tyr
    1025                1030                1035

Ala Gln Gln Thr Arg Gly Leu Leu Gly Ala Ile Val Val Ser Met
    1040                1045                1050

Thr Gly Arg Asp Arg Thr Glu Gln Ala Gly Glu Val Gln Ile Leu
    1055                1060                1065

Ser Thr Val Ser Gln Ser Phe Leu Gly Thr Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Pro Gly Thr Lys Ser Leu Glu Pro
    1115                1120                1125

Cys Lys Cys Gly Ala Val Asp Leu Tyr Leu Val Thr Arg Asn Ala
    1130                1135                1140

Asp Val Ile Pro Ala Arg Arg Gly Asp Lys Arg Gly Ala Leu
    1145                1150                1155

Leu Ser Pro Arg Pro Ile Ser Thr Leu Lys Gly Ser Ser Gly Gly
    1160                1165                1170

Pro Val Leu Cys Pro Arg Gly His Val Val Gly Leu Phe Arg Ala
    1175                1180                1185

Ala Val Cys Ser Arg Gly Val Ala Lys Ser Ile Asp Phe Ile Pro
    1190                1195                1200

Val Glu Thr Leu Asp Val Val Thr Arg Ser Pro Thr Phe Ser Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Lys Val Pro Val
    1235                1240                1245

Ala Tyr Ala Ala Gln Gly Tyr Lys Val Leu Val Leu Asn Pro Ser
    1250                1255                1260

Val Ala Ala Thr Leu Gly Phe Gly Ala Tyr Leu Ser Lys Ala His
    1265                1270                1275

Gly Ile Asn Pro Asn Ile Arg Thr Gly Val Arg Thr Val Met Thr
```

-continued

```
            1280                1285                1290

Gly Glu Ala Ile Thr Tyr Ser Thr Tyr Gly Lys Phe Leu Ala Asp
    1295                1300                1305

Gly Gly Cys Ala Ser Gly Ala Tyr Asp Ile Ile Ile Cys Asp Glu
    1310                1315                1320

Cys His Ala Val Asp Ala Thr Ser Ile Leu Gly Ile Gly Thr Val
    1325                1330                1335

Leu Asp Gln Ala Glu Thr Ala Gly Val Arg Leu Thr Val Leu Ala
    1340                1345                1350

Thr Ala Thr Pro Pro Gly Ser Val Thr Thr Pro His Pro Asp Ile
    1355                1360                1365

Glu Glu Val Gly Leu Gly Arg Glu Gly Glu Ile Pro Phe Tyr Gly
    1370                1375                1380

Arg Ala Ile Pro Leu Ser Cys Ile Lys Gly Gly Arg His Leu Ile
    1385                1390                1395

Phe Cys His Ser Lys Lys Lys Cys Asp Glu Leu Ala Ala Ala Leu
    1400                1405                1410

Arg Gly Met Gly Leu Asn Ala Val Ala Tyr Tyr Arg Gly Leu Asp
    1415                1420                1425

Val Ser Ile Ile Pro Ala Gln Gly Asp Val Val Val Val Ala Thr
    1430                1435                1440

Asp Ala Leu Met Thr Gly Tyr Thr Gly Asp Phe Asp Ser Val Ile
    1445                1450                1455

Asp Cys Asn Val Ala Val Thr Gln Ala Val Asp Phe Ser Leu Asp
    1460                1465                1470

Pro Thr Phe Thr Ile Thr Thr Gln Thr Val Pro Gln Asp Ala Val
    1475                1480                1485

Ser Arg Ser Gln Arg Arg Gly Arg Thr Gly Arg Gly Arg Leu Gly
    1490                1495                1500

Thr Tyr Arg Tyr Val Ser Thr Gly Glu Arg Ala Ser Gly Met Phe
    1505                1510                1515

Asp Ser Val Val Leu Cys Glu Cys Tyr Asp Ala Gly Ala Ala Trp
    1520                1525                1530

Tyr Asp Leu Thr Pro Ala Glu Thr Thr Val Arg Leu Arg Ala Tyr
    1535                1540                1545

Phe Asn Thr Pro Gly Leu Pro Val Cys Gln Asp His Leu Glu Phe
    1550                1555                1560

Trp Glu Ala Val Phe Thr Gly Leu Thr His Ile Asp Ala His Phe
    1565                1570                1575

Leu Ser Gln Thr Lys Gln Ala Gly Glu Asn Phe Ala Tyr Leu Val
    1580                1585                1590

Ala Tyr Gln Ala Thr Val Cys Ala Arg Ala Lys Ala Pro Pro Pro
    1595                1600                1605

Ser Trp Asp Ala Met Trp Lys Cys Leu Ala Arg Leu Lys Pro Thr
    1610                1615                1620

Leu Ala Gly Pro Thr Pro Leu Leu Tyr Arg Leu Gly Pro Ile Thr
    1625                1630                1635

Asn Glu Val Thr Leu Thr His Pro Gly Thr Lys Tyr Ile Ala Thr
    1640                1645                1650

Cys Met Gln Ala Asp Leu Glu Val Met Thr Ser Thr Trp Val Leu
    1655                1660                1665

Ala Gly Gly Val Leu Ala Ala Val Ala Ala Tyr Cys Leu Ala Thr
    1670                1675                1680
```

```
Gly Cys Val Ser Ile Ile Gly Arg Leu His Val Asn Gln Arg Val
    1685             1690                 1695

Val Val Ala Pro Asp Lys Glu Val Leu Tyr Glu Ala Phe Asp Glu
    1700             1705                 1710

Met Glu Glu Cys Ala Ser Arg Ala Ala Leu Ile Glu Glu Gly Gln
    1715             1720                 1725

Arg Ile Ala Glu Met Leu Lys Ser Lys Ile Gln Gly Leu Leu Gln
    1730             1735                 1740

Gln Ala Ser Lys Gln Ala Gln Asp Ile Gln Pro Ala Met Gln Ala
    1745             1750                 1755

Ser Trp Pro Lys Val Glu Gln Phe Trp Ala Arg His Met Trp Asn
    1760             1765                 1770

Phe Ile Ser Gly Ile Gln Tyr Leu Ala Gly Leu Ser Thr Leu Pro
    1775             1780                 1785

Gly Asn Pro Ala Val Ala Ser Met Met Ala Phe Ser Ala Ala Leu
    1790             1795                 1800

Thr Ser Pro Leu Ser Thr Ser Thr Thr Ile Leu Leu Asn Ile Met
    1805             1810                 1815

Gly Gly Trp Leu Ala Ser Gln Ile Ala Pro Pro Ala Gly Ala Thr
    1820             1825                 1830

Gly Phe Val Val Ser Gly Leu Val Gly Ala Ala Val Gly Ser Ile
    1835             1840                 1845

Gly Leu Gly Lys Val Leu Val Asp Ile Leu Ala Gly Tyr Gly Ala
    1850             1855                 1860

Gly Ile Ser Gly Ala Leu Val Ala Phe Lys Ile Met Ser Gly Glu
    1865             1870                 1875

Lys Pro Ser Met Glu Asp Val Ile Asn Leu Leu Pro Gly Ile Leu
    1880             1885                 1890

Ser Pro Gly Ala Leu Val Val Gly Val Ile Cys Ala Ala Ile Leu
    1895             1900                 1905

Arg Arg His Val Gly Pro Gly Glu Gly Ala Val Gln Trp Met Asn
    1910             1915                 1920

Arg Leu Ile Ala Phe Ala Ser Arg Gly Asn His Val Ala Pro Thr
    1925             1930                 1935

His Tyr Val Thr Glu Ser Asp Ala Ser Gln Arg Val Thr Gln Leu
    1940             1945                 1950

Leu Gly Ser Leu Thr Ile Thr Ser Leu Leu Arg Arg Leu His Asn
    1955             1960                 1965

Trp Ile Thr Glu Asp Cys Pro Ile Pro Cys Ser Gly Ser Trp Leu
    1970             1975                 1980

Arg Asp Val Trp Asp Trp Val Cys Thr Ile Leu Thr Asp Phe Lys
    1985             1990                 1995

Asn Trp Leu Thr Ser Lys Leu Phe Pro Lys Leu Pro Gly Leu Pro
    2000             2005                 2010

Phe Ile Ser Cys Gln Lys Gly Tyr Lys Gly Val Trp Ala Gly Thr
    2015             2020                 2025

Gly Ile Met Thr Thr Arg Cys Pro Cys Gly Ala Asn Ile Ser Gly
    2030             2035                 2040

Asn Val Arg Leu Gly Ser Met Arg Ile Thr Gly Pro Lys Thr Cys
    2045             2050                 2055

Met Asn Thr Trp Gln Gly Thr Phe Pro Ile Asn Cys Tyr Thr Glu
    2060             2065                 2070
```

```
Gly Gln Cys Ala Pro Lys Pro Pro Thr Asn Tyr Lys Thr Ala Ile
2075                 2080                 2085

Trp Arg Val Ala Ala Ser Glu Tyr Ala Glu Val Thr Gln His Gly
    2090                 2095                 2100

Ser Tyr Ser Tyr Val Thr Gly Leu Thr Thr Asp Asn Leu Lys Ile
    2105                 2110                 2115

Pro Cys Gln Leu Pro Ser Pro Glu Phe Phe Ser Trp Val Asp Gly
    2120                 2125                 2130

Val Gln Ile His Arg Phe Ala Pro Thr Pro Lys Pro Phe Phe Arg
    2135                 2140                 2145

Asp Glu Val Ser Phe Cys Val Gly Leu Asn Ser Tyr Ala Val Gly
    2150                 2155                 2160

Ser Gln Leu Pro Cys Glu Pro Glu Pro Asp Ala Asp Val Leu Arg
    2165                 2170                 2175

Ser Met Leu Thr Asp Pro Pro His Ile Thr Ala Glu Thr Ala Ala
    2180                 2185                 2190

Arg Arg Leu Ala Arg Gly Ser Pro Pro Ser Glu Ala Ser Ser Ser
    2195                 2200                 2205

Val Ser Gln Leu Ser Ala Pro Ser Leu Arg Ala Thr Cys Thr Thr
    2210                 2215                 2220

His Ser Asn Thr Tyr Asp Val Asp Met Val Asp Ala Asn Leu Leu
    2225                 2230                 2235

Met Glu Gly Gly Val Ala Gln Thr Glu Pro Glu Ser Arg Val Pro
    2240                 2245                 2250

Val Leu Asp Phe Leu Glu Pro Met Ala Glu Glu Ser Asp Leu
    2255                 2260                 2265

Glu Pro Ser Ile Pro Ser Glu Cys Met Leu Pro Arg Ser Gly Phe
    2270                 2275                 2280

Pro Arg Ala Leu Pro Ala Trp Ala Arg Pro Asp Tyr Asn Pro Pro
    2285                 2290                 2295

Leu Val Glu Ser Trp Arg Arg Pro Asp Tyr Gln Pro Pro Thr Val
    2300                 2305                 2310

Ala Gly Cys Ala Leu Pro Pro Lys Lys Ala Pro Thr Pro Pro
    2315                 2320                 2325

Pro Arg Arg Arg Arg Thr Val Gly Leu Ser Glu Ser Thr Ile Ser
    2330                 2335                 2340

Glu Ala Leu Gln Gln Leu Ala Ile Lys Thr Phe Gly Gln Pro Pro
    2345                 2350                 2355

Ser Ser Gly Asp Ala Gly Ser Ser Thr Gly Ala Gly Ala Ala Glu
    2360                 2365                 2370

Ser Gly Gly Pro Thr Ser Pro Gly Glu Pro Ala Pro Ser Glu Thr
    2375                 2380                 2385

Gly Ser Ala Ser Ser Met Pro Pro Leu Glu Gly Glu Pro Gly Asp
    2390                 2395                 2400

Pro Asp Leu Glu Ser Asp Gln Val Glu Leu Gln Pro Pro Pro Gln
    2405                 2410                 2415

Gly Gly Gly Val Ala Pro Gly Ser Gly Ser Gly Ser Trp Ser Thr
    2420                 2425                 2430

Cys Ser Glu Glu Asp Asp Thr Thr Val Cys Cys Ser Met Ser Tyr
    2435                 2440                 2445

Ser Trp Thr Gly Ala Leu Ile Thr Pro Cys Ser Pro Glu Glu Glu
    2450                 2455                 2460

Lys Leu Pro Ile Asn Pro Leu Ser Asn Ser Leu Leu Arg Tyr His
```

-continued

```
                2465                2470                2475
Asn  Lys  Val  Tyr  Cys  Thr  Thr  Ser  Lys  Ser  Ala  Ser  Gln  Arg  Ala
     2480                2485                2490

Lys  Lys  Val  Thr  Phe  Asp  Arg  Thr  Gln  Val  Leu  Asp  Ala  His  Tyr
     2495                2500                2505

Asp  Ser  Val  Leu  Lys  Asp  Ile  Lys  Leu  Ala  Ala  Ser  Lys  Val  Ser
     2510                2515                2520

Ala  Arg  Leu  Leu  Thr  Leu  Glu  Glu  Ala  Cys  Gln  Leu  Thr  Pro  Pro
     2525                2530                2535

His  Ser  Ala  Arg  Ser  Lys  Tyr  Gly  Phe  Gly  Ala  Lys  Glu  Val  Arg
     2540                2545                2550

Ser  Leu  Ser  Gly  Arg  Ala  Val  Asn  His  Ile  Lys  Ser  Val  Trp  Lys
     2555                2560                2565

Asp  Leu  Leu  Glu  Asp  Pro  Gln  Thr  Pro  Ile  Pro  Thr  Thr  Ile  Met
     2570                2575                2580

Ala  Lys  Asn  Glu  Val  Phe  Cys  Val  Asp  Pro  Ala  Lys  Gly  Gly  Lys
     2585                2590                2595

Lys  Pro  Ala  Arg  Leu  Ile  Val  Tyr  Pro  Asp  Leu  Gly  Val  Arg  Val
     2600                2605                2610

Cys  Glu  Lys  Met  Ala  Leu  Tyr  Asp  Ile  Thr  Gln  Lys  Leu  Pro  Gln
     2615                2620                2625

Ala  Val  Met  Gly  Ala  Ser  Tyr  Gly  Phe  Gln  Tyr  Ser  Pro  Ala  Gln
     2630                2635                2640

Arg  Val  Glu  Tyr  Leu  Leu  Lys  Ala  Trp  Ala  Glu  Lys  Lys  Asp  Pro
     2645                2650                2655

Met  Gly  Phe  Ser  Tyr  Asp  Thr  Arg  Cys  Phe  Asp  Ser  Thr  Val  Thr
     2660                2665                2670

Glu  Arg  Asp  Ile  Arg  Thr  Glu  Glu  Ser  Ile  Tyr  Gln  Ala  Cys  Ser
     2675                2680                2685

Leu  Pro  Glu  Glu  Ala  Arg  Thr  Ala  Ile  His  Ser  Leu  Thr  Glu  Arg
     2690                2695                2700

Leu  Tyr  Val  Gly  Gly  Pro  Met  Phe  Asn  Ser  Lys  Gly  Gln  Thr  Cys
     2705                2710                2715

Gly  Tyr  Arg  Arg  Cys  Arg  Ala  Ser  Gly  Val  Leu  Thr  Thr  Ser  Met
     2720                2725                2730

Gly  Asn  Thr  Ile  Thr  Cys  Tyr  Val  Lys  Ala  Leu  Ala  Ala  Cys  Lys
     2735                2740                2745

Ala  Ala  Gly  Ile  Val  Ala  Pro  Thr  Met  Leu  Val  Cys  Gly  Asp  Asp
     2750                2755                2760

Leu  Val  Val  Ile  Ser  Glu  Ser  Gln  Gly  Thr  Glu  Glu  Asp  Glu  Arg
     2765                2770                2775

Asn  Leu  Arg  Ala  Phe  Thr  Glu  Ala  Met  Thr  Arg  Tyr  Ser  Ala  Pro
     2780                2785                2790

Pro  Gly  Asp  Pro  Pro  Arg  Pro  Glu  Tyr  Asp  Leu  Glu  Leu  Ile  Thr
     2795                2800                2805

Ser  Cys  Ser  Ser  Asn  Val  Ser  Val  Ala  Leu  Gly  Pro  Arg  Gly  Arg
     2810                2815                2820

Arg  Arg  Tyr  Tyr  Leu  Thr  Arg  Asp  Pro  Thr  Thr  Pro  Leu  Ala  Arg
     2825                2830                2835

Ala  Ala  Trp  Glu  Thr  Val  Arg  His  Ser  Pro  Ile  Asn  Ser  Trp  Leu
     2840                2845                2850

Gly  Asn  Ile  Ile  Gln  Tyr  Ala  Pro  Thr  Ile  Trp  Val  Arg  Met  Val
     2855                2860                2865
```

```
Leu Met Thr His Phe Phe Ser Ile Leu Met Val Gln Asp Thr Leu
        2870                2875                2880

Asp Gln Asn Leu Asn Phe Glu Met Tyr Gly Ser Val Tyr Ser Val
    2885                2890                2895

Asn Pro Leu Asp Leu Pro Ala Ile Ile Glu Arg Leu His Gly Leu
    2900                2905                2910

Asp Ala Phe Ser Met His Thr Tyr Ser His His Glu Leu Thr Arg
    2915                2920                2925

Val Ala Ser Ala Leu Arg Lys Leu Gly Ala Pro Pro Leu Arg Val
    2930                2935                2940

Trp Lys Ser Arg Ala Arg Ala Val Arg Ala Ser Leu Ile Ser Arg
    2945                2950                2955

Gly Gly Lys Ala Ala Val Cys Gly Arg Tyr Leu Phe Asn Trp Ala
    2960                2965                2970

Val Lys Thr Lys Leu Lys Leu Thr Pro Leu Pro Glu Ala Arg Leu
    2975                2980                2985

Leu Asp Leu Ser Ser Trp Phe Thr Val Gly Ala Gly Gly Gly Asp
    2990                2995                3000

Ile Phe His Ser Val Ser Arg Ala Arg Pro Arg Ser Leu Leu Phe
    3005                3010                3015

Gly Leu Leu Leu Leu Phe Val Gly Val Gly Leu Phe Leu Leu Pro
    3020                3025                3030

Ala Arg
    3035

<210> SEQ ID NO 13
<211> LENGTH: 9684
<212> TYPE: DNA
<213> ORGANISM: Hepatitis C virus

<400> SEQUENCE: 13
acctgcccct aatagggcg acactccgcc atgaatcact ccctgtgag gaactactgt        60 cttcacgcag aaagcgccta gccatggcgt tagtatgagt gtcgtacagc ctccaggccc      120 cccctcccg ggagagccat agtggtctgc ggaaccggtg agtacaccgg aattgccggg      180
aagactgggt cctttcttgg ataaacccac tctatgcccg ccatttggg cgtgcccccg       240 caagactgct agccgagtag cgttgggttg cgaaaggcct tgtggtactg cctgataggg      300
tgcttgcgag tgccccggga ggtctcgtag accgtgcacc atgagcacac ttcctaaacc      360
tcaaagaaaa accaaaagaa acaccatccg tcgcccacag gacgttaagt tcccgggtgg      420
cggacagatc gttggtggag tatacgtgtt gccgcgcagg ggcccacgat gggtgtgcg      480 cgcgacgcgt aaaacttctg aacggtcaca gcctcgcgga cgacgacagc ctatccccaa      540
ggcgcgtcgg agcgaaggcc ggtcctgggc tcagcccggg tacccttggc ccctctatgg      600
taatgagggc tgcgggtggg cagggtggct cctgtcccg cgcggctccc gtccatcttg       660
gggcccaaac gaccccggc ggaggtcccg caatttgggt aaagtcatcg ataccttac       720 gtgcggattc gccgacctca tggggtacat ccgctcgtc ggcgctcccg taggaggcgt      780
cgcaagagcc ctcgcgcatg gcgtgagggc ccttgaagac gggataaatt ttgcaacagg     840
gaacttgccc ggttgctcct tttctatctt ccttcttgct ctgttctcct gcttagttca     900
tcctgcagct agtcttgagt ggcggaatac gtctggcctc tatgtcctta ccaacgactg     960
ttccaatagc agtattgtgt atgaggccga tgacgtcatt ctgcacacac ccggctgtgt    1020
```

```
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agcctttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
ggggtggggc cccttgacag atgctaacat caccggtcct tctgatgata daccgtattg   1800
ctggcactac gcacctagac cttgtagtgt tgtcccggca tcaagtgtct gcggccctgt   1860
gtactgcttc acaccatcgc cagtggtcgt aggcactact gatatcaaag caagccgac   1920
ctacaactgg ggtgagaatg agacagatgt gttcctgctg gagtccctgc ggcctcccag   1980
tggccggtgg tttggatgcg cgtggatgaa ctccacgggg ttcctcaaga cgtgtggagc   2040
tcccccttgt aacatctatg ggggtgaggg ggatcccgaa aatgagacag acctcttctg   2100
ccccaccgac tgcttcagga aacatcctga ggccacatac agccggtgtg gtgcggggcc   2160
ctggttgaca cctcgctgca tggtcgacta tccataccgg ctttggcatt acccatgtac   2220
agtcaatttc acattgttca aggtgaggat gtttgtgggc ggatttgaac accggtttac   2280
cgccgcttgt aactggacca gggggagcg ctgcaatatc gaggatcgtg atcgcagcga   2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct tggagaacct tgtcacgctg aacgccgtcg ctgctgctgg   2640
gacacatggt attggttggt acctggtagc cttttgcgcg cgtggtacg tgcggggtaa   2700
acttgtcccg ctgacgagct acggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttaccct atcaccctgg tacaagcatt ggatcggccg   2880
cctcatgtgg tggaaccagt acactatatg tagatgcgag gccgcccttc aagtgtgggt   2940
ccccccctta cttgcacgcg ggagtaggga cggtgtcatc ctgctaacaa gcttgctta   3000
tccatcctta atttttgaca tcactaagct gctgatagca gtaataggcc cattatactt   3060
aatacaggct gccatcacta ccacccccta ctttgtgcgc gcacatgtac tggtccgcct   3120
ttgcatgctc gtgcgctccg tgatgggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcgggctgcc   3360
ggtctccgcg cgattaggcc gtgaggtatt gttgggacct gctgatgatt atcgggaaat   3420
```

```
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcgggggttt tgtggactgt   3600
ttaccacgga gctggcaaca agactctagc cggcttacgg ggtccggtca cgcagatgta   3660
ctcgagtgct gagggggact tggtaggctg gcccagcccc cctgggacca agtctttgga   3720
gccgtgcaag tgtggagccg tcgacctata tctggtcacg cggaacgctg atgtcatccc   3780
ggctcggaga cgcggggaca agcggggagc attgctctcc ccgagaccca tttcgacctt   3840 gaagggggtcc tcgggggggc cggtgctctg ccctaggggc cacgtcgttg ggctcttccg   3900
agcagctgtg tgctctcggg gcgtggccaa atccatcgat ttcatccccg ttgagacact   3960
cgacgttgtt acaaggtctc ccactttcag tgacaacagc acgccaccgg ctgtgcccca   4020
gacctatcag gtcgggtact tgcatgctcc aactggcagt ggaaagagca ccaaggtccc   4080
tgtcgcgtat gccgcccagg ggtacaaagt actagtgctt aaccccctcgg tagctgccac   4140 cctggggttt ggggcgtacc tatccaaggc acatggcatc aatcccaaca ttaggactgg   4200
agtcaggacc gtgatgaccg gggaggccat cacgtactcc acatatggca aatttctcgc   4260 cgatggggc tgcgctagcg gcgcctatga catcatcata tgcgatgaat gccacgctgt   4320
ggatgctacc tccattctcg gcatcggaac ggtccttgat caagcagaga cagccggggt   4380
cagactaact gtgctggcta cggccacacc ccccgggtca gtgacaaccc cccatcccga   4440
tatagaagag gtaggcctcg gcgggagggg tgagatcccc ttctatggga gggcgattcc   4500
cctatcctgc atcaagggag ggagacacct gattttctgc cactcaaagc aaaagtgtga   4560
cgagctcgcg gcggcccttc ggggcatggg cttgaatgcc gtggcatact atagagggtt   4620
ggacgtctcc ataataccag ctcagggaga tgtggtggtc gtcgccaccg acgccctcat   4680
gacggggtac actggagact ttgactccgt gatcgactgc aatgtagcgg tcacccaagc   4740
tgtcgacttc agcctggacc ccaccttcac tataaccaca cagactgtcc cacaagacgc   4800
tgtctcacgc agtcagcgcc gcgggcgcac aggtagagga agacagggca cttataggta   4860
tgtttccact ggtgaacgag cctcaggaat gtttgacagt gtagtgcttt gtgagtgcta   4920
cgacgcaggg gctgcgtggt acgatctcac accagcggag accaccgtca ggcttagagc   4980
gtatttcaac acgcccggcc tacccgtgtg tcaagaccat cttgaatttt gggaggcagt   5040
tttcaccggc ctcacacaca tagacgccca cttcctctcc caaacaaagc aagcgggga   5100 gaacttcgcg tacctagtag cctaccaagc tacggtgtgc gccagagcca aggcccctcc   5160
cccgtcctgg gacgccatgt ggaagtgcct ggcccgactc aagcctacgc ttgcgggccc   5220
cacacctctc ctgtaccgtt tgggccctat taccaatgag gtcaccctca cacaccctgg   5280
gacgaagtac atcgccacat gcatgcaagc tgaccttgag gtcatgacca gcacgtgggt   5340
cctagctgga ggagtcctgg cagccgtcgc cgcatattgc ctggcgactg gatgcgtttc   5400
catcatcggc cgcttgcacg tcaaccagcg agtcgtcgtt gcgccggata aggaggtcct   5460
gtatgaggct tttgatgaga tggaggaatg cgcctctagg gcggctctca tcgaagaggg   5520
gcagcggata gccgagatgt tgaagtccaa gatccaaggc ttgctgcagc aggcctctaa   5580
gcaggcccag gacatacaac ccgctatgca ggcttcatgg cccaaagtgg aacaattttg   5640
ggccagacac atgtggaact tcattagcgg catccaatac ctcgcaggat tgtcaacact   5700
gccagggaac cccgcggtgg cttccatgat ggcattcagt gccgccctca ccagtccgtt   5760
```

```
gtcgaccagt accaccatcc ttctcaacat catgggaggc tggttagcgt cccagatcgc    5820
accacccgcg ggggccaccg gctttgtcgt cagtggcctg gtgggggctg ccgtgggcag    5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cgggggaggg cgcggtccaa tggatgaaca ggcttattgc    6120 cttttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaggggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc    6540
tatcaattgc tacacggagg ccagtgcgcg ccgaaacccc ccacgaact  acaagaccgc    6600 catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtgacggtg  tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctccccagg agcgggtttc cacgggcctt    7200
accggcttgg gcacggcctg actacaaccc gccgctcgtg gaatcgtgga ggaggccaga    7260
ttaccaaccg cccaccgttg ctggttgtgc tctcccccc  cccaagaagg ccccgacgcc    7320 tccccccaagg agacgccgga cagtgggtct gagcgagagc accatatcag aagccctcca    7380
gcaactggcc atcaagacct tggccagcc  cccctcgagc ggtgatgcag gctcgtccac    7440
gggggcgggc gccgccgaat ccggcggtcc gacgtcccct ggtgagccgg cccctcaga    7500 gacaggttcc gcctcctcta tgccccccct cgagggggag cctggagatc cggacctgga    7560
gtctgatcag gtagagcttc aacctccccc ccagggggg  ggggtagctc ccggttcggg    7620
ctcggggtct tggtctactt gctccgagga ggacgatacc accgtgtgct gctccatgtc    7680
atactcctgg accggggctc taataactcc ctgtagcccc gaagaggaaa agttgccaat    7740 caacccttg  agtaactcgc tgttgcgata ccataacaag gtgtactgta caacatcaaa    7800
gagcgcctca cagagggcta aaaggtaac  ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca gtatggatt    7980 cggggccaag gaggtccgca gcttgtccgg gagggccgtt aaccacatca gtccgtgtg    8040 gaaggacctc ctgaagacc  cacaaacacc aattcccaca accatcatgg ccaaaaatga    8100
ggtgttctgc gtggaccccg ccaaggggggg taagaaacca gctcgcctca tcgtttaccc    8160
```

```
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
agggcccatg ttcaacagca agggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc cccagaccg gaatatgacc tggagctaat    8760
aacatcctgt tcctcaaatg tgtctgtggc gttgggcccg cggggccgcc gcagatacta    8820
cctgaccaga gacccaacca ctccactcgc ccgggctgcc tgggaaacag ttagacactc    8880
ccctatcaat tcatggctgg aaacatcat ccagtatgct ccaaccatat gggttcgcat    8940
ggtcctaatg acacacttct tctccattct catggtccaa gacaccctgg accagaacct    9000
caactttgag atgtatggat cagtatactc cgtgaatcct ttggaccttc cagccataat    9060
tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttcacag    9360 cgtgtcgcgc gcccgacccc gctcattact cttcggccta ctcctacttt tcgtaggggt    9420
aggcctcttc ctactcccg ctcggtagag cggcacacac taggtacact ccatagctaa    9480
ctgttccttt tttttttttt tttttttttt tttttttttt tttttttttt ctttttttt    9540 ttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                          9684
```

<210> SEQ ID NO 14
<211> LENGTH: 3035
<212> TYPE: PRT
<213> ORGANISM: Hepatitis C virus

<400> SEQUENCE: 14

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

```
Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
            195                 200                 205

Asn Ser Ser Ile Val Tyr Glu Ala Asp Asp Val Ile Leu His Thr Pro
            210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
            275                 280                 285

Gln Ala Phe Thr Phe Arg Pro Arg Arg His Gln Thr Val Gln Thr Cys
        290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
    370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Lys Pro Thr Tyr
```

```
            515                 520                 525
Asn Trp Gly Glu Asn Glu Thr Asp Val Phe Leu Leu Glu Ser Leu Arg
    530                 535                 540
Pro Pro Ser Gly Arg Trp Phe Gly Cys Ala Trp Met Asn Ser Thr Gly
545                 550                 555                 560
Phe Leu Lys Thr Cys Gly Ala Pro Pro Cys Asn Ile Tyr Gly Gly Glu
                565                 570                 575
Gly Asp Pro Glu Asn Glu Thr Asp Leu Phe Cys Pro Thr Asp Cys Phe
                580                 585                 590
Arg Lys His Pro Glu Ala Thr Tyr Ser Arg Cys Gly Ala Gly Pro Trp
                595                 600                 605
Leu Thr Pro Arg Cys Met Val Asp Tyr Pro Tyr Arg Leu Trp His Tyr
    610                 615                 620
Pro Cys Thr Val Asn Phe Thr Leu Phe Lys Val Arg Met Phe Val Gly
625                 630                 635                 640
Gly Phe Glu His Arg Phe Thr Ala Ala Cys Asn Trp Thr Arg Gly Glu
                645                 650                 655
Arg Cys Asn Ile Glu Asp Arg Asp Arg Ser Glu Gln His Pro Leu Leu
                660                 665                 670
His Ser Thr Thr Glu Leu Ala Ile Leu Pro Cys Ser Phe Thr Pro Met
    675                 680                 685
Pro Ala Leu Ser Thr Gly Leu Ile His Leu His Gln Asn Ile Val Asp
690                 695                 700
Val Gln Tyr Leu Tyr Gly Val Gly Ser Asp Met Val Gly Trp Ala Leu
705                 710                 715                 720
Lys Trp Glu Phe Val Ile Leu Val Phe Leu Leu Leu Ala Asp Ala Arg
                725                 730                 735
Val Cys Val Ala Leu Trp Leu Met Leu Met Val Ser Gln Ala Glu Ala
                740                 745                 750
Ala Leu Glu Asn Leu Val Thr Leu Asn Ala Val Ala Ala Ala Gly Thr
                755                 760                 765
His Gly Ile Gly Trp Tyr Leu Val Ala Phe Cys Ala Ala Trp Tyr Val
    770                 775                 780
Arg Gly Lys Leu Val Pro Leu Thr Ser Tyr Gly Leu Thr Gly Leu Trp
785                 790                 795                 800
Ser Leu Ala Leu Leu Val Leu Leu Pro Gln Arg Ala Tyr Ala Trp
                805                 810                 815
Ser Gly Glu Asp Ser Ala Thr Leu Gly Ala Gly Val Leu Ala Leu Phe
                820                 825                 830
Gly Phe Phe Thr Leu Ser Pro Trp Tyr Lys His Trp Ile Gly Arg Leu
                835                 840                 845
Met Trp Trp Asn Gln Tyr Thr Ile Cys Arg Cys Glu Ala Ala Leu Gln
    850                 855                 860
Val Trp Val Pro Pro Leu Leu Ala Arg Gly Ser Arg Asp Gly Val Ile
865                 870                 875                 880
Leu Leu Thr Ser Leu Leu Tyr Pro Ser Leu Ile Phe Asp Ile Thr Lys
                885                 890                 895
Leu Leu Ile Ala Val Ile Gly Pro Leu Tyr Leu Ile Gln Ala Ala Ile
                900                 905                 910
Thr Thr Thr Pro Tyr Phe Val Arg Ala His Val Leu Val Arg Leu Cys
                915                 920                 925
Met Leu Val Arg Ser Val Met Gly Gly Lys Tyr Phe Gln Met Ala Ile
    930                 935                 940
```

```
Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
        995                 1000                1005

Ser Ala Arg Leu Gly Arg Glu Val Leu Leu Gly Pro Ala Asp Asp
    1010                1015            1020

Tyr Arg Glu Met Gly Trp Arg Leu Leu Ala Pro Ile Thr Ala Tyr
    1025                1030            1035

Ala Gln Gln Thr Arg Gly Leu Leu Gly Ala Ile Val Val Ser Met
    1040                1045            1050

Thr Gly Arg Asp Arg Thr Glu Gln Ala Gly Glu Val Gln Ile Leu
    1055                1060            1065

Ser Thr Val Ser Gln Ser Phe Leu Gly Thr Thr Ile Ser Gly Val
    1070                1075            1080

Leu Trp Thr Val Tyr His Gly Ala Gly Asn Lys Thr Leu Ala Gly
    1085                1090            1095

Leu Arg Gly Pro Val Thr Gln Met Tyr Ser Ser Ala Glu Gly Asp
    1100                1105            1110

Leu Val Gly Trp Pro Ser Pro Pro Gly Thr Lys Ser Leu Glu Pro
    1115                1120            1125

Cys Lys Cys Gly Ala Val Asp Leu Tyr Leu Val Thr Arg Asn Ala
    1130                1135            1140

Asp Val Ile Pro Ala Arg Arg Gly Asp Lys Arg Gly Ala Leu
    1145                1150            1155

Leu Ser Pro Arg Pro Ile Ser Thr Leu Lys Gly Ser Ser Gly Gly
    1160                1165            1170

Pro Val Leu Cys Pro Arg Gly His Val Val Gly Leu Phe Arg Ala
    1175                1180            1185

Ala Val Cys Ser Arg Gly Val Ala Lys Ser Ile Asp Phe Ile Pro
    1190                1195            1200

Val Glu Thr Leu Asp Val Val Thr Arg Ser Pro Thr Phe Ser Asp
    1205                1210            1215

Asn Ser Thr Pro Pro Ala Val Pro Gln Thr Tyr Gln Val Gly Tyr
    1220                1225            1230

Leu His Ala Pro Thr Gly Ser Gly Lys Ser Thr Lys Val Pro Val
    1235                1240            1245

Ala Tyr Ala Ala Gln Gly Tyr Lys Val Leu Val Leu Asn Pro Ser
    1250                1255            1260

Val Ala Ala Thr Leu Gly Phe Gly Ala Tyr Leu Ser Lys Ala His
    1265                1270            1275

Gly Ile Asn Pro Asn Ile Arg Thr Gly Val Arg Thr Val Met Thr
    1280                1285            1290

Gly Glu Ala Ile Thr Tyr Ser Thr Tyr Gly Lys Phe Leu Ala Asp
    1295                1300            1305

Gly Gly Cys Ala Ser Gly Ala Tyr Asp Ile Ile Cys Asp Glu
    1310                1315            1320

Cys His Ala Val Asp Ala Thr Ser Ile Leu Gly Ile Gly Thr Val
    1325                1330            1335
```

-continued

```
Leu Asp Gln Ala Glu Thr Ala Gly Val Arg Leu Thr Val Leu Ala
1340                1345                1350

Thr Ala Thr Pro Pro Gly Ser Val Thr Thr Pro His Pro Asp Ile
1355                1360                1365

Glu Glu Val Gly Leu Gly Arg Glu Gly Glu Ile Pro Phe Tyr Gly
1370                1375                1380

Arg Ala Ile Pro Leu Ser Cys Ile Lys Gly Gly Arg His Leu Ile
1385                1390                1395

Phe Cys His Ser Lys Gln Lys Cys Asp Glu Leu Ala Ala Ala Leu
1400                1405                1410

Arg Gly Met Gly Leu Asn Ala Val Ala Tyr Tyr Arg Gly Leu Asp
1415                1420                1425

Val Ser Ile Ile Pro Ala Gln Gly Asp Val Val Val Ala Thr
1430                1435                1440

Asp Ala Leu Met Thr Gly Tyr Thr Gly Asp Phe Asp Ser Val Ile
1445                1450                1455

Asp Cys Asn Val Ala Val Thr Gln Ala Val Asp Phe Ser Leu Asp
1460                1465                1470

Pro Thr Phe Thr Ile Thr Thr Gln Thr Val Pro Gln Asp Ala Val
1475                1480                1485

Ser Arg Ser Gln Arg Arg Gly Arg Thr Gly Arg Gly Arg Gln Gly
1490                1495                1500

Thr Tyr Arg Tyr Val Ser Thr Gly Glu Arg Ala Ser Gly Met Phe
1505                1510                1515

Asp Ser Val Val Leu Cys Glu Cys Tyr Asp Ala Gly Ala Ala Trp
1520                1525                1530

Tyr Asp Leu Thr Pro Ala Glu Thr Thr Val Arg Leu Arg Ala Tyr
1535                1540                1545

Phe Asn Thr Pro Gly Leu Pro Val Cys Gln Asp His Leu Glu Phe
1550                1555                1560

Trp Glu Ala Val Phe Thr Gly Leu Thr His Ile Asp Ala His Phe
1565                1570                1575

Leu Ser Gln Thr Lys Gln Ala Gly Glu Asn Phe Ala Tyr Leu Val
1580                1585                1590

Ala Tyr Gln Ala Thr Val Cys Ala Arg Ala Lys Ala Pro Pro Pro
1595                1600                1605

Ser Trp Asp Ala Met Trp Lys Cys Leu Ala Arg Leu Lys Pro Thr
1610                1615                1620

Leu Ala Gly Pro Thr Pro Leu Leu Tyr Arg Leu Gly Pro Ile Thr
1625                1630                1635

Asn Glu Val Thr Leu Thr His Pro Gly Thr Lys Tyr Ile Ala Thr
1640                1645                1650

Cys Met Gln Ala Asp Leu Glu Val Met Thr Ser Thr Trp Val Leu
1655                1660                1665

Ala Gly Gly Val Leu Ala Ala Val Ala Ala Tyr Cys Leu Ala Thr
1670                1675                1680

Gly Cys Val Ser Ile Ile Gly Arg Leu His Val Asn Gln Arg Val
1685                1690                1695

Val Val Ala Pro Asp Lys Glu Val Leu Tyr Glu Ala Phe Asp Glu
1700                1705                1710

Met Glu Glu Cys Ala Ser Arg Ala Ala Leu Ile Glu Glu Gly Gln
1715                1720                1725

Arg Ile Ala Glu Met Leu Lys Ser Lys Ile Gln Gly Leu Leu Gln
```

```
            1730               1735                1740
Gln Ala Ser Lys Gln Ala Gln Asp Ile Gln Pro Ala Met Gln Ala
            1745               1750                1755
Ser Trp Pro Lys Val Glu Gln Phe Trp Ala Arg His Met Trp Asn
            1760               1765                1770
Phe Ile Ser Gly Ile Gln Tyr Leu Ala Gly Leu Ser Thr Leu Pro
            1775               1780                1785
Gly Asn Pro Ala Val Ala Ser Met Met Ala Phe Ser Ala Ala Leu
            1790               1795                1800
Thr Ser Pro Leu Ser Thr Ser Thr Thr Ile Leu Leu Asn Ile Met
            1805               1810                1815
Gly Gly Trp Leu Ala Ser Gln Ile Ala Pro Pro Ala Gly Ala Thr
            1820               1825                1830
Gly Phe Val Val Ser Gly Leu Val Gly Ala Ala Val Gly Ser Ile
            1835               1840                1845
Gly Leu Gly Lys Val Leu Val Asp Ile Leu Ala Gly Tyr Gly Ala
            1850               1855                1860
Gly Ile Ser Gly Ala Leu Val Ala Phe Lys Ile Met Ser Gly Glu
            1865               1870                1875
Lys Pro Ser Met Glu Asp Val Ile Asn Leu Leu Pro Gly Ile Leu
            1880               1885                1890
Ser Pro Gly Ala Leu Val Val Gly Val Ile Cys Ala Ala Ile Leu
            1895               1900                1905
Arg Arg His Val Gly Pro Gly Glu Gly Ala Val Gln Trp Met Asn
            1910               1915                1920
Arg Leu Ile Ala Phe Ala Ser Arg Gly Asn His Val Ala Pro Thr
            1925               1930                1935
His Tyr Val Thr Glu Ser Asp Ala Ser Gln Arg Val Thr Gln Leu
            1940               1945                1950
Leu Gly Ser Leu Thr Ile Thr Ser Leu Leu Arg Arg Leu His Asn
            1955               1960                1965
Trp Ile Thr Glu Asp Cys Pro Ile Pro Cys Ser Gly Ser Trp Leu
            1970               1975                1980
Arg Asp Val Trp Asp Trp Val Cys Thr Ile Leu Thr Asp Phe Lys
            1985               1990                1995
Asn Trp Leu Thr Ser Lys Leu Phe Pro Lys Leu Pro Gly Leu Pro
            2000               2005                2010
Phe Ile Ser Cys Gln Lys Gly Tyr Lys Gly Val Trp Ala Gly Thr
            2015               2020                2025
Gly Ile Met Thr Thr Arg Cys Pro Cys Gly Ala Asn Ile Ser Gly
            2030               2035                2040
Asn Val Arg Leu Gly Ser Met Arg Ile Thr Gly Pro Lys Thr Cys
            2045               2050                2055
Met Asn Thr Trp Gln Gly Thr Phe Pro Ile Asn Cys Tyr Thr Glu
            2060               2065                2070
Gly Gln Cys Ala Pro Lys Pro Pro Thr Asn Tyr Lys Thr Ala Ile
            2075               2080                2085
Trp Arg Val Ala Ala Ser Glu Tyr Ala Glu Val Thr Gln His Gly
            2090               2095                2100
Ser Tyr Ser Tyr Val Thr Gly Leu Thr Thr Asp Asn Leu Lys Ile
            2105               2110                2115
Pro Cys Gln Leu Pro Ser Pro Glu Phe Phe Ser Trp Val Asp Gly
            2120               2125                2130
```

```
Val Gln Ile His Arg Phe Ala Pro Thr Pro Lys Pro Phe Phe Arg
    2135            2140            2145

Asp Glu Val Ser Phe Cys Val Gly Leu Asn Ser Tyr Ala Val Gly
    2150            2155            2160

Ser Gln Leu Pro Cys Glu Pro Glu Pro Asp Ala Asp Val Leu Arg
    2165            2170            2175

Ser Met Leu Thr Asp Pro Pro His Ile Thr Ala Glu Thr Ala Ala
    2180            2185            2190

Arg Arg Leu Ala Arg Gly Ser Pro Pro Ser Glu Ala Ser Ser Ser
    2195            2200            2205

Val Ser Gln Leu Ser Ala Pro Ser Leu Arg Ala Thr Cys Thr Thr
    2210            2215            2220

His Ser Asn Thr Tyr Asp Val Asp Met Val Asp Ala Asn Leu Leu
    2225            2230            2235

Met Glu Gly Gly Val Ala Gln Thr Glu Pro Glu Ser Arg Val Pro
    2240            2245            2250

Val Leu Asp Phe Leu Glu Pro Met Ala Glu Glu Glu Ser Asp Leu
    2255            2260            2265

Glu Pro Ser Ile Pro Ser Glu Cys Met Leu Pro Arg Ser Gly Phe
    2270            2275            2280

Pro Arg Ala Leu Pro Ala Trp Ala Arg Pro Asp Tyr Asn Pro Pro
    2285            2290            2295

Leu Val Glu Ser Trp Arg Arg Pro Asp Tyr Gln Pro Pro Thr Val
    2300            2305            2310

Ala Gly Cys Ala Leu Pro Pro Lys Lys Ala Pro Thr Pro Pro
    2315            2320            2325

Pro Arg Arg Arg Arg Thr Val Gly Leu Ser Glu Ser Thr Ile Ser
    2330            2335            2340

Glu Ala Leu Gln Gln Leu Ala Ile Lys Thr Phe Gly Gln Pro Pro
    2345            2350            2355

Ser Ser Gly Asp Ala Gly Ser Ser Thr Gly Ala Gly Ala Ala Glu
    2360            2365            2370

Ser Gly Gly Pro Thr Ser Pro Gly Glu Pro Ala Pro Ser Glu Thr
    2375            2380            2385

Gly Ser Ala Ser Ser Met Pro Pro Leu Glu Gly Glu Pro Gly Asp
    2390            2395            2400

Pro Asp Leu Glu Ser Asp Gln Val Glu Leu Gln Pro Pro Pro Gln
    2405            2410            2415

Gly Gly Gly Val Ala Pro Gly Ser Gly Ser Gly Ser Trp Ser Thr
    2420            2425            2430

Cys Ser Glu Glu Asp Asp Thr Thr Val Cys Cys Ser Met Ser Tyr
    2435            2440            2445

Ser Trp Thr Gly Ala Leu Ile Thr Pro Cys Ser Pro Glu Glu Glu
    2450            2455            2460

Lys Leu Pro Ile Asn Pro Leu Ser Asn Ser Leu Leu Arg Tyr His
    2465            2470            2475

Asn Lys Val Tyr Cys Thr Thr Ser Lys Ser Ala Ser Gln Arg Ala
    2480            2485            2490

Lys Lys Val Thr Phe Asp Arg Thr Gln Val Leu Asp Ala His Tyr
    2495            2500            2505

Asp Ser Val Leu Lys Asp Ile Lys Leu Ala Ala Ser Lys Val Ser
    2510            2515            2520
```

```
Ala Arg Leu Leu Thr Leu Glu Glu Ala Cys Gln Leu Thr Pro Pro
2525                2530                2535

His Ser Ala Arg Ser Lys Tyr Gly Phe Gly Ala Lys Glu Val Arg
2540                2545                2550

Ser Leu Ser Gly Arg Ala Val Asn His Ile Lys Ser Val Trp Lys
2555                2560                2565

Asp Leu Leu Glu Asp Pro Gln Thr Pro Ile Pro Thr Thr Ile Met
2570                2575                2580

Ala Lys Asn Glu Val Phe Cys Val Asp Pro Ala Lys Gly Gly Lys
2585                2590                2595

Lys Pro Ala Arg Leu Ile Val Tyr Pro Asp Leu Gly Val Arg Val
2600                2605                2610

Cys Glu Lys Met Ala Leu Tyr Asp Ile Thr Gln Lys Leu Pro Gln
2615                2620                2625

Ala Val Met Gly Ala Ser Tyr Gly Phe Gln Tyr Ser Pro Ala Gln
2630                2635                2640

Arg Val Glu Tyr Leu Leu Lys Ala Trp Ala Glu Lys Lys Asp Pro
2645                2650                2655

Met Gly Phe Ser Tyr Asp Thr Arg Cys Phe Asp Ser Thr Val Thr
2660                2665                2670

Glu Arg Asp Ile Arg Thr Glu Glu Ser Ile Tyr Gln Ala Cys Ser
2675                2680                2685

Leu Pro Glu Glu Ala Arg Thr Ala Ile His Ser Leu Thr Glu Arg
2690                2695                2700

Leu Tyr Val Gly Gly Pro Met Phe Asn Ser Lys Gly Gln Thr Cys
2705                2710                2715

Gly Tyr Arg Arg Cys Arg Ala Ser Gly Val Leu Thr Thr Ser Met
2720                2725                2730

Gly Asn Thr Ile Thr Cys Tyr Val Lys Ala Leu Ala Ala Cys Lys
2735                2740                2745

Ala Ala Gly Ile Val Ala Pro Thr Met Leu Val Cys Gly Asp Asp
2750                2755                2760

Leu Val Val Ile Ser Glu Ser Gln Gly Thr Glu Glu Asp Glu Arg
2765                2770                2775

Asn Leu Arg Ala Phe Thr Glu Ala Met Thr Arg Tyr Ser Ala Pro
2780                2785                2790

Pro Gly Asp Pro Pro Arg Pro Glu Tyr Asp Leu Glu Leu Ile Thr
2795                2800                2805

Ser Cys Ser Ser Asn Val Ser Val Ala Leu Gly Pro Arg Gly Arg
2810                2815                2820

Arg Arg Tyr Tyr Leu Thr Arg Asp Pro Thr Thr Pro Leu Ala Arg
2825                2830                2835

Ala Ala Trp Glu Thr Val Arg His Ser Pro Ile Asn Ser Trp Leu
2840                2845                2850

Gly Asn Ile Ile Gln Tyr Ala Pro Thr Ile Trp Val Arg Met Val
2855                2860                2865

Leu Met Thr His Phe Phe Ser Ile Leu Met Val Gln Asp Thr Leu
2870                2875                2880

Asp Gln Asn Leu Asn Phe Glu Met Tyr Gly Ser Val Tyr Ser Val
2885                2890                2895

Asn Pro Leu Asp Leu Pro Ala Ile Ile Glu Arg Leu His Gly Leu
2900                2905                2910

Asp Ala Phe Ser Met His Thr Tyr Ser His His Glu Leu Thr Arg
```

```
                 2915                 2920                 2925
Val Ala Ser Ala Leu Arg Lys Leu Gly Ala Pro Pro Leu Arg Val
        2930                 2935                 2940
Trp Lys Ser Arg Ala Arg Ala Val Arg Ala Ser Leu Ile Ser Arg
        2945                 2950                 2955
Gly Gly Lys Ala Ala Val Cys Gly Arg Tyr Leu Phe Asn Trp Ala
        2960                 2965                 2970
Val Lys Thr Lys Leu Lys Leu Thr Pro Leu Pro Glu Ala Arg Leu
        2975                 2980                 2985
Leu Asp Leu Ser Ser Trp Phe Thr Val Gly Ala Gly Gly Gly Asp
        2990                 2995                 3000
Ile Phe His Ser Val Ser Arg Ala Arg Pro Arg Ser Leu Leu Phe
        3005                 3010                 3015
Gly Leu Leu Leu Leu Phe Val Gly Val Gly Leu Phe Leu Leu Pro
        3020                 3025                 3030
Ala Arg
    3035

<210> SEQ ID NO 15
<211> LENGTH: 9684
<212> TYPE: DNA
<213> ORGANISM: Hepatitis C virus

<400> SEQUENCE: 15
acctgcccct aatagggcg acactccgcc atgaatcact ccctgtgag gaactactgt    60
cttcacgcag aaagcgccta gccatggcgt tagtatgagt gtcgtacagc ctccaggccc   120
cccctcccg ggagagccat agtggtctgc ggaaccggtg agtacaccgg aattgccggg   180
aagactgggt cctttcttgg ataaacccac tctatgcccg ccatttggg cgtgcccccg   240
caagactgct agccgagtag cgttgggttg cgaaaggcct tgtggtactg cctgataggg   300
tgcttgcgag tgccccggga ggtctcgtag accgtgcacc atgagcacac ttcctaaacc   360
tcaaagaaaa accaaaagaa acaccatccg tcgcccacag gacgttaagt tcccgggtgg   420
cggacagatc gttggtggag tatacgtgtt gccgcgcagg ggcccacgat gggtgtgcg   480
cgcgacgcgt aaaacttctg aacggtcaca gcctcgcgga cgacgacagc ctatccccaa   540
ggcgcgtcgg agcgaaggcc ggtcctgggc tcagcccggg tacccttggc ccctctatgg   600
taatgagggc tgcgggtggg cagggtggct cctgtccccg cgcggctccc gtccatcttg   660
ggcccaaac gaccccggc ggaggtcccg caatttgggt aaagtcatcg ataccctttac   720
gtgcggattc gccgacctca tggggtacat cccgctcgtc ggcgctcccg taggaggcgt   780
cgcaagagcc ctcgcgcatg gcgtgagggc ccttgaagac gggataaatt ttgcaacagg   840
gaacttgccc ggttgctcct tttctatctt ccttcttgct ctgttctcct gcttagttca   900
tcctgcagct agtcttgagt ggcggaatac gtctggcctc tatgtcctta ccaacgactg   960
ttccaatagc agtattgtgt atgaggccga tgacgtcatt ctgcacacac ccggctgtgt  1020
accttgtgtt caggacgaca atacatccac gtgctggacc ccagtgacac ctacggtggc  1080
agtcaggtac gtcggagcaa ccaccgcttc gatacgcagt catgtggacc tattagtggg  1140
cgcggccacg ctgtgctctg cgctctatgt gggtgatatg tgtgggccg tctttctcgt  1200
gggacaagcc ttcacgttca gacctcgtcg ccatcaaacg gtccagacct gtaactgctc  1260
gctgtaccca ggccatgttt caggacatcg aatggcttgg gatatgatga tgaattggtc  1320
ccccgctgtg ggtatggtgg tggcgcacat cctgcgattg ccccagacct tgtttgacat  1380
```

```
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agccttttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
caactctact ggatgtcctc aaaggcttag cagctgcaag cccatcattt ccttcaggca   1740
ggggtggggc cccttgacag atgctaacat caccggtcct tctgatgata accgtattg    1800 ctggcactac gcacctagac cttgtagtgt tgtcccggca tcaagtgtct gcggccctgt   1860
gtactgcttc acaccatcgc cagtggtcgt aggcactact gatatcaaag caagccgac    1920 ctacaactgg ggtgagaatg agacagatgt gttcctgctg gagtccctgc ggcctcccag   1980
tggccggtgg tttggatgcg cgtggatgaa ctccacgggg ttcctcaaga cgtgtggagc   2040
tcccccttgt aacatctatg ggggtgaggg ggatcccgaa aatgagacag acctcttctg   2100
ccccaccgac tgcttcagga acatcctga ggccacatac agccggtgtg gtgcggggcc    2160
ctggttgaca cctcgctgca tggtcgacta tccataccgg cttggcatt acccatgtac    2220 agtcaatttc acattgttca aggtgaggat gtttgtgggc ggatttgaac accggtttac   2280
cgccgcttgt aactgaacca gggggagcg ctgcaatatc gaggatcgtg atcgcagcga    2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc ctttggctga tgctgatggt   2580
atcacaagca gaagcagcct ggagaacct tgtcacgctg aacgccgtcg ctgctgctgg    2640
gacacatggt attggttggt acctggtagc cttttgcgcg cgtggtacg tgcggggtaa    2700 acttgtcccg ctgacgagct acggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940
ccccccctta cttgcacgcg ggagtaggga cggtgtcatc ctgctaacaa gcttgcttta   3000
tccatcctta atttttgaca tcactaagct gctgatagca gtaataggcc cattatactt   3060
aatacaggct gccatcacta ccaccccta cttttgtgcgc gcacatgtac tggtccgcct   3120
ttgcatgctc gtgcgctccg tgatgggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcgggctgcc   3360
ggtctccgcg cgattaggcc gtgaggtatt gttgggacct gctgatgatt atcgggaaat   3420
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcggggttt tgtggactgt    3600 ttaccacgga gctggcaaca agactctagc cggcttacgg ggtccggtca cgcagatgta   3660
ctcgagtgct gaggggggact tggtaggctg gcccagcccc cctgggacca agtctttgga   3720
```

```
gccgtgcaag tgtggagccg tcgacctata tctggtcacg cggaacgctg atgtcatccc    3780
ggctcggaga cgcggggaca agcggggagc attgctctcc ccgagaccca tttcgacctt    3840
gaagggtcc tcgggggggc cggtgctctg ccctagggc cacgtcgttg ggctcttccg      3900
agcagctgtg tgctctcggg gcgtggccaa atccatcgat ttcatcccg ttgagacact     3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aaccctcgg tagctgccac     4140
cctgggtt ggggcgtacc tatccaaggc acatggcatc aatcccaaca ttaggactgg      4200
agtcaggacc gtgatgaccg gggaggccat cacgtactcc acatatggca aatttctcgc    4260
cgatggggc tgcgctagcg cgcctatga catcatcata tgcgatgaat gccacgctgt      4320
ggatgctacc tccattctcg gcatcggaac ggtccttgat caagcagaga cagccgggt    4380
cagactaact gtgctggcta cggccacacc ccccggtca gtgacaaccc ccatcccga     4440
tatagaagag gtaggcctcg gcggagggg tgagatcccc ttctatggga gggcgattcc    4500
cctatcctgc atcaagggag ggagacacct gattttctgc cactcaaaga aaaagtgtga   4560
cgagctcgcg gcggcccttc ggggcatggg cttgaatgcc gtggcatact atagagggtt   4620
ggacgtctcc ataataccag ctcagggaga tgtggtggtc gtcgccaccg acgccctcat   4680
gacggggtac actggagact ttgactccgt gatcgactgc aatgtagcgg tcacccaagc   4740
tgtcgacttc agcctggacc ccaccttcac tataaccaca cagactgtcc cacaagacgc   4800
tgtctcacgc agtcagcgcc gcgggcgcac aggtagagga agacagggca cttataggta   4860
tgtttccact ggtgaacgag cctcaggaat gtttgacagt gtagtgcttt gtgagtgcta   4920
cgacgcaggg gctgcgtggt acgatctcac accagcggag accaccgtca ggcttagagc   4980
gtatttcaac acgcccggcc tacccgtgtg tcaagaccat cttgaattt gggaggcagt    5040
tttcaccggc ctcacacaca tagacgccca cttcctctcc caaacaaagc aagcgggga    5100
gaacttcgcg tacctagtag cctaccaagc tacggtgtgc gccagagcca aggcccctcc   5160
cccgtcctgg gacgccatgt ggaagtgcct ggcccgactc aagcctacgc ttgcgggcc    5220
cacacctctc ctgtaccgtt tgggccctat taccaatgag gtcacctca cacaccctgg    5280
gacgaagtac atcgccacat gcatgcaagc tgaccttgag gtcatgacca gcacgtgggt   5340
cctagctgga ggagtcctgg cagccgtcgc cgcatattgc ctggcgactg gatgcgtttc   5400
catcatcggc cgcttgcacg tcaaccgcg agtcgtcgtt cgccggata aggaggtcct    5460
gtatgaggct tttgatgaga tggaggaatg cgcctctagg gcggctctca tcgaagaggg   5520
gcagcggata gccgagatgt tgaagtccaa gatccaaggc ttgctgcagc aggcctctaa   5580
gcaggccag acatacaac ccgctatgca ggcttcatgg cccaaagtgg aacaattttg     5640
ggccagacac atgtggaact tcattagcgg catccaatac ctcgcaggat tgtcaacact   5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accaccgcg ggggccaccg gctttgtcgt cagtggcctg gtggggctg ccgtgggcag     5880
cataggcctg ggtaaggtgc tggtggacat cctggcagga tatggtgcgg gcatttcggg   5940
ggccctcgtc gcattcaaga tcatgtctgg cgagaagccc tctatggaag atgtcatcaa   6000
tctactgcct gggatcctgt ctcccgggagc cctggtggtg gggtcatct gcgcggccat   6060
tctgcgccgc cacgtgggac cgggggaggg cgcggtccaa tggatgaaca ggcttattgc   6120
```

```
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaggggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc    6540
tatcaattgc tacacggagg gccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctccccagg agcgggtttc cacgggcctt    7200
accggcttgg gcacggcctg actacaaccc gccgctcgtg gaatcgtgga ggaggccaga    7260
ttaccaaccg cccaccgttg ctggttgtgc tctcccccc cccaagaagg ccccgacgcc    7320
tcccccaagg agacgccgga cagtgggtct gagcgagagc accatatcag aagccctcca    7380
gcaactggcc atcaagacct ttggccagcc cccctcgagc ggtgatgcag gctcgtccac    7440
gggggcgggc gccgccgaat ccggcggtcc gacgtcccct ggtgagccgg cccctcaga    7500 gacaggttcc gcctcctcta tgcccccct cgagggggag cctggagatc cggacctgga    7560
gtctgatcag gtagagcttc aacctccccc ccagggggggg gggtagctc ccggttcggg    7620 ctcggggtct tggtctactt gctccgagga ggacgatacc accgtgtgct gctccatgtc    7680
atactcctgg accggggctc taataactcc ctgtagcccc gaagaggaaa agttgccaat    7740 caacccttg agtaactcgc tgttgcgata ccataacaag gtgtactgta caacatcaaa    7800
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc accccattct gcaagatcca gtatggatt    7980 cggggccaag gaggtccgca gcttgtccgg gagggccgtt aaccacatca gtccgtgtg    8040 gaaggacctc ctggaagacc cacaaacacc aattcccaca accatcatgg ccaaaaatga    8100
ggtgttctgc gtggaccccg ccaagggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
```

```
agggcccatg ttcaacagca agggtcaaac ctgcggttac agacgttgcc gcgccagcgg      8520
ggtgctaacc actagcatgg gtaacaccat cacatgctat gtgaaagccc tagcggcctg      8580
caaggctgcg gggatagttg cgcccacaat gctggtatgc ggcgatgacc tagtagtcat      8640
ctcagaaagc caggggactg aggaggacga gcggaacctg agagccttca cggaggccat      8700
gaccaggtac tctgcccctc ctggtgatcc ccccagaccg gaatatgacc tggagctaat      8760
aacatcctgt tcctcaaatg tgtctgtggc gttgggcccg cggggccgcc gcagatacta      8820
cctgaccaga gacccaacca ctccactcgc ccgggctgcc tgggaaacag ttagacactc      8880
ccctatcaat tcatggctgg gaaacatcat ccagtatgct ccaaccatat gggttcgcat      8940
ggtcctaatg acacacttct tctccattct catggtccaa gacaccctgg accagaacct      9000
caactttgag atgtatggat cagtatactc cgtgaatcct ttggaccttc agccataat       9060 tgagaggtta cacgggcttg acgccttttc tatgcacaca tactctcacc acgaactgac      9120
gcgggtggct tcagccctca gaaacttggg ggcgccaccc ctcagggtgt ggaagagtcg      9180
ggctcgcgca gtcagggcgt ccctcatctc ccgtggaggg aaagcggccg tttgcggccg      9240
atatctcttc aattgggcgg tgaagaccaa gctcaaactc actccattgc cggaggcgcg      9300
cctactggac ttatccagtt ggttcaccgt cggcgccggc gggggcgaca ttttttcacag     9360 cgtgtcgcgc gcccgacccc gctcattact cttcggccta ctcctacttt tcgtagggt      9420 aggcctcttc ctactccccg ctcggtagag cggcacacac taggtacact ccatagctaa      9480
ctgttccttt tttttttttt tttttttttt tttttttttt tttttttttt cttttttttt      9540
tttttccctc tttcttccct tctcatctta ttctactttc tttcttggtg gctccatctt      9600
agccctagtc acggctagct gtgaaaggtc cgtgagccgc atgactgcag agagtgccgt      9660
aactggtctc tctgcagatc atgt                                             9684
```

<210> SEQ ID NO 16
<211> LENGTH: 3035
<212> TYPE: PRT
<213> ORGANISM: Hepatitis C virus

<400> SEQUENCE: 16

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160
```

```
Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
                260                 265                 270

Ser Ala Leu Tyr Val Gly Asp Met Cys Gly Ala Val Phe Leu Val Gly
            275                 280                 285

Gln Ala Phe Thr Phe Arg Pro Arg His Gln Thr Val Gln Thr Cys
        290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
                340                 345                 350

Trp Gly Ile Leu Ala Gly Leu Ala Tyr Tyr Ser Met Gln Gly Asn Trp
            355                 360                 365

Ala Lys Val Ala Ile Val Met Ile Met Phe Ser Gly Val Asp Ala Glu
        370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
            435                 440                 445

Ser Thr Gly Cys Pro Gln Arg Leu Ser Ser Cys Lys Pro Ile Ile Ser
        450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Gly Thr Thr Asp Ile Lys Gly Lys Pro Thr Tyr
        515                 520                 525

Asn Trp Gly Glu Asn Glu Thr Asp Val Phe Leu Leu Glu Ser Leu Arg
530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575
```

```
Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
        660                 665                 670

His Ser Thr Thr Glu Leu Ala Ile Leu Pro Cys Ser Phe Thr Pro Met
    675                 680                 685

Pro Ala Leu Ser Thr Gly Leu Ile His Leu His Gln Asn Ile Val Asp
690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Ala Gly Thr
        755                 760                 765

His Gly Ile Gly Trp Tyr Leu Val Ala Phe Cys Ala Ala Trp Tyr Val
    770                 775                 780

Arg Gly Lys Leu Val Pro Leu Thr Ser Tyr Gly Leu Thr Gly Leu Trp
785                 790                 795                 800

Ser Leu Ala Leu Leu Val Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
    850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
            900                 905                 910

Thr Thr Thr Pro Tyr Phe Val Arg Ala His Val Leu Val Arg Leu Cys
        915                 920                 925

Met Leu Val Arg Ser Val Met Gly Gly Lys Tyr Phe Gln Met Ala Ile
    930                 935                 940

Leu Ser Ile Gly Arg Trp Phe Asn Thr Tyr Leu Tyr Asp His Leu Ala
945                 950                 955                 960

Pro Met Gln His Trp Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly  Asp Ile Leu Cys Gly  Leu Pro Val
```

```
                995                 1000                1005
Ser Ala Arg Leu Gly Arg Glu Val Leu Gly Pro Ala Asp Asp
    1010                1015                1020

Tyr Arg Glu Met Gly Trp Arg Leu Leu Ala Pro Ile Thr Ala Tyr
    1025                1030                1035

Ala Gln Gln Thr Arg Gly Leu Leu Gly Ala Ile Val Val Ser Met
    1040                1045                1050

Thr Gly Arg Asp Arg Thr Glu Gln Ala Gly Glu Val Gln Ile Leu
    1055                1060                1065

Ser Thr Val Ser Gln Ser Phe Leu Gly Thr Thr Ile Ser Gly Val
    1070                1075                1080

Leu Trp Thr Val Tyr His Gly Ala Gly Asn Lys Thr Leu Ala Gly
    1085                1090                1095

Leu Arg Gly Pro Val Thr Gln Met Tyr Ser Ser Ala Glu Gly Asp
    1100                1105                1110

Leu Val Gly Trp Pro Ser Pro Pro Gly Thr Lys Ser Leu Glu Pro
    1115                1120                1125

Cys Lys Cys Gly Ala Val Asp Leu Tyr Leu Val Thr Arg Asn Ala
    1130                1135                1140

Asp Val Ile Pro Ala Arg Arg Arg Gly Asp Lys Arg Gly Ala Leu
    1145                1150                1155

Leu Ser Pro Arg Pro Ile Ser Thr Leu Lys Gly Ser Ser Gly Gly
    1160                1165                1170

Pro Val Leu Cys Pro Arg Gly His Val Val Gly Leu Phe Arg Ala
    1175                1180                1185

Ala Val Cys Ser Arg Gly Val Ala Lys Ser Ile Asp Phe Ile Pro
    1190                1195                1200

Val Glu Thr Leu Asp Val Val Thr Arg Ser Pro Thr Phe Ser Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Lys Val Pro Val
    1235                1240                1245

Ala Tyr Ala Ala Gln Gly Tyr Lys Val Leu Val Leu Asn Pro Ser
    1250                1255                1260

Val Ala Ala Thr Leu Gly Phe Gly Ala Tyr Leu Ser Lys Ala His
    1265                1270                1275

Gly Ile Asn Pro Asn Ile Arg Thr Gly Val Arg Thr Val Met Thr
    1280                1285                1290

Gly Glu Ala Ile Thr Tyr Ser Thr Tyr Gly Lys Phe Leu Ala Asp
    1295                1300                1305

Gly Gly Cys Ala Ser Gly Ala Tyr Asp Ile Ile Ile Cys Asp Glu
    1310                1315                1320

Cys His Ala Val Asp Ala Thr Ser Ile Leu Gly Ile Gly Thr Val
    1325                1330                1335

Leu Asp Gln Ala Glu Thr Ala Gly Val Arg Leu Thr Val Leu Ala
    1340                1345                1350

Thr Ala Thr Pro Pro Gly Ser Val Thr Thr Pro His Pro Asp Ile
    1355                1360                1365

Glu Glu Val Gly Leu Gly Arg Glu Gly Glu Ile Pro Phe Tyr Gly
    1370                1375                1380

Arg Ala Ile Pro Leu Ser Cys Ile Lys Gly Gly Arg His Leu Ile
    1385                1390                1395
```

-continued

```
Phe Cys His Ser Lys Lys Lys Cys Asp Glu Leu Ala Ala Ala Leu
    1400            1405                1410

Arg Gly Met Gly Leu Asn Ala Val Ala Tyr Tyr Arg Gly Leu Asp
    1415            1420                1425

Val Ser Ile Ile Pro Ala Gln Gly Asp Val Val Val Ala Thr
    1430            1435                1440

Asp Ala Leu Met Thr Gly Tyr Thr Gly Asp Phe Asp Ser Val Ile
    1445            1450                1455

Asp Cys Asn Val Ala Val Thr Gln Ala Val Asp Phe Ser Leu Asp
    1460            1465                1470

Pro Thr Phe Thr Ile Thr Thr Gln Thr Val Pro Gln Asp Ala Val
    1475            1480                1485

Ser Arg Ser Gln Arg Arg Gly Arg Thr Gly Arg Gly Arg Gln Gly
    1490            1495                1500

Thr Tyr Arg Tyr Val Ser Thr Gly Glu Arg Ala Ser Gly Met Phe
    1505            1510                1515

Asp Ser Val Val Leu Cys Glu Cys Tyr Asp Ala Gly Ala Ala Trp
    1520            1525                1530

Tyr Asp Leu Thr Pro Ala Glu Thr Thr Val Arg Leu Arg Ala Tyr
    1535            1540                1545

Phe Asn Thr Pro Gly Leu Pro Val Cys Gln Asp His Leu Glu Phe
    1550            1555                1560

Trp Glu Ala Val Phe Thr Gly Leu Thr His Ile Asp Ala His Phe
    1565            1570                1575

Leu Ser Gln Thr Lys Gln Ala Gly Glu Asn Phe Ala Tyr Leu Val
    1580            1585                1590

Ala Tyr Gln Ala Thr Val Cys Ala Arg Ala Lys Ala Pro Pro Pro
    1595            1600                1605

Ser Trp Asp Ala Met Trp Lys Cys Leu Ala Arg Leu Lys Pro Thr
    1610            1615                1620

Leu Ala Gly Pro Thr Pro Leu Leu Tyr Arg Leu Gly Pro Ile Thr
    1625            1630                1635

Asn Glu Val Thr Leu Thr His Pro Gly Thr Lys Tyr Ile Ala Thr
    1640            1645                1650

Cys Met Gln Ala Asp Leu Glu Val Met Thr Ser Thr Trp Val Leu
    1655            1660                1665

Ala Gly Gly Val Leu Ala Ala Val Ala Ala Tyr Cys Leu Ala Thr
    1670            1675                1680

Gly Cys Val Ser Ile Ile Gly Arg Leu His Val Asn Gln Arg Val
    1685            1690                1695

Val Val Ala Pro Asp Lys Glu Val Leu Tyr Glu Ala Phe Asp Glu
    1700            1705                1710

Met Glu Glu Cys Ala Ser Arg Ala Ala Leu Ile Glu Glu Gly Gln
    1715            1720                1725

Arg Ile Ala Glu Met Leu Lys Ser Lys Ile Gln Gly Leu Leu Gln
    1730            1735                1740

Gln Ala Ser Lys Gln Ala Gln Asp Ile Gln Pro Ala Met Gln Ala
    1745            1750                1755

Ser Trp Pro Lys Val Glu Gln Phe Trp Ala Arg His Met Trp Asn
    1760            1765                1770

Phe Ile Ser Gly Ile Gln Tyr Leu Ala Gly Leu Ser Thr Leu Pro
    1775            1780                1785
```

```
Gly Asn Pro Ala Val Ala Ser Met Met Ala Phe Ser Ala Ala Leu
    1790            1795                1800

Thr Ser Pro Leu Ser Thr Ser Thr Thr Ile Leu Leu Asn Ile Met
    1805            1810                1815

Gly Gly Trp Leu Ala Ser Gln Ile Ala Pro Pro Ala Gly Ala Thr
    1820            1825                1830

Gly Phe Val Val Ser Gly Leu Val Gly Ala Ala Val Gly Ser Ile
    1835            1840                1845

Gly Leu Gly Lys Val Leu Val Asp Ile Leu Ala Gly Tyr Gly Ala
    1850            1855                1860

Gly Ile Ser Gly Ala Leu Val Ala Phe Lys Ile Met Ser Gly Glu
    1865            1870                1875

Lys Pro Ser Met Glu Asp Val Ile Asn Leu Leu Pro Gly Ile Leu
    1880            1885                1890

Ser Pro Gly Ala Leu Val Val Gly Val Ile Cys Ala Ala Ile Leu
    1895            1900                1905

Arg Arg His Val Gly Pro Gly Glu Gly Ala Val Gln Trp Met Asn
    1910            1915                1920

Arg Leu Ile Ala Phe Ala Ser Arg Gly Asn His Val Ala Pro Thr
    1925            1930                1935

His Tyr Val Thr Glu Ser Asp Ala Ser Gln Arg Val Thr Gln Leu
    1940            1945                1950

Leu Gly Ser Leu Thr Ile Thr Ser Leu Leu Arg Arg Leu His Asn
    1955            1960                1965

Trp Ile Thr Glu Asp Cys Pro Ile Pro Cys Ser Gly Ser Trp Leu
    1970            1975                1980

Arg Asp Val Trp Asp Trp Val Cys Thr Ile Leu Thr Asp Phe Lys
    1985            1990                1995

Asn Trp Leu Thr Ser Lys Leu Phe Pro Lys Leu Pro Gly Leu Pro
    2000            2005                2010

Phe Ile Ser Cys Gln Lys Gly Tyr Lys Gly Val Trp Ala Gly Thr
    2015            2020                2025

Gly Ile Met Thr Thr Arg Cys Pro Cys Gly Ala Asn Ile Ser Gly
    2030            2035                2040

Asn Val Arg Leu Gly Ser Met Arg Ile Thr Gly Pro Lys Thr Cys
    2045            2050                2055

Met Asn Thr Trp Gln Gly Thr Phe Pro Ile Asn Cys Tyr Thr Glu
    2060            2065                2070

Gly Gln Cys Ala Pro Lys Pro Pro Thr Asn Tyr Lys Thr Ala Ile
    2075            2080                2085

Trp Arg Val Ala Ala Ser Glu Tyr Ala Glu Val Thr Gln His Gly
    2090            2095                2100

Ser Tyr Ser Tyr Val Thr Gly Leu Thr Thr Asp Asn Leu Lys Ile
    2105            2110                2115

Pro Cys Gln Leu Pro Ser Pro Glu Phe Phe Ser Trp Val Asp Gly
    2120            2125                2130

Val Gln Ile His Arg Phe Ala Pro Thr Pro Lys Pro Phe Phe Arg
    2135            2140                2145

Asp Glu Val Ser Phe Cys Val Gly Leu Asn Ser Tyr Ala Val Gly
    2150            2155                2160

Ser Gln Leu Pro Cys Glu Pro Glu Pro Asp Ala Asp Val Leu Arg
    2165            2170                2175

Ser Met Leu Thr Asp Pro Pro His Ile Thr Ala Glu Thr Ala Ala
```

-continued

```
                2180                2185                2190
Arg Arg Leu Ala Arg Gly Ser Pro Pro Ser Glu Ala Ser Ser Ser
        2195                2200                2205
Val Ser Gln Leu Ser Ala Pro Ser Leu Arg Ala Thr Cys Thr Thr
        2210                2215                2220
His Ser Asn Thr Tyr Asp Val Asp Met Val Asp Ala Asn Leu Leu
        2225                2230                2235
Met Glu Gly Gly Val Ala Gln Thr Glu Pro Glu Ser Arg Val Pro
        2240                2245                2250
Val Leu Asp Phe Leu Glu Pro Met Ala Glu Glu Ser Asp Leu
        2255                2260                2265
Glu Pro Ser Ile Pro Ser Glu Cys Met Leu Pro Arg Ser Gly Phe
        2270                2275                2280
Pro Arg Ala Leu Pro Ala Trp Ala Arg Pro Asp Tyr Asn Pro Pro
        2285                2290                2295
Leu Val Glu Ser Trp Arg Arg Pro Asp Tyr Gln Pro Pro Thr Val
        2300                2305                2310
Ala Gly Cys Ala Leu Pro Pro Lys Lys Ala Pro Thr Pro Pro
        2315                2320                2325
Pro Arg Arg Arg Arg Thr Val Gly Leu Ser Glu Ser Thr Ile Ser
        2330                2335                2340
Glu Ala Leu Gln Gln Leu Ala Ile Lys Thr Phe Gly Gln Pro Pro
        2345                2350                2355
Ser Ser Gly Asp Ala Gly Ser Ser Thr Gly Ala Gly Ala Ala Glu
        2360                2365                2370
Ser Gly Gly Pro Thr Ser Pro Gly Glu Pro Ala Pro Ser Glu Thr
        2375                2380                2385
Gly Ser Ala Ser Ser Met Pro Pro Leu Glu Gly Glu Pro Gly Asp
        2390                2395                2400
Pro Asp Leu Glu Ser Asp Gln Val Glu Leu Gln Pro Pro Pro Gln
        2405                2410                2415
Gly Gly Gly Val Ala Pro Gly Ser Gly Ser Gly Ser Trp Ser Thr
        2420                2425                2430
Cys Ser Glu Glu Asp Asp Thr Thr Val Cys Cys Ser Met Ser Tyr
        2435                2440                2445
Ser Trp Thr Gly Ala Leu Ile Thr Pro Cys Ser Pro Glu Glu Glu
        2450                2455                2460
Lys Leu Pro Ile Asn Pro Leu Ser Asn Ser Leu Leu Arg Tyr His
        2465                2470                2475
Asn Lys Val Tyr Cys Thr Thr Ser Lys Ser Ala Ser Gln Arg Ala
        2480                2485                2490
Lys Lys Val Thr Phe Asp Arg Thr Gln Val Leu Asp Ala His Tyr
        2495                2500                2505
Asp Ser Val Leu Lys Asp Ile Lys Leu Ala Ala Ser Lys Val Ser
        2510                2515                2520
Ala Arg Leu Leu Thr Leu Glu Glu Ala Cys Gln Leu Thr Pro Pro
        2525                2530                2535
His Ser Ala Arg Ser Lys Tyr Gly Phe Gly Ala Lys Glu Val Arg
        2540                2545                2550
Ser Leu Ser Gly Arg Ala Val Asn His Ile Lys Ser Val Trp Lys
        2555                2560                2565
Asp Leu Leu Glu Asp Pro Gln Thr Pro Ile Pro Thr Thr Ile Met
        2570                2575                2580
```

-continued

```
Ala Lys Asn Glu Val Phe Cys Val Asp Pro Ala Lys Gly Gly Lys
2585                2590                2595

Lys Pro Ala Arg Leu Ile Val Tyr Pro Asp Leu Gly Val Arg Val
2600                2605                2610

Cys Glu Lys Met Ala Leu Tyr Asp Ile Thr Gln Lys Leu Pro Gln
2615                2620                2625

Ala Val Met Gly Ala Ser Tyr Gly Phe Gln Tyr Ser Pro Ala Gln
2630                2635                2640

Arg Val Glu Tyr Leu Leu Lys Ala Trp Ala Glu Lys Lys Asp Pro
2645                2650                2655

Met Gly Phe Ser Tyr Asp Thr Arg Cys Phe Asp Ser Thr Val Thr
2660                2665                2670

Glu Arg Asp Ile Arg Thr Glu Glu Ser Ile Tyr Gln Ala Cys Ser
2675                2680                2685

Leu Pro Glu Glu Ala Arg Thr Ala Ile His Ser Leu Thr Glu Arg
2690                2695                2700

Leu Tyr Val Gly Gly Pro Met Phe Asn Ser Lys Gly Gln Thr Cys
2705                2710                2715

Gly Tyr Arg Arg Cys Arg Ala Ser Gly Val Leu Thr Thr Ser Met
2720                2725                2730

Gly Asn Thr Ile Thr Cys Tyr Val Lys Ala Leu Ala Ala Cys Lys
2735                2740                2745

Ala Ala Gly Ile Val Ala Pro Thr Met Leu Val Cys Gly Asp Asp
2750                2755                2760

Leu Val Val Ile Ser Glu Ser Gln Gly Thr Glu Glu Asp Glu Arg
2765                2770                2775

Asn Leu Arg Ala Phe Thr Glu Ala Met Thr Arg Tyr Ser Ala Pro
2780                2785                2790

Pro Gly Asp Pro Pro Arg Pro Glu Tyr Asp Leu Glu Leu Ile Thr
2795                2800                2805

Ser Cys Ser Ser Asn Val Ser Val Ala Leu Gly Pro Arg Gly Arg
2810                2815                2820

Arg Arg Tyr Tyr Leu Thr Arg Asp Pro Thr Thr Pro Leu Ala Arg
2825                2830                2835

Ala Ala Trp Glu Thr Val Arg His Ser Pro Ile Asn Ser Trp Leu
2840                2845                2850

Gly Asn Ile Ile Gln Tyr Ala Pro Thr Ile Trp Val Arg Met Val
2855                2860                2865

Leu Met Thr His Phe Phe Ser Ile Leu Met Val Gln Asp Thr Leu
2870                2875                2880

Asp Gln Asn Leu Asn Phe Glu Met Tyr Gly Ser Val Tyr Ser Val
2885                2890                2895

Asn Pro Leu Asp Leu Pro Ala Ile Ile Glu Arg Leu His Gly Leu
2900                2905                2910

Asp Ala Phe Ser Met His Thr Tyr Ser His His Glu Leu Thr Arg
2915                2920                2925

Val Ala Ser Ala Leu Arg Lys Leu Gly Ala Pro Pro Leu Arg Val
2930                2935                2940

Trp Lys Ser Arg Ala Arg Ala Val Arg Ala Ser Leu Ile Ser Arg
2945                2950                2955

Gly Gly Lys Ala Ala Val Cys Gly Arg Tyr Leu Phe Asn Trp Ala
2960                2965                2970
```

```
Val Lys Thr Lys Leu Lys Leu Thr Pro Leu Pro Glu Ala Arg Leu
    2975                2980                2985

Leu Asp Leu Ser Ser Trp Phe Thr Val Gly Ala Gly Gly Gly Asp
    2990                2995                3000

Ile Phe His Ser Val Ser Arg Ala Arg Pro Arg Ser Leu Leu Phe
    3005                3010                3015

Gly Leu Leu Leu Leu Phe Val Gly Val Gly Leu Phe Leu Leu Pro
    3020                3025                3030

Ala Arg
    3035

<210> SEQ ID NO 17
<211> LENGTH: 9684
<212> TYPE: DNA
<213> ORGANISM: Hepatitis C virus

<400> SEQUENCE: 17
acctgcccct aatagggggcg acactccgcc atgaatcact cccctgtgag gaactactgt     60
cttcacgcag aaagcgccta gccatggcgt tagtatgagt gtcgtacagc ctccaggccc    120 cccctcccg  ggagagccat agtggtctgc ggaaccggtg agtacaccgg aattgccggg    180 aagactggt  cctttcttgg ataaacccac tctatgcccg ccatttgggg cgtgccccg     240 caagactgct agccgagtag cgttgggttg cgaaaggcct tgtggtactg cctgataggg    300
tgcttgcgag tgccccggga ggtctcgtag accgtgcacc atgagcacac ttcctaaacc    360
tcaaagaaaa accaaaagaa acaccatccg tcgcccacag gacgttaagt tcccgggtgg    420
cggacagatc gttggtggag tatacgtgtt gccgcgcagg ggcccacgat tgggtgtgcg    480
cgcgacgcgt aaaacttctg aacggtcaca gcctcgcgga cgacgacagc ctatccccaa    540
ggcgcgtcgg agcgaaggcc ggtcctgggc tcagcccggg tacccttggc ccctctatgg    600
taatgagggc tgcggggtggg caggtggct  cctgtcccg  cgcggctccc gtccatcttg    660
gggcccaaac gacccccggc ggaggtcccg caatttgggt aaagtcatcg ataccctttac    720 gtgcggattc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agccttttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgttttatt accataagtt   1680
```

| | |
|---|---|
| caactctact ggatgtcctc aaaggcttag cagctgcaag cccatcattt ccttcaggca | 1740 |
| ggggtggggc cccttgacag atgctaacat caccggtcct tctgatgata gaccgtattg | 1800 |
| ctggcactac gcacctagac cttgtagtgt tgtcccggca tcaagtgtct gcggccctgt | 1860 |
| gtactgcttc acaccatcgc cagtggtcgt aggcactact gatatcaaag gcaagccgac | 1920 |
| ctacaactgg ggtgagaatg agacagatgt gttcctgctg gagtccctgc ggcctcccag | 1980 |
| tggccggtgt tttggatgcg cgtggatgaa ctccacgggg ttcctcaaga cgtgtgggagc | 2040 |
| tccccttgt aacatctatg ggggtgaggg ggatcccgaa aatgagacag acctcttctg | 2100 |
| ccccaccgac tgcttcagga aacatcctga ggccacatac agccggtgtg gtgcggggcc | 2160 |
| ctggttgaca cctcgctgca tggtcgacta tccataccgg ctttggcatt acccatgtac | 2220 |
| agtcaatttc acattgttca aggtgaggat gtttgtgggc ggatttgaac accggtttac | 2280 |
| cgccgcttgt aactggacca ggggggagcg ctgcaatatc gaggatcgtg atcgcagcga | 2340 |
| gcaacatccg ctgctgcatt caacaactga gcttgctata ctgccttgct ctttcacgcc | 2400 |
| catgcctgca ttgtcaacag gtctaataca cctccaccaa aatatcgtgg atgtccaata | 2460 |
| cctttatggt gttggatctg acatggtggg atgggcgctg aaatgggagt tcgtcatcct | 2520 |
| cgttttcctc ctcctggcag acgcacgcgt gtgcgttgcc ctttggctga tgctgatggt | 2580 |
| atcacaagca gaagcagcct tggagaacct tgtcacgctg aacgccgtcg ctgctgctgg | 2640 |
| gacacatggt attggttggt acctggtagc cttttgcgcg cgtggtacg tgcggggtaa | 2700 |
| acttgtcccg ctgacgatct acggcctgac gggtctttgg tccctagcat tgcttgtcct | 2760 |
| cttgctcccc caacgggcgt atgcttggtc gggtgaagac agcgctactc tcggcgctgg | 2820 |
| ggtcttggcc ctcttcggct tctttacctt atcaccctgg tacaagcatt ggatcggccg | 2880 |
| cctcatgtgt tggaaccagt acactatatg tagatgcgag gccgcccttc aagtgtgggt | 2940 |
| cccccccctta cttgcacgcg ggagtaggga cggtgtcatc ctgctaacaa gcttgcttta | 3000 |
| tccatcctta attttttgaca tcactaagct gctgatagca gtaataggcc cattatactt | 3060 |
| aatacaggct gccatcacta ccacccccta ctttgtgcgc gcacatgtac tggtccgcct | 3120 |
| ttgcatgctc gtgcgctccg tgatgggggg aaagtacttc cagatggcca tactgagcat | 3180 |
| tggcagatgg ttcaacacct acctatatga ccacctagcg ccaatgcaac attgggccgc | 3240 |
| agctggcctc aaagacctag cagtggccac tgaacctgta atatttagtc ccatggaaat | 3300 |
| taaggtcatc acctggggcg cggacacagc ggcttgcgga gatattcttt gcgggctgcc | 3360 |
| ggtctccgcg cgattaggcc gtgaggtatt gttgggacct gctgatgatt atcgggaaat | 3420 |
| gggttggcgt ctgttggctc ccatcactgc ttatgcccag caaacacgag gcctcctggg | 3480 |
| cgccatagtg gtgagtatga cggggcgtga caggacagaa caggccgggg aagtccaaat | 3540 |
| cctgtccaca gtctctcagt ccttcctcgg aacaaccatc tcgggggttt tgtggactgt | 3600 |
| ttaccacgga gctggcaaca agactctagc cggcttacgg ggtccggtca cgcagatgta | 3660 |
| ctcgagtgct gagggggact tggtaggctg gcccagcccc cctgggacca agtctttgga | 3720 |
| gccgtgcaag tgtggagccg tcgacctata tctggtcacg cggaacgctg atgtcatccc | 3780 |
| ggctcggaga cgcggggaca agcggggagc attgctctcc ccgagaccca tttcgacctt | 3840 |
| gaaggggtcc tcgggggggc cggtgctctg ccctagggc cacgtcgttg ggctcttccg | 3900 |
| agcagctgtg tgctctcggg gcgtggcaa atccatcgat ttcatccccg ttgagacact | 3960 |
| cgacgttgtt acaaggtctc ccactttcag tgacaacagc acgccaccgg ctgtgcccca | 4020 |
| gacctatcag gtcgggtact tgcatgctcc aactggcagt ggaaagagca caaggtccc | 4080 |

```
tgtcgcgtat gccgcccagg ggtacaaagt actagtgctt aaccctcgg tagctgccac    4140 cctggggttt ggggcgtacc tatccaaggc acatggcatc aatcccaaca ttaggactgg    4200
agtcaggacc gtgatgaccg gggaggccat cacgtactcc acatatggca aatttctcgc    4260 cgatggggc tgcgctagcg gcgcctatga catcatcata tgcgatgaat gccacgctgt    4320
ggatgctacc tccattctcg gcatcggaac ggtccttgat caagcagaga cagccggggt    4380
cagactaact gtgctggcta cggccacacc ccccgggtca gtgacaaccc cccatcccga    4440
tatagaagag gtaggcctcg gcgggaggg tgagatcccc ttctatggga gggcgattcc    4500
cctatcctgc atcaagggag ggagacacct gattttctgc cactcaaagc aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgccggcc tacccgtgtg tcaagaccat cttgaattt gggaggcagt    5040 tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggcccctat taccaatgag gtcacccctca cacaccctgg    5280 gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggagc tggttagcgt cccagatcgc    5820
accacccgcg ggggccaccg gctttgtcgt cagtggcctg gtgggggctg ccgtgggcag    5880
cataggcctg gtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg gggtcatct gcgcggccat    6060 tctgcgccgc cacgtgggac cggggagg gcgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300 ggactgggt tgcaccatct tgacagactt caaaaattgg ctgacctcta aattgttccc    6360
caagctgccc ggcctccct tcatctcttg tcaaaagggg tacaagggtg tgtgggccgg    6420
```

```
cactggcatc atgaccacgc gctgcccttg cggcgccaac atctctggca atgtccgcct    6480
gggctctatg aggatcacag ggcctaaaac ctgcatgaac acctggcagg ggacctttcc    6540
tatcaattgc tacacggagg gccagtgcgc gccgaaaccc cccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
gcctgagtcc agggtgcccg ttctggactt tctcgagcca atggccgagg aagagagcga    7140
ccttgagccc tcaataccat cggagtgcat gctccccagg agcgggtttc cacgggcctt    7200
accggcttgg gcacggcctg actacaaccc gccgctcgtg gaatcgtgga ggaggccaga    7260
ttaccaaccg cccaccgttg ctggttgtgc tctcccccc cccaagaagg ccccgacgcc    7320
tcccccaagg agacgccgga cagtgggtct gagcgagagc accatatcag aagccctcca    7380
gcaactggcc atcaagacct ttggccagcc cccctcgagc ggtgatgcag gctcgtccac    7440
gggggcgggc gccgccgaat ccggcggtcc gacgtcccct ggtgagccgg cccctcaga    7500
gacaggttcc gcctcctcta tgcccccct cgagggggag cctggagatc cggacctgga    7560
gtctgatcag gtagagcttc aacctccccc ccagggggg ggggtagctc ccggttcggg    7620
ctcgggtct tggtctactt gctccgagga ggacgatacc accgtgtgct gctccatgtc    7680
atactcctgg accggggctc taataactcc ctgtagcccc gaagaggaaa agttgccaat    7740
caacccttg agtaactcgc tgttcgata ccataacaag gtgtactgta caacatcaaa    7800
gagcgcctca cagagggcta aaaaggtaac ttttgacagg acgcaagtgc tcgacgccca    7860
ttatgactca gtcttaaagg acatcaagct agcggcttcc aaggtcagcg caaggctcct    7920
caccttggag gaggcgtgcc agttgactcc acccccattct gcaagatcca agtatggatt    7980
cggggccaag gaggtccgca gcttgtccgg gagggccgtt aaccacatca agtccgtgtg    8040
gaaggacctc ctggaagacc cacaaacacc aattcccaca accatcatgg ccaaaaatga    8100
ggtgttctgc gtggacccg ccaaggggg taagaaacca gctcgcctca tcgtttaccc    8160
tgacctcggc gtccgggtct gcgagaaaat ggccctctat gacattacac aaaagcttcc    8220
tcaggcggta atgggagctt cctatggctt ccagtactcc cctgcccaac gggtggagta    8280
tctcttgaaa gcatgggcgg aaaagaagga ccccatgggt ttttcgtatg atacccgatg    8340
cttcgactca accgtcactg agagagacat caggaccgag gagtccatat accaggcctg    8400
ctccctgccc gaggaggccc gcactgccat acactcgctg actgagagac tttacgtagg    8460
agggcccatg ttcaacagca agggtcaaac ctgcggttac agacgttgcc gcgccagcgg    8520
ggtgctaacc actagcatgg gtaacaccat cacatgctat gtgaaagccc tagcggcctg    8580
caaggctgcg gggatagttg cgcccacaat gctggtatgc ggcgatgacc tagtagtcat    8640
ctcagaaagc caggggactg aggaggacga gcggaacctg agagccttca cggaggccat    8700
gaccaggtac tctgcccctc ctggtgatcc ccccagaccg gaatatgacc tggagctaat    8760
aacatcctgt tcctcaaatg tgtctgtggc gttgggcccg cggggccgcc gcagatacta    8820
```

```
cctgaccaga gacccaacca ctccactcgc ccgggctgcc tgggaaacag ttagacactc    8880
ccctatcaat tcatggctgg gaaacatcat ccagtatgct ccaaccatat gggttcgcat    8940
ggtcctaatg acacacttct tctccattct catggtccaa gacaccctgg accagaacct    9000
caactttgag atgtatggat cagtatactc cgtgaatcct ttggaccttc agccataat    9060 tgagaggtta cacgggcttg acgccttttc tatgcacaca tactctcacc acgaactgac    9120
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttcacag    9360 cgtgtcgcgc gcccgacccc gctcattact cttcggccta ctcctacttt cgtaggggt    9420 aggcctcttc ctactccccg ctcggtagag cggcacacac taggtacact ccatagctaa    9480
ctgttccttt tttttttttt tttttttttt tttttttttt tttttttttt cttttttttt    9540 ttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                          9684
```

<210> SEQ ID NO 18  
<211> LENGTH: 3035  
<212> TYPE: PRT  
<213> ORGANISM: Hepatitis C virus

<400> SEQUENCE: 18

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
```

```
              210                 215                 220
Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
                260                 265                 270

Ser Ala Leu Tyr Val Gly Asp Met Cys Gly Ala Val Phe Leu Val Gly
                275                 280                 285

Gln Ala Phe Thr Phe Arg Pro Arg His Gln Thr Val Gln Thr Cys
290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Ala His
                325                 330                 335

Ile Leu Arg Leu Pro Gln Thr Leu Phe Asp Ile Leu Ala Gly Ala His
                340                 345                 350

Trp Gly Ile Leu Ala Gly Leu Ala Tyr Tyr Ser Met Gln Gly Asn Trp
                355                 360                 365

Ala Lys Val Ala Ile Val Met Ile Met Phe Ser Gly Val Asp Ala Glu
370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
                435                 440                 445

Ser Thr Gly Cys Pro Gln Arg Leu Ser Ser Cys Lys Pro Ile Ile Ser
                450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
                500                 505                 510

Ser Pro Val Val Gly Thr Thr Asp Ile Lys Gly Lys Pro Thr Tyr
                515                 520                 525

Asn Trp Gly Glu Asn Glu Thr Asp Val Phe Leu Leu Glu Ser Leu Arg
530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
                580                 585                 590

Arg Lys His Pro Glu Ala Thr Tyr Ser Arg Cys Gly Ala Gly Pro Trp
                595                 600                 605

Leu Thr Pro Arg Cys Met Val Asp Tyr Pro Tyr Arg Leu Trp His Tyr
                610                 615                 620

Pro Cys Thr Val Asn Phe Thr Leu Phe Lys Val Arg Met Phe Val Gly
625                 630                 635                 640
```

```
Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Gly Thr
        755                 760                 765

His Gly Ile Gly Trp Tyr Leu Val Ala Phe Cys Ala Ala Trp Tyr Val
    770                 775                 780

Arg Gly Lys Leu Val Pro Leu Thr Ile Tyr Gly Leu Thr Gly Leu Trp
785                 790                 795                 800

Ser Leu Ala Leu Leu Val Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
    850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
            900                 905                 910

Thr Thr Thr Pro Tyr Phe Val Arg Ala His Val Leu Val Arg Leu Cys
        915                 920                 925

Met Leu Val Arg Ser Val Met Gly Gly Lys Tyr Phe Gln Met Ala Ile
    930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
        995                 1000                1005

Ser Ala Arg Leu Gly Arg Glu Val Leu Leu Gly Pro Ala Asp Asp
        1010                1015                1020

Tyr Arg Glu Met Gly Trp Arg Leu Leu Ala Pro Ile Thr Ala Tyr
        1025                1030                1035

Ala Gln Gln Thr Arg Gly Leu Leu Gly Ala Ile Val Val Ser Met
        1040                1045                1050
```

```
Thr Gly Arg Asp Arg Thr Glu Gln Ala Gly Glu Val Gln Ile Leu
    1055            1060            1065

Ser Thr Val Ser Gln Ser Phe Leu Gly Thr Thr Ile Ser Gly Val
    1070            1075            1080

Leu Trp Thr Val Tyr His Gly Ala Gly Asn Lys Thr Leu Ala Gly
    1085            1090            1095

Leu Arg Gly Pro Val Thr Gln Met Tyr Ser Ser Ala Glu Gly Asp
    1100            1105            1110

Leu Val Gly Trp Pro Ser Pro Pro Gly Thr Lys Ser Leu Glu Pro
    1115            1120            1125

Cys Lys Cys Gly Ala Val Asp Leu Tyr Leu Val Thr Arg Asn Ala
    1130            1135            1140

Asp Val Ile Pro Ala Arg Arg Gly Asp Lys Arg Gly Ala Leu
    1145            1150            1155

Leu Ser Pro Arg Pro Ile Ser Thr Leu Lys Gly Ser Ser Gly Gly
    1160            1165            1170

Pro Val Leu Cys Pro Arg Gly His Val Val Gly Leu Phe Arg Ala
    1175            1180            1185

Ala Val Cys Ser Arg Gly Val Ala Lys Ser Ile Asp Phe Ile Pro
    1190            1195            1200

Val Glu Thr Leu Asp Val Val Thr Arg Ser Pro Thr Phe Ser Asp
    1205            1210            1215

Asn Ser Thr Pro Pro Ala Val Pro Gln Thr Tyr Gln Val Gly Tyr
    1220            1225            1230

Leu His Ala Pro Thr Gly Ser Gly Lys Ser Thr Lys Val Pro Val
    1235            1240            1245

Ala Tyr Ala Ala Gln Gly Tyr Lys Val Leu Val Leu Asn Pro Ser
    1250            1255            1260

Val Ala Ala Thr Leu Gly Phe Gly Ala Tyr Leu Ser Lys Ala His
    1265            1270            1275

Gly Ile Asn Pro Asn Ile Arg Thr Gly Val Arg Thr Val Met Thr
    1280            1285            1290

Gly Glu Ala Ile Thr Tyr Ser Thr Tyr Gly Lys Phe Leu Ala Asp
    1295            1300            1305

Gly Gly Cys Ala Ser Gly Ala Tyr Asp Ile Ile Cys Asp Glu
    1310            1315            1320

Cys His Ala Val Asp Ala Thr Ser Ile Leu Gly Ile Gly Thr Val
    1325            1330            1335

Leu Asp Gln Ala Glu Thr Ala Gly Val Arg Leu Thr Val Leu Ala
    1340            1345            1350

Thr Ala Thr Pro Pro Gly Ser Val Thr Thr Pro His Pro Asp Ile
    1355            1360            1365

Glu Glu Val Gly Leu Gly Arg Glu Gly Glu Ile Pro Phe Tyr Gly
    1370            1375            1380

Arg Ala Ile Pro Leu Ser Cys Ile Lys Gly Gly Arg His Leu Ile
    1385            1390            1395

Phe Cys His Ser Lys Gln Lys Cys Asp Glu Leu Ala Ala Ala Leu
    1400            1405            1410

Arg Gly Met Gly Leu Asn Ala Val Ala Tyr Tyr Arg Gly Leu Asp
    1415            1420            1425

Val Ser Ile Ile Pro Ala Gln Gly Asp Val Val Val Ala Thr
    1430            1435            1440

Asp Ala Leu Met Thr Gly Tyr Thr Gly Asp Phe Asp Ser Val Ile
```

```
                    1445                1450                1455

Asp  Cys  Asn  Val  Ala  Val  Thr  Gln  Ala  Val  Asp  Phe  Ser  Leu  Asp
          1460                1465                1470

Pro  Thr  Phe  Thr  Ile  Thr  Thr  Gln  Thr  Val  Pro  Gln  Asp  Ala  Val
     1475                1480                1485

Ser  Arg  Ser  Gln  Arg  Arg  Gly  Arg  Thr  Gly  Arg  Gly  Arg  Gln  Gly
     1490                1495                1500

Thr  Tyr  Arg  Tyr  Val  Ser  Thr  Gly  Glu  Arg  Ala  Ser  Gly  Met  Phe
     1505                1510                1515

Asp  Ser  Val  Val  Leu  Cys  Glu  Cys  Tyr  Asp  Ala  Gly  Ala  Ala  Trp
     1520                1525                1530

Tyr  Asp  Leu  Thr  Pro  Ala  Glu  Thr  Thr  Val  Arg  Leu  Arg  Ala  Tyr
     1535                1540                1545

Phe  Asn  Thr  Pro  Gly  Leu  Pro  Val  Cys  Gln  Asp  His  Leu  Glu  Phe
     1550                1555                1560

Trp  Glu  Ala  Val  Phe  Thr  Gly  Leu  Thr  His  Ile  Asp  Ala  His  Phe
     1565                1570                1575

Leu  Ser  Gln  Thr  Lys  Gln  Ala  Gly  Glu  Asn  Phe  Ala  Tyr  Leu  Val
     1580                1585                1590

Ala  Tyr  Gln  Ala  Thr  Val  Cys  Ala  Arg  Ala  Lys  Ala  Pro  Pro  Pro
     1595                1600                1605

Ser  Trp  Asp  Ala  Met  Trp  Lys  Cys  Leu  Ala  Arg  Leu  Lys  Pro  Thr
     1610                1615                1620

Leu  Ala  Gly  Pro  Thr  Pro  Leu  Leu  Tyr  Arg  Leu  Gly  Pro  Ile  Thr
     1625                1630                1635

Asn  Glu  Val  Thr  Leu  Thr  His  Pro  Gly  Thr  Lys  Tyr  Ile  Ala  Thr
     1640                1645                1650

Cys  Met  Gln  Ala  Asp  Leu  Glu  Val  Met  Thr  Ser  Thr  Trp  Val  Leu
     1655                1660                1665

Ala  Gly  Gly  Val  Leu  Ala  Ala  Val  Ala  Ala  Tyr  Cys  Leu  Ala  Thr
     1670                1675                1680

Gly  Cys  Val  Ser  Ile  Ile  Gly  Arg  Leu  His  Val  Asn  Gln  Arg  Val
     1685                1690                1695

Val  Val  Ala  Pro  Asp  Lys  Glu  Val  Leu  Tyr  Glu  Ala  Phe  Asp  Glu
     1700                1705                1710

Met  Glu  Glu  Cys  Ala  Ser  Arg  Ala  Ala  Leu  Ile  Glu  Glu  Gly  Gln
     1715                1720                1725

Arg  Ile  Ala  Glu  Met  Leu  Lys  Ser  Lys  Ile  Gln  Gly  Leu  Leu  Gln
     1730                1735                1740

Gln  Ala  Ser  Lys  Gln  Ala  Gln  Asp  Ile  Gln  Pro  Ala  Met  Gln  Ala
     1745                1750                1755

Ser  Trp  Pro  Lys  Val  Glu  Gln  Phe  Trp  Ala  Arg  His  Met  Trp  Asn
     1760                1765                1770

Phe  Ile  Ser  Gly  Ile  Gln  Tyr  Leu  Ala  Gly  Leu  Ser  Thr  Leu  Pro
     1775                1780                1785

Gly  Asn  Pro  Ala  Val  Ala  Ser  Met  Met  Ala  Phe  Ser  Ala  Ala  Leu
     1790                1795                1800

Thr  Ser  Pro  Leu  Ser  Thr  Ser  Thr  Thr  Ile  Leu  Leu  Asn  Ile  Met
     1805                1810                1815

Gly  Gly  Trp  Leu  Ala  Ser  Gln  Ile  Ala  Pro  Pro  Ala  Gly  Ala  Thr
     1820                1825                1830

Gly  Phe  Val  Val  Ser  Gly  Leu  Val  Gly  Ala  Ala  Val  Gly  Ser  Ile
     1835                1840                1845
```

```
Gly Leu Gly Lys Val Leu Val Asp Ile Leu Ala Gly Tyr Gly Ala
1850                1855                1860

Gly Ile Ser Gly Ala Leu Val Ala Phe Lys Ile Met Ser Gly Glu
1865                1870                1875

Lys Pro Ser Met Glu Asp Val Ile Asn Leu Leu Pro Gly Ile Leu
1880                1885                1890

Ser Pro Gly Ala Leu Val Val Gly Val Ile Cys Ala Ala Ile Leu
1895                1900                1905

Arg Arg His Val Gly Pro Gly Glu Gly Ala Val Gln Trp Met Asn
1910                1915                1920

Arg Leu Ile Ala Phe Ala Ser Arg Gly Asn His Val Ala Pro Thr
1925                1930                1935

His Tyr Val Thr Glu Ser Asp Ala Ser Gln Arg Val Thr Gln Leu
1940                1945                1950

Leu Gly Ser Leu Thr Ile Thr Ser Leu Leu Arg Arg Leu His Asn
1955                1960                1965

Trp Ile Thr Glu Asp Cys Pro Ile Pro Cys Ser Gly Ser Trp Leu
1970                1975                1980

Arg Asp Val Trp Asp Trp Val Cys Thr Ile Leu Thr Asp Phe Lys
1985                1990                1995

Asn Trp Leu Thr Ser Lys Leu Phe Pro Lys Leu Pro Gly Leu Pro
2000                2005                2010

Phe Ile Ser Cys Gln Lys Gly Tyr Lys Gly Val Trp Ala Gly Thr
2015                2020                2025

Gly Ile Met Thr Thr Arg Cys Pro Cys Gly Ala Asn Ile Ser Gly
2030                2035                2040

Asn Val Arg Leu Gly Ser Met Arg Ile Thr Gly Pro Lys Thr Cys
2045                2050                2055

Met Asn Thr Trp Gln Gly Thr Phe Pro Ile Asn Cys Tyr Thr Glu
2060                2065                2070

Gly Gln Cys Ala Pro Lys Pro Pro Thr Asn Tyr Lys Thr Ala Ile
2075                2080                2085

Trp Arg Val Ala Ala Ser Glu Tyr Ala Glu Val Thr Gln His Gly
2090                2095                2100

Ser Tyr Ser Tyr Val Thr Gly Leu Thr Thr Asp Asn Leu Lys Ile
2105                2110                2115

Pro Cys Gln Leu Pro Ser Pro Glu Phe Phe Ser Trp Val Asp Gly
2120                2125                2130

Val Gln Ile His Arg Phe Ala Pro Thr Pro Lys Pro Phe Phe Arg
2135                2140                2145

Asp Glu Val Ser Phe Cys Val Gly Leu Asn Ser Tyr Ala Val Gly
2150                2155                2160

Ser Gln Leu Pro Cys Glu Pro Glu Pro Asp Ala Asp Val Leu Arg
2165                2170                2175

Ser Met Leu Thr Asp Pro Pro His Ile Thr Ala Glu Thr Ala Ala
2180                2185                2190

Arg Arg Leu Ala Arg Gly Ser Pro Pro Ser Glu Ala Ser Ser Ser
2195                2200                2205

Val Ser Gln Leu Ser Ala Pro Ser Leu Arg Ala Thr Cys Thr Thr
2210                2215                2220

His Ser Asn Thr Tyr Asp Val Asp Met Val Asp Ala Asn Leu Leu
2225                2230                2235
```

```
Met Glu Gly Gly Val Ala Gln Thr Glu Pro Glu Ser Arg Val Pro
    2240                2245                2250

Val Leu Asp Phe Leu Glu Pro Met Ala Glu Glu Ser Asp Leu
    2255                2260                2265

Glu Pro Ser Ile Pro Ser Glu Cys Met Leu Pro Arg Ser Gly Phe
    2270                2275                2280

Pro Arg Ala Leu Pro Ala Trp Ala Arg Pro Asp Tyr Asn Pro Pro
    2285                2290                2295

Leu Val Glu Ser Trp Arg Arg Pro Asp Tyr Gln Pro Pro Thr Val
    2300                2305                2310

Ala Gly Cys Ala Leu Pro Pro Lys Lys Ala Pro Thr Pro Pro
    2315                2320                2325

Pro Arg Arg Arg Arg Thr Val Gly Leu Ser Glu Ser Thr Ile Ser
    2330                2335                2340

Glu Ala Leu Gln Gln Leu Ala Ile Lys Thr Phe Gly Gln Pro Pro
    2345                2350                2355

Ser Ser Gly Asp Ala Gly Ser Ser Thr Gly Ala Gly Ala Ala Glu
    2360                2365                2370

Ser Gly Gly Pro Thr Ser Pro Gly Glu Pro Ala Pro Ser Glu Thr
    2375                2380                2385

Gly Ser Ala Ser Ser Met Pro Pro Leu Glu Gly Glu Pro Gly Asp
    2390                2395                2400

Pro Asp Leu Glu Ser Asp Gln Val Glu Leu Gln Pro Pro Pro Gln
    2405                2410                2415

Gly Gly Gly Val Ala Pro Gly Ser Gly Ser Gly Ser Trp Ser Thr
    2420                2425                2430

Cys Ser Glu Glu Asp Asp Thr Thr Val Cys Cys Ser Met Ser Tyr
    2435                2440                2445

Ser Trp Thr Gly Ala Leu Ile Thr Pro Cys Ser Pro Glu Glu Glu
    2450                2455                2460

Lys Leu Pro Ile Asn Pro Leu Ser Asn Ser Leu Leu Arg Tyr His
    2465                2470                2475

Asn Lys Val Tyr Cys Thr Thr Ser Lys Ser Ala Ser Gln Arg Ala
    2480                2485                2490

Lys Lys Val Thr Phe Asp Arg Thr Gln Val Leu Asp Ala His Tyr
    2495                2500                2505

Asp Ser Val Leu Lys Asp Ile Lys Leu Ala Ala Ser Lys Val Ser
    2510                2515                2520

Ala Arg Leu Leu Thr Leu Glu Glu Ala Cys Gln Leu Thr Pro Pro
    2525                2530                2535

His Ser Ala Arg Ser Lys Tyr Gly Phe Gly Ala Lys Glu Val Arg
    2540                2545                2550

Ser Leu Ser Gly Arg Ala Val Asn His Ile Lys Ser Val Trp Lys
    2555                2560                2565

Asp Leu Leu Glu Asp Pro Gln Thr Pro Ile Pro Thr Thr Ile Met
    2570                2575                2580

Ala Lys Asn Glu Val Phe Cys Val Asp Pro Ala Lys Gly Gly Lys
    2585                2590                2595

Lys Pro Ala Arg Leu Ile Val Tyr Pro Asp Leu Gly Val Arg Val
    2600                2605                2610

Cys Glu Lys Met Ala Leu Tyr Asp Ile Thr Gln Lys Leu Pro Gln
    2615                2620                2625

Ala Val Met Gly Ala Ser Tyr Gly Phe Gln Tyr Ser Pro Ala Gln
```

-continued

```
            2630                2635                2640
Arg Val Glu Tyr Leu Leu Lys Ala Trp Ala Glu Lys Lys Asp Pro
            2645                2650                2655
Met Gly Phe Ser Tyr Asp Thr Arg Cys Phe Asp Ser Thr Val Thr
            2660                2665                2670
Glu Arg Asp Ile Arg Thr Glu Glu Ser Ile Tyr Gln Ala Cys Ser
            2675                2680                2685
Leu Pro Glu Glu Ala Arg Thr Ala Ile His Ser Leu Thr Glu Arg
            2690                2695                2700
Leu Tyr Val Gly Gly Pro Met Phe Asn Ser Lys Gly Gln Thr Cys
            2705                2710                2715
Gly Tyr Arg Arg Cys Arg Ala Ser Gly Val Leu Thr Thr Ser Met
            2720                2725                2730
Gly Asn Thr Ile Thr Cys Tyr Val Lys Ala Leu Ala Ala Cys Lys
            2735                2740                2745
Ala Ala Gly Ile Val Ala Pro Thr Met Leu Val Cys Gly Asp Asp
            2750                2755                2760
Leu Val Val Ile Ser Glu Ser Gln Gly Thr Glu Glu Asp Glu Arg
            2765                2770                2775
Asn Leu Arg Ala Phe Thr Glu Ala Met Thr Arg Tyr Ser Ala Pro
            2780                2785                2790
Pro Gly Asp Pro Pro Arg Pro Glu Tyr Asp Leu Glu Leu Ile Thr
            2795                2800                2805
Ser Cys Ser Ser Asn Val Ser Val Ala Leu Gly Pro Arg Gly Arg
            2810                2815                2820
Arg Arg Tyr Tyr Leu Thr Arg Asp Pro Thr Thr Pro Leu Ala Arg
            2825                2830                2835
Ala Ala Trp Glu Thr Val Arg His Ser Pro Ile Asn Ser Trp Leu
            2840                2845                2850
Gly Asn Ile Ile Gln Tyr Ala Pro Thr Ile Trp Val Arg Met Val
            2855                2860                2865
Leu Met Thr His Phe Phe Ser Ile Leu Met Val Gln Asp Thr Leu
            2870                2875                2880
Asp Gln Asn Leu Asn Phe Glu Met Tyr Gly Ser Val Tyr Ser Val
            2885                2890                2895
Asn Pro Leu Asp Leu Pro Ala Ile Ile Glu Arg Leu His Gly Leu
            2900                2905                2910
Asp Ala Phe Ser Met His Thr Tyr Ser His His Glu Leu Thr Arg
            2915                2920                2925
Val Ala Ser Ala Leu Arg Lys Leu Gly Ala Pro Pro Leu Arg Val
            2930                2935                2940
Trp Lys Ser Arg Ala Arg Ala Val Arg Ala Ser Leu Ile Ser Arg
            2945                2950                2955
Gly Gly Lys Ala Ala Val Cys Gly Arg Tyr Leu Phe Asn Trp Ala
            2960                2965                2970
Val Lys Thr Lys Leu Lys Leu Thr Pro Leu Pro Glu Ala Arg Leu
            2975                2980                2985
Leu Asp Leu Ser Ser Trp Phe Thr Val Gly Ala Gly Gly Gly Asp
            2990                2995                3000
Ile Phe His Ser Val Ser Arg Ala Arg Pro Arg Ser Leu Leu Phe
            3005                3010                3015
Gly Leu Leu Leu Leu Phe Val Gly Val Gly Leu Phe Leu Leu Pro
            3020                3025                3030
```

Ala Arg
   3035

<210> SEQ ID NO 19
<211> LENGTH: 9684
<212> TYPE: DNA
<213> ORGANISM: Hepatitis C virus

<400> SEQUENCE: 19

| | | | | | |
|---|---|---|---|---|---|
| acctgcccct | aatagggggcg | acactccgcc | atgaatcact | cccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gccatttggg | cgtgcccccg | 240 |
| caagactgct | agccgagtag | cgttgggttg | cgaaaggcct | tgtggtactg | cctgataggg | 300 |
| tgcttgcgag | tgccccggga | ggtctcgtag | accgtgcacc | atgagcacac | ttcctaaacc | 360 |
| tcaaagaaaa | accaaaagaa | acaccatccg | tcgcccacag | gacgttaagt | tcccgggtgg | 420 |
| cggacagatc | gttggtggag | tatacgtgtt | gccgcgcagg | ggcccacgat | tgggtgtgcg | 480 |
| cgcgacgcgt | aaaacttctg | aacggtcaca | gcctcgcgga | cgacgacagc | ctatccccaa | 540 |
| ggcgcgtcgg | agcgaaggcc | ggtcctgggc | tcagcccggg | tacccttggc | ccctctatgg | 600 |
| taatgagggc | tgcgggtggg | cagggtggct | cctgtccccg | cgcggctccc | gtccatcttg | 660 |
| gggcccaaac | gaccccggc | ggaggtcccg | caatttgggt | aaagtcatcg | ataccttac | 720 |
| gtgcggattc | gccgacctca | tggggtacat | cccgctcgtc | ggcgctcccg | taggaggcgt | 780 |
| cgcaagagcc | ctcgcgcatg | gcgtgagggc | ccttgaagac | gggataaatt | ttgcaacagg | 840 |
| gaacttgccc | ggttgctcct | tttctatctt | ccttcttgct | ctgttctcct | gcttagttca | 900 |
| tcctgcagct | agtcttgagt | ggcggaatac | gtctggcctc | tatgtcctta | ccaacgactg | 960 |
| ttccaatagc | agtattgtgt | atgaggccga | tgacgtcatt | ctgcacacac | ccggctgtgt | 1020 |
| accttgtgtt | caggacgaca | atacatccac | gtgctggacc | ccagtgacac | ctacggtggc | 1080 |
| agtcaggtac | gtcggagcaa | ccaccgcttc | gatacgcagt | catgtggacc | tattagtggg | 1140 |
| cgcggccacg | ctgtgctctg | cgctctatgt | gggtgatatg | tgtgggccg | tctttctcgt | 1200 |
| gggacaagcc | ttcacgttca | gacctcgtcg | ccatcaaacg | gtccagacct | gtaactgctc | 1260 |
| gctgtaccca | ggccatgttt | caggacatcg | aatggcttgg | gatatgatga | tgaattggtc | 1320 |
| ccccgctgtg | ggtatggtgg | tggcgcacat | cctgcgattg | ccccagacct | tgtttgacat | 1380 |
| actggccggg | gcccattggg | gcatcttggc | gggcctagcc | tattattcta | tgcagggcaa | 1440 |
| ctgggccaag | gtcgctattg | tcatgattat | gttttcaggg | gtcgatgctg | aaacatatgt | 1500 |
| caccggtggc | agtgtagctc | atagtgccag | agggttaact | agccttttta | gtatgggcgc | 1560 |
| caagcagaaa | ctgcaattgg | tcaacaccaa | tggctcgtgg | cacatcaaca | gtactgccct | 1620 |
| gaactgcaat | gagtccataa | acaccgggtt | catagctggg | ttgttttatt | accataagtt | 1680 |
| caactctact | ggatgtcctc | aaaggcttag | cagctgcaag | cccatcattt | ccttcaggca | 1740 |
| ggggtggggc | cccttgacag | atgctaacat | caccggtcct | tctgatgata | accgtattg | 1800 |
| ctggcactac | gcacctagac | cttgtagtgt | tgtcccggca | tcaagtgtct | gcggccctgt | 1860 |
| gtactgcttc | acaccatcgc | cagtggtcgt | aggcactact | gatatcaaag | gcaagccgac | 1920 |
| ctacaactgg | ggtgagaatg | agacagatgt | gttcctgctg | gagtccctgc | ggcctccag | 1980 |
| tggccggtgg | tttggatgcg | cgtggatgaa | ctccacgggg | ttcctcaaga | cgtgtggagc | 2040 |

```
tcccccttgt aacatctatg ggggtgaggg ggatcccgaa aatgagacag acctcttctg   2100
ccccaccgac tgcttcagga aacatcctga ggccacatac agccggtgtg gtgcggggcc   2160
ctggttgaca cctcgctgca tggtcgacta tccataccgg ctttggcatt acccatgtac   2220
agtcaatttc acattgttca aggtgaggat gtttgtgggc ggatttgaac accggtttac   2280
cgccgcttgt aactggacca ggggggagcg ctgcaatatc gaggatcgtg atcgcagcga   2340
gcaacatccg ctgctgcatt caacaactga gcttgctata ctgccttgct ctttcacgcc   2400
catgcctgca ttgtcaacag gtctaataca cctccaccaa aatatcgtgg atgtccaata   2460
cctttatggt gttggatctg acatggtggg atgggcgctg aaatgggagt tcgtcatcct   2520
cgttttcctc ctcctggcag acgcacgcgt gtgcgttgcc cttttggctga tgctgatggt   2580
atcacaagca gaagcagcct tggagaacct tgtcacgctg aacgccgtcg ctgctgctgg   2640
gacacatggt attggttggt acctggtagc cttttgcgcg gcgtggtacg tgcggggtaa   2700
acttgtcccg ctgacgagct acggcctgac gggtctttgg tccctagcat tgcttgtcct   2760
cttgctcccc caacgggcgt atgcttggtc gggtgaagac agcgctactc tcggcgctgg   2820
ggtcttggcc ctcttcggct tctttacctt atcaccctgg tacaagcatt ggatcggccg   2880
cctcatgtgg tggaaccagt acactatatg tagatgcgag gccgcccttc aagtgtgggt   2940
ccccccctta cttgcacgcg ggagtaggga cggtgtcatc ctgctaacaa gcttgcttta   3000
tccatcctta atttttgaca tcactaagct gctgatagca gtaataggcc cattatactt   3060
aatacaggct gccatcacta ccaccccta ctttgtgcgc gcacatgtac tggtccgcct   3120
ttgcatgctc gtgcgctccg tgatggggg aaagtacttc cagatggcca tactgagcat   3180
tggcagatgg ttcaacacct acctatatga ccacctagcg ccaatgcaac attgggccgc   3240
agctggcctc aaagacctag cagtggccac tgaacctgta atatttagtc ccatggaaat   3300
taaggtcatc acctggggcg cggacacagc ggcttgcgga gatattcttt gcggggctgcc   3360
ggtctccgcg cgattaggcc gtgaggtatt gttgggacct gctgatgatt atcgggaaat   3420
gggttggcgt ctgttggctc ccatcactgc ttatgcccag caaacacgag gcctcctggg   3480
cgccatagtg gtgagtatga cggggcgtga caggacagaa caggccgggg aagtccaaat   3540
cctgtccaca gtctctcagt ccttcctcgg aacaaccatc tcggggggttt tgtggactgt   3600
ttaccacgga gctggcaaca agactctagc cggcttacgg ggtccggtca cgcagatgta   3660
ctcgagtgct gaggggact tggtaggctg gcccagcccc cctgggacca agtctttgga   3720
gccgtgcaag tgtggagccg tcgacctata tctggtcacg cggaacgctg atgtcatccc   3780
ggctcggaga cgcggggaca agcggggagc attgctctcc ccgagaccca tttcgacctt   3840
gaagggcc tcggggggc cggtgctctg cccctagggc cacgtcgttg ggctcttccg   3900
agcagctgtg tgctctcggg gcgtggccaa atccatcgat ttcatccccg ttgagacact   3960
cgacgttgtt acaaggtctc ccactttcag tgacaacagc acgccaccgg ctgtgcccca   4020
gacctatcag gtcgggtact tgcatgctcc aactggcagt ggaaagagca ccaaggtccc   4080
tgtcgcgtat gccgcccagg gtacaaaagt actagtgctt aaccctcgg tagctgccac   4140
cctgggttt gggggcgtacc tatccaaggc acatggcatc aatcccaaca ttaggactgg   4200
agtcaggacc gtgatgaccg gggaggccat cacgtactcc acatatggca aatttctcgc   4260
cgatgggggc tgcgctagcg gcgccctatga catcatcata tgcgatgaat gccacgctgt   4320
ggatgctacc tccattctcg gcatcggaac ggtccttgat caagcagaga cagccggggt   4380
```

```
cagactaact gtgctggcta cggccacacc ccccgggtca gtgacaaccc cccatcccga    4440
tatagaagag gtaggcctcg ggcgggaggg tgagatcccc ttctatggga gggcgattcc    4500
cctatcctgc atcaagggag ggagacacct gattttctgc cactcaaaga aaaagtgtga    4560
cgagctcgcg gcggcccttc ggggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg cggctctca tcgaagaggg    5520
```

(Note: verifying line at 5520 — "cgcctctagg gcggctctca tcgaagaggg")

```
gcagcggata ccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820 accaccgcg ggggccaccg gctttgtcgt cagtggcctg gtgggggctg ccgtgggcag    5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggagagg cgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctccccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag gcctaaaac ctgcatgaac acctggcagg gacctttcc    6540 tatcaattgc tacacggagg ccagtgcgc gccgaaaccc ccacgaact acaagaccgc    6600 catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
```

```
ccgggatgag gtctcgttct gcgttgggct taattcctat gctgtcgggt cccagcttcc   6840
ctgtgaacct gagcccgacg cagacgtatt gaggtccatg ctaacagatc cgccccacat   6900
cacggcggag actgcggcgc ggcgcttggc acggggatca cctccatctg aggcgagctc   6960
ctcagtgagc cagctatcag caccgtcgct gcgggccacc tgcaccaccc acagcaacac   7020
ctatgacgtg gacatggtcg atgccaacct gctcatggag ggcggtgtgg ctcagacaga   7080
gcctgagtcc agggtgcccg ttctggactt tctcgagcca atggccgagg aagagagcga   7140
ccttgagccc tcaataccac cggagtgcat gctccccagg agcgggtttc cacgggcctt   7200
accggcttgg gcacggcctg actacaaccc gccgctcgtg aatcgtgga ggaggccaga    7260 ttaccaaccg cccaccgttg ctggttgtgc tctcccccc cccaagaagg ccccgacgcc    7320
tcccccaagg agacgccgga cagtgggtct gagcgagagc accatatcag aagccctcca   7380
gcaactggcc atcaagacct ttggccagcc cccctcgagc ggtgatgcag gctcgtccac   7440
gggggcgggc gccgccgaat ccggcggtcc gacgtcccct ggtgagccgg ccccctcaga   7500
gacaggttcc gcctcctcta tgccccccct cgagggggag cctggagatc cggacctgga   7560
gtctgatcag gtagagcttc aacctccccc ccagggggg ggggtagctc ccggttcggg    7620
ctcggggtct tggtctactt gctccgagga ggacgatacc accgtgtgct gctccatgtc   7680
atactcctgg accggggctc taataactcc ctgtagcccc gaagaggaaa agttgccaat   7740 caacccttg agtaactcgc tgttgcgata ccataacaag gtgtactgta caacatcaaa    7800
gagcgcctca cagagggcta aaaggtaac ttttgacagg acgcaagtgc tcgacgccca    7860
ttatgactca gtcttaaagg acatcaagct agcggcttcc aaggtcagcg caaggctcct   7920
caccttggag gaggcgtgcc agttgactcc accccattct gcaagatcca agtatggatt   7980
cggggccaag gaggtccgca gcttgtccgg gagggccgtt aaccacatca gtccgtgtg    8040 gaaggacctc ctggaagacc cacaaacacc aattcccaca accatcatgg ccaaaaatga   8100
ggtgttctgc gtggacccccg ccaagggggg taagaaacca gctcgcctca tcgtttaccc   8160
tgacctcggc gtccgggtct gcgagaaaat ggccctctat gacattacac aaaagcttcc   8220
tcaggcggta atgggagctt cctatggctt ccagtactcc cctgcccaac gggtggagta   8280
tctcttgaaa gcatgggcgg aaaagaagga ccccatgggt ttttcgtatg atacccgatg   8340
cttcgactca accgtcactg agagagacat caggaccgag gagtccatat accaggcctg   8400
ctccctgccc gaggaggccc gcactgccat acactcgctg actgagagac tttacgtagg   8460
agggcccatg ttcaacagca agggtcaaac ctgcggttac agacgttgcc gcgccagcgg   8520
ggtgctaacc actagcatgg gtaacaccat cacatgctat gtgaaagccc tagcggcctg   8580
caaggctgcg gggatagttg cgcccacaat gctggtatgc ggcgatgacc tagtagtcat   8640
ctcagaaagc caggggactg aggaggacga gcggaacctg agagccttca cggaggccat   8700
gaccaggtac tctgcccctc ctggtgatcc cccagaccg gaatatgacc tggagctaat    8760
aacatcctgt tcctcaaatg tgtctgtggc gttgggcccg cggggccgcc gcagatacta   8820
cctgaccaga gacccaacca ctccactcgc ccgggctgcc tgggaaacag ttagacactc   8880
ccctatcaat tcatggctgg gaaacatcat ccagtatgct ccaaccatat gggttcgcat   8940
ggtcctaatg acacacttct tctccattct catggtccaa gacaccctgg accagaacct   9000
caactttgag atgtatggat cagtatactc cgtgaatccc ttggaccttc agccataat    9060 tgagaggtta cacgggcttg acgccttttc tatgcacaca tactctcacc acgaactgac   9120
```

```
gcgggtggct tcagccctca gaaaacttgg ggcgccaccc ctcagggtgt ggaagagtcg    9180
ggctcgcgca gtcagggcgt ccctcatctc ccgtggaggg aaagcggccg tttgcggccg    9240
atatctcttc aattgggcgg tgaagaccaa gctcaaactc actccattgc cggaggcgcg    9300
cctactggac ttatccagtt ggttcaccgt cggcgccggc gggggcgaca ttttcacag    9360 cgtgtcgcgc gcccgacccc gctcattact cttcggccta ctcctacttt tcgtaggggt    9420
aggcctcttc ctactcccg ctcggtagag cggcacacac taggtacact ccatagctaa    9480
ctgttccttt tttttttttt tttttttttt tttttttttt tttttttttt ctttttttt    9540 tttttccctc tttcttccct tctcatctta ttctactttc tttcttggtg gctccatctt    9600
agccctagtc acggctagct gtgaaaggtc cgtgagccgc atgactgcag agagtgccgt    9660
aactggtctc tctgcagatc atgt                                          9684
```

<210> SEQ ID NO 20
<211> LENGTH: 3035
<212> TYPE: PRT
<213> ORGANISM: Hepatitis C virus

<400> SEQUENCE: 20

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270
```

-continued

```
Ser Ala Leu Tyr Val Gly Asp Met Cys Gly Ala Val Phe Leu Val Gly
            275                 280                 285
Gln Ala Phe Thr Phe Arg Pro Arg His Gln Thr Val Gln Thr Cys
290                 295                 300
Asn Cys Ser Leu Tyr Pro Gly His Val Ser Gly His Arg Met Ala Trp
305                 310                 315                 320
Asp Met Met Met Asn Trp Ser Pro Ala Val Gly Met Val Val Ala His
                325                 330                 335
Ile Leu Arg Leu Pro Gln Thr Leu Phe Asp Ile Leu Ala Gly Ala His
            340                 345                 350
Trp Gly Ile Leu Ala Gly Leu Ala Tyr Tyr Ser Met Gln Gly Asn Trp
        355                 360                 365
Ala Lys Val Ala Ile Val Met Ile Met Phe Ser Gly Val Asp Ala Glu
    370                 375                 380
Thr Tyr Val Thr Gly Gly Ser Val Ala His Ser Ala Arg Gly Leu Thr
385                 390                 395                 400
Ser Leu Phe Ser Met Gly Ala Lys Gln Lys Leu Gln Leu Val Asn Thr
                405                 410                 415
Asn Gly Ser Trp His Ile Asn Ser Thr Ala Leu Asn Cys Asn Glu Ser
            420                 425                 430
Ile Asn Thr Gly Phe Ile Ala Gly Leu Phe Tyr Tyr His Lys Phe Asn
        435                 440                 445
Ser Thr Gly Cys Pro Gln Arg Leu Ser Ser Cys Lys Pro Ile Ile Ser
    450                 455                 460
Phe Arg Gln Gly Trp Gly Pro Leu Thr Asp Ala Asn Ile Thr Gly Pro
465                 470                 475                 480
Ser Asp Asp Arg Pro Tyr Cys Trp His Tyr Ala Pro Arg Pro Cys Ser
                485                 490                 495
Val Val Pro Ala Ser Ser Val Cys Gly Pro Val Tyr Cys Phe Thr Pro
            500                 505                 510
Ser Pro Val Val Val Gly Thr Thr Asp Ile Lys Gly Lys Pro Thr Tyr
        515                 520                 525
Asn Trp Gly Glu Asn Glu Thr Asp Val Phe Leu Leu Glu Ser Leu Arg
    530                 535                 540
Pro Pro Ser Gly Arg Trp Phe Gly Cys Ala Trp Met Asn Ser Thr Gly
545                 550                 555                 560
Phe Leu Lys Thr Cys Gly Ala Pro Pro Cys Asn Ile Tyr Gly Gly Glu
                565                 570                 575
Gly Asp Pro Glu Asn Glu Thr Asp Leu Phe Cys Pro Thr Asp Cys Phe
            580                 585                 590
Arg Lys His Pro Glu Ala Thr Tyr Ser Arg Cys Gly Ala Gly Pro Trp
        595                 600                 605
Leu Thr Pro Arg Cys Met Val Asp Tyr Pro Tyr Arg Leu Trp His Tyr
    610                 615                 620
Pro Cys Thr Val Asn Phe Thr Leu Phe Lys Val Arg Met Phe Val Gly
625                 630                 635                 640
Gly Phe Glu His Arg Phe Thr Ala Ala Cys Asn Trp Thr Arg Gly Glu
                645                 650                 655
Arg Cys Asn Ile Glu Asp Arg Asp Arg Ser Gln His Pro Leu Leu
            660                 665                 670
His Ser Thr Thr Glu Leu Ala Ile Leu Pro Cys Ser Phe Thr Pro Met
        675                 680                 685
Pro Ala Leu Ser Thr Gly Leu Ile His Leu His Gln Asn Ile Val Asp
```

```
                690                 695                 700
Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Val Ser Gln Ala Glu Ala
                740                 745                 750

Ala Leu Glu Asn Leu Val Thr Leu Asn Ala Val Ala Ala Gly Thr
                755                 760                 765

His Gly Ile Gly Trp Tyr Leu Val Ala Phe Cys Ala Ala Trp Tyr Val
                770                 775                 780

Arg Gly Lys Leu Val Pro Leu Thr Ser Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
                820                 825                 830

Gly Phe Phe Thr Leu Ser Pro Trp Tyr Lys His Trp Ile Gly Arg Leu
                835                 840                 845

Met Trp Trp Asn Gln Tyr Thr Ile Cys Arg Cys Glu Ala Ala Leu Gln
                850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
                900                 905                 910

Thr Thr Thr Pro Tyr Phe Val Arg Ala His Val Leu Val Arg Leu Cys
                915                 920                 925

Met Leu Val Arg Ser Val Met Gly Gly Lys Tyr Phe Gln Met Ala Ile
                930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
                980                 985                 990

Gly Ala Asp Thr Ala Ala Cys Gly Asp Ile Leu Cys Gly Leu Pro Val
                995                 1000                1005

Ser Ala Arg Leu Gly Arg Glu Val Leu Leu Gly Pro Ala Asp Asp
                1010                1015                1020

Tyr Arg Glu Met Gly Trp Arg Leu Leu Ala Pro Ile Thr Ala Tyr
                1025                1030                1035

Ala Gln Gln Thr Arg Gly Leu Leu Gly Ala Ile Val Ser Met
                1040                1045                1050

Thr Gly Arg Asp Arg Thr Glu Gln Ala Gly Glu Val Gln Ile Leu
                1055                1060                1065

Ser Thr Val Ser Gln Ser Phe Leu Gly Thr Ile Ser Gly Val
                1070                1075                1080

Leu Trp Thr Val Tyr His Gly Ala Gly Asn Lys Thr Leu Ala Gly
                1085                1090                1095

Leu Arg Gly Pro Val Thr Gln Met Tyr Ser Ser Ala Glu Gly Asp
                1100                1105                1110
```

-continued

```
Leu Val Gly Trp Pro Ser Pro Pro Gly Thr Lys Ser Leu Glu Pro
1115                1120                1125

Cys Lys Cys Gly Ala Val Asp Leu Tyr Leu Val Thr Arg Asn Ala
1130                1135                1140

Asp Val Ile Pro Ala Arg Arg Gly Asp Lys Arg Gly Ala Leu
1145                1150                1155

Leu Ser Pro Arg Pro Ile Ser Thr Leu Lys Gly Ser Ser Gly Gly
1160                1165                1170

Pro Val Leu Cys Pro Arg Gly His Val Val Gly Leu Phe Arg Ala
1175                1180                1185

Ala Val Cys Ser Arg Gly Val Ala Lys Ser Ile Asp Phe Ile Pro
1190                1195                1200

Val Glu Thr Leu Asp Val Val Thr Arg Ser Pro Thr Phe Ser Asp
1205                1210                1215

Asn Ser Thr Pro Pro Ala Val Pro Gln Thr Tyr Gln Val Gly Tyr
1220                1225                1230

Leu His Ala Pro Thr Gly Ser Gly Lys Ser Thr Lys Val Pro Val
1235                1240                1245

Ala Tyr Ala Ala Gln Gly Tyr Lys Val Leu Val Leu Asn Pro Ser
1250                1255                1260

Val Ala Ala Thr Leu Gly Phe Gly Ala Tyr Leu Ser Lys Ala His
1265                1270                1275

Gly Ile Asn Pro Asn Ile Arg Thr Gly Val Arg Thr Val Met Thr
1280                1285                1290

Gly Glu Ala Ile Thr Tyr Ser Thr Tyr Gly Lys Phe Leu Ala Asp
1295                1300                1305

Gly Gly Cys Ala Ser Gly Ala Tyr Asp Ile Ile Ile Cys Asp Glu
1310                1315                1320

Cys His Ala Val Asp Ala Thr Ser Ile Leu Gly Ile Gly Thr Val
1325                1330                1335

Leu Asp Gln Ala Glu Thr Ala Gly Val Arg Leu Thr Val Leu Ala
1340                1345                1350

Thr Ala Thr Pro Pro Gly Ser Val Thr Thr Pro His Pro Asp Ile
1355                1360                1365

Glu Glu Val Gly Leu Gly Arg Glu Gly Glu Ile Pro Phe Tyr Gly
1370                1375                1380

Arg Ala Ile Pro Leu Ser Cys Ile Lys Gly Gly Arg His Leu Ile
1385                1390                1395

Phe Cys His Ser Lys Lys Lys Cys Asp Glu Leu Ala Ala Ala Leu
1400                1405                1410

Arg Gly Met Gly Leu Asn Ala Val Ala Tyr Tyr Arg Gly Leu Asp
1415                1420                1425

Val Ser Ile Ile Pro Ala Gln Gly Asp Val Val Val Ala Thr
1430                1435                1440

Asp Ala Leu Met Thr Gly Tyr Thr Gly Asp Phe Asp Ser Val Ile
1445                1450                1455

Asp Cys Asn Val Ala Val Thr Gln Ala Val Asp Phe Ser Leu Asp
1460                1465                1470

Pro Thr Phe Thr Ile Thr Thr Gln Thr Val Pro Gln Asp Ala Val
1475                1480                1485

Ser Arg Ser Gln Arg Arg Gly Arg Thr Gly Arg Gly Arg Gln Gly
1490                1495                1500
```

```
Thr Tyr Arg Tyr Val Ser Thr Gly Glu Arg Ala Ser Gly Met Phe
1505                1510                1515

Asp Ser Val Val Leu Cys Glu Cys Tyr Asp Ala Gly Ala Ala Trp
1520                1525                1530

Tyr Asp Leu Thr Pro Ala Glu Thr Thr Val Arg Leu Arg Ala Tyr
1535                1540                1545

Phe Asn Thr Pro Gly Leu Pro Val Cys Gln Asp His Leu Glu Phe
1550                1555                1560

Trp Glu Ala Val Phe Thr Gly Leu Thr His Ile Asp Ala His Phe
1565                1570                1575

Leu Ser Gln Thr Lys Gln Ala Gly Glu Asn Phe Ala Tyr Leu Val
1580                1585                1590

Ala Tyr Gln Ala Thr Val Cys Ala Arg Ala Lys Ala Pro Pro Pro
1595                1600                1605

Ser Trp Asp Ala Met Trp Lys Cys Leu Ala Arg Leu Lys Pro Thr
1610                1615                1620

Leu Ala Gly Pro Thr Pro Leu Leu Tyr Arg Leu Gly Pro Ile Thr
1625                1630                1635

Asn Glu Val Thr Leu Thr His Pro Gly Thr Lys Tyr Ile Ala Thr
1640                1645                1650

Cys Met Gln Ala Asp Leu Glu Val Met Thr Ser Thr Trp Val Leu
1655                1660                1665

Ala Gly Gly Val Leu Ala Ala Val Ala Ala Tyr Cys Leu Ala Thr
1670                1675                1680

Gly Cys Val Ser Ile Ile Gly Arg Leu His Val Asn Gln Arg Val
1685                1690                1695

Val Val Ala Pro Asp Lys Glu Val Leu Tyr Glu Ala Phe Asp Glu
1700                1705                1710

Met Glu Glu Cys Ala Ser Arg Ala Ala Leu Ile Glu Glu Gly Gln
1715                1720                1725

Arg Ile Ala Glu Met Leu Lys Ser Lys Ile Gln Gly Leu Leu Gln
1730                1735                1740

Gln Ala Ser Lys Gln Ala Gln Asp Ile Gln Pro Ala Met Gln Ala
1745                1750                1755

Ser Trp Pro Lys Val Glu Gln Phe Trp Ala Arg His Met Trp Asn
1760                1765                1770

Phe Ile Ser Gly Ile Gln Tyr Leu Ala Gly Leu Ser Thr Leu Pro
1775                1780                1785

Gly Asn Pro Ala Val Ala Ser Met Met Ala Phe Ser Ala Ala Leu
1790                1795                1800

Thr Ser Pro Leu Ser Thr Ser Thr Thr Ile Leu Leu Asn Ile Met
1805                1810                1815

Gly Gly Trp Leu Ala Ser Gln Ile Ala Pro Pro Ala Gly Ala Thr
1820                1825                1830

Gly Phe Val Val Ser Gly Leu Val Gly Ala Ala Val Gly Ser Ile
1835                1840                1845

Gly Leu Gly Lys Val Leu Val Asp Ile Leu Ala Gly Tyr Gly Ala
1850                1855                1860

Gly Ile Ser Gly Ala Leu Val Ala Phe Lys Ile Met Ser Gly Glu
1865                1870                1875

Lys Pro Ser Met Glu Asp Val Ile Asn Leu Leu Pro Gly Ile Leu
1880                1885                1890

Ser Pro Gly Ala Leu Val Val Gly Val Ile Cys Ala Ala Ile Leu
```

-continued

```
              1895                1900                1905
Arg Arg His Val Gly Pro Gly Glu Gly Ala Val Gln Trp Met Asn
    1910                1915                1920
Arg Leu Ile Ala Phe Ala Ser Arg Gly Asn His Val Ala Pro Thr
    1925                1930                1935
His Tyr Val Thr Glu Ser Asp Ala Ser Gln Arg Val Thr Gln Leu
    1940                1945                1950
Leu Gly Ser Leu Thr Ile Thr Ser Leu Leu Arg Arg Leu His Asn
    1955                1960                1965
Trp Ile Thr Glu Asp Cys Pro Ile Pro Cys Ser Gly Ser Trp Leu
    1970                1975                1980
Arg Asp Val Trp Asp Trp Val Cys Thr Ile Leu Thr Asp Phe Lys
    1985                1990                1995
Asn Trp Leu Thr Ser Lys Leu Phe Pro Lys Leu Pro Gly Leu Pro
    2000                2005                2010
Phe Ile Ser Cys Gln Lys Gly Tyr Lys Gly Val Trp Ala Gly Thr
    2015                2020                2025
Gly Ile Met Thr Thr Arg Cys Pro Cys Gly Ala Asn Ile Ser Gly
    2030                2035                2040
Asn Val Arg Leu Gly Ser Met Arg Ile Thr Gly Pro Lys Thr Cys
    2045                2050                2055
Met Asn Thr Trp Gln Gly Thr Phe Pro Ile Asn Cys Tyr Thr Glu
    2060                2065                2070
Gly Gln Cys Ala Pro Lys Pro Pro Thr Asn Tyr Lys Thr Ala Ile
    2075                2080                2085
Trp Arg Val Ala Ala Ser Glu Tyr Ala Glu Val Thr Gln His Gly
    2090                2095                2100
Ser Tyr Ser Tyr Val Thr Gly Leu Thr Thr Asp Asn Leu Lys Ile
    2105                2110                2115
Pro Cys Gln Leu Pro Ser Pro Glu Phe Phe Ser Trp Val Asp Gly
    2120                2125                2130
Val Gln Ile His Arg Phe Ala Pro Thr Pro Lys Pro Phe Phe Arg
    2135                2140                2145
Asp Glu Val Ser Phe Cys Val Gly Leu Asn Ser Tyr Ala Val Gly
    2150                2155                2160
Ser Gln Leu Pro Cys Glu Pro Glu Pro Asp Ala Asp Val Leu Arg
    2165                2170                2175
Ser Met Leu Thr Asp Pro Pro His Ile Thr Ala Glu Thr Ala Ala
    2180                2185                2190
Arg Arg Leu Ala Arg Gly Ser Pro Pro Ser Glu Ala Ser Ser Ser
    2195                2200                2205
Val Ser Gln Leu Ser Ala Pro Ser Leu Arg Ala Thr Cys Thr Thr
    2210                2215                2220
His Ser Asn Thr Tyr Asp Val Asp Met Val Asp Ala Asn Leu Leu
    2225                2230                2235
Met Glu Gly Gly Val Ala Gln Thr Glu Pro Glu Ser Arg Val Pro
    2240                2245                2250
Val Leu Asp Phe Leu Glu Pro Met Ala Glu Glu Ser Asp Leu
    2255                2260                2265
Glu Pro Ser Ile Pro Pro Glu Cys Met Leu Pro Arg Ser Gly Phe
    2270                2275                2280
Pro Arg Ala Leu Pro Ala Trp Ala Arg Pro Asp Tyr Asn Pro Pro
    2285                2290                2295
```

-continued

```
Leu Val Glu Ser Trp Arg Arg Pro Asp Tyr Gln Pro Pro Thr Val
    2300              2305              2310

Ala Gly Cys Ala Leu Pro Pro Lys Lys Ala Pro Thr Pro Pro
    2315              2320              2325

Pro Arg Arg Arg Arg Thr Val Gly Leu Ser Glu Ser Thr Ile Ser
    2330              2335              2340

Glu Ala Leu Gln Gln Leu Ala Ile Lys Thr Phe Gly Gln Pro Pro
    2345              2350              2355

Ser Ser Gly Asp Ala Gly Ser Ser Thr Gly Ala Gly Ala Ala Glu
    2360              2365              2370

Ser Gly Gly Pro Thr Ser Pro Gly Glu Pro Ala Pro Ser Glu Thr
    2375              2380              2385

Gly Ser Ala Ser Ser Met Pro Pro Leu Glu Gly Glu Pro Gly Asp
    2390              2395              2400

Pro Asp Leu Glu Ser Asp Gln Val Glu Leu Gln Pro Pro Pro Gln
    2405              2410              2415

Gly Gly Gly Val Ala Pro Gly Ser Gly Ser Gly Ser Trp Ser Thr
    2420              2425              2430

Cys Ser Glu Glu Asp Asp Thr Thr Val Cys Cys Ser Met Ser Tyr
    2435              2440              2445

Ser Trp Thr Gly Ala Leu Ile Thr Pro Cys Ser Pro Glu Glu Glu
    2450              2455              2460

Lys Leu Pro Ile Asn Pro Leu Ser Asn Ser Leu Leu Arg Tyr His
    2465              2470              2475

Asn Lys Val Tyr Cys Thr Thr Ser Lys Ser Ala Ser Gln Arg Ala
    2480              2485              2490

Lys Lys Val Thr Phe Asp Arg Thr Gln Val Leu Asp Ala His Tyr
    2495              2500              2505

Asp Ser Val Leu Lys Asp Ile Lys Leu Ala Ala Ser Lys Val Ser
    2510              2515              2520

Ala Arg Leu Leu Thr Leu Glu Glu Ala Cys Gln Leu Thr Pro Pro
    2525              2530              2535

His Ser Ala Arg Ser Lys Tyr Gly Phe Gly Ala Lys Glu Val Arg
    2540              2545              2550

Ser Leu Ser Gly Arg Ala Val Asn His Ile Lys Ser Val Trp Lys
    2555              2560              2565

Asp Leu Leu Glu Asp Pro Gln Thr Pro Ile Pro Thr Thr Ile Met
    2570              2575              2580

Ala Lys Asn Glu Val Phe Cys Val Asp Pro Ala Lys Gly Gly Lys
    2585              2590              2595

Lys Pro Ala Arg Leu Ile Val Tyr Pro Asp Leu Gly Val Arg Val
    2600              2605              2610

Cys Glu Lys Met Ala Leu Tyr Asp Ile Thr Gln Lys Leu Pro Gln
    2615              2620              2625

Ala Val Met Gly Ala Ser Tyr Gly Phe Gln Tyr Ser Pro Ala Gln
    2630              2635              2640

Arg Val Glu Tyr Leu Leu Lys Ala Trp Ala Glu Lys Lys Asp Pro
    2645              2650              2655

Met Gly Phe Ser Tyr Asp Thr Arg Cys Phe Asp Ser Thr Val Thr
    2660              2665              2670

Glu Arg Asp Ile Arg Thr Glu Glu Ser Ile Tyr Gln Ala Cys Ser
    2675              2680              2685
```

-continued

| | | | | | | | | | | | |
|---|---|---|---|---|---|---|---|---|---|---|---|
| Leu | Pro | Glu | Glu | Ala | Arg | Thr | Ala | Ile | His | Ser | Leu | Thr | Glu | Arg |

```
Leu Pro Glu Glu Ala Arg Thr Ala Ile His Ser Leu Thr Glu Arg
2690              2695              2700

Leu Tyr Val Gly Gly Pro Met Phe Asn Ser Lys Gly Gln Thr Cys
2705              2710              2715

Gly Tyr Arg Arg Cys Arg Ala Ser Gly Val Leu Thr Thr Ser Met
2720              2725              2730

Gly Asn Thr Ile Thr Cys Tyr Val Lys Ala Leu Ala Ala Cys Lys
2735              2740              2745

Ala Ala Gly Ile Val Ala Pro Thr Met Leu Val Cys Gly Asp Asp
2750              2755              2760

Leu Val Val Ile Ser Glu Ser Gln Gly Thr Glu Glu Asp Glu Arg
2765              2770              2775

Asn Leu Arg Ala Phe Thr Glu Ala Met Thr Arg Tyr Ser Ala Pro
2780              2785              2790

Pro Gly Asp Pro Pro Arg Pro Glu Tyr Asp Leu Glu Leu Ile Thr
2795              2800              2805

Ser Cys Ser Ser Asn Val Ser Val Ala Leu Gly Pro Arg Gly Arg
2810              2815              2820

Arg Arg Tyr Tyr Leu Thr Arg Asp Pro Thr Thr Pro Leu Ala Arg
2825              2830              2835

Ala Ala Trp Glu Thr Val Arg His Ser Pro Ile Asn Ser Trp Leu
2840              2845              2850

Gly Asn Ile Ile Gln Tyr Ala Pro Thr Ile Trp Val Arg Met Val
2855              2860              2865

Leu Met Thr His Phe Phe Ser Ile Leu Met Val Gln Asp Thr Leu
2870              2875              2880

Asp Gln Asn Leu Asn Phe Glu Met Tyr Gly Ser Val Tyr Ser Val
2885              2890              2895

Asn Pro Leu Asp Leu Pro Ala Ile Ile Glu Arg Leu His Gly Leu
2900              2905              2910

Asp Ala Phe Ser Met His Thr Tyr Ser His His Glu Leu Thr Arg
2915              2920              2925

Val Ala Ser Ala Leu Arg Lys Leu Gly Ala Pro Pro Leu Arg Val
2930              2935              2940

Trp Lys Ser Arg Ala Arg Ala Val Arg Ala Ser Leu Ile Ser Arg
2945              2950              2955

Gly Gly Lys Ala Ala Val Cys Gly Arg Tyr Leu Phe Asn Trp Ala
2960              2965              2970

Val Lys Thr Lys Leu Lys Leu Thr Pro Leu Pro Glu Ala Arg Leu
2975              2980              2985

Leu Asp Leu Ser Ser Trp Phe Thr Val Gly Ala Gly Gly Gly Asp
2990              2995              3000

Ile Phe His Ser Val Ser Arg Ala Arg Pro Arg Ser Leu Leu Phe
3005              3010              3015

Gly Leu Leu Leu Leu Phe Val Gly Val Gly Leu Phe Leu Leu Pro
3020              3025              3030

Ala Arg
3035
```

<210> SEQ ID NO 21
<211> LENGTH: 9684
<212> TYPE: DNA
<213> ORGANISM: Hepatitis C virus

<400> SEQUENCE: 21

```
acctgcccct aatagggcg acactccgcc atgaatcact cccctgtgag gaactactgt      60
cttcacgcag aaagcgccta gccatggcgt tagtatgagt gtcgtacagc ctccaggccc    120
cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacac ttcctaaacc    360
tcaaagaaaa accaaaagaa acaccatccg tcgcccacag gacgttaagt tcccgggtgg    420
cggacagatc gttggtggag tatacgtgtt gccgcgcagg ggcccacgat tgggtgtgcg    480
cgcgacgcgt aaaacttctg aacggtcaca gcctcgcgga cgacgacagc ctatccccaa    540
ggcgcgtcgg agcgaaggcc ggtcctgggc tcagcccggg tacccttggc ccctctatgg    600
taatgagggc tgcgggtggg cagggtggct cctgtcccg cgcggctccc gtccatcttg    660
gggcccaaac gaccccggc ggaggtcccg caatttgggt aaagtcatcg atacccttac    720
gtgcggattc gccgacctca tggggtacat cccgctcgtc ggcgctcccg taggaggcgt    780
cgcaagagcc ctcgcgcatg gcgtgagggc ccttgaagac gggataaatt ttgcaacagg    840
gaacttgccc ggttgctcct tttctatctt ccttcttgct ctgttctcct gcttagttca    900
tcctgcagct agtcttgagt ggcggaatac gtctggcctc tatgtcctta ccaacgactg    960
ttccaatagc agtattgtgt atgaggccga tgacgtcatt ctgcacacac ccggctgtgt   1020
accttgtgtt caggacgaca atacatccac gtgctggacc ccagtgacac ctacggtggc   1080
agtcaggtac gtcggagcaa ccaccgcttc gatacgcagt catgtggacc tattagtggg   1140
cgcggccacg ctgtgctctg cgctctatgt gggtgatatg tgtggggccg tctttctcgt   1200
gggacaagcc ttcacgttca gacctcgtcg ccatcaaacg gtccagacct gtaactgctc   1260
gctgtaccca ggccatgttt caggacatcg aatggcttgg gatatgatga tgaattggtc   1320
ccccgctgtg ggtatggtgg tggcgcacat cctgcgattg ccccagacct tgtttgacat   1380
actggccggg gcccattggg gcatcttggc gggcctagcc tattattcta tgcagggcaa   1440
ctgggccaag gtcgctattg tcatgattat gttttcaggg gtcgatgctg aaacatatgt   1500
caccggtggc agtgtagctc atagtgccag agggttaact agcctttta gtatgggcgc   1560
caagcagaaa ctgcaattgg tcaacaccaa tggctcgtgg cacatcaaca gtactgccct   1620
gaactgcaat gagtccataa acaccgggtt catagctggg ttgtttttatt accataagtt   1680
caactctact ggatgtcctc aaaggcttag cagctgcaag cccatcattt ccttcaggca   1740
ggggtggggc cccttgacag atgctaacat caccggtcct tctgatgata ccgtattg   1800
ctggcactac gcacctagac cttgtagtgt tgtcccggca tcaagtgtct gcggccctgt   1860
gtactgcttc acaccatcgc cagtggtcgt aggcactact gatatcaaag gcaagccgac   1920
ctacaactgg ggtgagaatg agacagatgt gttcctgctg gagtccctgc ggcctcccag   1980
tggccggtgg tttggatgcg cgtggatgaa ctccacgggg ttcctcaaga cgtgtggagc   2040
tccccctgt aacatctatg ggggtgaggg ggatcccgaa aatgagacag acctcttctg   2100
ccccaccgac tgcttcagga acatcctga ggccacatac agccggtgtg gtgcgggcc   2160
ctggttgaca cctcgctgca tggtcgacta tccataccgg ctttggcatt acccatgtac   2220
agtcaatttc acattgttca aggtgaggat gttttgtggggc ggatttgaac accggtttac   2280
cgccgcttgt aactggacca ggggggagcg ctgcaatatc gaggatcgtg atcgcagcga   2340
```

```
gcaacatccg ctgctgcatt caacaactga gcttgctata ctgccttgct ctttcacgcc    2400
catgcctgca ttgtcaacag gtctaataca cctccaccaa aatatcgtgg atgtccaata    2460
cctttatggt gttggatctg acatggtggg atgggcgctg aaatgggagt tcgtcatcct    2520
cgttttcctc ctcctggcag acgcacgcgt gtgcgttgcc ctttggctga tgctgatggt    2580
atcacaagca gaagcagcct tggagaacct tgtcacgctg aacgccgtcg ctgctgctgg    2640
gacacatggg attggttggt acctggtagc cttttgcgcg gcgtggtacg tgcggggtaa    2700
acttgtcccg ctgacgacct acggcctgac gggtctttgg tccctagcat tgcttgtcct    2760
cttgctcccc caacgggcgt atgcttggtc gggtgaagac agcgctactc tcggcgctgg    2820
ggtcttggcc ctcttcggct tctttacctt atcaccctgg tacaagcatt ggatcggccg    2880
cctcatgtgg tggaaccagt acactatatg tagatgcgag gccgcccttc aagtgtgggt    2940
ccccccctta cttgcacgcg ggagtaggga cggtgtcatc ctgctaacaa gcttgcttta    3000
tccatcctta attttgaca tcactaagct gctgatagca gtaataggcc cattatactt    3060
aatacaggct gccatcacta ccacccccta ctttgtgcgc gcacatgtac tggtccgcct    3120
ttgcatgctc gtgcgctccg tgatgggggg aaagtacttc cagatggcca tactgagcat    3180
tggcagatgg ttcaacacct acctatatga ccacctagcg ccaatgcaac attgggccgc    3240
agctggcctc aaagacctag cagtggccac tgaacctgta atatttagtc ccatggaaat    3300
taaggtcatc acctggggcg cggacacagc ggcttgcgga gatattcttt gcgggctgcc    3360
ggtctccgcg cgattaggcc gtgaggtatt gttgggacct gctgatgatt atcgggaaat    3420
gggttggcgt ctgttggctc ccatcactgc ttatgcccag caaacacgag gcctcctggg    3480
cgccatagtg gtgagtatga cggggcgtga caggacagaa caggccgggg aagtccaaat    3540
cctgtccaca gtctctcagt ccttcctcgg aacaaccatc tcgggggttt tgtggactgt    3600
ttaccacgga gctggcaaca agactctagc cggcttacgg ggtccggtca cgcagatgta    3660
ctcgagtgct gaggggact tggtaggctg gcccagcccc cctgggacca agtctttgga    3720
gccgtgcaag tgtggagccg tcgacctata tctggtcacg cggaacgctg atgtcatccc    3780
ggctcggaga cgcggggaca agcgggagc attgctctcc ccgagaccca tttcgacctt    3840
gaaggggtcc tcgggggggc cggtgctctg ccctagggc cacgtcgttg gctcttccg    3900 agcagctgtg tgctctcggg gcgtggccaa atccatcgat ttcatccccg ttgagacact    3960
cgacgttgtt acaaggtctc ccactttcag tgacaacagc acgccaccgg ctgtgcccca    4020
gacctatcag gtcgggtact tgcatgctcc aactggcagt ggaaagagca ccaaggtccc    4080
tgtcgcgtat gccgcccagg ggtacaaagt actagtgctt aaccctcgg tagctgccac    4140 cctgggttt ggggcgtacc tatccaaggc acatggcatc aatcccaaca ttaggactgg    4200
agtcaggacc gtgatgaccg ggaggccat cacgtactcc acatatggca aatttctcgc    4260 cgatggggc tgcgctagcg gcgcctatga catcatcata tgcgatgaat gccacgctgt    4320
ggatgctacc tccattctcg gcatcggaac ggtccttgat caagcagaga cagccggggt    4380
cagactaact gtgctggcta cggccacacc ccccgggtca gtgacaaccc cccatcccga    4440
tatagaagag gtaggcctcg gcggggaggg tgagatcccc ttctatggga gggcgattcc    4500
cctatcctgc atcaagggag ggagacacct gattttctgc cactcaaagc aaaagtgtga    4560
cgagctcgcg gcggcccttc gggcatggg cttgaatgcc gtggcatact atagagggtt    4620
ggacgtctcc ataataccag ctcagggaga tgtggtggtc gtcgccaccg acgccctcat    4680
gacggggtac actggagact ttgactccgt gatcgactgc aatgtagcgg tcacccaagc    4740
```

```
tgtcgacttc agcctggacc ccaccttcac tataaccaca cagactgtcc cacaagacgc    4800
tgtctcacgc agtcagcgcc gcgggcgcac aggtagagga agacagggca cttataggta    4860
tgtttccact ggtgaacgag cctcaggaat gtttgacagt gtagtgcttt gtgagtgcta    4920
cgacgcaggg gctgcgtggt acgatctcac accagcggag accaccgtca ggcttagagc    4980
gtatttcaac acgcccggcc tacccgtgtg tcaagaccat cttgaatttt gggaggcagt    5040
tttcaccggc ctcacacaca tagacgccca cttcctctcc caaacaaagc aagcggggga    5100
gaacttcgcg tacctagtag cctaccaagc tacggtgtgc gccagagcca aggcccctcc    5160
cccgtcctgg gacgccatgt ggaagtgcct ggcccgactc aagcctacgc ttgcgggccc    5220
cacacctctc ctgtaccgtt tgggccctat taccaatgag gtcaccctca cacaccctgg    5280
gacgaagtac atcgccacat gcatgcaagc tgaccttgag gtcatgacca gcacgtgggt    5340
cctagctgga ggagtcctgg cagccgtcgc cgcatattgc ctggcgactg gatgcgtttc    5400
catcatcggc cgcttgcacg tcaaccagcg agtcgtcgtt gcgccggata aggaggtcct    5460
gtatgaggct tttgatgaga tggaggaatg cgcctctagg gcggctctca tcgaagaggg    5520
gcagcggata gccgagatgt tgaagtccaa gatccaaggc ttgctgcagc aggcctctaa    5580
gcaggcccag gacatacaac ccgctatgca ggcttcatgg cccaaagtgg aacaattttg    5640
ggccagacac atgtggaact tcattagcgg catccaatac ctcgcaggat tgtcaacact    5700
gccagggaac cccgcggtgg cttccatgat ggcattcagt gccgccctca ccagtccgtt    5760
gtcgaccagt accaccatcc ttctcaacat catgggaggc tggttagcgt cccagatcgc    5820
accacccgcg ggggccaccg gctttgtcgt cagtggcctg gtggggcctg ccgtgggcag    5880
cataggcctg ggtaaggtgc tggtggacat cctggcagga tatggtgcgg gcatttcggg    5940
ggccctcgtc gcattcaaga tcatgtctgg cgagaagccc tctatggaag atgtcatcaa    6000
tctactgcct gggatcctgt ctccgggagc cctggtggtg ggggtcatct gcgcggccat    6060
tctgcgccgc cacgtgggac cggggagggg cgcggtccaa tggatgaaca ggcttattgc    6120
ctttgcttcc agaggaaacc acgtcgcccc tactcactac gtgacggagt cggatgcgtc    6180
gcagcgtgtg acccaactac ttggctctct tactataacc agcctactca gaagactcca    6240
caattggata actgaggact gccccatccc atgctccgga tcctggctcc gcgacgtgtg    6300
ggactgggtt tgcaccatct tgacagactt caaaaattgg ctgacctcta aattgttccc    6360
caagctgccc ggcctcccct tcatctcttg tcaaaagggg tacaagggtg tgtgggccgg    6420
cactggcatc atgaccacgc gctgcccttg cggcgccaac atctctggca atgtccgcct    6480
gggctctatg aggatcacag ggcctaaaac ctgcatgaac acctggcagg gaccttttcc    6540
tatcaattgc tacacggagg gccagtgcgc gccgaaaccc ccacgaact acaagaccgc    6600
catctggagg gtggcggcct cggagtacgc ggaggtgacg cagcatgggt cgtactccta    6660
tgtaacagga ctgaccactg acaatctgaa aattccttgc caactacctt ctccagagtt    6720
tttctcctgg gtggacggtg tgcagatcca taggtttgca cccacaccaa agccgttttt    6780
ccgggatgag gtctcgttct gcgttgggct taattcctat gctgtcgggt cccagcttcc    6840
ctgtgaacct gagcccgacg cagacgtatt gaggtccatg ctaacagatc cgccccacat    6900
cacggcggag actgcggcgc ggcgcttggc acggggatca cctccatctg aggcgagctc    6960
ctcagtgagc cagctatcag caccgtcgct gcgggccacc tgcaccaccc acagcaacac    7020
ctatgacgtg gacatggtcg atgccaacct gctcatggag ggcggtgtgg ctcagacaga    7080
```

-continued

```
gcctgagtcc agggtgcccg ttctggactt tctcgagcca atggccgagg aagagagcga   7140
ccttgagccc tcaataccat cggagtgcat gctccccagg agcgggtttc cacgggcctt   7200
accggcttgg gcacggcctg actacaaccc gccgctcgtg aatcgtgga ggaggccaga    7260
ttaccaaccg cccaccgttg ctggttgtgc tctcccccc cccaagaagg ccccgacgcc    7320
tcccccaagg agacgccgga cagtgggtct gagcgagagc accatatcag aagccctcca   7380
gcaactggcc atcaagacct ttggccagcc cccctcgagc ggtgatgcag gctcgtccac   7440
gggggcgggc gccgccgaat ccggcggtcc gacgtcccct ggtgagccgg cccctcaga    7500
gacaggttcc gcctcctcta tgccccccct cgagggggag cctggagatc cggacctgga   7560
gtctgatcag gtagagcttc aacctccccc ccagggggg gggtagctc ccggttcggg    7620
ctcggggtct tggtctactt gctccgagga ggacgatacc accgtgtgct gctccatgtc   7680
atactcctgg accggggctc taataactcc ctgtagcccc gaagaggaaa agttgccaat   7740
caacccttg agtaactcgc tgttgcgata ccataacaag gtgtactgta caacatcaaa    7800
gagcgcctca cagagggcta aaaggtaac ttttgacagg acgcaagtgc tcgacgccca    7860
ttatgactca gtcttaaagg acatcaagct agcggcttcc aaggtcagcg caaggctcct   7920
caccttggag gaggcgtgcc agttgactcc accccattct gcaagatcca agtatggatt   7980
cggggccaag gaggtccgca gcttgtccgg gagggccgtt aaccacatca agtccgtgtg   8040
gaaggacctc ctggaagacc cacaaacacc aattcccaca accatcatgg ccaaaaatga   8100
ggtgttctgc gtggaccccg ccaagggggg taagaaacca gctcgcctca tcgtttaccc   8160
tgacctcggc gtccgggtct gcgagaaaat ggccctctat gacattacac aaaagcttcc   8220
tcaggcggta atgggagctt cctatggctt ccagtactcc cctgcccaac gggtggagta   8280
tctcttgaaa gcatgggcgg aaaagaagga ccccatgggg ttttcgtatg atacccgatg   8340
cttcgactca accgtcactg agagagacat caggaccgag gagtccatat accaggcctg   8400
ctccctgccc gaggaggccc gcactgccat acactcgctg actgagagac tttacgtagg   8460
agggcccatg ttcaacagca agggtcaaac ctgcggttac agacgttgcc gcgccagcgg   8520
ggtgctaacc actagcatgg gtaacaccat cacatgctat gtgaaagccc tagcggcctg   8580
caaggctgcg gggatagttg cgcccacaat gctggtatgc ggcgatgacc tagtagtcat   8640
ctcagaaagc cagggggactg aggaggacga gcggaacctg agagccttca cggaggccat   8700
gaccaggtac tctgcccctc ctggtgatcc ccccagaccg gaatatgacc tggagctaat   8760
aacatcctgt tcctcaaatg tgtctgtggc gttgggcccg cggggccgcc gcagatacta   8820
cctgaccaga gacccaacca ctccactcgc ccgggctgcc tgggaaacag ttagacactc   8880
ccctatcaat tcatggctgg gaaacatcat ccagtatgct ccaaccatat gggttcgcat   8940
ggtcctaatg acacacttct tctccattct catggtccaa gacaccctgg accagaacct   9000
caactttgag atgtatggat cagtatactc cgtgaatcct ttggaccttc agccataat    9060
tgagaggtta cacgggcttg acgccttttc tatgcacaca tactctcacc acgaactgac   9120
gcgggtggct tcagccctca gaaaacttgg ggcgccaccc ctcagggtgt ggaagagtcg   9180
ggctcgcgca gtcagggcgt ccctcatctc cgtggaggg aaagcggccg tttgcggccg    9240
atatctcttc aattgggcgg tgaagaccaa gctcaaactc actccattgc cggaggcgcg   9300
cctactggac ttatccagtt ggttcaccgt cggcgccggc gggggcgaca ttttcacag     9360
cgtgtcgcgc gcccgacccc gctcattact cttcggccta ctcctacttt tcgtagggg    9420
aggcctcttc ctactccccg ctcggtagag cggcacacac taggtacact ccatagctaa   9480
```

```
ctgttcctt  tttttttttt  tttttttttt  tttttttttt  tttttttttt  ctttttttt       9540 tttttccctc  ttcttcccct  tctcatctta  ttctactttc  tttcttggtg  gctccatctt     9600
agccctagtc  acggctagct  gtgaaaggtc  cgtgagccgc  atgactgcag  agagtgccgt     9660
aactggtctc  tctgcagatc  atgt                                                9684
```

<210> SEQ ID NO 22
<211> LENGTH: 3035
<212> TYPE: PRT
<213> ORGANISM: Hepatitis C virus

<400> SEQUENCE: 22

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335
```

```
Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Val Met Ile Met Phe Ser Gly Val Asp Ala Glu
            370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
                435                 440                 445

Ser Thr Gly Cys Pro Gln Arg Leu Ser Ser Cys Lys Pro Ile Ile Ser
            450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Lys Pro Thr Tyr
            515                 520                 525

Asn Trp Gly Glu Asn Glu Thr Asp Val Phe Leu Leu Glu Ser Leu Arg
            530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
                660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
            690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750
```

```
Ala Leu Glu Asn Leu Val Thr Leu Asn Ala Val Ala Ala Gly Thr
            755                 760                 765

His Gly Ile Gly Trp Tyr Leu Ala Phe Cys Ala Ala Trp Tyr Val
770                 775                 780

Arg Gly Lys Leu Val Pro Leu Thr Thr Tyr Gly Leu Thr Gly Leu Trp
785                 790                 795                 800

Ser Leu Ala Leu Leu Val Leu Leu Pro Gln Arg Ala Tyr Ala Trp
                805                 810                 815

Ser Gly Glu Asp Ser Ala Thr Leu Gly Ala Gly Val Leu Ala Leu Phe
                820                 825                 830

Gly Phe Phe Thr Leu Ser Pro Trp Tyr Lys His Trp Ile Gly Arg Leu
            835                 840                 845

Met Trp Trp Asn Gln Tyr Thr Ile Cys Arg Cys Glu Ala Ala Leu Gln
850                 855                 860

Val Trp Val Pro Pro Leu Leu Ala Arg Gly Ser Arg Asp Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
                900                 905                 910

Thr Thr Thr Pro Tyr Phe Val Arg Ala His Val Leu Val Arg Leu Cys
            915                 920                 925

Met Leu Val Arg Ser Val Met Gly Gly Lys Tyr Phe Gln Met Ala Ile
930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
                995                1000                1005

Ser Ala Arg Leu Gly Arg Glu Val Leu Leu Gly Pro Ala Asp Asp
      1010                1015                1020

Tyr Arg Glu Met Gly Trp Arg Leu Leu Ala Pro Ile Thr Ala Tyr
      1025                1030                1035

Ala Gln Gln Thr Arg Gly Leu Leu Gly Ala Ile Val Val Ser Met
      1040                1045                1050

Thr Gly Arg Asp Arg Thr Glu Gln Ala Gly Glu Val Gln Ile Leu
      1055                1060                1065

Ser Thr Val Ser Gln Ser Phe Leu Gly Thr Thr Ile Ser Gly Val
      1070                1075                1080

Leu Trp Thr Val Tyr His Gly Ala Gly Asn Lys Thr Leu Ala Gly
      1085                1090                1095

Leu Arg Gly Pro Val Thr Gln Met Tyr Ser Ser Ala Glu Gly Asp
      1100                1105                1110

Leu Val Gly Trp Pro Ser Pro Gly Thr Lys Ser Leu Glu Pro
      1115                1120                1125

Cys Lys Cys Gly Ala Val Asp Leu Tyr Leu Val Thr Arg Asn Ala
      1130                1135                1140

Asp Val Ile Pro Ala Arg Arg Arg Gly Asp Lys Arg Gly Ala Leu
      1145                1150                1155

Leu Ser Pro Arg Pro Ile Ser Thr Leu Lys Gly Ser Ser Gly Gly
```

-continued

```
             1160                1165                1170
Pro Val Leu Cys Pro Arg Gly His Val Val Gly Leu Phe Arg Ala
        1175                1180                1185
Ala Val Cys Ser Arg Gly Val Ala Lys Ser Ile Asp Phe Ile Pro
        1190                1195                1200
Val Glu Thr Leu Asp Val Val Thr Arg Ser Pro Thr Phe Ser Asp
        1205                1210                1215
Asn Ser Thr Pro Pro Ala Val Pro Gln Thr Tyr Gln Val Gly Tyr
        1220                1225                1230
Leu His Ala Pro Thr Gly Ser Gly Lys Ser Thr Lys Val Pro Val
        1235                1240                1245
Ala Tyr Ala Ala Gln Gly Tyr Lys Val Leu Val Leu Asn Pro Ser
        1250                1255                1260
Val Ala Ala Thr Leu Gly Phe Gly Ala Tyr Leu Ser Lys Ala His
        1265                1270                1275
Gly Ile Asn Pro Asn Ile Arg Thr Gly Val Arg Thr Val Met Thr
        1280                1285                1290
Gly Glu Ala Ile Thr Tyr Ser Thr Tyr Gly Lys Phe Leu Ala Asp
        1295                1300                1305
Gly Gly Cys Ala Ser Gly Ala Tyr Asp Ile Ile Ile Cys Asp Glu
        1310                1315                1320
Cys His Ala Val Asp Ala Thr Ser Ile Leu Gly Ile Gly Thr Val
        1325                1330                1335
Leu Asp Gln Ala Glu Thr Ala Gly Val Arg Leu Thr Val Leu Ala
        1340                1345                1350
Thr Ala Thr Pro Pro Gly Ser Val Thr Thr Pro His Pro Asp Ile
        1355                1360                1365
Glu Glu Val Gly Leu Gly Arg Glu Gly Glu Ile Pro Phe Tyr Gly
        1370                1375                1380
Arg Ala Ile Pro Leu Ser Cys Ile Lys Gly Gly Arg His Leu Ile
        1385                1390                1395
Phe Cys His Ser Lys Gln Lys Cys Asp Glu Leu Ala Ala Ala Leu
        1400                1405                1410
Arg Gly Met Gly Leu Asn Ala Val Ala Tyr Tyr Arg Gly Leu Asp
        1415                1420                1425
Val Ser Ile Ile Pro Ala Gln Gly Asp Val Val Val Ala Thr
        1430                1435                1440
Asp Ala Leu Met Thr Gly Tyr Thr Gly Asp Phe Asp Ser Val Ile
        1445                1450                1455
Asp Cys Asn Val Ala Val Thr Gln Ala Val Asp Phe Ser Leu Asp
        1460                1465                1470
Pro Thr Phe Thr Ile Thr Thr Gln Thr Val Pro Gln Asp Ala Val
        1475                1480                1485
Ser Arg Ser Gln Arg Arg Gly Arg Thr Gly Arg Gly Arg Gln Gly
        1490                1495                1500
Thr Tyr Arg Tyr Val Ser Thr Gly Glu Arg Ala Ser Gly Met Phe
        1505                1510                1515
Asp Ser Val Val Leu Cys Glu Cys Tyr Asp Ala Gly Ala Ala Trp
        1520                1525                1530
Tyr Asp Leu Thr Pro Ala Glu Thr Thr Val Arg Leu Arg Ala Tyr
        1535                1540                1545
Phe Asn Thr Pro Gly Leu Pro Val Cys Gln Asp His Leu Glu Phe
        1550                1555                1560
```

-continued

Trp Glu Ala Val Phe Thr Gly Leu Thr His Ile Asp Ala His Phe
1565                1570                1575

Leu Ser Gln Thr Lys Gln Ala Gly Glu Asn Phe Ala Tyr Leu Val
1580                1585                1590

Ala Tyr Gln Ala Thr Val Cys Ala Arg Ala Lys Ala Pro Pro Pro
1595                1600                1605

Ser Trp Asp Ala Met Trp Lys Cys Leu Ala Arg Leu Lys Pro Thr
1610                1615                1620

Leu Ala Gly Pro Thr Pro Leu Leu Tyr Arg Leu Gly Pro Ile Thr
1625                1630                1635

Asn Glu Val Thr Leu Thr His Pro Gly Thr Lys Tyr Ile Ala Thr
1640                1645                1650

Cys Met Gln Ala Asp Leu Glu Val Met Thr Ser Thr Trp Val Leu
1655                1660                1665

Ala Gly Gly Val Leu Ala Ala Val Ala Ala Tyr Cys Leu Ala Thr
1670                1675                1680

Gly Cys Val Ser Ile Ile Gly Arg Leu His Val Asn Gln Arg Val
1685                1690                1695

Val Val Ala Pro Asp Lys Glu Val Leu Tyr Glu Ala Phe Asp Glu
1700                1705                1710

Met Glu Glu Cys Ala Ser Arg Ala Ala Leu Ile Glu Glu Gly Gln
1715                1720                1725

Arg Ile Ala Glu Met Leu Lys Ser Lys Ile Gln Gly Leu Leu Gln
1730                1735                1740

Gln Ala Ser Lys Gln Ala Gln Asp Ile Gln Pro Ala Met Gln Ala
1745                1750                1755

Ser Trp Pro Lys Val Glu Gln Phe Trp Ala Arg His Met Trp Asn
1760                1765                1770

Phe Ile Ser Gly Ile Gln Tyr Leu Ala Gly Leu Ser Thr Leu Pro
1775                1780                1785

Gly Asn Pro Ala Val Ala Ser Met Met Ala Phe Ser Ala Ala Leu
1790                1795                1800

Thr Ser Pro Leu Ser Thr Ser Thr Thr Ile Leu Leu Asn Ile Met
1805                1810                1815

Gly Gly Trp Leu Ala Ser Gln Ile Ala Pro Pro Ala Gly Ala Thr
1820                1825                1830

Gly Phe Val Val Ser Gly Leu Val Gly Ala Ala Val Gly Ser Ile
1835                1840                1845

Gly Leu Gly Lys Val Leu Val Asp Ile Leu Ala Gly Tyr Gly Ala
1850                1855                1860

Gly Ile Ser Gly Ala Leu Val Ala Phe Lys Ile Met Ser Gly Glu
1865                1870                1875

Lys Pro Ser Met Glu Asp Val Ile Asn Leu Leu Pro Gly Ile Leu
1880                1885                1890

Ser Pro Gly Ala Leu Val Val Gly Val Ile Cys Ala Ala Ile Leu
1895                1900                1905

Arg Arg His Val Gly Pro Gly Glu Gly Ala Val Gln Trp Met Asn
1910                1915                1920

Arg Leu Ile Ala Phe Ala Ser Arg Gly Asn His Val Ala Pro Thr
1925                1930                1935

His Tyr Val Thr Glu Ser Asp Ala Ser Gln Arg Val Thr Gln Leu
1940                1945                1950

```
Leu Gly Ser Leu Thr Ile Thr Ser Leu Leu Arg Arg Leu His Asn
1955                1960                1965

Trp Ile Thr Glu Asp Cys Pro Ile Pro Cys Ser Gly Ser Trp Leu
1970                1975                1980

Arg Asp Val Trp Asp Trp Val Cys Thr Ile Leu Thr Asp Phe Lys
1985                1990                1995

Asn Trp Leu Thr Ser Lys Leu Phe Pro Lys Leu Pro Gly Leu Pro
2000                2005                2010

Phe Ile Ser Cys Gln Lys Gly Tyr Lys Gly Val Trp Ala Gly Thr
2015                2020                2025

Gly Ile Met Thr Thr Arg Cys Pro Cys Gly Ala Asn Ile Ser Gly
2030                2035                2040

Asn Val Arg Leu Gly Ser Met Arg Ile Thr Gly Pro Lys Thr Cys
2045                2050                2055

Met Asn Thr Trp Gln Gly Thr Phe Pro Ile Asn Cys Tyr Thr Glu
2060                2065                2070

Gly Gln Cys Ala Pro Lys Pro Pro Thr Asn Tyr Lys Thr Ala Ile
2075                2080                2085

Trp Arg Val Ala Ala Ser Glu Tyr Ala Glu Val Thr Gln His Gly
2090                2095                2100

Ser Tyr Ser Tyr Val Thr Gly Leu Thr Thr Asp Asn Leu Lys Ile
2105                2110                2115

Pro Cys Gln Leu Pro Ser Pro Glu Phe Phe Ser Trp Val Asp Gly
2120                2125                2130

Val Gln Ile His Arg Phe Ala Pro Thr Pro Lys Pro Phe Phe Arg
2135                2140                2145

Asp Glu Val Ser Phe Cys Val Gly Leu Asn Ser Tyr Ala Val Gly
2150                2155                2160

Ser Gln Leu Pro Cys Glu Pro Glu Pro Asp Ala Asp Val Leu Arg
2165                2170                2175

Ser Met Leu Thr Asp Pro Pro His Ile Thr Ala Glu Thr Ala Ala
2180                2185                2190

Arg Arg Leu Ala Arg Gly Ser Pro Pro Ser Glu Ala Ser Ser Ser
2195                2200                2205

Val Ser Gln Leu Ser Ala Pro Ser Leu Arg Ala Thr Cys Thr Thr
2210                2215                2220

His Ser Asn Thr Tyr Asp Val Asp Met Val Asp Ala Asn Leu Leu
2225                2230                2235

Met Glu Gly Gly Val Ala Gln Thr Glu Pro Glu Ser Arg Val Pro
2240                2245                2250

Val Leu Asp Phe Leu Glu Pro Met Ala Glu Glu Ser Asp Leu
2255                2260                2265

Glu Pro Ser Ile Pro Ser Glu Cys Met Leu Pro Arg Ser Gly Phe
2270                2275                2280

Pro Arg Ala Leu Pro Ala Trp Ala Arg Pro Asp Tyr Asn Pro Pro
2285                2290                2295

Leu Val Glu Ser Trp Arg Arg Pro Asp Tyr Gln Pro Pro Thr Val
2300                2305                2310

Ala Gly Cys Ala Leu Pro Pro Pro Lys Lys Ala Pro Thr Pro Pro
2315                2320                2325

Pro Arg Arg Arg Arg Thr Val Gly Leu Ser Glu Ser Thr Ile Ser
2330                2335                2340

Glu Ala Leu Gln Gln Leu Ala Ile Lys Thr Phe Gly Gln Pro Pro
```

-continued

```
            2345                2350                2355
Ser  Ser  Gly  Asp  Ala  Gly  Ser  Ser  Thr  Gly  Ala  Gly  Ala  Ala  Glu
            2360                2365                2370
Ser  Gly  Gly  Pro  Thr  Ser  Pro  Gly  Glu  Pro  Ala  Pro  Ser  Glu  Thr
            2375                2380                2385
Gly  Ser  Ala  Ser  Ser  Met  Pro  Pro  Leu  Glu  Gly  Glu  Pro  Gly  Asp
            2390                2395                2400
Pro  Asp  Leu  Glu  Ser  Asp  Gln  Val  Glu  Leu  Gln  Pro  Pro  Pro  Gln
            2405                2410                2415
Gly  Gly  Gly  Val  Ala  Pro  Gly  Ser  Gly  Ser  Gly  Ser  Trp  Ser  Thr
            2420                2425                2430
Cys  Ser  Glu  Glu  Asp  Asp  Thr  Thr  Val  Cys  Cys  Ser  Met  Ser  Tyr
            2435                2440                2445
Ser  Trp  Thr  Gly  Ala  Leu  Ile  Thr  Pro  Cys  Ser  Pro  Glu  Glu  Glu
            2450                2455                2460
Lys  Leu  Pro  Ile  Asn  Pro  Leu  Ser  Asn  Ser  Leu  Leu  Arg  Tyr  His
            2465                2470                2475
Asn  Lys  Val  Tyr  Cys  Thr  Thr  Ser  Lys  Ser  Ala  Ser  Gln  Arg  Ala
            2480                2485                2490
Lys  Lys  Val  Thr  Phe  Asp  Arg  Thr  Gln  Val  Leu  Asp  Ala  His  Tyr
            2495                2500                2505
Asp  Ser  Val  Leu  Lys  Asp  Ile  Lys  Leu  Ala  Ala  Ser  Lys  Val  Ser
            2510                2515                2520
Ala  Arg  Leu  Leu  Thr  Leu  Glu  Glu  Ala  Cys  Gln  Leu  Thr  Pro  Pro
            2525                2530                2535
His  Ser  Ala  Arg  Ser  Lys  Tyr  Gly  Phe  Gly  Ala  Lys  Glu  Val  Arg
            2540                2545                2550
Ser  Leu  Ser  Gly  Arg  Ala  Val  Asn  His  Ile  Lys  Ser  Val  Trp  Lys
            2555                2560                2565
Asp  Leu  Leu  Glu  Asp  Pro  Gln  Thr  Pro  Ile  Pro  Thr  Thr  Ile  Met
            2570                2575                2580
Ala  Lys  Asn  Glu  Val  Phe  Cys  Val  Asp  Pro  Ala  Lys  Gly  Gly  Lys
            2585                2590                2595
Lys  Pro  Ala  Arg  Leu  Ile  Val  Tyr  Pro  Asp  Leu  Gly  Val  Arg  Val
            2600                2605                2610
Cys  Glu  Lys  Met  Ala  Leu  Tyr  Asp  Ile  Thr  Gln  Lys  Leu  Pro  Gln
            2615                2620                2625
Ala  Val  Met  Gly  Ala  Ser  Tyr  Gly  Phe  Gln  Tyr  Ser  Pro  Ala  Gln
            2630                2635                2640
Arg  Val  Glu  Tyr  Leu  Leu  Lys  Ala  Trp  Ala  Glu  Lys  Lys  Asp  Pro
            2645                2650                2655
Met  Gly  Phe  Ser  Tyr  Asp  Thr  Arg  Cys  Phe  Asp  Ser  Thr  Val  Thr
            2660                2665                2670
Glu  Arg  Asp  Ile  Arg  Thr  Glu  Glu  Ser  Ile  Tyr  Gln  Ala  Cys  Ser
            2675                2680                2685
Leu  Pro  Glu  Glu  Ala  Arg  Thr  Ala  Ile  His  Ser  Leu  Thr  Glu  Arg
            2690                2695                2700
Leu  Tyr  Val  Gly  Gly  Pro  Met  Phe  Asn  Ser  Lys  Gly  Gln  Thr  Cys
            2705                2710                2715
Gly  Tyr  Arg  Arg  Cys  Arg  Ala  Ser  Gly  Val  Leu  Thr  Thr  Ser  Met
            2720                2725                2730
Gly  Asn  Thr  Ile  Thr  Cys  Tyr  Val  Lys  Ala  Leu  Ala  Ala  Cys  Lys
            2735                2740                2745
```

```
Ala Ala Gly Ile Val Ala Pro Thr Met Leu Val Cys Gly Asp Asp
        2750            2755                2760

Leu Val Val Ile Ser Glu Ser Gln Gly Thr Glu Glu Asp Glu Arg
        2765            2770                2775

Asn Leu Arg Ala Phe Thr Glu Ala Met Thr Arg Tyr Ser Ala Pro
        2780            2785                2790

Pro Gly Asp Pro Pro Arg Pro Glu Tyr Asp Leu Glu Leu Ile Thr
        2795            2800                2805

Ser Cys Ser Ser Asn Val Ser Val Ala Leu Gly Pro Arg Gly Arg
        2810            2815                2820

Arg Arg Tyr Tyr Leu Thr Arg Asp Pro Thr Thr Pro Leu Ala Arg
        2825            2830                2835

Ala Ala Trp Glu Thr Val Arg His Ser Pro Ile Asn Ser Trp Leu
        2840            2845                2850

Gly Asn Ile Ile Gln Tyr Ala Pro Thr Ile Trp Val Arg Met Val
        2855            2860                2865

Leu Met Thr His Phe Phe Ser Ile Leu Met Val Gln Asp Thr Leu
        2870            2875                2880

Asp Gln Asn Leu Asn Phe Glu Met Tyr Gly Ser Val Tyr Ser Val
        2885            2890                2895

Asn Pro Leu Asp Leu Pro Ala Ile Ile Glu Arg Leu His Gly Leu
        2900            2905                2910

Asp Ala Phe Ser Met His Thr Tyr Ser His His Glu Leu Thr Arg
        2915            2920                2925

Val Ala Ser Ala Leu Arg Lys Leu Gly Ala Pro Pro Leu Arg Val
        2930            2935                2940

Trp Lys Ser Arg Ala Arg Ala Val Arg Ala Ser Leu Ile Ser Arg
        2945            2950                2955

Gly Gly Lys Ala Ala Val Cys Gly Arg Tyr Leu Phe Asn Trp Ala
        2960            2965                2970

Val Lys Thr Lys Leu Lys Leu Thr Pro Leu Pro Glu Ala Arg Leu
        2975            2980                2985

Leu Asp Leu Ser Ser Trp Phe Thr Val Gly Ala Gly Gly Gly Asp
        2990            2995                3000

Ile Phe His Ser Val Ser Arg Ala Arg Pro Arg Ser Leu Leu Phe
        3005            3010                3015

Gly Leu Leu Leu Leu Phe Val Gly Val Gly Leu Phe Leu Leu Pro
        3020            3025                3030

Ala Arg
        3035

<210> SEQ ID NO 23
<211> LENGTH: 58
<212> TYPE: DNA
<213> ORGANISM: Artificial Sequence
<220> FEATURE:
<223> OTHER INFORMATION: oligoDNA primer

<400> SEQUENCE: 23
aaggaaaaaa gcggccgcta atacgactca ctatagcctg cctcttacga ggcgacac      58

<210> SEQ ID NO 24
<211> LENGTH: 34
<212> TYPE: DNA
<213> ORGANISM: Artificial Sequence
<220> FEATURE:
```

<223> OTHER INFORMATION: oligoDNA primer

<400> SEQUENCE: 24
ttggcgcgcc catctcccga tagtcatcag cagg                          34

<210> SEQ ID NO 25
<211> LENGTH: 41
<212> TYPE: DNA
<213> ORGANISM: Artificial Sequence
<220> FEATURE:
<223> OTHER INFORMATION: oligeDNA primer

<400> SEQUENCE: 25
aaggaaaaaa gcggccgccg gagatattct ttgcgggctg c                  41

<210> SEQ ID NO 26
<211> LENGTH: 33
<212> TYPE: DNA
<213> ORGANISM: Artificial Sequence
<220> FEATURE:
<223> OTHER INFORMATION: oligoDNA primer

<400> SEQUENCE: 26
ttggcgcgcc gtgttggctt aagccgcacg aga                           33

<210> SEQ ID NO 27
<211> LENGTH: 24
<212> TYPE: DNA
<213> ORGANISM: Artificial Sequence
<220> FEATURE:
<223> OTHER INFORMATION: oligoDNA primer

<400> SEQUENCE: 27
ctatggagtg tacctagtgt gtgc                                     24

<210> SEQ ID NO 28
<211> LENGTH: 22
<212> TYPE: DNA
<213> ORGANISM: Artificial Sequence
<220> FEATURE:
<223> OTHER INFORMATION: oligoDNA primer

<400> SEQUENCE: 28
gtaggtgtca ctggggtcca gc                                       22

<210> SEQ ID NO 29
<211> LENGTH: 30
<212> TYPE: DNA
<213> ORGANISM: Artificial Sequence
<220> FEATURE:
<223> OTHER INFORMATION: oligoDNA primer

<400> SEQUENCE: 29
tcatgcggct cacggacctt tcacagctag                               30

<210> SEQ ID NO 30
<211> LENGTH: 24
<212> TYPE: DNA
<213> ORGANISM: Artificial Sequence
<220> FEATURE:
<223> OTHER INFORMATION: oligoDNA primer

<400> SEQUENCE: 30
ggccattttc tcgcagaccc ggac                                     24

```
<210> SEQ ID NO 31
<211> LENGTH: 30
<212> TYPE: DNA
<213> ORGANISM: Artificial Sequence
<220> FEATURE:
<223> OTHER INFORMATION: oligoDNA primer

<400> SEQUENCE: 31
actgtcttca cgcagaaagc gcctagccat                                    30

<210> SEQ ID NO 32
<211> LENGTH: 22
<212> TYPE: DNA
<213> ORGANISM: Artificial Sequence
<220> FEATURE:
<223> OTHER INFORMATION: oligoDNA primer

<400> SEQUENCE: 32
gaaatttatc ccgtcttcaa gg                                            22

<210> SEQ ID NO 33
<211> LENGTH: 26
<212> TYPE: DNA
<213> ORGANISM: Artificial Sequence
<220> FEATURE:
<223> OTHER INFORMATION: oligoDNA primer

<400> SEQUENCE: 33
acctgcccct aatagggggcg acactc                                       26

<210> SEQ ID NO 34
<211> LENGTH: 30
<212> TYPE: DNA
<213> ORGANISM: Artificial Sequence
<220> FEATURE:
<223> OTHER INFORMATION: oligoDNA primer

<400> SEQUENCE: 34
ggcgccggcg ggggcgacat ttttcacagc                                    30

<210> SEQ ID NO 35
<211> LENGTH: 24
<212> TYPE: DNA
<213> ORGANISM: Artificial Sequence
<220> FEATURE:
<223> OTHER INFORMATION: oligoDNA primer

<400> SEQUENCE: 35
gaagctctac ctgatcagac tcca                                          24

<210> SEQ ID NO 36
<211> LENGTH: 24
<212> TYPE: DNA
<213> ORGANISM: Artificial Sequence
<220> FEATURE:
<223> OTHER INFORMATION: oligoDNA primer

<400> SEQUENCE: 36
ggtctacgag rcctcccggg gcac                                          24

<210> SEQ ID NO 37
<211> LENGTH: 25
<212> TYPE: DNA
<213> ORGANISM: Artificial Sequence
<220> FEATURE:
<223> OTHER INFORMATION: oligoDNA primer
```

```
<400> SEQUENCE: 37
cgcaagcrcc ctatcaggca gtacc                                          25

<210> SEQ ID NO 38
<211> LENGTH: 19
<212> TYPE: DNA
<213> ORGANISM: Artificial Sequence
<220> FEATURE:
<223> OTHER INFORMATION: oligoDNA primer

<400> SEQUENCE: 38
cggtgtactc accggttcc                                                 19

<210> SEQ ID NO 39
<211> LENGTH: 40
<212> TYPE: DNA
<213> ORGANISM: Artificial Sequence
<220> FEATURE:
<223> OTHER INFORMATION: oligoDNA primer

<400> SEQUENCE: 39
gtagcgttgg gttgcgaaag gccttgtggt actgcctgat                          40

<210> SEQ ID NO 40
<211> LENGTH: 22
<212> TYPE: DNA
<213> ORGANISM: Artificial Sequence
<220> FEATURE:
<223> OTHER INFORMATION: oligoDNA primer

<400> SEQUENCE: 40
gtggcggaat acgtctggcc tc                                             22

<210> SEQ ID NO 41
<211> LENGTH: 23
<212> TYPE: DNA
<213> ORGANISM: Artificial Sequence
<220> FEATURE:
<223> OTHER INFORMATION: oligoDNA primer

<400> SEQUENCE: 41
gtctaggtgc gtagtgccag cag                                            23

<210> SEQ ID NO 42
<211> LENGTH: 25
<212> TYPE: DNA
<213> ORGANISM: Artificial Sequence
<220> FEATURE:
<223> OTHER INFORMATION: oligoDNA primer

<400> SEQUENCE: 42
cgaatggctt gggatatgat gatga                                          25

<210> SEQ ID NO 43
<211> LENGTH: 23
<212> TYPE: DNA
<213> ORGANISM: Artificial Sequence
<220> FEATURE:
<223> OTHER INFORMATION: oligoDNA primer

<400> SEQUENCE: 43
atgggcgtga aagagcaagg cag                                            23

<210> SEQ ID NO 44
<211> LENGTH: 21
```

```
<212> TYPE: DNA
<213> ORGANISM: Artificial Sequence
<220> FEATURE:
<223> OTHER INFORMATION: oligoDNA primer

<400> SEQUENCE: 44
gcaactggac caggggggag c                                              21

<210> SEQ ID NO 45
<211> LENGTH: 23
<212> TYPE: DNA
<213> ORGANISM: Artificial Sequence
<220> FEATURE:
<223> OTHER INFORMATION: oligoDNA primer

<400> SEQUENCE: 45
tcccgatagt catcagcagg tcc                                            23

<210> SEQ ID NO 46
<211> LENGTH: 23
<212> TYPE: DNA
<213> ORGANISM: Artificial Sequence
<220> FEATURE:
<223> OTHER INFORMATION: oligoDNA primer

<400> SEQUENCE: 46
cggagatatt ctttgcgggc tgc                                            23

<210> SEQ ID NO 47
<211> LENGTH: 26
<212> TYPE: DNA
<213> ORGANISM: Artificial Sequence
<220> FEATURE:
<223> OTHER INFORMATION: oligoDNA primer

<400> SEQUENCE: 47
cgcccgaggc ctacctcttc tatatc                                         26

<210> SEQ ID NO 48
<211> LENGTH: 24
<212> TYPE: DNA
<213> ORGANISM: Artificial Sequence
<220> FEATURE:
<223> OTHER INFORMATION: oligoDNA primer

<400> SEQUENCE: 48
cccatcacgt actccacata tggc                                           24

<210> SEQ ID NO 49
<211> LENGTH: 22
<212> TYPE: DNA
<213> ORGANISM: Artificial Sequence
<220> FEATURE:
<223> OTHER INFORMATION: oligoDNA primer

<400> SEQUENCE: 49
gcgcacaccg tagcttggta gg                                             22

<210> SEQ ID NO 50
<211> LENGTH: 25
<212> TYPE: DNA
<213> ORGANISM: Artificial Sequence
<220> FEATURE:
<223> OTHER INFORMATION: oligoDNA primer

<400> SEQUENCE: 50
```

```
gagcgagcct caggaatgtt tgaca                                              25

<210> SEQ ID NO 51
<211> LENGTH: 24
<212> TYPE: DNA
<213> ORGANISM: Artificial Sequence
<220> FEATURE:
<223> OTHER INFORMATION: oligoDNA primer

<400> SEQUENCE: 51
tgatgttgag aaggatggtg gtac                                               24

<210> SEQ ID NO 52
<211> LENGTH: 24
<212> TYPE: DNA
<213> ORGANISM: Artificial Sequence
<220> FEATURE:
<223> OTHER INFORMATION: OligoDNA primer

<400> SEQUENCE: 52
tggcccaaag tggaacaatt ttgg                                               24

<210> SEQ ID NO 53
<211> LENGTH: 24
<212> TYPE: DNA
<213> ORGANISM: Artificial Sequence
<220> FEATURE:
<223> OTHER INFORMATION: oligoDNA primer

<400> SEQUENCE: 53
caacgcagaa cgagacctca tccc                                               24

<210> SEQ ID NO 54
<211> LENGTH: 24
<212> TYPE: DNA
<213> ORGANISM: Artificial Sequence
<220> FEATURE:
<223> OTHER INFORMATION: OligoDNA primer

<400> SEQUENCE: 54
gacctttcct atcaattgct acac                                               24

<210> SEQ ID NO 55
<211> LENGTH: 20
<212> TYPE: DNA
<213> ORGANISM: Artificial Sequence
<220> FEATURE:
<223> OTHER INFORMATION: OligoDNA primer

<400> SEQUENCE: 55
tgggcacggc ctgactacaa                                                    20

<210> SEQ ID NO 56
<211> LENGTH: 24
<212> TYPE: DNA
<213> ORGANISM: Artificial Sequence
<220> FEATURE:
<223> OTHER INFORMATION: OligoDNA primer

<400> SEQUENCE: 56
atggccaaaa atgaggtgtt ctgc                                               24

<210> SEQ ID NO 57
<211> LENGTH: 24
<212> TYPE: DNA
<213> ORGANISM: Artificial Sequence
```

```
<220> FEATURE:
<223> OTHER INFORMATION: OligoDNA primer

<400> SEQUENCE: 57
aaggtccaaa ggattcacgg agta                                          24

<210> SEQ ID NO 58
<211> LENGTH: 26
<212> TYPE: DNA
<213> ORGANISM: Artificial Sequence
<220> FEATURE:
<223> OTHER INFORMATION: OligoDNA primer

<400> SEQUENCE: 58
ggtcaaacct gcggttacag acgttg                                        26

<210> SEQ ID NO 59
<211> LENGTH: 24
<212> TYPE: DNA
<213> ORGANISM: Artificial Sequence
<220> FEATURE:
<223> OTHER INFORMATION: OligoDNA primer

<400> SEQUENCE: 59
gtgtacctag tgtgtgccgc tcta                                          24

<210> SEQ ID NO 60
<211> LENGTH: 26
<212> TYPE: DNA
<213> ORGANISM: Artificial Sequence
<220> FEATURE:
<223> OTHER INFORMATION: OligoDNA primer

<400> SEQUENCE: 60
tttgcccacg ctccctgcat agagaa                                        26

<210> SEQ ID NO 61
<211> LENGTH: 24
<212> TYPE: DNA
<213> ORGANISM: Artificial Sequence
<220> FEATURE:
<223> OTHER INFORMATION: OligoDNA primer

<400> SEQUENCE: 61
caccgcatgg cgtgggacat gatg                                          24

<210> SEQ ID NO 62
<211> LENGTH: 23
<212> TYPE: DNA
<213> ORGANISM: Artificial Sequence
<220> FEATURE:
<223> OTHER INFORMATION: OligoDNA primer

<400> SEQUENCE: 62
tgcacgtcca cgatgttttg gtg                                           23

<210> SEQ ID NO 63
<211> LENGTH: 26
<212> TYPE: DNA
<213> ORGANISM: Artificial Sequence
<220> FEATURE:
<223> OTHER INFORMATION: OligoDNA primer

<400> SEQUENCE: 63
tacaggctct ggcattaccc ctgcac                                        26
```

```
<210> SEQ ID NO 64
<211> LENGTH: 24
<212> TYPE: DNA
<213> ORGANISM: Artificial Sequence
<220> FEATURE:
<223> OTHER INFORMATION: OligoDNA primer

<400> SEQUENCE: 64
agcgtgagcc ctgacgaagt acgg                                          24

<210> SEQ ID NO 65
<211> LENGTH: 33
<212> TYPE: DNA
<213> ORGANISM: Artificial Sequence
<220> FEATURE:
<223> OTHER INFORMATION: OligoDNA primer

<400> SEQUENCE: 65
tagcattgcc ccaacaggct tatgcttatg acg                                33

<210> SEQ ID NO 66
<211> LENGTH: 29
<212> TYPE: DNA
<213> ORGANISM: Artificial Sequence
<220> FEATURE:
<223> OTHER INFORMATION: OligoDNA primer

<400> SEQUENCE: 66
gggatgacat cagcgttccg cgtgaccag                                     29

<210> SEQ ID NO 67
<211> LENGTH: 25
<212> TYPE: DNA
<213> ORGANISM: Artificial Sequence
<220> FEATURE:
<223> OTHER INFORMATION: OligoDNA primer

<400> SEQUENCE: 67
ggagtcttct cgctcccatc actgc                                         25
```

CELL CULTURE SYSTEM OF A HEPATITIS C GENOTYPE 3A AND 2A CHIMERA

CROSS REFERENCE TO RELATED APPLICATIONS

This application claims the benefit of priority to and is a U.S. National Phase Application of PCT International Application Number PCT/DK2008/050083, filed on Apr. 11, 2008, designating the United States of America and published in the English language, which is an International Application of and claims the benefit of priority to Danish Patent Application No. PA 2007 00544, filed on Apr. 13, 2007, and Danish Patent Application No. PA 2007 01100, filed on Jul. 27, 2007, The disclosures of the above-referenced applications are hereby expressly incorporated by reference in their entireties.

FIELD OF THE INVENTION

This invention provides infectious recombinant hepatitis C viruses (HCV), and vectors, cells and animals comprising the same. The present invention provides methods of producing the infectious recombinant HCV, and their use in identifying anti-HCV therapeutic and including for use in vaccines and diagnostics and, as well as sequences of HCV associated with HCV pathogenesis.

BACKGROUND

Hepatitis C virus (HCV) is one of the most widespread infectious diseases in the world. About 170 million people are infected with HCV worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and posttranslationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 6 major HCV genotypes (genotypes 1-6) have been identified, which differ by 31-33% at the nucleotide level. In addition, there are numerous subtypes (a, b, c, etc.). In general different subtypes and isolates differ respectively by 20-25% and 2-8% at the nucleotide level. In the U.S., the majority of HCV infected individuals has genotype 1 (1a or 1b), while most others are infected with genotype 2 (2a or 2b) or 3a. Genotype 3a is more prevalent in Europe infecting up to 50% of patients in several countries with a high prevalence in specific risk groups, such as intravenous drug users and its prevalence in Europe is expected to rise.

Furthermore, genotype 3a is very prevalent in many highly populated countries in Asia such as India and Pakistan, as well as the former USSR, Australia and Brazil. In HCV infected patients, genotype 3 was found to be associated with more pronounced hepatic steatosis compared to other genotypes. The only approved therapy for HCV, combination therapy with interferon and ribavirin, is expensive and associated with severe side effects and contraindications. Sustained viral response can be achieved in only about 55% of treated patients in general, in 85-90% of patients infected with genotypes 2 and 3 and only in 40-50% of patients infected with genotype 1. There is no vaccine against HCV.

Since its discovery in 1989, research on HCV has been hampered by the lack of appropriate cell culture systems allowing for research on the complete viral life cycle as well as new therapeutics and vaccines. Full-length consensus cDNA clones of HCV strain H77 (genotype 1a) and J6 (genotype 2a) shown to be infectious in the chimpanzee model, were apparently not infectious in vitro. Replicon systems permitted the study of HCV RNA replication in cell culture using the human liver hepatoma cell line Huh7 but were dependent on adaptive mutations that were deleterious for infectivity in vivo.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells and the derived Huh7.5.1 (Wakita et al., 2005) (Zhong et al., 2005).

At the same time, Lindenbach et al. demonstrated that the intragenotypic 2a/2a recombinant genome (J6/JFH1), in which the structural genes (C, E1, E2), p7 and NS2 of JFH1 were replaced by the corresponding genes of the infectious cDNA clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo (Lindenbach et al., 2006). Intragenotypic and intergenotypic recombinant HCV genomes are naturally occurring. Interestingly, in several of these isolates the recombination breakpoint apparently maps in close proximity to the NS2/NS3 junction, the site of recombination in the J6/JFH genomes.

Despite the importance of the described cell culture systems they represent only a single subtype (genotype 2a) of HCV.

Pietschmann et al. 2006 disclose the construction and characterization of infectious intragenotypic and intergenotypic hepatitis C virus recombinants. The authors created a series of recombinant genomes allowing production of infectious viral particles containing Core through NS2 of genotype 1a, 1b, 2a and 3a by constructing intra- and intergenotypic recombinant genomes between the JFH1 isolate and the HCV isolates: H77 (genotype 1a), Con1 (genotype 1b), J6 (genotype 2a) and 452 (genotype 3a) respectively. Thus, disclosing a genotype 3a isolate completely different from the isolate disclosed in the present application.

The infectious titers of the 1a, 1b and 3a genotypes disclosed in Pietschmann et al. 2006 are not at a level sufficiently high for practical utilization in functional analysis, drug and vaccine development or most other applications. For such applications, including screening of potential drugs and development of potential vaccine candidates the skilled person will know that infectivity titers below $10^3$ $TCID_{50}$/mL contain insufficient amounts of infectious virus. Besides from disclosing a genotype 3a isolate different from the genotype 3a isolate disclosed in the present application Pietschmann et al. 2006 provides no sequence data of the virus produced in the cell culture. Accordingly, the study does not attempt cell culture adaptation of the genotype recombinants, e.g. by serial passage of cell culture derived viruses to naïve cells and it is not investigated whether adaptive mutations developed after transfection in cell culture.

In fact, Pietschmann et al does not even provide any sequence data of the virus produced in the cell culture.

SUMMARY OF THE INVENTION

It is important to develop cell culture systems for representative strains of other HCV genotypes with infectious titers enabling in vitro studies, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as ne when incubated with undiluted supernatant derived on day 9 from cells transfected with RNA transcripts ofpS52/JFH1 resulting in a non-determinable TCID5O. # None of 6 replicate wells was showing infection when incubated with undiluted supernatant derived on day 3, 7, and 9 from Huh7.5 cells transfected with RNA transcripts ofpS52/JFH1(GND). $P7_{2718}$ indicates the nucleotide change T2718G.

Figure 5:
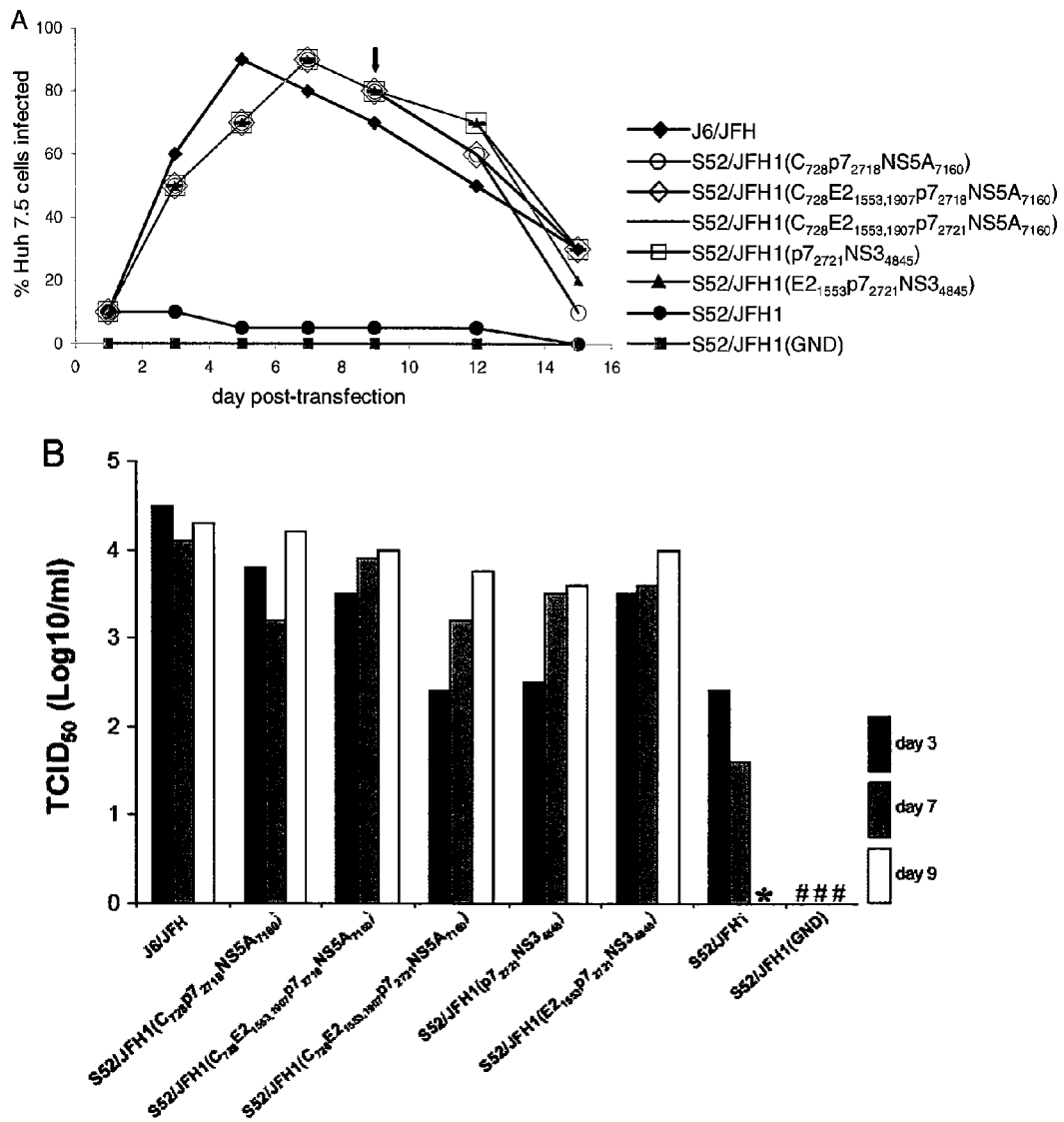

FIG. 6A-C. First passage of five adapted S52/JFH1 viruses in naïve Huh7.5 cells. Huh7.5 cells were incubated for 24 hrs with 1 ml (~$10^4$TCID$_{50}$) of filtered supernatant derived from day 9 of the cultures transfected with RNA transcripts of the five S52/JFH1 recombinants (SEQ ID NO: 3, 5, 7, 9, 11) (FIG. 5). (A) After immuno-staining for Core antigen, the percentage of infected cells was determined with confocal fluorescence microscopy (Leica). (B) HCV RNA titers in supernatants were determined by an HCV TaqMan assay. nd; not detected. (C) Twelve days post-infection cells were plated on chamber slides and subsequently stained with anti-Core primary and Alexa594 fluorochrome coupled secondary antibody. Cell nuclei were counterstained with Hoechst reagent. Pictures were taken using a Leica confocal fluorescence microscope. $P7_{2718}$ indicates the nucleotide change T2718G.

Figure 7:
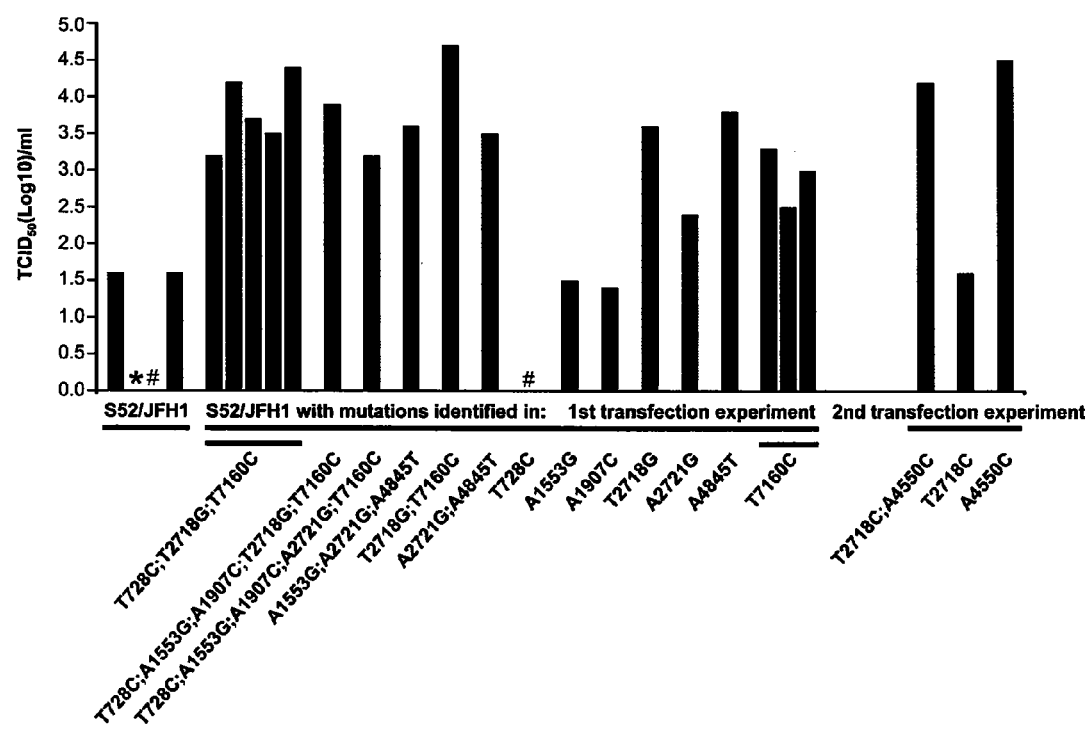

FIG. 7. Infectivity titers after transfection of Huh7.5 cells with S52/JFH1 recombinants with putative adaptive mutations identified in the 1st and 2nd transfection experiment (Table 5). TCID$_{50}$ values were determined on day 7 supernatant. Data were generated in 5 different experiments (including experiment shown in FIG. 5); S52/JFH1(T728C;T2718G; T7160C) (SEQ ID NO: 7) was included in five, S52/JFH1 in four, and S52/JFH1(T7160C) in three experiments. *One/ #None of 6 replicate wells infected after incubation with undiluted supernatant.

Figure 8:
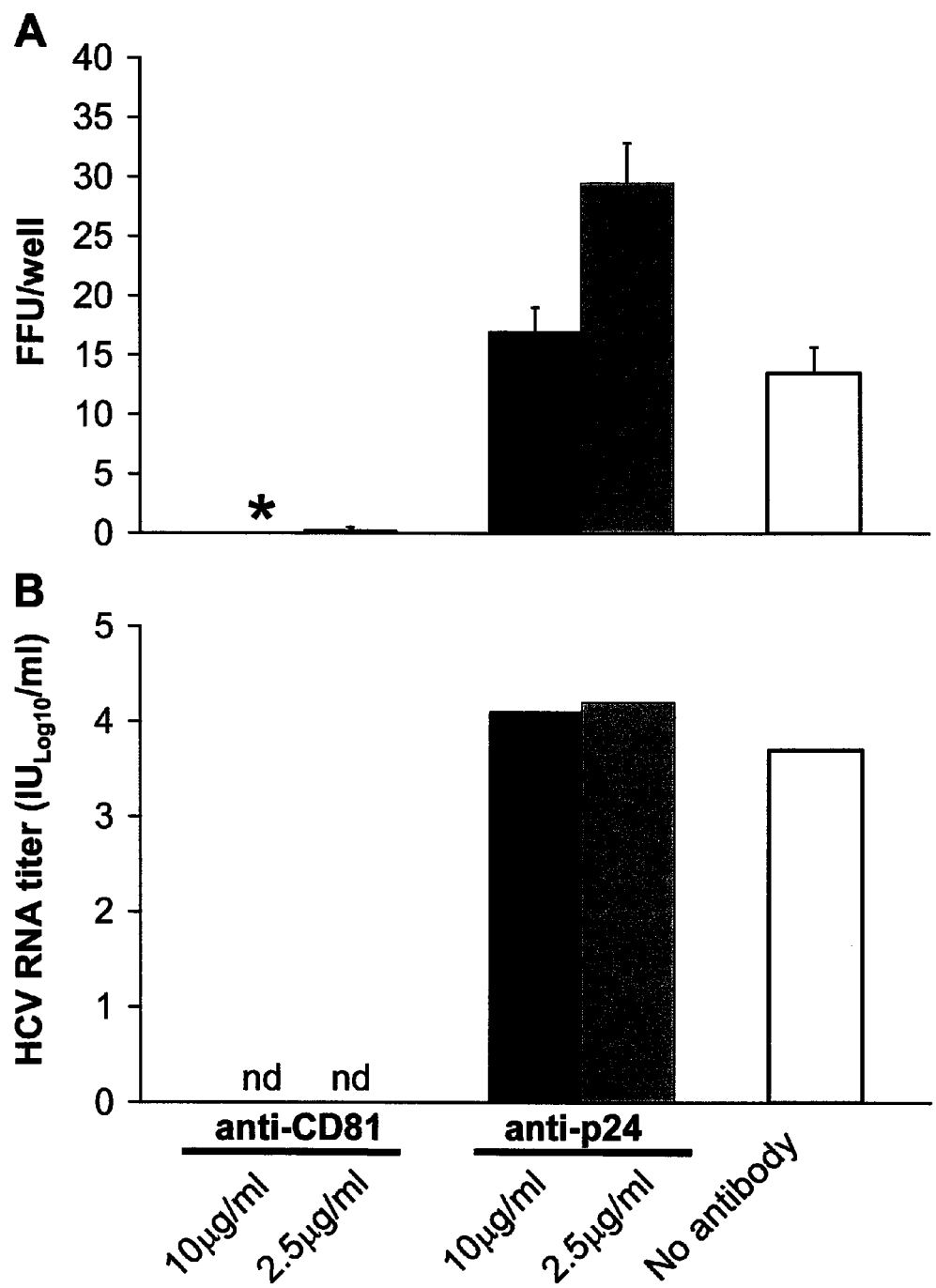

FIG. 8A-B. S52/JFH1 infection depends on CD81. After pre-incubation with anti-CD81 or isotype matched control antibody (anti-p24), $6\times10^3$ Huh7.5 cells/well of a 96 well dish were inoculated with 100 TCID$_{50}$ of S52/JFH1(T728C; T2718G;T7160C). A: Numbers of focus forming units (FFU) per well determined by HCV NS5A staining on day 3. Mean values calculated from four independent infections, error bars indicate standard errors of the mean. B: HCV RNA titers were determined on pooled supernatants from the four different infection experiments on day 3. FFU observed. nd; not detected FIG. 9. S52/JFH1 infection depends on SR-BI. After 1 hr pre-incubation with indicated dilutions of anti-SRBI serum or control serum (Ctr), 6 $\times10^3$ Huh7.5 cells/well of a 96-well dish were inoculated with 150 focus forming units (FFU) of S52/JFH1(T2718G;A4550C) or J6/JFH1. The number of FFUs per well was determined by HCV NS5A staining on day 2. % inhibition was calculated referring to the mean FFU count of non-treated but with the respective virus infected wells. Mean values were calculated from 3 independent infections, error bars indicate standard errors of the mean.

Figure 10:
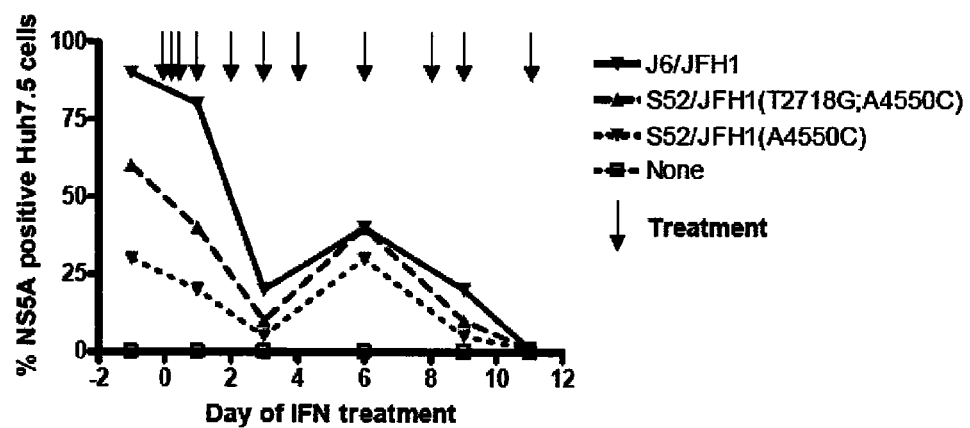

FIG. 10. S52/JFH1 viruses are sensitive to treatment with Interferon alfa. $3\times^6$ Huh7.5 cells were infected with $10^4$ TCID$_{50}$ (MOI 0,003) of the indicated viruses. On day 5 after infection, cultures were evaluated for % of NS5A positive cells (first datapoint) and $4\times10^5$ cells of the respective culture were plated per well of a 6-well dish. After 24 hrs incubation, treatment with cell culture medium containing 500 IU/mL interferon alfa 2b was started. Interferon containing medium was replaced at the time points indicated by arrows. Cultures were evaluated for the % of NS5A positive cells at the indicated timepoints.

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

Nucleotide Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA comprising the structural genes (Core, E1, E2), p7 and non-structural gene NS2 of genotype 3a (e.g. strain S52) and the non-structural genes NS3, NS4A, NS4B, NS5A and NS5B from the JFH1 strain.

The invention provides an isolated nucleic acid molecule encoding an infectious recombinant HCV genome, which nucleic acid comprises an intergenotypic HCV genome. In one embodiment, the intergenotypic HCV genome comprises sequences encoding structural genes (Core, E1, E2), p7 and nonstructural gene (NS2) from a first HCV strain, and sequences encoding the 5' untranslated region (UTR), non-structural genes NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain S52, and in another embodiment, the second HCV strain is strain JFH1.

Importantly, the present inventors demonstrated that J6/JFH viruses recovered from Huh7.5 cells had the original J6/JFH open reading frame sequence after one cell free passage, thus confirming the robustness of this system. This is in contrast to the JFH1 system described by Zhong et al., in which the establishment of sustained infection depends on the acquisition of adaptive mutations.

As observed for JFH1, the present inventors found that J6/JFH viruses at the peak of infection exerted a cytopathic effect on Huh7.5 cells. This was subsequently demonstrated also for the present S52/JFH1 intergenotypic viruses.

In one embodiment, the HCV nucleic acid molecule of the present invention comprises the nucleic acid sequence (cDNA) of SEQ ID NO: 1. In another embodiment the nucleic acid molecule has at least a functional portion of a sequence as shown in SEQ ID NO: 1, which represents a specific embodiment of the present invention exemplified herein.

In another embodiment, the nucleic acid comprises a sequence sharing at least 90% identity with that set forth in SEQ ID NO: 1, such as 90% identity, 91% identity, 92% identity, 93% identity, 94% identity, 95% identity, 96% identity, 97% identity, 98% identity, or 99% identity.

In another embodiment the nucleic acid comprises at least 90% sequence identity to that of SEQ ID NO: 1.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO: 1 is a DNA sequence, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID NO: 1.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 1. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 1 or the said nucleic acid sequence with any mutation described in this document is obtained by any other means than what is described above. Thus, one aspect of the present invention relates to any of the nucleic acid sequence disclosed herein, such as but not limited to SEQ ID NO: 1, 3, 5, 7, 9, 11, 13, 15, 17, 19 and 21.

In another embodiment, the complementary DNA (cDNA) clone, which encodes human hepatitis C virus of genotype 3a/JFH1 (e.g. S52/JFH1), wherein said molecule is capable of expressing said virus when transfected into cells and further capable of infectivity in vivo and wherein said molecule encodes the amino acid sequence of SEQ ID NO: 2.

In yet another embodiment, the complementary DNA (cDNA) clone, which encodes human hepatitis C virus of genotype 3a/JFH1 (e.g. S52/JFH1), wherein said molecule is capable of expressing said virus when transfected into cells and further capable of infectivity in vivo and wherein said molecule encodes the amino acid sequence with at least 90% sequence identity to that of SEQ ID NO: 2.

In another embodiment, the amino acid sequence comprises a sequence sharing at least 90% identity with that set forth in SEQ ID NO: 2, such as 90% identity, 91% identity, 92% identity, 93% identity, 94% identity, 95% identity, 96% identity, 97% identity, 98% identity, or 99% identity.

It is to be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

According to an aspect of the invention, HCV nucleic acid, including the polyprotein coding region, may be mutated or engineered to produce variants or derivatives with, e.g., silent mutations, conservative mutations, etc. In a further embodiment, silent nucleotide changes in the polyprotein coding regions (i.e., variations of the first, second or third base of a codon leading to a new codon that encodes the same amino acid) are incorporated as markers of specific HCV clones.

In another embodiment, the nucleic acid molecule in any form with any changes from SEQ ID NO: 1 encodes the amino acid sequence of SEQ ID NO: 2 or the said amino acid with any mutation described in this document including conservative amino acid mutations as described.

In a further embodiment, the amino acid sequence of SEQ ID NO: 2 or the said amino acid with any mutation described in this document is obtained by any other means than what is described above. Thus, one aspect of the present invention relates to any of the amino acid sequences disclosed herein, such as but not limited to SEQ ID NO: 2, 4, 6, 8, 10, 12, 14, 16, 18, 20 and 22.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventor here reports adaptive mutations, which allow efficient formation and release of viral particles in cell culture, and thus the present invention relates to these adaptive mutation in the present use as well as use in other strains.

After transfection of S52/JFH1 RNA transcripts into Huh7.5 cells, the present inventors observed in six independent experiments (FIG. 1A, FIG. 2A, FIG. 5A, FIG. 7) a significant delay in virus spread compared to the J6/JFH positive control culture, which indicates dependence on the acquisition of adaptive mutations.

A group of preferred HCV-cDNA constructs, HCV-RNA full-length genomes with the ability to release viral particles in cell culture, which are consequently highly suitable for practical use is characterized in that it contains one, several or all of the nucleic acid exchanges listed below and/or one, several or all of the following amino acid exchanges.

Direct genome sequencing of recovered S52/JFH1 viruses indicated the occurrence of different adaptive mutations during the first transfection experiment and consecutive viral passages (TABLE 5 and below).

Thus in one embodiment, the present invention relates to nucleic acid molecules according to the present invention, wherein said molecule comprises adaptive mutations in Core, E2, p7, NS3 and NS5A singly or in combination, such as but not limited to sequences with SEQ ID NO: 3, 5, 7, 9, 11, 13, 15, 17, 19, 21.

In the context of the present invention the term "adaptive mutation" is meant to cover mutations identified in passaged S52/JFH1 viruses that provide the original S52/JFH1 genome and any other HCV sequence the ability to grow efficiently in culture. Furthermore all introductions of mutations into the S52/JFH1 sequence described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins. For example mutations in Core could increase Core stability and target Core more efficiently to lipid droplets, which could be exploited in in vitro Core expression systems. Mutations in NS3 and NS5A could increase replication capacity, which could be expoited in studies using the replicon system.

Thus in one embodiment, the present invention relates to other HCV genomes with adaptive mutations, all of them, combinations of them or individual mutations, that grow in culture. In this case the titers might be lower than those listed.

It should be understood that any feature and/or aspect discussed above in connection with the mutations according to the invention apply by analogy to both single mutation and any combination of the mutations.

Clonal analysis confirmed the presence of several different adapted genomes in 2nd passage cell culture supernatant and supported the hypothesis, that a primary viable genome (with mutations in E2, p7, and/or N3) might have been outnumbered by a set of even fitter genomes with key mutations in Core, p7, and NS5A (TABLE 5).

A hallmark in this clonal analysis was the occurrence of a p7 mutation in all genomes, either T2718G (7/9 clones) or A2721G (2/9 clones). The mutations in p7 were always combined with one mutation in the JFH1 part of the genome, either in NS3 (A4845T; 1/9 clones) or NS5A (T7160C; 8/9 clones). T7160C in NS5A always occurred together with T728C in Core.

Five recombinant S52/JFH1 genomes with the identified combinations of adaptive mutations (SEQ ID NO: 3, 5, 7, 9, 11) performed as efficiently in Huh7.5 cells as J6/JFH (FIG. 5, FIG. 6), and in contrast to the original S52/JFH1 the resulting S52/JFH1 viruses could be passaged without acquiring additional mutations. Genomes with just two mutations, in p7 and NS3 (SEQ ID NO: 11), or with three mutations, in Core, p7, and NS5A (SEQ ID NO: 7), were fully viable. It did not appear to make a difference which of the two p7 mutations identified was combined with the Core and NS5A mutations. The identified mutations in E2 did apparently not improve growth of these recombinants.

Furthermore the following mutations were identified in passaged S52/JFH1 viruses and are therefore considered as adaptive mutations in the context of this invention 1. identified in the $1^{st}$ passage of the $2^{nd}$ transfection experiment by direct sequencing: T2718C and A4550C
2. identified in the $2^{nd}$ passage of the $1^{st}$ transfection experiment by direct sequencing: mutations in E1 and NS5A (T1191C and G7182A) as well as noncoding mutations in Core and NS5A (C688A and T6685C).
3. identified only by clonal analysis. The following nucleotide changes occurred in more than one clone and are therefore more likely to contribute to cell culture adaptation, even though they were not prominent in direct sequencing: A824G (occurred in 3/9 clones), A1937G (2/9 clones), G2916A (2/9 clones), C6328T (3/9 clones).
4. identified in transfection or $1^{st}$ passage of viruses containing single adaptive mutations (Table 5A): C1527T, A2297T, T2720A, A3023C, A3748G, G4464T, G4464A, A4552C, A4552T, C5407T, A7154C.

The present inventors constructed up to seven recombinant S52/JFH1 genomes with combinations of adaptive mutations; four with the combinations suggested by clonal analysis (SEQ ID NO: 3, 5, 7, 9) and three with one p7 mutation combined with another mutation either in NS3 or NS5A (SEQ ID NO: 11, 19, 21) (Table 5A). These recombinants performed as efficiently as J6/JFH in Huh7.5 cells (FIGS. 5, 6, 7) and the resulting S52/JFH1 viruses could be passaged without acquiring additional mutations. In contrast 7/9 S52/JFH1 recombinants with single mutations acquired additional nucleotide changes in cell culture, in most instances at positions at which adaptive mutations had been detected previously and with a preference for the combination of one mutation in p7 with a second mutation in NS3 or NS5A (Table 5A). Only two S52/JFH1 recombinants with single mutations did not require additional nucleotide changes: T2718G (I793S) in p7 (SEQ ID 15) and A4550C (K1404Q) in NS3 (SEQ ID 17), respectively. Interestingly, these were the two amino acid changes conferring viability to S52/JFH1 (T728C) 25 days after transfection (Table 5B). It is of note, that neither of these two mutated nucleotides/corresponding amino acids is found in other HCV isolates (156 and 204 isolates deposited in a ready-made alignment of NS3 and p7, respectively, as provided by the American HCV database website by Jun. 14, 2007).

T2718G in p7 and A4550C in NS3 were the only adaptive mutations able to individually confer cell culture adaptation of S52/JFH1. S52/JFH1(T2718G; A4550C) (SEQ ID 13) was constructed in order to test if combination of T2718G and A4550C on one S52/JFH1 genome was possible. After transfection and passage in Huh7.5 cells S52/JFH1(T2718G; A4550C) viruses yielded infectivity titers between $10^4$ and $10^5$ TCID$_{50}$/mL; additionally, direct sequencing of the complete ORF of S52/JFH1(T2718G; A4550C) genomes revealed that these viruses were genetically stable after passage in Huh7.5 cells. Thus, it was shown that the S52/JFH1 (T2718G; A4550C) genome (SEQ ID 13), combining the two adaptive mutations, which were able to individually provide adaptation of the S52/JFH1 genome, is viable and efficient in Huh7.5 cell culture.

One embodiment of the present invention relates to adaptive mutations, wherein said adaptive mutation is at least one of the replacements of the first said nucleotide at the said position of SEQ ID NO: 1 by the following said nucleotide selected from the group consisting of C688A, T728C, A824G, T1191C, C1527T, A1553G, A1907C, A1937G, A2297T, T2718C, T2720A, T2718G, A2721G, G2916A, A3023C, A3748G, G4464T, G4464A, A4550C, A4552C, A4552T, A4845T, C5407T, C6328T, T6685C, A7154C, T7160C and G7182A.

One embodiment of the present invention relates to adaptive mutations, wherein said adaptive mutation is at least one of the replacements of the first said nucleotide at the said position of SEQ ID NO: 1 by the following said nucleotide selected from the group consisting of T728C, A1553G, A1907C, T2718C, T2718G, A2721G, A4550C, A4845T and T7160C.

One embodiment of the present invention relates to adaptive mutations, wherein said adaptive mutation is at least one of the replacements of the first said nucleotide at the said position of SEQ ID NO: 1 by the following said nucleotide selected from the group consisting of T728C, A1553G, A1907C, T2718G and T7160C. The resulting sequence is shown in SEQ ID NO: 3

One embodiment of the present invention relates to adaptive mutations, wherein said adaptive mutation is at least one of the replacements of the first said nucleotide at the said position of SEQ ID NO: 1 by the following said nucleotide selected from the group consisting of T728C, A1553G, A1907C, T2721G and T7160C. The resulting sequence is shown in SEQ ID NO: 5

One embodiment of the present invention relates to adaptive mutations, wherein said adaptive mutation is at least one of the replacements of the first said nucleotide at the said position of SEQ ID NO: 1 by the following said nucleotide selected from the group consisting of T728C, T2718G, and T7160C. The resulting sequence is shown in SEQ ID NO: 7

One embodiment of the present invention relates to adaptive mutations, wherein said adaptive mutation is at least one of the replacements of the first said nucleotide at the said position of SEQ ID NO: 1 by the following said nucleotide selected from the group consisting of A1553G, A2721G and A4845T. The resulting sequence is shown in SEQ ID NO: 9

One embodiment of the present invention relates to adaptive mutations, wherein said adaptive mutation is at least one of the replacements of the first said nucleotide at the said position of SEQ ID NO: 1 by the following said nucleotide selected from the group consisting of A2721G and A4845T. The resulting sequence is shown in SEQ ID NO: 11 One embodiment of the present invention relates to adaptive mutations, wherein said adaptive mutations is a replacement of T in position 2718 of SEQ ID NO: 1 with G and a replacement of T in position 7160 of SEQ ID NO: 1 with C. The resulting sequence is shown in SEQ ID NO: 19.

One embodiment of the present invention relates to adaptive mutations, wherein said adaptive mutations is a replacement of T in position 2718 of SEQ ID NO: 1 with C and a replacement of A in position 4550 of SEQ ID NO: 1 with C. The resulting sequence is shown in SEQ ID NO: 21.

One embodiment of the present invention relates to adaptive mutations, wherein said adaptive mutations is a replacement of T in position 2718 of SEQ ID NO: 1 with G and a replacement of A in position 4550 of SEQ ID NO: 1 with C. The resulting sequence is shown in SEQ ID NO: 13.

One embodiment of the present invention relates to adaptive mutations, wherein said adaptive mutation is a replacement of T in position 728 of SEQ ID NO: 1 with C.

One embodiment of the present invention relates to adaptive mutations, wherein said adaptive mutation is a replacement of C in position 1527 of SEQ ID NO: 1 with T.

One embodiment of the present invention relates to adaptive mutations, wherein said adaptive mutation is a replacement of A in position 1553 of SEQ ID NO: 1 with G.

One embodiment of the present invention relates to adaptive mutations, wherein said adaptive mutation is a replacement of A in position 1907 of SEQ ID NO: 1 with C.

One embodiment of the present invention relates to adaptive mutations, wherein said adaptive mutation is a replacement of A in position 2297 of SEQ ID NO: 1 with T.

One embodiment of the present invention relates to adaptive mutations, wherein said adaptive mutation is a replacement of T in position 2718 of SEQ ID NO: 1 with G. The resulting sequence is shown in SEQ ID NO: 15.

One embodiment of the present invention relates to adaptive mutations, wherein said adaptive mutation is a replacement of T in position 2718 of SEQ ID NO: 1 with C.

One embodiment of the present invention relates to adaptive mutations, wherein said adaptive mutation is a replacement of T in position 2720 of SEQ ID NO: 1 with A.

One embodiment of the present invention relates to adaptive mutations, wherein said adaptive mutation is a replacement of A in position 2721 of SEQ ID NO: 1 with G.

One embodiment of the present invention relates to adaptive mutations, wherein said adaptive mutation is a replacement of A in position 3023 of SEQ ID NO: 1 with C.

One embodiment of the present invention relates to adaptive mutations, wherein said adaptive mutation is a replacement of A in position 3748 of SEQ ID NO: 1 with G.

One embodiment of the present invention relates to adaptive mutations, wherein said adaptive mutation is a replacement of G in position 4464 of SEQ ID NO: 1 with T.

One embodiment of the present invention relates to adaptive mutations, wherein said adaptive mutation is a replacement of G in position 4464 of SEQ ID NO: 1 with A.

One embodiment of the present invention relates to adaptive mutations, wherein said adaptive mutation is a replacement of A in position 4550 of SEQ ID NO: 1 with C. The resulting sequence is shown in SEQ ID NO: 17.

One embodiment of the present invention relates to adaptive mutations, wherein said adaptive mutation is a replacement of A in position 4552 of SEQ ID NO: 1 with C.

One embodiment of the present invention relates to adaptive mutations, wherein said adaptive mutation is a replacement of A in position 4552 of SEQ ID NO: 1 with T.

One embodiment of the present invention relates to adaptive mutations, wherein said adaptive mutation is a replacement of A in position 4845 of SEQ ID NO: 1 with T.

One embodiment of the present invention relates to adaptive mutations, wherein said adaptive mutation is a replacement of C in position 5407 of SEQ ID NO: 1 with T.

One embodiment of the present invention relates to adaptive mutations, wherein said adaptive mutation is a replacement of A in position 7154 of SEQ ID NO: 1 with C.

One embodiment of the present invention relates to adaptive mutations, wherein said adaptive mutation is a replacement of T in position 7160 of SEQ ID NO: 1 with C.

In another embodiment all the amino acid changes observed herein are provided by the present application. The skilled addressee can easily obtain the same amino acid change by mutating another base of the codon and hence all means of obtaining the given amino acid sequence is intended.

One embodiment of the present invention relates to adaptive mutations, wherein said adaptive mutation is at least one of the replacements of the first said amino acid at the said position of SEQ ID NO: 2 by the following said amino acid selected from the group consisting of F130L, I162V, V284A, A396V, M405V, K523Q, N533D, T653S, I793S, I793T, Y794C, Y794N, C859Y, T895P, R1375L, R1375Q, K1404N, K1404Q, Q1502L, I2272L, S2274P and S2281N.

One embodiment of the present invention relates to adaptive mutations, wherein said adaptive mutation is at least one of the replacements of the first said amino acid at the said position of SEQ ID NO: 2 by the following said amino acid selected from the group consisting of F130L, M405V, K523Q, I793S, I793T, Y794C, K1404Q, Q1502L and S2274P.

One embodiment of the present invention relates to adaptive mutations, wherein said adaptive mutation is at least one of the replacements of the first said amino acid at the said position of SEQ ID NO: 2 by the following said amino acid selected from the group consisting of F130L, M405V, K523Q, I793S, and S2274P. The resulting sequence is shown in SEQ ID NO: 4

One embodiment of the present invention relates to adaptive mutations, wherein said adaptive mutation is at least one of the replacements of the first said amino acid at the said position of SEQ ID NO: 2 by the following said amino acid selected from the group consisting of F130L, I793S, and S2274P. The resulting sequence is shown in SEQ ID NO: 8

One embodiment of the present invention relates to adaptive mutations, wherein said adaptive mutation is at least one of the replacements of the first said amino acid at the said position of SEQ ID NO: 2 by the following said amino acid selected from the group consisting of F130L, M405V, K523Q, Y794C and S2274P. The resulting sequence is shown in SEQ ID NO: 6

One embodiment of the present invention relates to adaptive mutations, wherein said adaptive mutation is at least one of the replacements of the first said amino acid at the said position of SEQ ID NO: 2 by the following said amino acid selected from the group consisting of M405V, Y794C, and Q1502L The resulting sequence is shown in SEQ ID NO: 10

One embodiment of the present invention relates to adaptive mutations, wherein said adaptive mutation is at least one of the replacements of the first said amino acid at the said position of SEQ ID NO: 2 by the following said amino acid selected from the group consisting of Y794C, and Q1502L The resulting sequence is shown in SEQ ID NO: 12

One embodiment of the present invention relates to adaptive mutations, wherein said adaptive mutations is a replacement of I in position 793 of SEQ ID NO: 2 with S and a replacement of S in position 2274 of SEQ ID NO: 2 with P. The resulting sequence is shown in SEQ ID NO: 20.

One embodiment of the present invention relates to adaptive mutations, wherein said adaptive mutations is a replacement of I in position 793 of SEQ ID NO: 2 with T and a replacement of K in position 1404 of SEQ ID NO: 2 with Q. The resulting sequence is shown in SEQ ID NO: 22.

One embodiment of the present invention relates to adaptive mutations, wherein said adaptive mutations is a replacement of I in position 793 of SEQ ID NO: 2 with S and a replacement of K in position 1404 of SEQ ID NO: 1 with Q. The resulting sequence is shown in SEQ ID NO: 14.

Another embodiment of the present invention relates said adaptive mutation is a replacement of F in position 130 of SEQ ID NO: 2 with L.

Another embodiment of the present invention relates said adaptive mutation is a replacement of A in position 396 of SEQ ID NO: 2 with V.

Another embodiment of the present invention relates said adaptive mutation is a replacement of M in position 405 of SEQ ID NO: 2 with V.

Another embodiment of the present invention relates said adaptive mutation is a replacement of K in position 523 of SEQ ID NO: 2 with Q.

Another embodiment of the present invention relates said adaptive mutation is a replacement of T in position 653 of SEQ ID NO: 2 with S.

Another embodiment of the present invention relates said adaptive mutation is a replacement of I in position 793 of SEQ ID NO: 2 with S. The resulting sequence is shown as SEQ ID NO: 16.

Another embodiment of the present invention relates said adaptive mutation is a replacement of I in position 793 of SEQ ID NO: 2 with T.

Another embodiment of the present invention relates said adaptive mutation is a replacement of Y in position 794 of SEQ ID NO: 2 with C.

Another embodiment of the present invention relates said adaptive mutation is a replacement of Y in position 794 of SEQ ID NO: 2 with N.

Another embodiment of the present invention relates said adaptive mutation is a replacement of T in position 895 of SEQ ID NO: 2 with P.

Another embodiment of the present invention relates said adaptive mutation is a replacement of R in position 1375 of SEQ ID NO: 2 with L.

Another embodiment of the present invention relates said adaptive mutation is a replacement of R in position 1375 of SEQ ID NO: 2 with O.

Another embodiment of the present invention relates said adaptive mutation is a replacement of K in position 1404 of SEQ ID NO: 2 with Q. The resulting sequence is shown as SEQ ID NO: 18.

Another embodiment of the present invention relates said adaptive mutation is a replacement of K in position 1404 of SEQ ID NO: 2 with N.

Another embodiment of the present invention relates said adaptive mutation is a replacement of Q in position 1502 of SEQ ID NO: 2 with L.

Another embodiment of the present invention relates said adaptive mutation is a replacement of I in position 2272 of SEQ ID NO: 2 with L.

Another embodiment of the present invention relates said adaptive mutation is a replacement of S in position 2274 of SEQ ID NO: 2 with P.

Possible Mechanisms of Identified Adaptive Mutations

Q1502L in the JFH1 NS3 portion of our S52/JFH1 viruses might facilitate interaction with genotype 3a proteins or optimize the JFH1 NS3 protein, since 6/6 genotype 3a and 43/45 genotype 2 isolates (published as confirmed in euHCVdb18) also encode L at this amino acid position, respectively. However, Q1502L was not selected in J6/JFH cultures. NS3 and NS5A proteins have been hot spots for cell culture adaptation in the replicon system. A leucine substitution at amino acid 470 (referring to H77 and S52/JFH1 NS3 protein and corresponding to position 1502 on the S52/JFH1 polyprotein) has been implied in cell culture adaptation of the H77 replicon. Concerning NS5A it is intriguing that S2274P, observed in S52/JFH1 viruses, localizes immediately downstream of a cluster of conserved serine residues involved in NS5A hyperphosphorylation and thus regulation of replication. Even though not conserved for all genotypes, S is conserved for all 45 genotype 2 isolates.

F130L is located in domain 2 of Core, which is supposed to be critical for Core stability and localization to lipid droplets. At position 130, F is conserved in most isolates, while L is only rarely occurring. In future studies it would be interesting to test, if F130L can enhance Core stability and thus lead to greater amounts of intracellular Core, which is thought to be of importance for production of infectious viral particles.

The crucial role of adaptive mutations for the viability of intergenotypic recombinant viruses has recently been found also by others. After transfection of intergenotypic 1a/2a (H77/JFH1) recombinants, a lag phase was observed following transfection before infectious viruses were produced yielding infectivity titers of $10^4$-$10^5$ FFU/ml. It is difficult to evaluate the performance of the 1a/2a recombinants, since the original non-adapted JFH1 genome was used as reference system, which has been shown to perform sub-optimally in the absence of adaptive mutations.

Further the efficiency of the 1/2a recombinants cannot be directly compared with that of the recombinants used in this study, because it has not been clarified, how different measures of infectivity (FFU versus $TCID_{50}$) compare. The viability of the 1a/2a recombinant featuring the same junction (NS2/NS3) as our S52/JFH1 virus appeared to depend on a single mutation in NS3.

However, this conclusion was drawn by studying a timeframe of only 72 hours post-transfection, and the sequence of viruses present in this culture was not determined. Thus, it is possible that additional mutations, accounting for viability, had been acquired. In the present study, we found that a mutation in NS3, probably in combination with one of the mutations observed in p7, is sufficient but not required to confer viability to an intergenotypic (3a/2a) recombinant genome featuring the NS2/NS3 junction.

Figure 3:
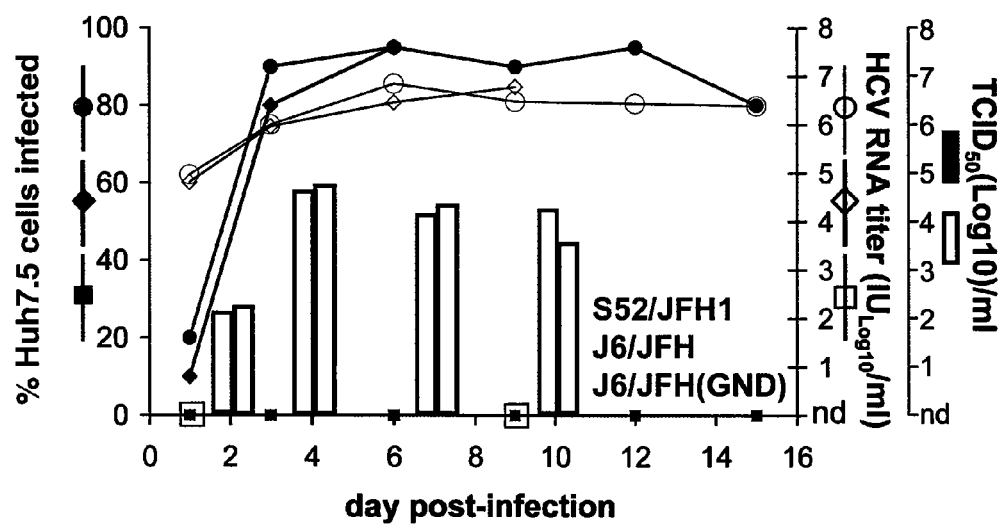
Figure 6:
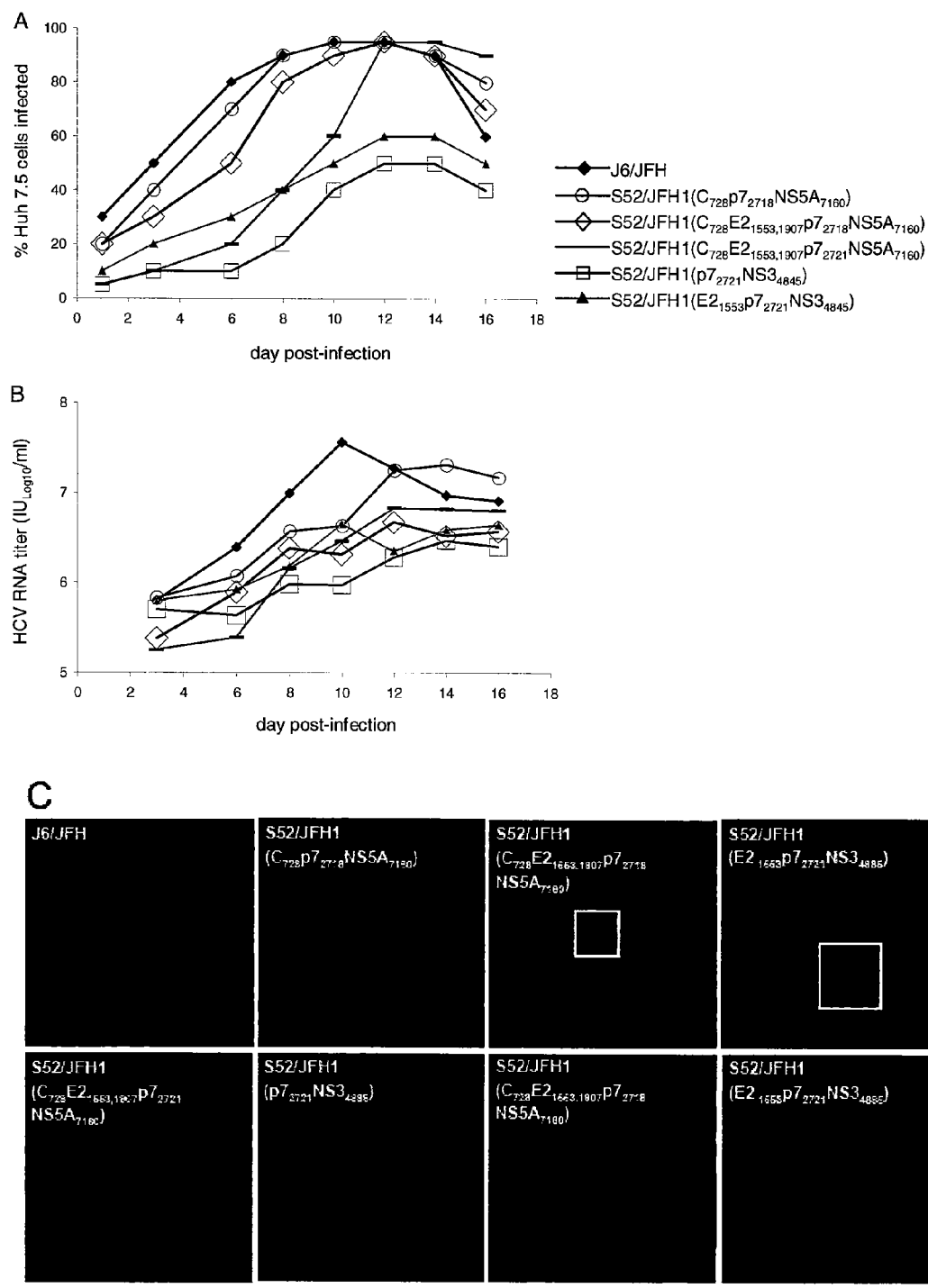

Polyclonal 2nd passage viruses, as well as recombinant adapted S52/JFH1 viruses, performed as efficiently as the J6/JFH reference viruses with respect to peak genome and infectivity titers as well as growth kinetics (TABLE 4, FIG. 3, FIG. 5, FIG. 6). This is in contrast to a recently described intergenotypic recombinant 3a/JFH1 virus based on genotype 3a strain HCV-452, which performs with poor efficiency in cell culture leading to low infectivity titers (<$10^2$ $TCID_{50}$/ml) when compared to J6/JFH recombinant genomes (Pietschmann et al. 2006). These differences might be due to differential assembly capabilities of the structural proteins of different isolates. However, since a timeframe of only 96 hours post-transfection was studied, this could also indicate a low infectivity of the original 3a/2a viruses in the absence of adaptive mutations.

Our study also points to a low infectivity of the original S52/JFH1 virus. First, the present inventors found comparable to the previously described study low infectivity titers shortly after transfection with pS52/JFH1 in vitro transcripts (FIG. 5B), which eventually became undeterminable. Second, the original pS52/JFH1 sequence could not be detected in clonal analysis of virus genomes derived from a 2nd viral passage. Thus, the original S52/JFH1 viruses seem to be viable but unable to establish sustained infection in cell culture.

In summary, the present inventors have provided the first efficient HCV genotype 3a cell culture system leading to sustained infection in Huh7.5 cell culture. The present inventors have developed an intergenotypic recombinant, containing the Core through NS2 sequence of the S52 reference genome on a JFH1 backbone.

The present inventors have identified and characterized combinations of adaptive mutations, which allow efficient growth of S52/JFH1 viruses. The recombinant adapted S52/JFH1 genomes will be valuable tools for genotype 3a specific in vitro studies of Core through NS2 involved in viral entry, assembly and release as well as related therapeutics. Furthermore they will permit studies of genotype specific interactions and functions and might further the development of a genotype 3a full-length cell culture system.

The skilled addressee may use the present invention to determine whether the identified sets of mutations can confer viability to other JFH1 based intergenotypic genotype 3a recombinants, which would allow in vitro studies of any patient 3a isolate of interest, or to other JFH1 based intergenotypic genotype recombinants or to any other HCV isolate.

Finally, it would be interesting to elucidate the mechanism of action of the identified mutations. In principle they might enable efficient intergenotypic protein interaction and/or lead to improvement of protein function independent of these intergenotypic interactions, for example by influencing interactions with host cell proteins.

Titer

To determine the efficiency of the developed system, HCV RNA titers are determined in IU/ml (international units/ml) with Taq-Man Real-Time-PCR and infectious titers are determined with a tissue culture infectious dose-50 method. This titer indicates the dilution of the examined viral stock, at which 50% of the replicate cell cultures used in the essay become infected and is given in $TCID_{50}$/ml.

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

Thus such molecules which following transfection and/or subsequent viral passage, are capable of generating a HCV infectivity titer of $10^2$ $TCID_{50}$/ml (50% tissue culture infectious doses)/ml or above using the assay described in this text or what is equivalent to this titer determined by any method.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient, which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non-hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 3a/JFH1 RNA and produces a virus particle comprising introducing the said RNA according to the invention into a cell.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein. Such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle or parts thereof, comprising culturing a cell or an animal to allow either to produce the virus.

In another embodiment the invention provides a hepatitis C virus particle obtainable by the method described.

Because the invention provides, inter alia, infectious HCV RNA, the invention provides a method for infecting an animal with HCV, which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further it will be important to determine the viability of the developed viruses in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for anti-viral drugs and the determination of drug resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the genomes obtained in the present study may prove useful for different research topics. Genomes with the original S52 Core could be applied to examine genotype 3a specific features of Core, such as its presumed role in the development of hepatocellular steatosis.

The systems developed in this study are ideal candidates for the genotype 3a specific testing of therapeutics targeting viral entry, assembly and release. Genomes with the original S52 E1 and E2 are valuable for testing of neutralizing antibodies and other drugs acting on entry level, such as fusion inhibitors.

In one embodiment the present invention related to a method for screening new HCV genotype 1a/1b, 2a, 3a, 4a, 5a, 6a and/or 7a inhibitors or neutralizing antibodies, comprising:
  a. culturing at least one selected from the group consisting of a cell according to the present invention, a hepatitis C virus infected cell according to the present invention and a hepatitis C virus particle obtainable by the present invention together with a hepatitis C virus permissive cell,
  b. subjecting said virus or virus infected cell culture to a blood sample or derivatives thereof or synthetically produced equivalents from a HCV genotype 1a/1b, 2a, 3a, 4a, 5a, 6a and/or 7a infected patient, and
detecting the amount of replicating RNA and/or the virus particles.

As proof of principle of using the present invention in testing of anti-hepatitis C virus substances, the effects of interferon alfa, currently used in combination therapy for HCV, were tested on the infected cell culture. Previously, replication of different HCV replicons as well as of the J6/JFH1 virus have been shown to be sensitive to treatment with interferon. Thus we treated Huh7.5 cell cultures infected with J6/JFH1, S52/JFH1(T2718G; A4550C) and S52/JFH1 (A4550C) with cell culture medium containing 5001 U/mL interferon alfa 2b (FIG. 10). After initiation of treatment, we observed for all cultures a fast decline of HCV antigen positive cells. Thus, for J6/JFH1 and S52/JFH1(T2718G; A4550C) the percentage of NS5A positive cells was 90 and 60 the day prior to treatment, whereas only 20% and 10% NS5A positive cells were detected in the respective cultures on day 3 of treatment (FIG. 5). Interestingly, prolonged treatment intervals were followed by an increase in NS5A positive cells; thus, on day 6, when the cultures had not been treated for 48 hrs, 40% of cells in the J6/JFH1 and S52/JFH1 (T2718G; A4550C) cultures were NS5A positive.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. The p7 mutations observed in this study map to TM2, and enables interactions between the S52 p7 and p7-associated JFH1 derived proteins. Hence, new compounds targeting the putative p7 ion-channel, protease inhibitors interfering with NS2, and drugs targeting cellular proteins involved in the described processes can be tested.

Thus, one embodiment of the present invention relates to a method for screening an anti-hepatitis C virus substance, comprising
  a) culturing at least one selected from the group consisting of a cell according to claim 17, a hepatitis C virus infected cell according to claim 21 and a hepatitis C virus particle obtainable by claim 18 together with a hepatitis C virus permissive cell, and
  b) detecting the replicating RNA and/or the virus particles in the resulting culture.
detecting the replicating RNA and/or the virus particles in the resulting culture.

In another embodiment the present invention relates to a method for screening an anti-hepatitis C virus substance, comprising
  a. culturing at least one selected from the group consisting of a cell according to claim 17, a hepatitis C virus infected cell according to claim 21 and a hepatitis C virus particle obtainable by claim 18 together with a hepatitis C virus permissive cell, and
  b. subjecting said virus or virus infected cell culture to the anti-hepatitis C virus substance, and
  c. detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labeled for easier detection, including radiolabeled, antibody labeled for fluorescently labeled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology indicates a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, the SCID-uPA mouse model or a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus indicates the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus indicates that the HCV variant has improved growth in cell culture. In some embodiments, HCV variants are selected for enhanced replication, over a long course of time, in in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference does not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

The invention will hereinafter be described by way of the following non-limiting Figures and Examples.

Sequences

SEQ ID NO: 1: S52-JFH1—DNA
SEQ ID NO: 2: S52-JFH1—Amino Acid Sequence
SEQ ID NO: 3: S52-JFH1-Core(728)E2(1553,1907)p7(T2718G)NS5A(7160)—DNA
SEQ ID NO: 4: S52-JFH1-Core(728)E2(1553,1907)p7(T2718G)NS5A(7160)—Amino Acid Sequence
SEQ ID NO: 5: S52-JFH1-Core(728)E2(1553,1907)p7(2721)NS5A(7160)—DNA
SEQ ID NO: 6: S52-JFH1-Core(728)E2(1553,1907)p7(2721)NS5A(7160)—Amino Acid Sequence
SEQ ID NO: 7: 7: S52-JFH1-Core(728)p7(T2718G)NS5A(7160)—DNA
SEQ ID NO: 8: S52-JFH1-Core(728)p7(T2718G)NS5A(7160)—Amino Acid Sequence
SEQ ID NO: 9: S52-JFH1-E2(1553)p7(2721)NS3(4845)—DNA
SEQ ID NO: 10: S52-JFH1-E2(1553)p7(2721)NS3(4845)—Amino Acid Sequence
SEQ ID NO: 11: S52-JFH1-p7(2721)NS3(4845)—DNA
SEQ ID NO: 12: S52-JFH1-p7(2721)NS3(4845)—Amino Acid Sequence
SEQ ID NO: 13: S52-JFH1-p7(T2718G)NS3(4550)—DNA
SEQ ID NO: 14: S52-JFH1-p7(T2718G)NS3(4550)—Amino Acid Sequence
SEQ ID NO: 15: S52-JFH1-p7(T2718G)—DNA
SEQ ID NO: 16: S52-JFH1-p7(T2718G)—Amino Acid Sequence
SEQ ID NO: 17: S52-JFH1-NS3(4550)—DNA
SEQ ID NO: 18: S52-JFH1-NS3(4550)—Amino Acid Sequence
SEQ ID NO: 19: S52-JFH1-p7(T2718G)NS5A(7160)—DNA
SEQ ID NO: 20: S52-JFH1-p7(T2718G)NS5A(7160)—Amino Acid Sequence
SEQ ID NO: 21: S52-JFH1-p7(T2718C)NS3(4550)—DNA
SEQ ID NO: 22: S52-JFH1-p7(T2718C)NS3(4550)—Amino Acid Sequence
SEQ ID NO: 23: HCV3aF1T7NotI-G
SEQ ID NO: 24: HCV3aR3420BsaBIAscI
SEQ ID NO: 25: HCV3aF3336NotIBsaBI
SEQ ID NO: 26: HCV3aR5209AflIIAscI
SEQ ID NO: 27: 9470R(24)_JFH1
SEQ ID NO: 28: HCV3aCoSeR1072
SEQ ID NO: 29: H39X58R
SEQ ID NO: 30: 7848R_JFH1
SEQ ID NO: 31: −285S_HCV-MOD
SEQ ID NO: 32: HCV3aSeqR831
SEQ ID NO: 33: Chim seq JFH F1
SEQ ID NO: 34: HCV2aF9251
SEQ ID NO: 35: 7234R_JFH1
SEQ ID NO: 36: HCVconsR337
SEQ ID NO: 37: HCVconsR312
SEQ ID NO: 38: HCVconsR169
SEQ ID NO: 39: −84S_HCV-MOD
SEQ ID NO: 40: HCV3aCoSeF918
SEQ ID NO: 41: HCV3aCoSeR1819
SEQ ID NO: 42: HCV3aCoSeF1288
SEQ ID NO: 43: HCV3aCoSeR2402
SEQ ID NO: 44: HCV3aCoSeF2288
SEQ ID NO: 45: HCV3aCoSeR3416
SEQ ID NO: 46: HCV3aCoSeF3336
SEQ ID NO: 47: 4118R_JFH1
SEQ ID NO: 48: 3880S_J6
SEQ ID NO: 49: 4796R_JFH1
SEQ ID NO: 50: 4528S_J6
SEQ ID NO: 51: 5446R_JFH1
SEQ ID NO: 52: 5272S_JFH1
SEQ ID NO: 53: 6460R_J6
SEQ ID NO: 54: 6186S_JFH1
SEQ ID NO: 55: 6862S_JFH1
SEQ ID NO: 56: 7741S_J6
SEQ ID NO: 57: 8703R_JFH1
SEQ ID NO: 58: 8137S_JFH1
SEQ ID NO: 59: 9464R(24)_JFH1
SEQ ID NO: 60: 1109R_J6
SEQ ID NO: 61: 946S_J6
SEQ ID NO: 62: 2111R_J6
SEQ ID NO: 63: 1849S_J6
SEQ ID NO: 64: 2763R_J6
SEQ ID NO: 65: 2754S_J6

SEQ ID NO: 66: 3774R_J6
SEQ ID NO: 67: 3081S_J6/JFH1

EXAMPLES

Materials and Methods

Source of HCV Genotype 3a.

A plasma pool of strain S52 was prepared from acute-phase plasmapheresis units collected from a chimpanzee experimentally infected with serum of an Italian patient chronically infected with hepatitis C virus genotype 3a (strain S52). This HCV pool has an HCV RNA titer of approximately $10^4$ IU/ml and an infectivity titer of approximately $10^3$ chimpanzee infectious doses/ml.

Sequencing of Core Through NS2 of Strain S52.

Total RNA from 200 μl of the S52 plasma was extracted using High Pure Viral Nucleic Acid Kit (Roche) and eluted in 20 μl of elution buffer. RT-PCR was performed on RNA equivalent to 100 μl plasma using random hexamers (TAG Copenhagen) and SuperScript II (Invitrogen) for one hour at 42° C. followed by inactivation of the enzyme for 10 min at 70° C. Remaining RNA templates were digested by incubation with RNAseH (4U, Invitrogen) and RNAseT1 (1000U, Ambion) for 20 min at 37° C. The region of interest was PCR amplified from cDNA in two overlapping fragments using BD Advantage 2 Polymerase Mix (Clontech). The first fragment spanning nucleotides (nts) 1-3404 (positions referring to S52 sequences correspond to the full-length genome sequence of reference isolate H77, accession number AF009606, as proposed by Kuiken et al.41) was amplified with primers HCV3aF1T7NotI-G (SEQ ID NO: 23) and HCV3aR3420BsaBIAscI (SEQ ID NO: 24) (TABLE 1) and the following cycling parameters: initial denaturation of 1 min at 95° C., 40 cycles with 30 sec at 95° C., 30 sec at 62° C., 8 min at 68° C., and final extension of 8 min at 68° C. The second fragment spanning nucleotide 3320 to 5193 was amplified with primers HCV3aF3336NotIBsaBI (SEQ ID NO: 25) and HCV3aR5209AflIIAscI (SEQ ID NO: 26) (TABLE 1) using cycling parameters as above with an annealing temperature of 62° C. Both amplicons were subcloned in pCR2.1 Topo (Invitrogen) and 5 clones were sequenced of each fragment to determine the consensus sequence of core through NS2 of strain S52 (nts 342-3419).

Construction of pS52/JFH1 and Recombinant Adapted Genomes.

For construction of pS52/JFH1 the S52 Core-NS2 fused to JFH1 5' UTR and NS3 was assembled in pGEM-9Zf(-) (Promega) using fusion PCR with Pfu DNA polymerase (Stratagene) and standard cloning procedures with appropriate restriction sites. S52 fragments were derived from the clones described above. The two JFH1 fragments used for fusion of JFH1-5'UTR/S52-Core and S52-NS2/JFH1-NS3, were amplified from plasmid pFL-J6/JFH (generous gift from Charles M. Rice, Rockefeller University) including the EcoRI (vector sequence upstream of JFH1 5' UTR) and AvrII (in NS3 of JFH1) sites, respectively. The S52 consensus XbaI site was removed by site directed mutagenesis (A916T) in order to permit XbaI linearization of pS52/JFH1 at the very 3' end of the 3' UTR prior to in vitro transcription75. The EcoRI/AvrII fragment of the resulting pGEM-9Zf(-) clone was finally inserted into pFL-J6/JFH. pS52/JFH1 contains the 5' UTR of the JFH1 isolate (nts 1-340), which differs from the sequence provided for JFH1 (accession number AB047639) at one position (C301T), Core through NS2 of S52 (nts 341-3436), and NS3 through 3' UTR of JFH1 (nts 3437-9684). pS52/JFH1(GND) has a single point mutation in NS5B (G8624A), which abolishes replication; it was created by transferring the EcoRI/AvrII fragment of pS52/JFH1 into pFL-J6/JFH(GND) (gift from Charles M. Rice, Rockefeller University). For construction of five recombinant adapted S52/JFH1 genomes mutations were introduced in pS52/JFH1 by fusion PCR (Pfu DNA polymerase, Stratagene) and standard cloning techniques using appropriate restriction sites. The HCV sequence of the described plasmids was verified by sequencing of the final DNA preparation (EndoFree Plasmid Maxi Kit, Qiagen). All sequencing reactions were carried out at Macrogen Inc., Seoul, South Korea.

In Vitro Transcription from Full-Length HCV cDNA Genomes.

Plasmid DNA was linearized with XbaI (New England BioLabs), gel purified (Wizard SV Gel and PCR Clean-Up System, Promega), and subjected to in vitro transcription with T7 RNA Polymerase (Promega) for 2 hours at 37° C. according to the manufacturers protocol. The amount of RNA transcripts was estimated by standard agarose gel electrophoresis.

Culture of Huh7.5 Cells.

The human hepatoma cell line Huh7.5 has been described previously (gift from Charles M. Rice, Rockefeller University). Cells were cultured in D-MEM+4500 mg/L Glucose+ GlutaMAX-I+Pyruvate (Gibco/Invitrogen Corporation) containing 10% heat inactivated fetal bovine serum (FBS) (Sigma), penicillin at 100 units/ml and streptomycin at 100 mg/ml (Gibco/Invitrogen Corporation) at 5% $CO_2$ and 37° C. Cells were split every 2nd to 3rd day at a ratio of 1:2 to 1:3.

Transfection of RNA Transcripts into Huh7.5 Cells.

24 hrs before transfection cells were washed with PBS (Dulbecco's Phosphate Buffered Saline; Sigma) and trypsinized (Trypsin/EDTA; Gibco/Invitrogen Corporation). $4 \times 10^5$ cells were plated per well of a 6 well plate in D-MEM supplemented with 10% FBS without antibiotics. Transfection was carried out by lipofection using 2.5 μg in vitro RNA transcripts and 5 μl Lipofectamine 2000 Transfection reagent (Invitrogen) for formation of lipofection complexes in serum free medium (Opti-MEM, Invitrogen). Cell cultures were incubated with lipofection complexes for ~12 hrs at 5% $CO_2$, at 37° C.

Infection of Huh7.5 Cells with Cell Culture Supernatants.

24 hrs before infection cells were washed with PBS and trypsinized. $4 \times 10^5$ cells were plated per well of a 6 well plate. On the day of infection growth medium was removed, cells were washed with PBS and incubated with the desired dilution of virus containing cell culture supernatants or negative control supernatants in complete growth medium. The incubation times for the respective experiments are given in the figure legends.

Collection of Viral Stock of Supernatants.

Cell culture supernatants of virus infected cell cultures or controls were rescued every 2-3 days. After filtration, cell free supernatants were aliquoted immediately and stored at −80° C.

Immuno-Histochemistry Staining for HCV NS5A.

Analyses were carried out as previously described with modifications. Huh7.5 cells were washed with PBS, trypsinized and plated on chamber slides (Nunc). After ~24 hours cells were washed twice with PBS and fixed 5 min with ice-cold methanol. After washing 2× with PBS and 1× with PBS/Tween (0.1% Tween-20), slides were blocked with PBS containing bovine serum albumin (BSA, 1%) and skim milk (0.2%) for 1 hour at room temperature. Endogenous peroxidase staining was reduced by adding 3% $H_2O_2$ in PBS for 5 min. After washing as above the 1st antibody (anti-NS5A, 9E10, a generous gift from Charles M. Rice, used at 1:200 in PBS/Tween) was added and incubated at 4° C. overnight. After washing slides were incubated with secondary antibody (ECLTM Anti-mouse IgG, horseradish peroxidase linked whole antibody, Amersham Biosciences, used at 1:300 in PBS/Tween) for 30 min at room temperature. After washing horseradish peroxidase substrate (DAB substrate kit, DAKO) was added. After incubation for 30 min, slides were washed with H2O, mounted with Fluoromount-G (Southern Biotech) and cover slipped. Percentage of infected cells was evaluated by light microscopy assigning values of 0% (no cells infected), 1%, 5%, 10-90% (in steps of 10%), 95% and 100% (all cells infected).

Immuno-Histochemistry Staining for HCV Core.

Huh7.5 cells were washed with PBS, trypsinized and plated on chamber slides. After ~24 hours cells were washed twice with PBS and fixed with acetone for 5 minutes. After washing 2× with PBS and 1× with PBS/Tween (0.1%), slides were incubated with 1st antibody (MAB Murine Anti-Human HCV (Core Protein) Clone B2, Anogen, used at 1:200 in PBS containing 5% BSA) for 20 min at room temperature. After washing as above secondary antibody (Alexa Fluor 594 goat anti-mouse IgG (H+L), Invitrogen, used at 1:500 in PBS/Tween) was added for 5 min. Cell nuclei were counterstained with Hoechst for 5 min. Finally slides were washed with PBS, mounted with Fluoromount-G and cover slipped. Percentage of infected cells was evaluated by fluorescence confocal microscopy as described above.

Staining and Quantification of Intracellular Lipid Droplets

Cells were fixed as described previously and incubated with anti-Core (as above) followed by incubation with 2nd antibody Alexa Fluor 488 goat anti-mouse IgG (H+L) (Invitrogen) at 1:300 in PBS containing 5% BSA. Lipid droplets were stained with oil red O (Fisher Scientific) as described previously. Cell nuclei were counterstained with Hoechst 33342. Images were obtained by confocal microscopy. For quantification of intracellular lipid contents pixel saturation of the oil red O signal was avoided and images were analyzed using MetaMorph (Universal Imaging). The relative amount of intracellular lipid per cell was determined as the intensity of oil red O signal per nucleus. Eight randomized areas were analyzed per infected/mock infected culture, each area representing 50 cells in average.

Determination of 50% Tissue Culture Infectious Doses ($TCID_{50}$)

In general, the $TCID_{50}$ of culture supernatants was determined as previously described. Huh7.5 cells were washed with PBS, trypsinized and plated at $6 \times 10^3$ cells per well of a poly-D-lysine coated 96 well plate (Nunc). After ~24 hrs cells were incubated with 10-fold serial dilutions of viral stock cell culture supernatant in complete growth medium. For each dilution, six replicate wells were inoculated. After incubation for 48 hrs the plate was subjected to immuno staining for NS5A as described above. Wells were evaluated by light microscopy and scored positive if at least one positive cell could be detected. $TCID_{50}$ values were calculated as described by Reed and Muench.

CD81 Blocking Assay $6 \times 10^3$ Huh7.5 cells were plated per well of a poly-D-lysine coated 96-well plate. After 24 hrs cells were incubated with anti-CD81 (JS-81, BD Pharmingen) or isotype matched control antibody (anti-HIV, p24, clone Kal-1, DAKO) for 1 hr. Subsequently cells were infected with 100 $TCID_{50}$ of S52/JFH1(T728C; T2718G; T7160C) for 3 hrs and washed with PBS. Supernatants were collected after 1, 2 and 3 days. Cells were stained for HCV NS5A after 3 days to determine the number of focus forming units (FFU) per well.

Real-time PCR (TaqMan) Assay for Determination of HCV RNA Titers.

RNA was purified from 200 µl of heat inactivated (56° C. for 30 min) cell culture supernatant and eluted in a final volume of 50 µl using the Total Nucleic Acid Isolation Kit (Roche) in combination with the Total NA Variable Elution Volume protocol on a MagNA Pure LC Instrument (Roche). As an internal control, Phocine Distemper Virus (PDV) was added to the lysis buffer in a concentration titrated to yield a Ct of ~32 upon real-time PCR analysis. In parallel to RNA purified from cell culture supernatants, a quantitative HCV standard panel covering RNA concentrations of 0 to $5 \times 10^6$ IU/ml in one log increments (OptiQuant HCV Panel, AcroMetrix) was analysed. Real-time PCR analyses of HCV and PDV RNA were carried out in two separate reactions using the TaqMan EZ RT-PCR Kit (Applied Biosystems). For HCV, primers and a FAM-labelled MGB-probe were directed against the 5' UTR and were previously shown to perform equivalently against a panel of the six major HCV genotypes in a different TaqMan assay (Engle R E, Bukh J, and Purcell R H, 2007) For PDV, a ready-to-use primer/probe mix was used (Dr. H. G. M. Niesters, Department of Virology, Erasmus Medical Centre, Rotterdam, The Netherlands). The PCR analysis was performed on a 7500 Real-Time PCR System (Applied Biosystems) using 50° C. for 2 min, 60° C. for 30 min and 95° C. for 5 min followed by 45 cycles of 94° C. for 20 sec and 62° C. for 1 min. HCV RNA titers (IU/ml) were calculated using a standard curve created from the known concentrations of the standard panel and their corresponding Ct values (cycle number, at which the normalised fluorescence signal rises above a fixed threshold of 0.2 being directly proportional to the amount of template in the PCR reaction). The reproducible detection limit of the assay was 500 IU/ml. In order to confirm successful purification, amplification and the absence of PCR inhibitors, the Ct value of the PDV reaction was compared to the expected Ct value (based on a mean of all previous runs; n>9) using the MedLab QC freeware programme. The results of samples with an actual Ct value within ±25D of the expected Ct value were accepted.

Direct Sequencing of the HCV ORF of Recovered Virus Genomes.

In order to determine the consensus sequence of the complete ORF, RNA was extracted from virus containing cell culture supernatant as described above. RT-PCR was performed using the gene specific primer 9470R(24)_JFH1 (SEQ ID NO: 27) (TABLE 2) and SuperScript III (Invitrogen) for one hour at 50° C. followed by 10 min incubation at 70° C. and treatment with RNAse H and RNAse T1 as described above. First round PCR was carried out with primers −285S_HCV-MOD (SEQ ID NO: 31) and 9470R (24)_ JFH1 (SEQ ID NO: 27) (TABLE 2) using BD Advantage 2 Polymerase Mix and the following cycling parameters: 35 cycles with denaturation at 99° C. for 35 sec, primer annealing at 67° C. for 30 sec and amplification at 68° C. for 10 min (5 cycles), 11 min (10 cycles), 12 min (10 cycles), 13 min (10 cycles). In a 2nd round PCR, 12 overlapping fragments spanning the complete ORF were generated with the primer combinations shown in TABLE 2 for S52/JFH1 and in TABLE 3 for J6/JFH with the following cycling parameters: initial denaturation of 35 sec at 99° C. and 35 cycles with 35 sec at 99° C., 30 sec at 67° C. and 6 min at 68° C. PCR products were agarose gel purified and directly sequenced in both directions.

Sequence Analysis of 5' and 3' UTR of Recovered S52/JFH1 Viruses.

RNA was extracted from cell culture supernatant as described above. RT was performed using primer HCV3aCoSeR1072 (SEQ ID NO: 28) (TABLE 1) for the 5' UTR and H39X58R (SEQ ID NO: 29) (TABLE 1) for the 3' UTR with SuperScript III for one hour at 50° C. followed by one hour at 55° C. For 2nd passage S52/JFH1 viruses a fragment spanning nts 56-832 was amplified with the primers −285S_HCV-MOD (SEQ ID NO: 31) (TABLE 2) and HCV3aSeqR831 (SEQ ID NO: 32) (TABLE 1) and for 1st passage recombinant adapted viruses a fragment from nts 1-832 was generated with the primers Chim seq JFH F1 (SEQ ID NO: 33) (TABLE 1) and HCV3aSeqR831 (SEQ ID NO: 32) (TABLE 1). PCR amplification was performed with BD Advantage 2 Polymerase Mix with the following cycling parameters: 3 min at 95° C. followed by 35 cycles with 40 sec at 95° C., 40 sec at 52° C., 3 min at 68° C., and final extension of 6 min at 68° C. For 2nd passage S52/JFH1 viruses a fragment spanning the variable region and the poly U tract (nts 9332-9644) of the 3' UTR was amplified with the primers HCV2aF9251 (SEQ ID NO: 34) and H39X58R (SEQ ID NO: 29) (TABLE 1) using the following cycling parameters: 10 min at 94° C., 45 cycles with 1 min at 94° C., 1 min at 60° C., 2 min at 68° C., and final extension of 2 min at 68° C. PCR products were agarose gel purified and directly sequenced.
Clonal Sequence Analysis of 2nd Viral Passage S52/JFH1 Viruses.

RNA was extracted as described above. RT was performed with the primer 7848R_JFH1 (SEQ ID NO: 30) (TABLE 2) and SuperScript III for one hour at 50° C. A long PCR product was generated with primers −285S_HCV-MOD (SEQ ID NO: 31) and 7234R_JFH1 (SEQ ID NO: 35) (TABLE 2) using BD Advantage 2 Polymerase Mix with the following cycling parameters: 1 min at 95° C., 40 cycles with 35 sec at 95° C., 35 sec at 67° C., 18 min at 68° C., and final extension of 18 min at 68° C. The resulting PCR product was gel purified, subcloned into pCR-XL-TOPO (Invitrogen), and the resulting clones were sequenced.

5' RACE (Rapid Amplification of cDNA Ends)

The extreme 5' end of 2nd passage S52/JFH1 viruses was determined using the 5' RACE System for Rapid Amplification of cDNA Ends, Version 2.0 (Invitrogen) with modifications. RNA was extracted using the Trizol (Invitrogen) protocol. First strand synthesis was carried out with primer HCVconsR337 (SEQ ID NO: 36) (TABLE 1) using SuperScriptIII for 40 min at 50° C. and 30 min at 55° C. To optimize binding on S.N.A.P. cDNA purification columns samples were reloaded twice, and 16.5 µl of the eluate were used for TdT-tailing according to the protocol. 1st round PCR was done according to the manufacturer's protocol using primer HCVconsR312 (SEQ ID NO: 37) (TABLE 1) and AmpliTaq Gold DNA Polymerase (Applied Biosystems). Cycle parameters were: initial denaturation of 10 min at 94° C. and 40 cycles of 45 sec at 94° C., 45 sec at 55° C. and 1 min 30 sec at 72° C. followed by a final extension of 10 min at 72° C. 2nd round PCR was done using primer HCVconsR169 (SEQ ID NO: 38) (TABLE 1) and cycle parameters as above. The consensus sequence of the amplified fragment was determined by direct sequencing and by sequencing of 4 clones obtained by subcloning into pCR2.1 Topo.

Sequence Analysis Software and Databases.

Sequence analysis was performed using Sequencher 4.6, Gene Codes Corporation and freeware BioEdit v. 7.0.5. HCV sequences used for alignments were retrieved from The European HCV database website (euHCVdb; http://euhcvdb.ib-cp.fr/euHCVdb/) and the American HCV database website (LANL; http://hcv.lanl.gov/content/hcv-db/index42).

Example 1

The J6/JFH Cell Culture System Yields High Viral Titers and Does Not Require Adaptive Mutations The intragenotypic 2a/2a recombinant J6/JFH, in which the structural genes (Core, E1 and E2), p7 and NS2 of JFH1 were replaced by the corresponding sequence of the infectious clone pJ6CF, produced infectious viral particles in the human hepatoma cell line Huh7.5. In our hands, transfection of J6/JFH RNA transcripts into Huh7.5 cells resulted in infection of most cells within 5 days as determined by NS5A immuno-staining (FIG. 1A), and J6/JFH virus from supernatant collected on day 6 readily infected naive Huh7.5 cells (data not shown). In supernatant from day 8 of this 1st passage the present inventors recorded an HCV infectivity titer of $10^{4.6}$ TCID$_{50}$/ml and an HCV RNA titer of $10^{7.2}$ IU/ml with a specific infectivity (infectious dose per genomes measured in IU) of 1:398 (TABLE 4). These results are comparable to those obtained by Lindenbach et al. The present inventors demonstrated that J6/JFH did not require mutations for efficient growth since the present inventors did not detect a single mutation compared to the original J6/JFH plasmid in the ORF consensus sequence of 1st passage virus recovered on day 8 post-infection.

After a subsequent transfection of Huh7.5 cells with J6/JFH, the culture was followed for 40 days (FIG. 2A). After rapid viral spread, massive cell death occurred, followed by recovery and decrease in percentage of infected cells, presumably caused by a lower susceptibility or permissiveness of the remaining cells.

Example 2

The intergenotypic 3a/2a recombinant S52/JFH1 is viable in Huh7.5 cells. To generate pS52/JFH1, the present inventors first determined the consensus sequence of Core through NS2 of HCV strain S52 (genotype 3a) by amplifying two overlapping fragments from the chimpanzee challenge pool (see Material and Methods), subcloning and analyses of 5 clones of each fragment. The final S52/JFH1 clone contains Core, E1, E2, p7 and NS2 genes of S52, and the 5' and 3' UTR, as well as the NS3, NS4A, NS4B, NS5A, and NS5B genes of JFH1. Compared to the S52 consensus sequence, pS52/JFH1 contains only noncoding nucleotide changes, which are present at 10 of 3096 (0.3%) nucleotide positions: A641G, A916T (introduced to eliminate an XbaI site), G1039A, C1490T, G1577A, C1709T, G1912A, C2639T, C2792T, C3053T (corresponding to H77 reference genome).

The delayed viral spread of S52/JFH1 compared to J6/JFH indicated selection of adaptive mutations. To further characterize the cell culture derived S52/JFH1 viruses the present inventors performed 1st and 2nd passages by inoculation of naïve Huh7.5 cells with filtered cell free supernatant derived from the transfection and the following transfection of Huh7.5 cells with RNA transcripts of pS52/JFH1, the present inventors found evidence of replication with ~10% NS5A antigen positive cells on day 1 (FIG. 1A). However, while infection with J6/JFH viruses spread to most Huh7.5 cells within 5 days, the percentage of NS5A positive cells decreased in the S52/JFH1 culture. Evidence of spread of S52/JFH1 virus was detected from day 8 post-transfection (FIG. 1A) and the present inventors recorded an HCV infectivity titer of $10^{2.5}$ TCID$_{50}$/ml in day 11 supernatant (TABLE 4). The present inventors did not detect NS5A positive cells in the negative control culture, transfected with RNA transcripts of the replication defective pFL-J6/JFH(GND).

The 1st passage, respectively (FIGS. 1B and C). On day 11, the 2nd passage S52/JFH1 culture had an infectivity titer of $10^{4.2}$ TCID$_{50}$/ml and an HCV RNA titer of $10^{6.9}$ IU/ml (specific infectivity 1:501) (TABLE 4). These values are comparable to those the present inventors (see above) and others found in the J6/JFH culture.

The delayed growth kinetic of S52/JFH1 initially observed was confirmed in a second transfection experiment (FIG. 2A). Spread of S52/JFH1 viruses was not observed until day 26 and reached its peak on day 33, yielding an infectivity titer of $10^{3.2}$ TCID$_{50}$/ml (TABLE 4). In contrast, the J6/JFH control virus had spread to most cells on day 5. In the S52/JFH1 culture the present inventors observed, similar to the J6/JFH cell culture, progressing cell death and decrease in percentage of NS5A positive cells after peak infection. In contrast to the delayed viral spread after transfection, S52/JFH1 viruses rescued on day 33 post-transfection infected a high percentage of naïve Huh7.5 cells within 6 to 8 days (FIG. 2B), with an infectivity titer of $10^{4.5}$ TCID$_{50}$/ml and an HCV RNA titer of $10^{7.2}$ IU/ml (TABLE 4).

Example 3

Similar Growth Kinetics of S52/JFH1 and J6/JFH Viruses

Naïve Huh7.5 cells were inoculated with ~$10^4$ TCID$_{50}$ of the S52/JFH13a/2a (2nd passage virus) and J6/JFH 2a/2a (1st passage virus), respectively (TABLE 4), and in both cultures >90% of cells became infected after 6 days (FIG. 3).

Furthermore, HCV RNA titers and infectivity titers of S52/JFH1 and J6/JFH were similar at all time points analyzed. HCV RNA titers peaked at close to $10^7$ copies/ml at day 6 and 9 and peak infectivity titers were detected on day 3 ($10^{4.6}$ TCID$_{50}$/ml for S52/JFH1 and $10^{4.7}$ TCID$_{50}$/ml for J6/JFH) (TABLE 4). When comparing specific infectivity, the present inventors recorded the highest values on day 3 post-infection (1:25 for S52/JFH1 and 1:20 for J6/JFH) and the lowest values on day 1 post-infection (1:794 for S52/JFH1 and 1:398 for J6/JFH). Growth kinetics of S52/JFH1 and J6/JFH viruses after infection with ~$10^3$ TCID$_{50}$ of the respective viruses were also comparable (data not shown).

Figure 4:
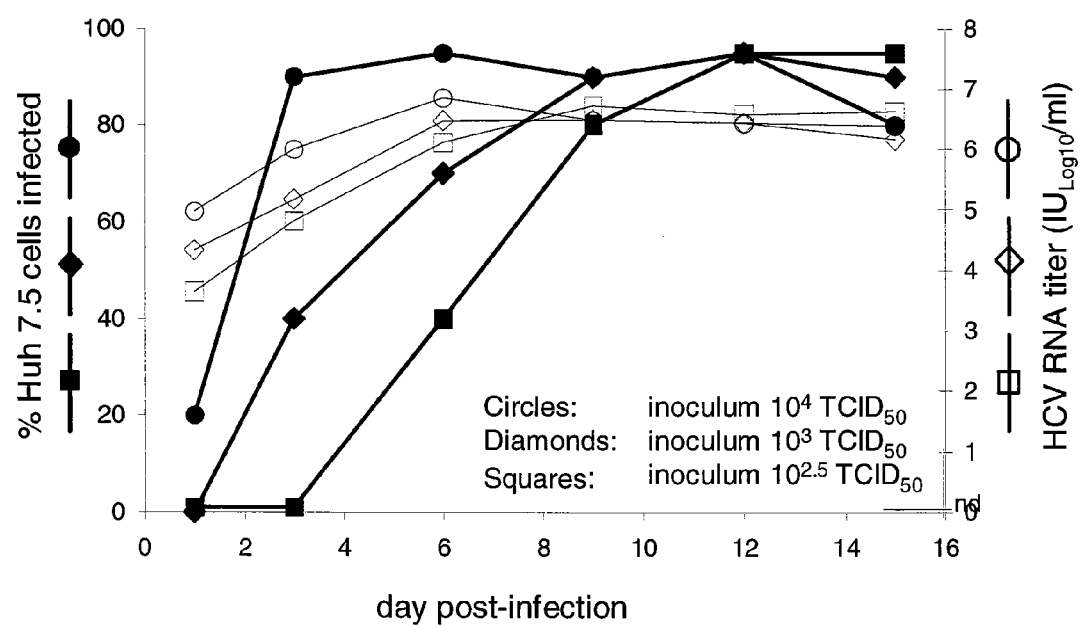

The kinetics of S52/JFH1 infection was dependent on the virus dose. After infection of naïve Huh7.5 cells with approximately $10^4$, $10^3$ and $10^{2.5}$ TCID50, the viruses spread to the entire culture after 3, 9, and 12 days, respectively, with differences reflected also in the HCV RNA titers (FIG. 4). Specific infectivities of S52/JFH1 viruses derived from these cell cultures at the peak of infection were comparable (TABLE 4).

Example 4

Identification of Several Adaptive Mutations in Serially Passaged S52/JFH1 Viruses The present inventors determined the consensus sequence of viral genomes recovered from cell culture supernatants derived from the first transfection experiment and consecutive 1st, 2nd and 3rd viral passages by direct sequencing of overlapping PCR fragments spanning the entire open reading frame (TABLE 5A). Analysis of S52/JFH1 genomes recovered on day 11 post-transfection (sample used for 1st viral passage; FIG. 1A) revealed coding mutations in p7 (A2721G) and NS3 (A4845T). Both occurred as quasispecies with the original pS52/JFH1 sequence. Sequence analysis of the day 21 1st viral passage viruses (used for the 2nd viral passage, FIG. 1B) demonstrated additional coding mutations in Core (T728C), E2 (A1553G, A1907C), p7 (T2718G) and NS5A (T7160C), again occurring as quasispecies with the pS52/JFH1 sequence. Analysis of day 11 2nd passage viruses (used for the 3rd viral passage/kinetic experiment) and 3rd passage viruses (FIG. 4) revealed mutations at all seven positions identified above, with the ones arisen during the 1st passage now showing a clear dominance over the original pS52/JFH1 sequences. For the 2nd viral passage virus the potential for mutations outside the ORF was examined by sequencing of the entire 5' UTR and partial 3' UTR (see Material and Methods); no mutations were found. Interestingly, the nucleotide changes at all seven positions with clear evidence of mutations resulted also in changes of the deduced amino acid sequence (TABLE 5B).

Another 2nd passage of S52/JFH1 conducted by inoculation with day 18 1st passage supernatant (FIG. 1B), showed in addition to the mutations identified above evidence of coding mutations in E1 and NS5A (T1191C/V284A and G7182A/S2281N) as well as noncoding mutations in Core and NS5A (C688A and T6685C).

To confirm the requirement for adaptive mutations, the present inventors determined the consensus sequence of S52/JFH1 viruses in day 8 supernatant from the 1st passage of the second transfection experiment (FIG. 2B). As for the passages derived from the 1st transfection experiment the present inventors found evidence of a mutation at position 2718 in p7 (T2718C coding for I793T) occurring as a 50/50 quasispecies with the pS52/JFH1 sequence. Additionally the present inventors detected a mutation in NS3 (A4550C coding for K1404Q), showing strong predominance of the mutated over the original pS52/JFH1 sequence. There was no evidence of mutation at this position in the consensus sequence data obtained from viruses recovered from the first transfection and consecutive passage experiments.

Example 5

Clonal analysis of adaptive mutations of 2nd viral passage S52/JFH1 viruses. The absence of an unambiguous consensus sequence in cell culture derived S52/JFH1 genomes could be explained in two ways: Either the original sequence was still present and/or different viral genomes coexisted, which had the detected mutations in various combinations. Thus, the present inventors performed clonal analysis of a long PCR fragment amplified from 2nd passage viral genomes, which contained all nucleotide positions, at which clear evidence of mutations had been observed. Interestingly, the clones represented several different viral genomes with specific combinations of the mutations identified by direct sequencing (TABLE 5). However, the present inventors could not identify any genomes with the original pS52/JFH1 sequence.

Overall this clonal analysis reflected the results of direct sequencing with the combination of mutations in Core (T728C), p7 (T2718G) and NS5A (T7160C), which dominated the direct sequencing of viruses derived from the 2nd and 3rd viral passage, being present in 7 of 9 clones analyzed. In one additional clone the mutations in Core and NS5A were combined with another p7 mutation (A2721G). Finally, one clone had a combination of A2721G in p7 and A4845T in NS3, which were present as a minor species in direct sequencing of the cloned 2nd passage virus. A1553G and A1907C in E2 occurred in about half of the clones analyzed, reflecting a 50/50 distribution in direct sequencing. In addition to the described mutations all 9 clones analyzed had nucleotide changes at other positions, which could at least partly have resulted from errors in the PCR amplification process. The following nucleotide changes occurred in more than one clone and are therefore more likely to contribute to cell culture adaptation, even though they were not prominent in direct sequencing: A824G in Core (I162V; 3/9 clones), A1937G in E2 (N533D; 2/9 clones), G2916A in NS2 (C859Y; 2/9 clones), C6328T in NS5A (no amino acid change; 3/9 clones). In summary the present inventors identified different adapted S52/JFH1 genomes coexisting in the 2nd viral passage cell culture supernatant.

Example 6

Recombinant Adapted S52/JFH1 Viruses Have Significantly Improved Growth Potential in Huh7.5 Cells In order to determine the influence of the described mutations on viability and efficiency of the S52/JFH1 genome, the present inventors constructed six S52/JFH1 cDNA clones with different combinations of the putative adaptive mutations: Four with three or more mutations in combinations identified in the clonal analysis (SEQ ID NO: 3, 5, 7, 9) and two with two mutations each, S52/JFH1(T2718G; T7160C) (SEQ ID NO: 19), and S52/JFH1(A2721G; A4845T) (SEQ ID NO: 11)(TABLE 5). Equal amounts of RNA transcripts of five of these constructs and the original pS52/JFH1 and pFL-J6/JFH were transfected into Huh7.5 cells (FIG. 5A). Following transfection, all five recombinant S52/JFH1 viruses infected, like J6/JFH viruses, 50% and 90% of the cells on day 3 and day 7, respectively, as measured by anti-Core staining. However, following transfection with RNA transcripts of the original pS52/JFH1, the percentage of infected cells decreased during the period of observation as previously observed. Peak infectivity titers of the different recombinant S52/JFH1 viruses were comparable to that of J6/JFH viruses, whereas the original S52/JFH1 viruses showed significantly lower titers, which decreased during the observation period and became undeterminable on day 9 post-transfection (FIG. 5B).

To examine, whether recombinant adapted S52/JFH1 viruses were genetically stable, the present inventors performed a 1st viral passage by transferring 1 ml of filtered supernatant (~$10^4$ TCID$_{50}$; rescued at day 9 post-transfection; FIG. 5A) onto naïve Huh7.5 cells. Although spread appeared to be somewhat slower for the recombinant adapted S52/JFH1 and the J6/JFH viruses (FIG. 6A) compared to the polyclonal 2nd passage S52/JFH1 and control J6/JFH viruses (FIG. 3), as measured with staining of Core and NS5A, respectively, the present inventors did not observe differences in the HCV RNA titers (FIG. 3 and FIG. 6B). For each of the adapted S52/JFH1 viruses, the present inventors demonstrated that the consensus sequence of nts 27-9445 including the entire ORF of the viral genomes present in 1st passage supernatants (derived on day 12; FIG. 6A) was identical to that of the parental plasmid used to generate the in vitro RNA transcripts for the transfection experiment. Thus, as was the case for J6/JFH cell culture derived viruses (see above), adapted S52/JFH1 viruses were genetically stable during transfection and 1st viral passage and did not require additional mutations for efficient growth in Huh7.5 cells.

To determine whether all mutations of each combination tested were required for S52/JFH1 viability we generated two S52/JFH1 recombinants with only two mutations: S52/JFH1 (T2718G; T7160C) (SEQ ID NO: 19) (FIG. 7) and S52/JFH1 (A2721G; A4845T) (SEQ ID NO: 11) (FIGS. 5, 6, 7).

We further developed seven S52/JFH1 recombinants containing the mutations identified during the first transfection experiment individually (Table 5A,B). On day 7 most cells of the cultures transfected with the two recombinants with two mutations each were HCV Core positive (data not shown) and showed relatively high infectivity titers (FIG. 7). In contrast, for recombinants with single mutations we observed significant variations in viral spread (data not shown) and infectivity titers (FIG. 7). To investigate the genetic stability of these genomes, we infected naïve Huh7.5 cells with day 7 supernatant and directly sequenced nts 297-9445 of 1st passage viral genomes, when most cells in these cultures had become HCV Core positive and yielded an HCV RNA titer of $10^7$ IU/ml. For recombinants containing single mutations in Core (T728C) or E2 (A1553G and A1907C), sequence analysis was performed on genomes derived from the transfection culture because of the long eclipse phase preceding viral spread (25, 13 and 13 days post-transfection, respectively) reducing the risk of obtaining input DNA/RNA sequences. Sequence analysis showed that in contrast to the two recombinants with combinations of two mutations (and the four recombinants with three or more mutations) only 1/7 recombinants with single mutations (T2718G in p7) (SEQ ID NO: 15) was genetically stable, although a minor quasispecies was detected at nt position 4552, which would lead to an aa change at the same position as A4550C, observed in the 2nd transfection experiment (Table 5A,B). In contrast, 6/7 recombinants with single mutations acquired additional nucleotide changes (present at least as a 50/50 quasispecies), notably frequently at positions, which also had acquired changes during the original experiments (Table 5A,B). Analysis of these mutation patterns showed a preference for the combination of mutations in p7 with a second mutation in either NS3 or NS5A. For example, S52/JFH1(T728C) acquired T2718G in p7 and A4550C in NS3, and two independent transfections with S52/JFH1(T7160C) resulted in the additional changes T2718G and T2718C, respectively.

We finally analyzed mutations identified in the 2nd transfection experiment. S52/JFH1 recombinants with A4550C in NS3, singly (SEQ ID NO: 17) or in combination with T2718C in p7, yielded infectivity titers of >$10^4$ TCID$_{50}$/ml on day 7 post-transfection (FIG. 7). These two viruses were also genetically stable after 1st passage, whereas the recombinant with the single p7 mutation T2718C had a lower infectivity titer at day 7 (FIG. 7) and acquired additional mutations (Table 5A,B).

Overall, 7/7 recombinants with combinations of the nine mutations identified in S52/JFH1, but only 2/9 recombinants with single mutations yielded relatively high infectivity titers 7 days post-transfection, and were genetically stable after a 1st viral passage. Single mutations able to confer viability to S52/JFH1 without an apparent requirement for additional mutations were T2718G (I793S) in p7 (SEQ ID NO: 15) and A4550C (K1404Q) in NS3 (SEQ ID NO: 17).

Because T2718G in p7 and A4550C in NS3 were the only adaptive mutations able to individually confer cell culture adaptation of S52/JFH1. S52/JFH1(T2718G; A4550C) (SEQ ID NO: 13) was constructed in order to test if combination of T2718G and A4550C on one S52/JFH1 genome was possible. After transfection and passage in Huh7.5 cells S52/JFH1 (T2718G; A4550C) viruses yielded infectivity titers between $10^4$ and $10^5$ TCID$_{50}$/mL; additionally, direct sequencing of the complete ORF of S52/JFH1(T2718G; A4550C) genomes revealed that these viruses were genetically stable after passage in Huh7.5 cells. Thus, it was shown that the S52/JFH1 (T2718G; A4550C) genome, combining the two adaptive mutations, which were able to individually provide adaptation of the S52/JFH1 genome, is viable and efficient in Huh7.5 cell culture.

Example 7

HCV Genotype 3a Infection Depends on CD81

It has previously been shown that HCV genotype 1a and 2a infection can be inhibited by blocking the tetraspanin and putative HCV co-receptor CD81 with specific antibodies. We examined whether genotype 3a entry also depended on CD81 and whether recombinant S52/JFH1 containing the authentic E1/E2 proteins could be used as a model system to study HCV entry events and interfering agents in a genotype 3a specific manner. Pretreatment of Huh7.5 cells with anti-CD81 could prevent infection with 100 $TCID_{50}$ of S52/JFH1(T728C; T2718G; T7160C) as determined by the number of FFU (FIG. 8A) and HCV RNA titers (FIG. 8B).

Example 8

Infection with S52/JFH1 Recombinants Leads to Redistribution of Intracellular Lipid Droplets and Co-Localization with HCV Core HCV genotype 3a infection is thought to be associated with increased hepatic steatosis. HCV Core co-localized with lipid droplets and recombinantly expressed genotype 3a Core was implicated in increased cellular lipid accumulation in vitro. However, these effects have not been studied on cells infected with HCV viruses expressing genotype 3a Core. We infected Huh7.5 cells with either J6/JFH, S52/JFH1 polyclonal 2nd passage viruses, S52/JFH1(T728C; T2718G; T7160C) or S52/JFH1(T2718G; T7160C). Confocal imaging revealed that in all HCV infected cells, in comparison to negative control cells mock infected with J6/JFH(GND) or S52/JFH1 (GND) culture supernatants, lipid droplets were often redistributed from the entire cytoplasm to a perinuclear area, typically asymmetrically centered on one side of the nucleus, and co-localized with HCV Core. By confocal microscopy based image analysis we determined the average lipid content per cell in cultures with most cells being HCV positive and with HCV RNA titers of $10^7$ IU/ml in culture supernatant. We could not detect any difference in lipid content between cells infected with the different viruses and mock infected cells. The Core mutation at aa 130, which as a single mutation was found not to influence viability of S52/JFH1, did not appear to influence lipid co-localization with S52 Core or lipid accumulation.

Example 9

S52/JFH1 Infection Depends on SR-BI

The inventors of the present invention have previously shown that S52/JFH1 infection of Huh7.5 cells was dependent on CD81 (see the previous examples).

Figure 9:
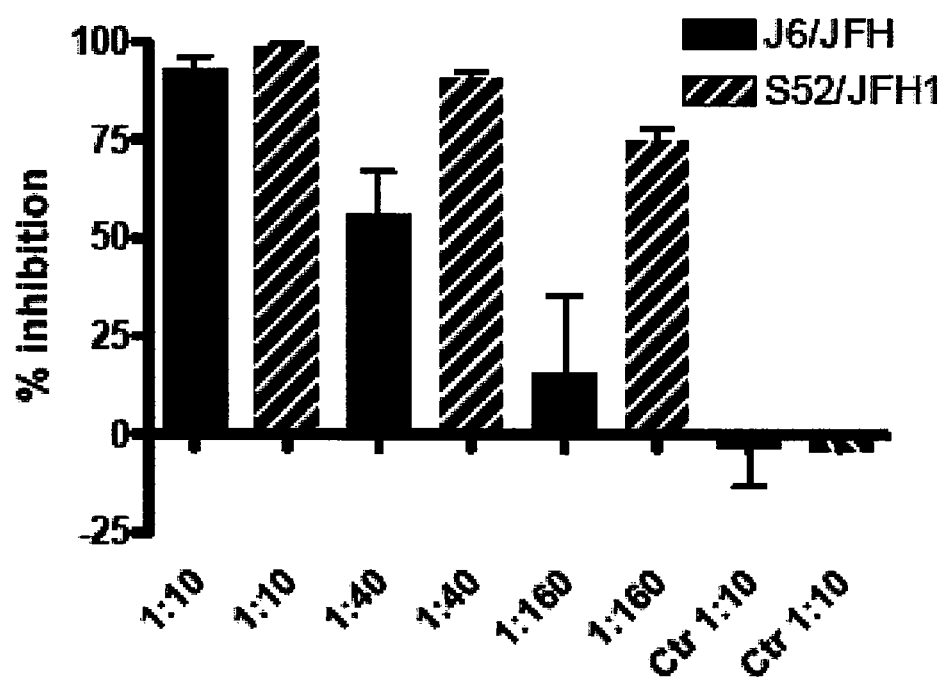

SR-BI is thought to be part of the HCV receptor complex. Using anti-SR-BI serum the present inventors showed that S52/JFH1(T2718G; A4550C) infection of Huh7.5 cells as well as infection with the reference virus J6/JFH1 depends on SR-BI (FIG. 9). This further underlines the importance of the developed model system for studies of HCV genotype 3a entry.

Example 10

S52/JFH1 Infection is Sensitive to Treatment with Interferon

HCV cell culture systems could be important tools for testing of antiviral therapeutics. Previously, replication of different HCV replicons as well as of the J6/JFH1 virus have been shown to be sensitive to treatment with interferon. Thus Huh7.5 cell cultures infected with J6/JFH1, S52/JFH1 (T2718G; A4550C) and S52/JFH1(A4550C) were treated with cell culture medium containing 5001 U/mL interferon alfa 2b. After initiation of treatment, a fast decline of HCV antigen positive cells was shown for all cultures. Thus, for J6/JFH1 and S52/JFH1(T2718G; A4550C) the percentage of NS5A positive cells was 90 and 60 the day prior to treatment, whereas only 20% and 10% NS5A positive cells were detected in the respective cultures on day 3 of treatment (FIG. 10). Interestingly, prolonged treatment intervals were followed by an increase in NS5A positive cells; thus, on day 6, when the cultures had not been treated for 48 hrs, 40% of cells in the J6/JFH1 and S52/JFH1(T2718G; A4550C) cultures were NS5A positive.

Tables

TABLE 1

Primers used for amplification of HCV strain S52 (genotype 3a) and generation of amplicons for analysis of S52/JFH1 5' and 3' UTR.

| Cloning primers | Primer sequence |
| --- | --- |
| HCV3aF1T7NotI-G (SEQ ID NO: 23) | 5'-AAGGAAAAAA<u>GCGGCCGC</u>*TAATACGACT CACTATAG*CCTGCCTCTTACGAGGCGACA C-3' |
| HCV3aR3420BsaBIAscI (SEQ ID NO: 24) | 5'-TT<u>GGCGCGCC</u>CATCTCCCGATAGTCATC AGCAGG-3' |
| HCV3aF3336NotIBsaBI (SEQ ID NO: 25) | 5'-AAGGAAAAAA<u>GCGGCCGC</u>CGGAGATATT CTTTGCGGGCTGC-3' |
| HCV3aR5209AflIIAscI (SEQ ID NO: 26) | 5'-TT<u>GGCGCGCC</u>GTGTTGGCTTAAGCCGCA CGAGA-3' |
| HCV3aCoSeR1072 (SEQ ID NO: 28) | 5'-GTAGGTGTCACTGGGGTCCAGC-3' |
| H39X58R (SEQ ID NO: 29) | 5'-TCATGCGGCTCACGGACCTTTCACAGCT AG-3' |
| HCV3aSeqR831 (SEQ ID NO: 32) | 5'-GAAATTTATCCCGTCTTCAAGG-3' |
| Chim seq JFH F1 (SEQ ID NO: 33) | 5'-ACCTGCCCCTAATAGGGGCGACACT C-3' |
| HCV2aF9251 (SEQ ID NO: 34) | 5'-GGCGCCGGCGGGGCGACATTTTCACAG C-3' |
| HCVconsR337 (SEQ ID NO: 36) | 5'-GGTCTACGAGRCCTCCCGGGGCAC-3' |
| HCVconsR312 (SEQ ID NO: 37) | 5'-CGCAAGCRCCCTATCAGGCAGTACC-3' |
| HCVconsR169 (SEQ ID NO: 38) | 5'-CGGTGTACTCACCGGTTCC-3' |

Underlined: introduced restriction sites. Italics: T7 promotor.

TABLE 2

Primers used for S52/JFH1 long RT-PCR procedure to generate amplicons for direct sequencing of the open reading frame.

| Amplification step and amplicon | Primer name | Primer sequence |
| --- | --- | --- |
| cDNA synthesis | 9470R(24)_JFH1 (SEQ ID NO: 27) | 5'-CTATGGAGTGTACCTAGTGTGTGC-3' |
| 1st round PCR | -285S_HCV_MOD (SEQ ID NO: 31) | 5'-ACTGTCTTCACGCAGAAAGCGCCTAGCCAT-3' |
| | 9470R(24)_JFH1 (SEQ ID NO: 27) | 5'-CTATGGAGTGTACCTAGTGTGTGC-3' |
| 2nd round PCR | | |
| Amplicon 1 | -84S_HCV-MOD (SEQ ID NO: 39) | 5'-GTAGCGTTGGGTTGCGAAAGGCCTTGTGGTACTGCCTGAT-3' |
| | HCV3aCoSeR1072 (SEQ ID NO: 28) | 5'-GTAGGTGTCACTGGGGTCCAGC-3' |
| Amplicon 2 | HCV3aCoSeF918 (SEQ ID NO: 40) | 5'-GTGGCGGAATACGTCTGGCCTC-3' |
| | HCV3aCoSeR1819 (SEQ ID NO: 41) | 5'-GTCTAGGTGCGTAGTGCCAGCAG-3' |
| Amplicon 3 | HCV3aCoSeF1288 (SEQ ID NO: 42) | 5'-CGAATGGCTTGGGATATGATGATGA-3' |
| | HCV3aCoSeR2402 (SEQ ID NO: 43) | 5'-ATGGGCGTGAAAGAGCAAGGCAG-3' |
| Amplicon 4 | HCV3aCoSeF2288 (SEQ ID NO: 44) | 5'-GCAACTGGACCAGGGGGGAGC-3' |
| | HCV3ACoSeR3416 (SEQ ID NO: 45) | 5'-TCCCGATAGTCATCAGCAGGTCC-3' |
| Amplicon 5 | HCV3aCoSeF3336 (SEQ ID NO: 46) | 5'-CGGAGATATTCTTTGCGGGCTGC-3' |
| | 4118R_JFH1 (SEQ ID NO: 47) | 5'-CGCCCGAGGCCTACCTCTTCTATATC-3' |
| Amplicon 6 | 3880S_J6 (SEQ ID NO: 48) | 5'-CCCATCACGTACTCCACATATGGC-3' |
| | 4796R_JFH1 (SEQ ID NO: 49) | 5'-GCGCACACCGTAGCTTGGTAGG-3' |
| Amplicon 7 | 4528S_J6 (SEQ ID NO: 50) | 5'-GAGCGAGCCTCAGGAATGTTTGACA-3' |
| | 5446R_JFH1 (SEQ ID NO: 51) | 5'-TGATGTTGAGAAGGATGGTGGTAC-3' |
| Amplicon 8 | 5272S_JFH1 (SEQ ID NO: 52) | 5'-TGGCCCAAAGTGGAACAATTTTGG-3' |
| | 6460R_J6 (SEQ ID NO: 53) | 5'-CAACGCAGAACGAGACCTCATCCC-3' |
| Amplicon 9 | 6186S_JFH1 (SEQ ID NO: 54) | 5'-GACCTTTCCTATCAATTGCTACAC-3' |
| | 7234R_JFH1 (SEQ ID NO: 35) | 5'-GAAGCTCTACCTGATCAGACTCCA-3' |
| Amplicon 10 | 6862S_JFH1 (SEQ ID NO: 55) | 5'-TGGGCACGGCCTGACTACAA-3' |
| | 7848R_JFH1 (SEQ ID NO: 30) | 5'-GGCCATTTTCTCGCAGACCCGGAC-3' |
| Amplicon 11 | 7741S_J6 (SEQ ID NO: 56) | 5'-ATGGCCAAAAATGAGGTGTTCTGC-3' |
| | 8703R_JFH1 (SEQ ID NO: 57) | 5'-AAGGTCCAAAGGATTCACGGAGTA-3' |
| Amplicon 12 | 8137S_JFH1 (SEQ ID NO: 58) | 5'-GGTCAAACCTGCGGTTACAGACGTTG-3' |
| | 9464(24)_JFH1 (SEQ ID NO: 59) | 5'-GTGTACCTAGTGTGTGCCGCTCTA-3' |

TABLE 3

Primers used for J6/JFH long RT-PCR procedure to generate amplicons for direct sequencing of the open reading frame.*

| Amplification step and amplicon | Primer name | Primer sequence |
|---|---|---|
| 2nd round PCR | | |
| Amplicon 1 | −84S_HCV-MOD (SEQ ID NO: 39) | 5'-GTAGCGTTGGGTTGCGAAAGGCCTTGTGGTACTGCCTGAT-3' |
| | 1109R_J6 (SEQ ID NO: 60) | 5'-TTTGCCCACGCTCCCTGCATAGAGAA-3' |
| Amplicon 2 | 946S_J6 (SEQ ID NO: 61) | 5'-CACCGCATGGCGTGGGACATGATG-3' |
| | 2111R_J6 (SEQ ID NO: 62) | 5'-TGCACGTCCACGATGTTTTGGTG-3' |
| Amplicon 3 | 1849S_J6 (SEQ ID NO: 63) | 5'-TACAGGCTCTGGCATTACCCCTGCAC-3' |
| | 2763R_J6 (SEQ ID NO: 64) | 5'-AGCGTGAGCCCTGACGAAGTACGG-3' |
| Amplicon 4 | 2754S_J6 (SEQ ID NO: 65) | 5'-TAGCATTGCCCCAACAGGCTTATGCTTATGACG-3' |
| | 3774R_J6 (SEQ ID NO: 66) | 5'-GGGATGACATCAGCGTTCCGCGTGACCAG-3' |
| Amplicon 5 | 3081S_J6/JFH1 (SEQ ID NO: 67) | 5'-GGAGTCTTCTCGCTCCCATCACTGC-3' |
| | 4118R_JFH1 (SEQ ID NO: 47) | 5'-CGCCCGAGGCCTACCTCTTCTATATC-3' |

*For cDNA synthesis, 1st round PCR, and 2nd round PCR amplicons 6-12 see TABLE 2.

TABLE 4

Representative infectivity and HCV RNA titers of J6/JFH and S52/JFH1 cultures.

| Viral isolate | Origin of supernatant | Experimental day | $TCID_{50}/ml$ | % infected cells | HCV RNA titer (IU/ml) | Specific infectivity |
|---|---|---|---|---|---|---|
| J6/JFH | 1st viral passage (used for kinetic experiment) | 8 | $10^{4.6}$† | 95 | $10^{7.2}$ | 1:398 |
| J6/JFH | 2nd viral passage (inoculated with $10^4$ $TCID_{50}$) | 3 | $10^{4.7}$+ | 80 | $10^{6.0}$ | 1:20 |
| S52/JFH1 | First experiment | | | | | |
| S52/JFH1 | Transfection | 11 | $10^{2.5}$* | 40 | | |
| S52/JFH1 | 2nd viral passage (used for kinetic experiment) | 11 | $10^{4.2}$* | 95 | $10^{6.9}$ | 1:501 |
| S52/JFH1 | 3rd viral passage (inoculated with $10^4$ $TCID_{50}$) | 3 | $10^{4.6}$+ | 90 | $10^{6.0}$ | 1:25 |
| S52/JFH1 | 3rd viral passage (inoculated with $10^{2.5}$ $TCID_{50}$) | 12 | $10^{4.7}$+ | 95 | $10^{6.6}$ | 1:79 |
| S52/JFH1 | Second experiment | | | | | |
| S52/JFH1 | Transfection | 33 | $10^{3.2}$+ | 70 | | |
| S52/JFH1 | 1st viral passage | 8 | $10^{4.5}$+ | 95 | $10^{7.2}$ | 1:501 |

For determination of $TCID_{50}$ Huh7.5 cells were plated at $6 \times 10^3$ cells/well on a poly-D-Lysine coated 96 well plate and infected with serial dilutions of virus containing cell culture supernatant in complete growth medium in replicates of 6 wells per dilution. After incubation for 48 hours cells were stained for NS5A expression. A well was counted positive, if at least one infected cell was visible. Calculation of $TCID_{50}$ was done as previously described by Reed et al. † Average of 3 independent determinations, * average of 2 independent determinations, +1 determination. HCV RNA titers were determined with an TaqMan assay. Supernatants from transfection experiments were not tested in TaqMan due to DNA/RNA input from the transfection procedure. Specific infectivity was calculated as infectious units ($TCID_{50}$/ml) per genome number (IU/ml).

Table 5 (below)

Adaptive nucleotide (A) and amino acid mutations (B) acquired by S52/JFH1 viruses during viral passage.

Direct sequence analysis was performed on viruses recovered from the first transfection experiment and the consecutive 1st, 2nd and 3rd viral passages (Table 4; FIG. 1; FIG. 4); on 1st viral passage viruses from the second transfection experiment (Table 4, FIG. 2); and on mutated viruses after 1st passage or transfection as indicated. Clonal analysis was performed on 2nd passage virus from the 1st transfection; all clones had in addition to the mutations shown changes at other positions, which could partly have resulted from errors in PCR. At the positions with evidence of mutations the S52 consensus sequence had the original pS52/JFH1 sequence with no heterogeneity among 5 clones. Capital letters indicate the presence of one determinate sequence peak. Two capital letters separated by a slash indicate the presence of a 50/50 quasispecies, whereas a capital letter separated by a slash from a lowercase letter indicates a quasispecies with a predominant versus a minor sequence. Criterion for listing of nt positions was the occurrence of a quasispecies in direct sequencing with the new sequence showing at least a 50/50 distribution in at least one experiment. Names of adapted S52/JFH1 recombinants engineered to contain mutations singly or in combination refer to the respective nt changes. # additional mutation C64T in the 5' UTR. Grey shading: engineered nt and deduced aa changes. ● nt/aa identical with pS52/JFH1 sequence. Numbers of nt/aa positions refer to pS52/JFH1. * nt/aa position in analogy to the H77 reference genome (accession number AF009606) determined as described. For aa positions the absolute (abs. ref. num.; referring to H77 polyprotein) and relative (rel. ref. num.; referring to the individual H77 protein) reference numbers are given

| | Core | | E2 | | | | | p7 | | | NS2 | | | NS3 | | | | NS4A | NS5A | |
|---|---|---|---|---|---|---|---|---|---|---|---|---|---|---|---|---|---|---|---|---|
| Nucleotide position S52/JFH1 | 728 | 1527 | 1553 | 1907 | 2297 | 2718 | 2720 | 2721 | 3023 | 3748 | 4464 | 4550 | 4552 | 4845 | 5407 | 7154 | 7160 |
| Nucleotide position H77 (AF009606)* | 729 | 1528 | 1554 | 1905 | 2280 | 2701 | 2703 | 2704 | 3006 | 3731 | 4447 | 4533 | 4535 | 4828 | 5390 | 7149 | 7155 |
| | T | C | A | A | A | T | A | A | A | A | G | A | A | A | C | A | T |

Sequence of pS52/JFH1

Sequence of viruses recovered from infected Huh7.5 cells

First transfection experiment with S52/JFH1
Direct Sequencing

| | Core | | E2 | | | | | p7 | | | NS2 | | | NS3 | | | | NS4A | NS5A | |
|---|---|---|---|---|---|---|---|---|---|---|---|---|---|---|---|---|---|---|---|---|
| Transfection, day 11 | . | . | . | . | . | . | . | . | . | . | . | . | . | . | . | . | . |
| 1st passage, day 21 | C/T | . | A/g | . | . | T/g | A/g | A/g | . | . | . | . | . | A/t | . | . | C/T |
| 2nd passage, day 11 | C/t | . | G/a | C/A | . | G/t | G/A | G/A | . | . | . | . | . | T/A | . | . | C |
| 3rd passage: Inoculum 1E2.5 TCID50, day 12 | C/t | . | G/A | C/A | . | G/T | A/g | A/g | . | . | . | . | . | A/t | . | . | C/t |
| 3rd passage: Inoculum 1E4 TCID50, day 3 | C/t | . | G/a | C/a | . | G/t | A/g | A/g | . | . | . | . | . | A/t | . | . | C/t |

Clonal sequence analysis of 2nd passage virus

| | | | | | | | | | | | | | | | | | |
|---|---|---|---|---|---|---|---|---|---|---|---|---|---|---|---|---|---|
| clone 5, 12 and 17 | C | . | . | C | . | G | G | G | . | . | . | . | . | . | . | . | C |
| clone 6, 13 and 18 | C | . | G | C | . | G | G | G | . | . | . | . | . | . | . | . | C |
| clone 11 | C | . | G | C | . | G | G | G | . | . | . | . | . | . | . | . | C |
| clone 2 | C | . | G | . | . | . | . | . | . | . | . | . | . | T | . | . | . |
| clone 1 | C | . | G | . | . | . | . | . | . | . | . | . | . | . | . | . | . |

Transfection experiment with mutated S52/JFH1

| | | | | | | | | | | | | | | | | | |
|---|---|---|---|---|---|---|---|---|---|---|---|---|---|---|---|---|---|
| SEQ ID NO 3: T728C;A1553G;A1907C;T2718G;T7160C #: 1st | C | . | G | C | . | G | . | . | . | . | . | . | . | . | . | . | C |
| SEQ ID NO 5: T728C;A1553G;A1907C;A2721G;T7160C #: 1st | C | . | G | C | . | G | . | G | . | . | . | . | . | T | . | . | C |
| SEQ ID NO 7: T728C;T2718G;T7160C: 1st passage | C | . | . | . | . | G | . | . | . | . | . | . | . | T | . | . | C |
| SEQ ID NO 9: A1553G;A2721G;A4845T: 1st passage | . | . | G | . | . | . | . | G | . | . | . | . | . | T | . | . | . |
| SEQ ID NO 19: T2718G;T7160C: 1st passage | . | . | . | . | . | G | . | . | . | . | . | . | . | . | . | . | C |
| SEQ ID NO 11: A2721G;A4845T: 1st passage | C | . | G | . | . | . | A/t | . | . | . | . | . | . | . | . | . | . |
| T728C: Transfection, day 32 | . | . | . | . | . | . | . | . | . | . | G | . | . | . | . | . | . |
| A1553G: Transfection, day 24 | . | . | . | . | . | . | . | . | . | T | A/G | . | . | . | . | . | . |
| A1907C: Transfection, day 24 | . | . | . | . | . | . | . | . | C/A | . | . | . | . | . | . | . | . |
| A2721G: 1st passage | . | . | . | . | . | . | . | . | . | . | . | A/c | T/A | . | . | . | . |
| SEQ ID NO 15: T2718G: 1st passage | . | . | . | . | . | . | . | . | . | . | . | . | . | . | . | . | . |
| A4845T: 1st passage | . | . | . | . | . | . | . | . | . | . | . | . | . | . | . | . | . |
| A4845T: 1st passage | . | . | . | . | . | . | . | . | . | . | . | . | . | . | . | . | . |
| T7160C: 1st passage | . | . | . | . | . | . | . | . | . | . | . | . | . | . | . | . | . |

Second transfection experiment with S52/JFH1
Direct sequencing

| | | | | | | | | | | | | | | | | | |
|---|---|---|---|---|---|---|---|---|---|---|---|---|---|---|---|---|---|
| 1st passage, day 8 | T/c | . | . | . | T/a | G/t | . | . | . | . | . | . | . | . | . | T/C | . |

Transfection experiment with mutated S52/JFH1

| | | | | | | | | | | | | | | | | | |
|---|---|---|---|---|---|---|---|---|---|---|---|---|---|---|---|---|---|
| SEQ ID NO 21: T2718C;A4550C: 1st passage | . | . | . | . | . | C/T | . | . | . | . | . | C | . | . | . | . | . |
| T2718C: 1st passage | . | . | . | . | . | C | . | . | . | . | . | C | . | . | . | . | . |
| A4550C: 1st passage | . | . | . | . | . | C | . | . | . | . | . | C | . | . | . | . | . |
| SEQ ID NO 17: A4550C: 1st passage | . | . | . | . | . | . | . | . | . | . | . | A/c | . | . | . | T/C | C/A |

-continued

| | Core | | E2 | | | p7 | | NS2 | | NS3 | | | NS4A | NS5A | |
|---|---|---|---|---|---|---|---|---|---|---|---|---|---|---|---|
| Amino acid position S52/JFH1 | 130 | 396 | 405 | 523 | 653 | 793 | 794 | 895 | 1136 | 1375 | 1404 | 1502 | 1689 | 2272 | 2274 |
| Amino acid position H77 (abs. ref. num.)* | 130 | 396 | 405 | 522 | 647 | 787 | 788 | 889 | 1130 | 1369 | 1398 | 1496 | 1683 | 2270 | 2272 |
| Amino acid position H77 (rel. ref. num.)* | 13 | 22 | 139 | 264 | | 41 | 42 | 80 | 104 | 343 | 372 | 470 | 26 | 298 | 300 |
| | F | A | M | K | T | I | Y | T | L | R | K | Q | I | I | S |
| *Sequence of S52/JFH1 polyprotein* | | | | | | | | | | | | | | | |
| First transfection experiment with S52/JFH1 | | | | | | | | | | | | | | | |
| *Direct Sequencing* | | | | | | | | | | | | | | | |
| Transfection, day 11 | . | . | . | . | . | . | . | . | . | . | . | . | . | . | . |
| 1st passage, day 21 | L/F | . | M/v | . | . | I/s | Y/c | . | . | . | . | Q/l | . | . | P/S |
| 2nd passage, day 11 | L/f | . | V/m | Q/K | . | s/i | C/Y | . | . | . | . | L/Q | . | . | P |
| 3rd passage: Inoculum 1E2.5 TCID50, day 12 | L/f | . | V/M | Q/K | . | s/I | Y/c | . | . | . | . | Q/l | . | . | P/s |
| 3rd passage: Inoculum 1E4 TCID50, day 3 | L/f | . | V/m | Q/k | . | s/I | Y/c | . | . | . | . | Q/l | . | . | P/s |
| *Sequence of viruses recovered from infected Huh7.5 cells* | | | | | | | | | | | | | | | |
| Clonal sequence analysis of 2nd passage virus | | | | | | | | | | | | | | | |
| clone 5, 12 and 17 | L | . | . | V | Q | . | S | . | . | . | . | . | . | . | P |
| clone 6, 13 and 18 | L | . | . | V | Q | . | S | . | . | . | . | . | . | . | P |
| clone 11 | L | . | . | V | Q | . | S | . | . | . | . | . | . | . | P |
| clone 2 | . | . | . | V | . | . | . | C | . | . | . | L | . | . | P |
| clone 1 | . | . | . | . | . | . | . | C | . | . | . | . | . | . | . |
| Transfection experiment with mutated S52/JFH1 | | | | | | | | | | | | | | | |
| SEQ ID NO 4: T728C;A1553G;A1907C;T2718G;T7160C #: 1st | L | . | V | Q | . | S | . | . | . | . | . | L | . | . | P |
| SEQ ID NO 6: T728C;A1553G;A1907C;A2721G;T7160C #: 1st | L | . | V | . | . | . | C | . | . | . | . | L | . | . | P |
| SEQ ID NO 8: T728C;T2718G;T7160C: 1st passage | . | . | V | . | . | S | . | . | . | . | . | . | . | . | . |
| SEQ ID NO 20: A1553G;A2721G;A4845T: 1st passage | . | . | . | . | . | S | C | . | . | . | . | . | . | . | . |
| SEQ ID NO 10: A1553G;A2721G;A4845T: 1st passage | . | . | V | . | . | S | C | . | . | Q/R | . | . | . | . | . |
| SEQ ID NO 12: A2721G;A4845T: 1st passage | . | . | . | . | . | S | . | . | . | . | Q | . | . | . | . |
| A1553G: Transfection, day 32 | . | . | . | . | . | . | N/y | P/T | L | Q/R | . | . | . | . | . |
| A1907C: Transfection, day 24 | . | . | . | . | . | . | . | . | . | N/K | K/h | . | . | . | . |
| A1907C: Transfection, day 24 | . | . | . | . | . | . | . | . | . | . | K/h | . | . | . | . |
| SEQ ID NO 15: T2718G: 1st passage | . | . | . | . | . | S/i | . | . | . | . | . | L | . | . | P |
| A2721G: 1st passage | . | . | . | . | . | T/i | . | . | . | . | . | . | . | . | . |
| A4845T: 1st passage | . | . | . | . | . | S/i | . | . | . | . | . | . | . | . | . |
| T7160C: 1st passage | . | . | . | . | . | . | . | . | . | . | . | . | . | . | . |
| T7160C: 1st passage | . | . | . | . | . | . | . | . | . | . | . | . | . | . | . |
| Second transfection experiment with S52/JFH1 | | | | | | | | | | | | | | | |
| *Direct sequencing* | | | | | | | | | | | | | | | |
| 1st passage, day 8 | . | . | . | . | . | . | . | . | . | . | . | . | . | . | . |
| Transfection experiment with mutated S52/JFH1 | | | | | | | | | | | | | | | |
| SEQ ID NO 22: T2718C;A4550C: 1st passage | . | V/a | . | . | . | T/I | . | . | . | Q | . | . | . | . | . |
| T2718C: 1st passage | . | . | . | . | s/t | T/i | . | . | . | Q | K/h | L | . | L/I | . |
| SEQ ID NO 18: A4550C: 1st passage | . | . | . | . | . | s/i | . | . | . | Q | . | . | . | . | . |

REFERENCES

Engle, R. E., Russell, R. S., Purcell, R. H., & Bukh, J. (2007). Development of a TaqMan Assay for the Six Major Genotypes of Hepatitis C Virus: Comparison With Commercial Assays. J Med Virol. 2008 January; 80(1):72-9.

Kato, T., T. Date, M. Miyamoto, A. Furusaka, K. Tokushige, M. Mizokami, and T. Wakita. 2003. Efficient replication of the genotype 2a hepatitis C virus subgenomic replicon. Gastroenterology 125:1808-1817.

Kato, T., A. Furusaka, M. Miyamoto, T. Date, K. Yasui, J. Hiramoto, K. Nagayama, T. Tanaka, and T. Wakita. 2001. Sequence analysis of hepatitis C virus isolated from a fulminant hepatitis patient. J Med Virol 64:334-339.

Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete replication of hepatitis C virus in cell culture. Science 309:623-626.

Lindenbach B D, Meuleman P, Ploss A, Vanwolleghem T, Syder A J, McKeating J A, Lanford R E, Feinstone S M, Major M E, Leroux-Roels G, Rice C M. Cell culture-grown hepatitis C virus is infectious in vivo and can be recultured in vitro. Proc Natl Acad Sci USA. 2006 Mar. 7; 103(10): 3805-9. Epub 2006 Feb. 16.

Wakita, T., T. Pietschmann, T. Kato, T. Date, M. Miyamoto, Z. Zhao, K. Murthy, A. Habermann, H. G. Krausslich, M. Mizokami, R. Bartenschlager, and T. J. Liang. 2005. Production of infectious hepatitis C virus in tissue culture from a cloned viral genome. Nat Med 11:791-796.

Zhong, J., P. Gastaminza, G. Cheng, S. Kapadia, T. Kato, D. R. Burton, S. F. Wieland, S. L. Uprichard, T. Wakita, and F. V. Chisari. 2005. Robust hepatitis C virus infection in vitro. Proc Natl Acad Sci USA 102:9294-9299.

The invention claimed is:

1. A recombinant nucleic acid molecule which encodes human hepatitis C virus of genotype 3a/JFH1, wherein said molecule:
   (i) is capable of expressing said virus when transfected into cells,
   (ii) is capable of infectivity in vivo, and
   (iii) encodes an amino acid sequence with at least 99% sequence identity to that of SEQ ID NO: 2, and which
   (iv) comprises sequences encoding structural genes (Core, E1, E2), p7 and nonstructural gene (NS2) from a genotype 3a HCV strain, and sequences encoding the 5' untranslated region (UTR), nonstructural genes NS3, NS4A, NS4B, NS5A, NS5B, and the 3' UTR from the JFH-1 HCV strain and either (a) at least one adaptive mutation in the amino acid sequences of p7 or NS3, selected from the group consisting of I793S, and K1404Q, or, (b) at least two adaptive mutations in the amino acid sequences of E2, p7, NS3 or NS5A selected from the group consisting of M405V, K523Q, I793S, I1793T, Y794C, K1404Q, Q1502L, and S2274P, wherein a p7 adaptive mutation is combined with another adaptive mutation in NS3 or NS5A, and wherein said mutation is numbered according to the HCV sequence of SEQ ID NO: 2.

2. The nucleic acid molecule of claim 1, wherein said molecule:
   (i) comprises at least 99% sequence identity to that of SEQ ID NO: 1, which
   (ii) comprises sequences encoding structural genes (Core, E1, E2), p7 and nonstructural gene (NS2) from a genotype 3a HCV strain, and sequences encoding the 5' untranslated region (UTR), nonstructural genes NS3, NS4A, NS4B, NS5A, NS5B, and the 3' UTR from the JFH-1 HCV strain and either at least one adaptive mutation in the nucleic acid sequence encoding p7 or NS3 proteins selected from the group consisting of T2718G, and A4550C; or, (b) at least two adaptive mutations in the nucleic acid sequences of E2, p7, NS3, or NS5A selected from the group consisting of A1553G, A1907C, T2718C, T2718G, A2721G, A4550C, A4845T and T7160C, wherein a p7 adaptive mutation is combined with another adaptive mutation in NS3 or NS5A, wherein said mutation is numbered according to the HCV sequence of SEQ ID NO: 1.

3. The nucleic acid molecule of claim 1, further comprising a pharmaceutically acceptable diluent or excipient.

4. The nucleic acid molecule of claim 1, further comprising an active promoter and a cassette vector for cloning viral genomes.

5. A method for producing a cell which replicates HCV 3a/JFH1 and produces a virus particle comprising:

(i) introducing the nucleic acid molecule of claim 1 into a hepatic cell, wherein said cell is susceptible to infection by, or propagation of, an HCV construct, virus or viral particle comprising said nucleic acid molecule and wherein said nucleic acid molecule; and, (ii) culturing the cell to allow the cell to produce the viral particle.

6. The method of claim 5, wherein the cell is Huh7.5.

7. The method of claim 5, further comprising isolating said viral particle.

8. The method of claim 5 further comprising culturing the cell and infecting other cells with the produced viral particle in the culture.

9. A method of screening for an anti-hepatitis C virus substance, comprising:

a) culturing a hepatic cell or a hepatitis C virus particle with a hepatitis C virus permissive cell and a candidate molecule, wherein said hepatic cell or hepatitis C virus particle comprises the recombinant nucleic acid of claim 1, b) detecting the replicating RNA or the virus particles in the resulting culture; and, c) determining the effects of the candidate molecule on HCV infection, replication, or cell-to-cell spread in the culture of step (b) as compared to a placebo treated culture, wherein a decrease in the level of HCV infection, replication, or cell-to-cell spread indicates the candidate molecule is an anti-hepatitis C virus substance.

10. An immunogenic composition comprising a hepatitis C virus particle that comprises the nucleic acid of claim 1.

11. The nucleic acid of claim 1, wherein said nucleic acid is selected from the group consisting of double stranded DNA, positive-sense cDNA, negative-sense cDNA, positive-sense RNA, negative-sense RNA, and double stranded RNA.

12. The nucleic acid of claim 11, wherein said nucleic acid is selected from the group consisting of double stranded DNA, positive-sense cDNA, and negative-sense cDNA.

13. The nucleic acid of claim 1, wherein said nucleic acid further comprises a reporter gene.

14. The nucleic acid of claim 1, wherein said nucleic acid is a DNA molecule comprising a promoter 5' of the 5'-UTR on positive-sense DNA, whereby transcription of template DNA from the promoter produces replication-competent RNA.

15. The nucleic acid of claim 14, wherein said promoter is selected from the group consisting of a eukaryotic promoter, yeast promoter, plant promoter, bacterial promoter, and a viral promoter.

* * * * *